US010988466B2

(12) United States Patent
Ma et al.

(10) Patent No.: US 10,988,466 B2

(45) Date of Patent: Apr. 27, 2021

(54) HETEROCYCLIC DERIVATIVES USEFUL AS SHP2 INHIBITORS

(71) Applicant: Jacobio Pharmaceuticals Co., Ltd., Beijing (CN)

(72) Inventors: Cunbo Ma, Beijing (CN); Panliang Gao, Beijing (CN); Shaojing Hu, Beijing (CN); Zilong Xu, Beijing (CN); Huifeng Han, Beijing (CN); Xinping Wu, Beijing (CN); Di Kang, Beijing (CN)

(73) Assignee: Jacobio Pharmaceuticals Co., Ltd., Beijing (CN)

( * ) Notice: Subject to any disclaimer, the term of this patent is extended or adjusted under 35 U.S.C. 154(b) by 39 days.

(21) Appl. No.: 16/496,655

(22) PCT Filed: Mar. 23, 2018

(86) PCT No.: PCT/IB2018/051973

§ 371 (c)(1),
(2) Date: Sep. 23, 2019

(87) PCT Pub. No.: WO2018/172984

PCT Pub. Date: Sep. 27, 2018

(65) Prior Publication Data

US 2020/0392128 A1 Dec. 17, 2020

(30) Foreign Application Priority Data

Mar. 23, 2017 (WO) .................. PCT/IB2017/051690

(51) Int. Cl.

| | |
|---|---|
| ***C07D 471/10*** | (2006.01) |
| ***C07D 413/14*** | (2006.01) |
| ***C07D 401/04*** | (2006.01) |
| ***C07D 401/14*** | (2006.01) |
| ***C07D 471/20*** | (2006.01) |
| ***C07D 491/107*** | (2006.01) |
| ***C07D 495/10*** | (2006.01) |
| ***C07D 513/10*** | (2006.01) |

(52) U.S. Cl.

CPC ......... *C07D 413/14* (2013.01); *C07D 401/04* (2013.01); *C07D 401/14* (2013.01); *C07D 471/10* (2013.01); *C07D 471/20* (2013.01); *C07D 491/107* (2013.01); *C07D 495/10* (2013.01); *C07D 513/10* (2013.01)

(58) Field of Classification Search

CPC .................................................... C07D 471/10

See application file for complete search history.

(56) References Cited

U.S. PATENT DOCUMENTS

| | | | |
|---|---|---|---|
| 5,876,628 | A | 3/1999 | Illian et al. |
| 6,025,382 | A | 2/2000 | Bastian et al. |
| 7,056,911 | B1 | 6/2006 | Rosowsky |
| 7,435,830 | B2 | 10/2008 | Pennell et al. |
| 7,435,831 | B2 | 10/2008 | Chen et al. |
| 7,439,374 | B2 | 10/2008 | Thurkauf et al. |
| 7,605,159 | B2 | 10/2009 | McInally et al. |
| 7,691,863 | B2 | 4/2010 | Dietz et al. |
| 7,723,369 | B2 | 5/2010 | Mjalli et al. |
| 7,790,929 | B2 | 9/2010 | Reiffenrath et al. |
| 7,838,523 | B2 | 11/2010 | Blomgren et al. |
| 8,012,983 | B2 | 9/2011 | Andrews et al. |
| 8,138,206 | B2 | 3/2012 | Ishikawa et al. |
| 8,153,635 | B2 | 4/2012 | Alper et al. |
| 8,252,803 | B2 | 8/2012 | Rivkin |
| 8,258,156 | B2 | 9/2012 | Alper et al. |
| 8,313,729 | B2 | 11/2012 | Neumann et al. |
| 8,338,437 | B2 | 12/2012 | Wahhab et al. |
| 8,389,533 | B2 | 3/2013 | Connors et al. |
| 8,404,731 | B2 | 3/2013 | Mjalli et al. |
| 8,431,575 | B2 | 4/2013 | Gohimukkula et al. |
| 8,450,327 | B2 | 5/2013 | Gottschling et al. |

(Continued)

FOREIGN PATENT DOCUMENTS

| | | | |
|---|---|---|---|
| CN | 1934100 | A | 3/2007 |
| CN | 103201267 | A | 7/2013 |

(Continued)

OTHER PUBLICATIONS

Ahronian, Leanne G., "Strategies for Monitoring and Combating Resistance to Combination Kinase Inhibitors for Cancer Therapy," Genome Medicine (2017) 9:37; DOI: 10.1186/s13073-017-0431-3 (12 pages).

(Continued)

*Primary Examiner* — Laura L Stockton

(74) *Attorney, Agent, or Firm* — Foley Hoag LLP

(57) ABSTRACT

This invention relates to certain novel pyrazine derivatives (Formula I) as SHP2 inhibitors which is shown as formula I, their synthesis and their use for treating a SHP2 mediated disorder. More particularly, this invention is directed to fused heterocyclic group derivatives useful as inhibitors of SHP2, methods for producing such compounds and methods for treating a SHP2-mediated disorder.

Formula I

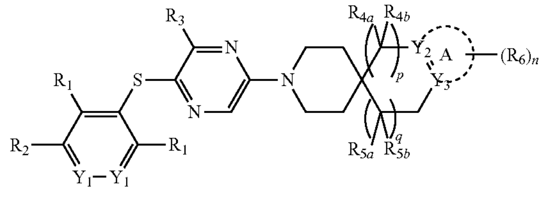

2 Claims, No Drawings

(56) References Cited

U.S. PATENT DOCUMENTS

| | | | |
|---|---|---|---|
| 8,461,329 | B2 | 6/2013 | Takayama et al. |
| 8,575,168 | B2 | 11/2013 | Azimioara et al. |
| 8,637,500 | B2 | 1/2014 | Allen et al. |
| 8,759,377 | B2 | 6/2014 | Conn et al. |
| 8,791,136 | B2 | 7/2014 | Goff et al. |
| 8,809,370 | B2 | 8/2014 | Goff et al. |
| 8,822,497 | B2 | 9/2014 | Burger et al. |
| 8,889,730 | B2 | 11/2014 | Bhattacharya et al. |
| 8,912,219 | B2 | 12/2014 | Fauber et al. |
| 8,952,014 | B2 | 2/2015 | Gottschling et al. |
| 8,980,921 | B2 | 3/2015 | Goff et al. |
| 8,987,303 | B2 | 3/2015 | Goff et al. |
| 9,062,015 | B2 | 6/2015 | Stieber et al. |
| 9,266,856 | B2 | 2/2016 | Goff et al. |
| 9,624,199 | B2 | 4/2017 | Becker-Pelster et al. |
| 9,663,496 | B2 | 5/2017 | Irving et al. |
| 9,815,813 | B2 | 11/2017 | Chen et al. |
| 9,969,719 | B2 | 5/2018 | Ding et al. |
| 10,077,276 | B2 | 9/2018 | Chen et al. |
| 10,253,046 | B2 | 4/2019 | Dahlgren et al. |
| 10,287,266 | B2 | 5/2019 | Chen et al. |
| 10,301,278 | B2 | 5/2019 | Chen et al. |
| 10,329,270 | B2 | 6/2019 | Qiu et al. |
| 10,377,742 | B2 | 8/2019 | Goff et al. |
| 10,463,662 | B2 | 11/2019 | Lu |
| 10,858,359 | B2 | 12/2020 | Ma et al. |
| 2007/0037794 | A1 | 2/2007 | Ungashe et al. |
| 2007/0043057 | A1 | 2/2007 | Matteucci et al. |
| 2008/0269217 | A1 | 10/2008 | Vos et al. |
| 2008/0269251 | A1 | 10/2008 | Andre-Gil et al. |
| 2009/0023701 | A1 | 1/2009 | Aungst et al. |
| 2009/0111801 | A1 | 4/2009 | Andres-Gil et al. |
| 2009/0281099 | A1 | 11/2009 | Andres-Gil et al. |
| 2009/0286831 | A1 | 11/2009 | Koegel et al. |
| 2010/0016319 | A1 | 1/2010 | Ohno et al. |
| 2010/0216816 | A1 | 8/2010 | Barrow et al. |
| 2011/0098269 | A1 | 4/2011 | Becknell et al. |
| 2011/0152246 | A1 | 6/2011 | Buckman et al. |
| 2012/0157471 | A1 | 6/2012 | Nair et al. |
| 2012/0184572 | A1 | 7/2012 | Song et al. |
| 2014/0005103 | A1 | 1/2014 | Coburn et al. |
| 2014/0142094 | A1 | 5/2014 | Reddy et al. |
| 2015/0087673 | A1 | 3/2015 | Hitoshi et al. |
| 2016/0057478 | A1 | 2/2016 | Mitchell et al. |
| 2016/0159773 | A1 | 6/2016 | Saitoh et al. |
| 2018/0207054 | A1 | 7/2018 | Sitsihovskiy et al. |
| 2019/0127378 | A1 | 5/2019 | Ma et al. |
| 2019/0300533 | A1 | 10/2019 | Wang et al. |

FOREIGN PATENT DOCUMENTS

| | | | |
|---|---|---|---|
| CN | 103201267 | B | 8/2016 |
| CN | 105899491 | A | 8/2016 |
| CN | 105899493 | A | 8/2016 |
| CN | 105916845 | A | 8/2016 |
| CN | 106232581 | A | 12/2016 |
| CN | 107286150 | A | 10/2017 |
| CN | 107922388 | A | 4/2018 |
| EP | 3290412 | A1 | 3/2018 |
| EP | 2985334 | B1 | 6/2018 |
| EP | 2883934 | B1 | 11/2019 |
| EP | 3608321 | A1 | 2/2020 |
| JP | 2007/13804 | A | 1/2007 |
| WO | WO-2002/032872 | A1 | 4/2002 |
| WO | WO-2003/059354 | A2 | 7/2003 |
| WO | WO-2003/072548 | A1 | 9/2003 |
| WO | WO-2004/033406 | A1 | 4/2004 |
| WO | WO-2004/046092 | A2 | 6/2004 |
| WO | WO-2004/071426 | A2 | 8/2004 |
| WO | WO-2004/074266 | A1 | 9/2004 |
| WO | WO-2004/099158 | A1 | 11/2004 |
| WO | WO-2004/085409 | A3 | 12/2004 |
| WO | WO-2005/004810 | A2 | 1/2005 |
| WO | WO-2005/005435 | A1 | 1/2005 |
| WO | WO-2005/033105 | A2 | 4/2005 |
| WO | WO-2005/044797 | A1 | 5/2005 |
| WO | WO-2005/066156 | A1 | 7/2005 |
| WO | WO-2006/012226 | A2 | 2/2006 |
| WO | WO-2006/045828 | A1 | 5/2006 |
| WO | WO-2006/067466 | A2 | 6/2006 |
| WO | WO-2006/071759 | A2 | 7/2006 |
| WO | WO-2006/084186 | A2 | 8/2006 |
| WO | WO-2006/087305 | A1 | 8/2006 |
| WO | WO-2007/045462 | A2 | 4/2007 |
| WO | WO-2007/046867 | A2 | 4/2007 |
| WO | WO-2007/057742 | A2 | 5/2007 |
| WO | WO-2007/057775 | A1 | 5/2007 |
| WO | WO-2007/063868 | A1 | 6/2007 |
| WO | WO-2007/084728 | A2 | 7/2007 |
| WO | WO-2008/008431 | A2 | 1/2008 |
| WO | WO-2007/103308 | A2 | 2/2008 |
| WO | WO-2008/033857 | A2 | 3/2008 |
| WO | WO-2008/100412 | A1 | 8/2008 |
| WO | WO-2008/112674 | A1 | 9/2008 |
| WO | WO-2009/033084 | A1 | 3/2009 |
| WO | WO-2009/036066 | A1 | 3/2009 |
| WO | WO-2009/108766 | A1 | 9/2009 |
| WO | WO-2010/008739 | A2 | 1/2010 |
| WO | WO-2010/020675 | A1 | 2/2010 |
| WO | WO-2010/036380 | A1 | 4/2010 |
| WO | WO-2010/070022 | A1 | 6/2010 |
| WO | WO-2010/074244 | A1 | 7/2010 |
| WO | WO-2010/085700 | A2 | 7/2010 |
| WO | WO-2010/086613 | A1 | 8/2010 |
| WO | WO-2010/103547 | A2 | 9/2010 |
| WO | WO-2011/004162 | A2 | 1/2011 |
| WO | WO-2011/022440 | A2 | 2/2011 |
| WO | WO-2011/072791 | A1 | 6/2011 |
| WO | WO-2011/103091 | A1 | 8/2011 |
| WO | WO-2011/130232 | A1 | 10/2011 |
| WO | WO-2011/135276 | A1 | 11/2011 |
| WO | WO-2011/146401 | A1 | 11/2011 |
| WO | WO-2011/150156 | A2 | 12/2011 |
| WO | WO-2012/016217 | A1 | 2/2012 |
| WO | WO-2012/026495 | A1 | 3/2012 |
| WO | WO-2012/041158 | A1 | 4/2012 |
| WO | WO-2012/069852 | A1 | 5/2012 |
| WO | WO-2012/088438 | A1 | 6/2012 |
| WO | WO-2012/080729 | A4 | 11/2012 |
| WO | WO-2012/158784 | A2 | 11/2012 |
| WO | WO-2013/017461 | A1 | 2/2013 |
| WO | WO-2013/039851 | A1 | 3/2013 |
| WO | WO-2013/090454 | A2 | 6/2013 |
| WO | WO-2013/124040 | A1 | 8/2013 |
| WO | WO-2013/139882 | A1 | 9/2013 |
| WO | WO-2013/161308 | A1 | 10/2013 |
| WO | WO-2013/167633 | A1 | 11/2013 |
| WO | WO-2014/000178 | A1 | 1/2014 |
| WO | WO-2014/001377 | A1 | 1/2014 |
| WO | WO-2014/004416 | A1 | 1/2014 |
| WO | WO-2014/028829 | A1 | 2/2014 |
| WO | WO-2014/043068 | A1 | 3/2014 |
| WO | WO-2014/140704 | A1 | 9/2014 |
| WO | WO-2014/144326 | A1 | 9/2014 |
| WO | WO-2014/184014 | A1 | 11/2014 |
| WO | WO-2014/184074 | A1 | 11/2014 |
| WO | WO-2014/191737 | A1 | 12/2014 |
| WO | WO-2014/201172 | A1 | 12/2014 |
| WO | WO-2015/003094 | A2 | 1/2015 |
| WO | WO-2015/016206 | A1 | 2/2015 |
| WO | WO-2015/017305 | A1 | 2/2015 |
| WO | WO-2015/048547 | A3 | 6/2015 |
| WO | WO-2015/091420 | A1 | 6/2015 |
| WO | WO-2015/107493 | A1 | 7/2015 |
| WO | WO 2015/107494 | A1 | 7/2015 |
| WO | WO 2015/107495 | A1 | 7/2015 |
| WO | WO-2015/123437 | A1 | 8/2015 |
| WO | WO-2015/123533 | A1 | 8/2015 |
| WO | WO-2015/148714 | A1 | 10/2015 |
| WO | WO-2015/155042 | A1 | 10/2015 |
| WO | WO-2015/177325 | A1 | 11/2015 |
| WO | WO-2016/015604 | A1 | 2/2016 |
| WO | WO-2016/022644 | A1 | 2/2016 |
| WO | WO-2016/022645 | A1 | 2/2016 |

(56) References Cited

FOREIGN PATENT DOCUMENTS

| | | | |
|---|---|---|---|
| WO | WO-2016/040449 | A1 | 3/2016 |
| WO | WO-2016/138352 | A1 | 9/2016 |
| WO | WO-2016/141881 | A1 | 9/2016 |
| WO | WO-2016/151501 | A1 | 9/2016 |
| WO | WO-2016/195776 | A1 | 12/2016 |
| WO | WO-2016/197027 | A1 | 12/2016 |
| WO | WO-2016/203404 | A1 | 12/2016 |
| WO | WO-2016/203405 | A1 | 12/2016 |
| WO | WO 2016/203406 | A1 | 12/2016 |
| WO | WO-2017/021784 | A2 | 2/2017 |
| WO | WO-2017/049321 | A1 | 3/2017 |
| WO | WO-2017/114351 | A1 | 7/2017 |
| WO | WO-2017/156397 | A1 | 9/2017 |
| WO | WO-2017/210134 | A1 | 12/2017 |
| WO | WO-2017/211303 | A1 | 12/2017 |
| WO | WO-2017/216706 | A1 | 12/2017 |
| WO | WO 2018/013597 | A1 | 1/2018 |
| WO | WO-2018/057884 | A1 | 3/2018 |
| WO | WO-2018/089433 | A1 | 5/2018 |
| WO | WO-2018/127801 | A1 | 7/2018 |
| WO | WO-2018/172984 | A1 | 9/2018 |
| WO | WO-2018/177403 | A1 | 10/2018 |
| WO | WO-2019/014427 | A1 | 1/2019 |
| WO | WO-2019/075265 | A1 | 4/2019 |
| WO | WO-2019/079783 | A1 | 4/2019 |
| WO | WO-2019/126696 | A1 | 6/2019 |
| WO | WO-2019/148132 | A1 | 8/2019 |
| WO | WO-2019/148136 | A1 | 8/2019 |
| WO | WO-2019/152454 | A1 | 8/2019 |
| WO | WO-2019/154950 | A1 | 8/2019 |
| WO | WO-2019/167000 | A1 | 9/2019 |
| WO | WO-2019/182924 | A1 | 9/2019 |

OTHER PUBLICATIONS

Bentires-Alj, Mohamed et al., "Activating Mutations of the Noonan Syndrome-Associated SHP2/PTPN11 Gene in Human Solid Tumors and Adult Acute Myelogenous Leukemia," Cancer Research 64, 8816-8820, Dec. 15, 2004.

Bunda, Severa et al., "Inhibition of SHP2-Mediated Dephosphorylation of Ras Suppresses Oncogenesis," Nature Communications, 6:8859 (2015), DOI: 10.1038/ncomms9859/www.nature.com/naturecommunications (12 pages).

Butterworth, Sam et al., "Targeting Protein Tyrosine Phosphatase SHP2 for Therapeutic Intervention," Future Med. Chem. 6(12), 1423-1437 (2014).

Chen, Chuan et al., "Discovery of a Novel Inhibitor of the Protein Tyrosine Phosphatase Shp2," Scientific Reports 5: 17626, DOI: 10:1038/srep 17626 (2015) (13 pages).

Chen, Liwei et al., "Discovery of a Novel Shp2 Protein Tyrosine Phosphatase Inhibitor," Molecular Pharmacology, vol. 70, No. 2 562-570 (2006).

Chen, Wendy S. et al., "Treating Leukemia at the Risk of Inducing Severe Anemia," Exp Henatol. 2016, 44(5): 329-331: doi:10.1016/j.exphem.2016.01.004.

Chen, Ying-Nan P., et al., "Allosteric Inhibition of SHP2 Phosphatase Inhibits Cancers Driven by Receptor Tyrosine Kinases," Nature 535, (17 pages) (2016).

Chichger, Havovi et al., "SH2-Domain-Containing Protein Tyrosine Phosphatase 2 and Focal Adhesion Kinase Protein Interactions Regulate Pulmonary Endothelium Barrier Function," Am. J. Respir. Cell Biol. vol. 52, Issue 6, 695-707, Jun. 2015.

Chio, Cynthia M. et al., "Targeting a Cryptic Allosteric Site for Selective Inhibition of the Oncogenic Protein Tyrosine Phosphatase Shp2," Biochemistry 54, 497-504 (2015).

Dardaei, Leila et al., "SHP2 Inhibition Restores Sensitivity in ALK-rearranged non-small-cell Lung Cancer Resistant to ALK Inhibitors," Nature Medicine, 24, (8 pages) (2018).

Dong, Lei et al., "Leukaemogenic Effects of Ptpn11 Activating Mutations in the Stem Cell Microenvironment," Nature, 539, (17 pages) (2016).

Extended European Search Report for EP Application No. 17809742.4 dated Mar. 25, 2019.

Extended European Search Report for EP Application No. 18770877.1 dated Apr. 17, 2020.

Fodor, Michelle et al., "Dual Allosteric Inhibition of SHP2 Phosphatase," ACS Chem. Biol. 2018, 13, 3, (34 pages).

Fortanet, Jorge Garcia et al., "Allosteric Inhibition of SHP2: Identification of a Potent, Selective, and Orally Efficacious Phosphatase Inhibitor," Journal of Medical Chemistry, 2016, 59, 17, (37 pages).

Frankson, Rochelle et al., "Therapeutic Targeting of Oncogenic Tyrosine Phosphatases," Cancer Res,Nov. 1, 2017, (77) (21) 5701-5705.

Grosskopf, Stefanie et al., "Selective Inhibitors of the Protein Tyrosine Phosphatase SHP2 Block Cellular Motility and Growth of Cancer Cells In Vitro and In Vivo," ChemMedChem 2015, 10, 815-826.

Guo, Wenjie et al., "Tyrosine Phosphatase SHP2 Negatively Regulates NLRP3 Inflammasome Activation via ANTI-dependent Mitochondrial Homeostasis," Nature Communications, 8:2168 (2017); (14 pages).

He, Rongjun et al., "Exploring the Existing Drug Space for Novel pTyr Mimetic and SHP2 Inhibitors," ACS Med. Chem. Lett. 2015, 6, 7, 782-786.

Hellmuth, Klaus et al., "Specific Inhibitors of the Protein Tyrosine Phosphatase Shp2 Identified by High-Throughput Docking," PNAS, May 20, 2008, vol. 105, No. 20, 7275-7280.

Huang, Wen-Qing et al., "Structure, Function, and Pathogensis of SHP2 in Developmental Disorders and Tumorigenesis," Current Cancer Drug Targets, 2014, 14, 567-588.

International Search Report and Written Opinion for International Application No. PCT/CN2017/087471 dated Aug. 18, 2017.

International Search Report and Written Opinion for International Application No. PCT/IB2018/051973 dated Jul. 11, 2018.

International Search Report for International Application No. PCT/CN2017/087471, dated Aug. 18, 2017. (5 pages).

Lappalainen, Ilkka et al., "Genome Wide Analysis of Pathogenic SH2 Domain Mutations," Proteins 2008; 72:779-792.

LaRochelle, J.R. et al., "Identification of an Allosteric Benzothiazoloprymidone Inhibitor of the Oncogenic Protein Tyrosine Phosphatase SHP2," Bioorganic & Medicinal Chemistry Letters, vol. 25, Issue 24, Dec. 15, 2017, (9 pages).

LaRochelle, Jonathan R., "Structural and Functional Consequences of Three Cancer-Associated Mutations of the Oncogenic Phosphatase SHP2," Biochemistry 55, 2269-2277 (2016).

Lawrence, Harshani R. et al., "Inhibitors of Src Homology-2 Domain Containing Protein Tyrosine Phosphatase-2 (Shp2) Based on Oxindole Scaffolds," J. Med. Chem 2008: 51 (16): (22 pages).

Leibowitz, Michael S. et al., "SHP2 is Overexpressed and Inhibits pSTAT1-Mediated APM Component Expression, T Cell Attracting Chemokine Secretion, and CTL Recognition in Head and Neck Cancer Cells," Clin Cancer Res. 19(4): (20 pages) (2013).

Li, Jing et al., "PD-1/SHP-2 Inhibits Tc1/Th1 Phenotypic Responses and the Activation of T Cells in the Tumor Microenvironment," Cancer Research, Feb. 1, 2015 (75) (3) 508-518.

Liu, Kun-Wei et al., "SHP-2/PTPN11 Mediates Gliomagenesis Driven by PDGFRA and /NK4A/ARF Aberrations in Mice and Humans," The Journal of Clinical Investigation, vol. 121, No. 3, Mar. 2011; pp. 905-917.

Liu, Wei et al., "Identification of Cryptotanshinone as an Inhibitor of Oncogenic Protein Tyrosine Phosphatase SHP2 (PTPN11)," J. Med. Chem. 2013; 56(18): (26 pages).

Liu, Wen et al., "T Lymphocyte SHP2-deficiency Triggers Anti-Tumor Immunity to Inhibit Colitis-Associated Cancer in Mice," Oncotarget, 2017, vol. 8, (No. 5), pp. 7586-7597.

Liu, Wen et al., "T Lymphocyte SHP2-deficiency Triggers Anti-Tumor Immunity to Inhibit Colitis-Associated Cancer in Mice," Oncotarget, Advance Publications 2016; (12 pages).

Manguso, Robert T. et al., "In vivo CRISPR Screening Identifies Ptpn2 as a Cancer Immunotherapy Target," Nature 2017, (17 pages).

Martin, Katie R. et al., "Integrating Virtual and Biochemical Screening for Protein Tyrosine Phosphatase Inhibitor Discovery," Methods, 65 (2014) 219-228.

(56) References Cited

OTHER PUBLICATIONS

Matozaki, Takashi et al., "Protein Tyrosine Phosphatase SHP-2: A Protooncogene Product that Promotes Ras Activation," Cancer Science, Oct. 2009, vol. 100, No. 10, 1786-1793.
Mazharian, Alexandra et al., "Megakaryocyte-specific Deletion of the Protein-Tyrosine Phosphatases Shp1 and Shp2 Causes Abnormal Megakaryocyte Development, Platelet Production, and Function," Blood. May 16, 2013; 121(20):4205-4220.
Meanwell., "Synopsis of Some Recent Tactical Application of Bioisosteres in Drug Design," Journal of Medicinal Chemistry, 54: 2529-2591 (2011).
Mohi, M. Golam et al., "The Role of Shp2 (PTPN11) in cancer," Current Opinion in Genetics & Development 2007, 17:23-30.
Nichols, Robert J. et al., "Efficacy of SHP2 Phosphatase Inhibition in Cancers With Nucleotide-Cycling Oncogenic RAS, RAS-GTP Dependent Oncogenic BRAF and NF1 Loss," BioRxiv Sep. 14, 2017 (16 pages).
Pandey, Ruchi et al., "Role of SHP2 in Hematopoiesis and Leukemogenesis," Curr Opin Hematol. Jul. 4, 2017(4):307-313.
Peled, Michael et al., "Affinity Purification Mass Spectrometry Analysis of PD-1 Uncovers SAP as a New Checkpoint Inhibitor," Proc Natl Acad Sci USA. Jan. 16, 2018;115(3):pp. E468-E477.
Prahallad, Anirudh et al., "PTPN11 Is a Central Node in Intrinsic and Acquired Resistance to Targeted Cancer Drugs," Cell Reports, 12, 1978-1985, Sep. 29, 2015.
Protein Tyrosine Phosphatase, PTPN11 (SHP-2) (Human), Dec. 2005 (1 page).
Qi, Chen et al., "Shp2 Inhibits Proliferation of Esophageal Squamous Cell Cancer via Dephosphorylation of Stat3," International Journal of Molecular Sciences, 18, 134 (2017) (12 pages).
Ran, Hao et al., "Sticking It to Cancer with Molecular Glue for SHP2," Cancer Cell 30, Aug. 8, 2016; 8;30(2):194-196.
Scott, Latanya M. et al., "Shp2 Protein Tyrosine Phosphatase Inhibitor Activity of Estramustine Phosphate and its Triterpenoid Analogs," Bioorg Med Chem Lett., 21 (2), (9 pages) Jan. 15, 2011.
Simoncic, Paul D., "T-Cell Protein Tyrosine Phosphatase (Tcptp) Is a Negative Regulator of Colony-Stimulating Factor 1 Signaling and Macrophage Differentiation," Molecular and Cellular Biology, vol. 26, No. 11, Jun. 2006, p. 4149-4160.
Stephan, Matthias T. et al., "Synapse-directed Delivery of Immunomodulators Using T-Cell-Conjugated Nanoparticles," Biomaterials 33, 5776-5787 (2012).
Sun, X. et al., "Selective Inhibition of Leukemia-Associated SHP2E59K Mutant by the Allosteric SHP2 Inhibitor SHP099," Leukemia, 32, (12 pages) (2018).
Supplementary European Search Report for corresponding EP Application No. EP 17809742 dated Mar. 15, 2019 (2 pages).
Wang, Wen-Long et al., "Benzo[c][1,2,5]thiadiazole Derivatives: A New Class of Potent Src Homology-2-domain Containing Protein Tyrosine Phosphatase-2 (SHP2) Inhibitors," Bioorganic & Medicinal Chemistry Letters Dec. 1, 2017;27(23): pp. 5154-5157.
Written Opinion of the International Search Authority for International Application No. PCT/CN2017/087471. (8 pages), dated Aug. 18, 2017.
Xie, Jingjing et al., "Allosteric Inhibitors of SHP2 with Therapeutic Potential for Cancer Treatment," Journal of Medicinal Chemistry, Nov. 20, 2017; 60, 24, (55 pages).
Xu, Jie et al., "Targeting SHP2 for EGFR Inhibitor Resistant Non-Small Cell Lung Carcinoma," Biochem Biophys Res Commun., 439(4), Oct. 4, 2013;439(4): (13 pages).
Yokosuka, Tadashi et al., "Programmed Cell Death 1 Forms Negative Costimulatory Microclusters that Directly Inhibit T Cell Receptor Signaling by Recruiting Phosphatase SHP2," J. Exp. Med., vol. 209, No. 6, 1201-1217 (2012).
Yu, Bing et al., "Targeting Protein Tyrosine Phosphatase SHP2 for the Treatment of PTPN11-Associated Malignancies," Mol Cancer Ther; 12(9) Sep. 2013 pp. 1738-1748.
Zeng, Li-Fan et al., "Therapeutic Potential of Targeting the Oncogenic SHP2 Phosphatase," J. Med Chem. 2014, 57, 6594-6609.
Zhang, Jie et al., "Functions of Shp2 in Cancer," J. Cell. Mol. Med. vol. 19, No. 9, pp. 2075-2083 (2015).
Zheng, Jian et al., "Pancreatic Cancer Risk Variant in LINC00673 Creates a miR-1231 Binding Site and Interferes with PTPN11 Degradation," Nature Genetics, vol. 48, No. 7, Jul. 2016; (14 pages).
Zhu, Helen He et al.,"Shp2 and Pten Have Antagonistic roles in Myeloproliferation but Cooperate to Promote Erythropoiesis in Mammals," PNAS, vol. 12, No. 43, 13342-13347, 2015.

HETEROCYCLIC DERIVATIVES USEFUL AS SHP2 INHIBITORS

This application is a national phase entry pursuant to 35 U.S.C. § 371 of International Application No. PCT/IB2018/051973, filed Mar. 23, 2018, which is incorporated herein by reference, which claims priority to International Application No. PCT/IB2017/051690, filed Mar. 23, 2017.

TECHNICAL FIELD

This invention relates to certain novel pyrazine derivatives (Formula I, II, III or IV) as SHP2 inhibitors which is shown as Formula I, II, III or IV, their synthesis and their use for treating a SHP2 mediated disorder. More particularly, this invention is directed to fused heterocyclic derivatives useful as inhibitors of SHP2, methods for producing such compounds and methods for treating a SHP2-mediated disorder.

BACKGROUND ART

SHP2 (The Src Homolgy-2 phosphatease) is a non-receptor protein tyrosine phosphatase encoded by the PTPN11 gene that harbors a classical tyrosine phosphatase domain and two N-terminal Src homology 2 (SH2) domains and a C-terminal tail. The two SH2 domains control the subcellular localization and functional regulation of SHP2. In its inactive state, the N-terminal SH2 domain blocks the PTP domain and this autoinhibition is relieved by binding of the SH2 domains to specific phosphotyrosine sites on receptors or receptor-associated adaptor proteins. The stimulation, for example, by cytokines or growth factors leads to exposure of the catalytic site resulting in enzymatic activation of SHP2.

SHP2 is widely expressed and participated in multiple cell signaling processes, such as the Ras-Erk, PI3K-Akt, Jak-Stat, Met, FGFR, EGFR, and insulin receptors and NF-kB pathways, in which plays an important role in proliferation, differentiation, cell cycle maintenance and migration.

The hyperactivation of SHP2 catalytic activity caused by either germline or somatic mutations in PTPN11 have been identified in patients with Noonan syndrome, Leopard syndrome, juvenile myelomonocytic leukemias, myelodysplastic syndrome, B cell acute lymphoblastic leukemia/lymphoma, and acute myeloid leukemia. In addition, activating mutations of PTPN11 have been found in solid tumors as well, such as lung cancer, colon cancer, melanoma, neuroblastoma, and hepatocellular carcinoma. Therefore, the presence of activated or up-regulated SHP2 protein in human cancers and other disease make SHP2 an excellent target for development of novel therapies. The compounds of the present invention fulfill the need of small molecules in order to inhibit the activity of SHP2.

SUMMARY OF INVENTION

The present invention relates to heterocyclic pyrazine compounds useful as SHP2 inhibitors and for the treatment of conditions mediated by SHP2. The compounds of the invention have the general structure as Formula I or a pharmaceutically acceptable salt:

I

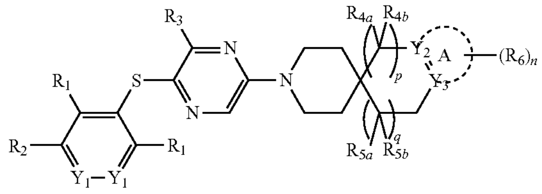

Each $R_1$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

$R_2$ is —H, halogen, —$NH_2$, —CN, —OH, —$NO_2$, —$N_3$, carboxyl, —$NHC_{1-6}$alkyl, —$N(C_{1-6}alkyl)_2$, —$CONH_2$, —$CONHC_{1-6}$alkyl, —$CON(C_{1-6}alkyl)_2$, —$COC_{1-6}$alkyl, —$NHCOC_{1-6}$alkyl, —$NC_{1-6}$alkyl-CO—$C_{1-6}$alkyl, substituted or unsubstituted —$C_{1-6}$alkoxy, substituted or unsubstituted —$C_{1-6}$alkyl or —$C_{5-10}$heterocyclic; or $R_2$ combines with $R_1$ to which is adjacent to form a 6-10 membered aryl, 5-10 membered heteroaryl or 5-10 membered heterocyclic ring, and each of the ring systems is independently optionally substituted;

Each $Y_1$ is independently N or $CR_{1a}$;

Each $R_{1a}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

$R_3$ is —H or —$NH_2$;

Each of $R_{4a}$ and $R_{4b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{4a}$ and $R_{4b}$ together with the carbon atom to which they are both attached form CO, C═NH, or C═N—OH;

p is 0, 1, 2 or 3;

Each of $R_{5a}$ and $R_{5b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{5a}$ and $R_{5b}$ together with the carbon atom to which they are both attached form a 3-10 membered heterocyclic or 5-10 membered heteroaryl or C═$NR_5$c, and $R_{5c}$ is —H, or —$C_{1-6}$alkyl; and each of the ring systems is independently optionally substituted;

q is 0, 1, 2, 3 or 4;

W is absent, —O, —S or —$NR_w$; and $R_w$ is —H, halogen, —$NH_2$, —CN, —OH, —$NO_2$, carboxyl, —CO—$C_{1-6}$alkyl, —CO—$OC_{1-6}$alkyl, —$C_{1-6}$alkyl-O— $C_{1-6}$alkoxy, substituted or unsubstituted —$C_{1-6}$alkoxy, or substituted or unsubstituted —$C_{1-6}$alkyl;

Ring A is absent or a 3-10 membered ring;

$\overline{\overline{---}}$ represents a single bond or a double bond;

When ring A is absent, $Y_2$ is $CR_{2a}R_{2b}$, $NR_{2a}$ or O, and $Y_3$ is $CR_{3a}R_{3b}$, $NR_{3a}$ or O;

When ring A is a 3-10 membered ring, i) $Y_2$ is $CR_{2a}$ or N, and $Y_3$ is $CR_{3a}$ or N, when $\overline{\overline{---}}$ represents a single bond; or ii) $Y_2$ is C, and $Y_3$ is C, when $\overline{\overline{---}}$ represents a double bond;

Each of $R_{2a}$ and $R_{2b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each of $R_{3a}$ and $R_{3b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each $R_6$ is independently —H, halogen, —$NR_{6a}R_{6b}$, —CN, —OH, —$NO_2$, oxo, =O, carboxyl, —$C_{1-6}$alkoxy, —$C_{1-6}$alkyl, —$C_{1-6}$alkylene-$NR_{6a}R_{6b}$, —$C_{1-6}$alkylene-O—$C_{1-6}$alkyl, —$C_{1-6}$alkylene-CO—$OR_{6a}$, —$C_{1-6}$alkylene-$C_{3-10}$heterocyclic, —$C_{1-6}$alkylene-$C_{5-10}$heteroaryl, —$C_{1-6}$alkylene-CO—$NR_{6a}R_{6b}$, —$C_{1-6}$alkylene-$NR_{6a}$—CO—$NR_{6a}R_{6b}$, —$C_{1-6}$alkylene-$NR_{6a}$—CO—$C_{1-6}$alkyl, —CO—$NR_{6a}R_{6b}$, —CO—CO—$NR_{6a}R_{6b}$, —$C_{3-10}$carbocyclic, —$C_{3-10}$heterocyclic, —CO—$C_{1-6}$alkyl, —CO—$C_{1-6}$alkylene-$NR_{6a}R_{6b}$, —CO—$NR_{6a}$—$C_{3-10}$heterocyclic, —CO—$NR_{6a}$—$C_{3-10}$heterocyclic, —CO—$C_{3-10}$heteocyclic, —O—$C_{1-6}$alkylene-CO—$OR_{6a}$, —O—$C_{1-6}$alkylene-CO—$NR_{6a}R_{6b}$, —O—$C_{1-6}$alkylene-$NR_{6a}R_{6b}$, —O—$C_{3-10}$carbocyclic, —O—$C_{3-10}$heterocyclic, —$NR_{6a}$—CO—$C_{1-6}$alkyl, —$NR_{6a}$—CO—$NR_{6a}R_{6b}$, —$NR_{6a}$—CO—$C_{5-10}$heteoaryl, —$NR_{6a}$—$C_{1-6}$alkylene-$NR_{6a}R_{6b}$, —$NR_{6a}$—$C_{1-6}$alkylene-$C_{3-10}$heterocyclic, —$NR_{6a}$—$C_{1-6}$alkylene-$C_{5-10}$heteroaryl, —$NR_{6a}$—$SO_2C_{1-6}$alkyl, —S—$C_{1-6}$alkyl, —$SONR_{6a}R_{6b}$, —$SO_2NR_{6a}R_{6b}$, —SO—$C_{1-6}$alkyl, —$SO_2C_{1-6}$alkyl, —PO($C_{1-6}$alkyl)$_2$, —PO($C_{1-6}$alkoxy)$_2$, —$C_{3-10}$heterocyclic or —$C_{5-10}$heteroaryl; each of which is independently optionally substituted; and n is 0, 1, 2, 3, 4, 5 or 6; or Two adjacent $R_6$ can be joined together to form a 6-membered aryl, 5-membered heteroaryl, 6-membered heteroaryl, —$C_{3-6}$heterocyclic or —$C_{3-6}$carbocyclic, and each of the ring systems is independently optionally substituted;

Each of $R_{6a}$ and $R_{6b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl.

The present invention further provides some preferred technical solutions with regard to compound of Formula I.

In some embodiments of Formula I:

Each $R_1$ is independently —H, halogen, —$NH_2$, —CN, —OH, —$NO_2$, carboxyl, substituted or unsubstituted —$C_{1-6}$alkoxy, or substituted or unsubstituted $C_{1-6}$alkyl;

$R_2$ is —H, halogen, —$NH_2$, —CN, —OH, —$NO_2$, —$N_3$, carboxyl, —$NHC_{1-6}$alkyl, —N($C_{1-6}$alkyl)$_2$, —$CONH_2$, —$CONHC_{1-6}$alkyl, —CON($C_{1-6}$alkyl)$_2$, —$COC_{1-6}$alkyl, —NH—CO—$C_{1-6}$alkyl, —$NC_{1-6}$alkyl-CO—$C_{1-6}$alkyl, substituted or unsubstituted —$C_{1-6}$alkoxy, substituted or unsubstituted —$C_{1-6}$alkyl or —$C_{5-10}$heterocyclic; or $R_2$ combines with $R_1$ to which is adjacent to form a 5-10 membered heteroaryl or 5-10 membered heterocyclic ring, and each of the ring systems is independently optionally substituted; Each $Y_1$ is independently N or $CR_{1a}$;

Each $R_{1a}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

$R_3$ is —H or —$NH_2$;

Each of $R_{4a}$ and $R_{4b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{4a}$ and $R_{4b}$ together with the carbon atom to which they are both attached form CO;

p is 0, 1, 2 or 3;

Each of $R_{5a}$ and $R_{5b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{5a}$ and $R_{5b}$ together with the carbon atom to which they are both attached form a 3-10 membered heterocyclic or 5-10 membered heteroaryl; and each of the ring systems is independently optionally substituted;

q is 1, 2, 3 or 4;

W is absent, O, NR, or S;

$R_w$ is —H, halogen, —$NH_2$, —CN, —OH, —$NO_2$, carboxyl, —CO—$C_{1-6}$alkyl, —CO—$OC_{1-6}$alkyl, substituted or unsubstituted —$C_{1-6}$alkoxy, or substituted or unsubstituted —$C_{1-6}$alkyl;

Ring A is absent or a 3-10 membered ring;

$\overset{---}{===}$ represents a single or double bond;

When ring A is absent, $Y_2$ is —$CR_{2a}R_{2b}$, —$NR_{2a}$ or —O, and $Y_3$ is —$CR_{3a}R_{3b}$, —$NR_{3a}$ or O;

When ring A is a 3-10 membered ring, i) $Y_2$ is $CR_{2a}$ or N, and $Y_3$ is $CR_{3a}$ or N, when $\overset{---}{===}$ represents a single bond; or ii) $Y_2$ is C, and $Y_3$ is C, when $\overset{---}{===}$ represents a double bond;

Each of $R_{2a}$ and $R_{2b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each of $R_{3a}$ and $R_{3b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each $R_6$ is independently —H, halogen, —$NR_{6a}R_{6b}$, —CN, —OH, —$NO_2$, oxo, =O, carboxyl, —$C_{1-6}$alkoxy, —$C_{1-6}$alkyl, —$C_{1-6}$alkylene-$NR_{6a}R_{6b}$, —$C_{1-6}$alkylene-O—$C_{1-6}$alkyl, —$C_{1-6}$alkylene-CO—$OR_{6a}$, —$C_{1-6}$alkylene-$C_{3-10}$heterocyclic, —$C_{1-6}$alkylene-$C_{5-10}$heteoaryl, —$C_{1-6}$alkylene-CO—$NR_{6a}R_{6b}$, —$C_{1-6}$alkylene-$NR_{6a}$—CO—$NR_{6a}R_{6b}$, —$C_{1-6}$alkylene-$NR_{6a}$—CO—$C_{1-6}$alkyl, —CO—$NR_{6a}R_{6b}$, —CO—CO—$NR_{6a}R_{6b}$, —CO—$C_{1-6}$alkyl, —CO—$C_{1-6}$alkylene-$NR_{6a}R_{6b}$, —CO—$NR_{6a}$—$C_{3-10}$heterocyclic, —CO—$NR_{6a}$—$C_{3-10}$heterocyclic, —CO—$C_{3-10}$heteocyclic, —O—$C_{1-6}$alkylene-CO—$OR_{6a}$, —O—$C_{1-6}$alkylene-CO—$NR_{6a}R_{6b}$, —O—$C_{1-6}$alkylene-$NR_{6a}R_{6b}$, —O—$C_{3-10}$carbocyclic, —$NR_{6a}$—CO—$C_{1-6}$alkyl, —$NR_{6a}$—CO—$NR_{6a}R_{6b}$, —$NR_{6a}$—CO—$C_{5-10}$heteoaryl, —$NR_{6a}$—$C_{1-6}$alkylene-$NR_{6a}R_{6b}$, —$NR_{6a}$—$C_{1-6}$alkylene-$C_{3-10}$heterocyclic, —$NR_{6a}$—$C_{1-6}$alkylene-$C_{5-10}$heteroaryl, —S—$C_{1-6}$alkyl, —$SONR_{6a}R_{6b}$, —$SO_2NR_{6a}R_{6b}$, —SO—$C_{1-6}$alkyl, —$SO_2C_{1-6}$alkyl, —PO($C_{1-6}$alkyl)$_2$, —$C_{3-10}$heterocyclic or —$C_{5-10}$heteroaryl, and each of which is independently optionally substituted; and n is 0, 1, 2, 3, 4, 5 or 6; or Two adjacent $R_6$ can be joined together to form a 6-membered aryl, 5-membered heteroaryl, 6-membered heteroaryl, —$C_{3-6}$heterocyclic or —$C_{3-6}$carbocyclic, and each of the ring system is independently optionally substituted;

Each of $R_{6a}$ and $R_{6b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula I, each $R_1$ is independently —H; —F; —Cl; —Br; —$NH_2$; —CN; —OH; —$NO_2$; carboxyl; —$C_{1-6}$alkyl; —$C_{1-6}$alkoxy; —$C_{1-6}$alkyl substituted with halogen, —$NH_2$, —CN, —OH, —$NO_2$, carboxyl, —$C_{1-3}$alkyl or —$C_{1-3}$alkoxy; or —$C_{1-6}$alkoxy substituted with halogen, —$NH_2$, —CN, —OH, —$NO_2$, carboxyl, —$C_{1-3}$alkyl or —$C_{1-3}$alkoxy.

In some embodiments of Formula I, each $R_1$ is independently —H; —F; —Cl; —Br; —$NH_2$; —CN; —OH; —$NO_2$; carboxyl; —$C_{1-3}$alkyl; —$C_{1-3}$alkoxy; —$C_{1-6}$alkyl substituted with —F, —Cl, —Br, —I, —$NH_2$, —CN, —OH, —$NO_2$, carboxyl, —$C_{1-3}$alkyl or —$C_{1-3}$alkoxy; or —$C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy.

In some embodiments of Formula I, each $R_1$ is independently —H; —F; —Cl; —Br; —$NH_2$; —CN; —OH; —$NO_2$; carboxyl; methyl; ethyl; propyl; isopropyl; methoxy; ethoxy; propoxy; isopropoxy; —$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or $C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, each $R_1$ is independently —H; —F; —Cl; —Br; —$NH_2$; —CN; —OH; methyl; ethyl; propyl; isopropyl; methoxy; ethoxy; propoxy; isopropoxy; or methyl substituted with one or more substituents each independently selected from —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, each $R_1$ is independently —Cl, or —H.

In some embodiments of Formula I, $R_2$ is —H; —F; —Cl; —Br; —$NH_2$; —CN; —OH; —$NO_2$; —$N_3$; carboxyl; —$C_{1-6}$alkyl; —$C_{1-6}$alkoxy; —$NHC_{1-6}$alkyl; —N($C_{1-6}$ alkyl)$_2$; —$CONH_2$; —$CONHC_{1-6}$alkyl; —CON($C_{1-6}$ alkyl)$_2$; —$COC_{1-6}$alkyl; —$NHCOC_{1-6}$alkyl; —N($C_{1-6}$alkyl)-CO—$C_{1-6}$alkyl; —$C_{5-10}$heterocyclic; —$C_{1-6}$alkyl substituted with halogen, —$NH_2$, —CN, —OH, —$NO_2$, carboxyl, —$C_{1-3}$alkyl or —$C_{1-3}$alkoxy; or —$C_{1-6}$alkoxy substituted with halogen, —$NH_2$, —CN, —OH, —$NO_2$, carboxyl, —$C_{1-3}$alkyl or —$C_{1-3}$alkoxy.

In some embodiments of Formula I, $R_2$ is —H; —F; —Cl; —Br; —$NH_2$; —CN; —OH; —$NO_2$; —$N_3$; carboxyl; —$C_{1-3}$alkyl; —$C_{1-3}$alkoxy; —$NHC_{1-3}$alkyl; —N($C_{1-3}$ alkyl)$_2$; —$CONH_2$; —$CONHC_{1-3}$alkyl; —CON($C_{1-3}$ alkyl)$_2$; —$COC_{1-3}$alkyl; —$NHCOC_{1-3}$alkyl; —N($C_{1-3}$alkyl)-CO—$C_{1-3}$alkyl; —$C_{5-10}$heterocyclic; —$C_{1-6}$alkyl substituted with —F, —Cl, —Br, —I, —$NH_2$, —CN, —OH, —$NO_2$, carboxyl, —$C_{1-3}$alkyl or —$C_{1-3}$alkoxy; or —$C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy.

In some embodiments of Formula I, $R_2$ is —H; —F; —Cl; —Br; —$NH_2$; —CN; —OH; —$NO_2$; —$N_3$; carboxyl; methyl; ethyl; propyl; isopropyl; methoxy; ethoxy; propoxy; isopropoxy; —$NHCH_3$; —N($CH_3$)$_2$; —$CONH_2$; —$CONHCH_3$; —CON($CH_3$)$_2$; —$COCH_3$; —NH—$COCH_3$; —N($CH_3$)—$COCH_3$;

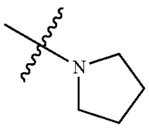 ; 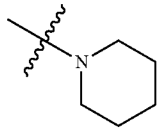 ; 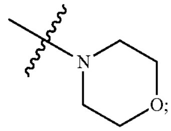 ;

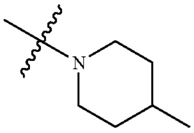 ;

—$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or $C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, $R_2$ is —H; —F; —Cl; —Br; —$NH_2$; —CN; —OH; —$NO_2$; carboxyl; methyl;

ethyl; propyl; isopropyl; methoxy; ethoxy; propoxy; isopropoxy; or methyl substituted with one or more substituents each independently selected from —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, $R_2$ is —$NH_2$.

In some embodiments of Formula I, $R_2$ combines with $R_1$ to which is adjacent to form a 5-10 membered heteroaryl or 5-10 membered heterocyclic ring, and each of the ring systems is independently optionally substituted with halogen, —$NH_2$, —CN, —OH, —$NO_2$, carboxyl, oxo, =O, —$CONH_2$, substituted or unsubstituted —$C_{1-6}$alkoxy, substituted or unsubstituted —$C_{1-6}$alkyl, —$C_{1-6}$alkylene-O—$C_{1-6}$alkyl, —$C_{1-6}$alkylene-COOH, —$C_{1-6}$alkylene-$NHCONH_2$, —CO—N($C_{1-6}$alky)$_2$, —$C_{1-6}$alkylene-NHCO—$C_{1-6}$alkyl, —CO—CO—N($C_{1-6}$alkyl)$_2$, —CO—$C_{1-6}$alkyl, —$SONH_2$, —$SO_2NH_2$, —$SOCH_3$, —$SO_2CH_3$, —$C_{5-10}$heterocyclic or —$C_{5-10}$heteroaryl.

In some embodiments of Formula I, $R_2$ combines with $R_1$ to which is adjacent to form a 5-membered heteroaryl, 6-membered heteroaryl, 7-membered heteroaryl, 8-membered heteroaryl, 9-membered heteroaryl, 5-membered heterocyclic, 6-membered heterocyclic, 7-membered heterocyclic, 8-membered heterocyclic or 9-membered heterocyclic; and each of the heteroaryl or heterocyclic contains 1 or 2 heteroatoms selected from N or O; and each of the ring systems is independently optionally substituted with —F, —Cl, —Br, —I, —$NH_2$, —CN, —OH, —$NO_2$, carboxyl, oxo, =O, —$CONH_2$, substituted or unsubstituted $C_{1-3}$alkoxy, substituted or unsubstituted $C_{1-3}$alkyl, —$C_{1-3}$alkylene-O—$C_{1-3}$alkyl, —$C_{1-3}$alkylene-COOH, —$C_{1-3}$alkylene-$NHCONH_2$, —CO—N($C_{1-3}$alky)$_2$, —$C_{1-3}$alkylene-NHCO—$C_{1-3}$alkyl, —CO—CO—N($C_{1-3}$alkyl)$_2$, —CO—$C_{1-3}$alkyl, —$SONH_2$, —$SO_2NH_2$, —$SOCH_3$ or —$SO_2CH_3$.

In some embodiments of Formula I, $R_2$ combines with $R_1$ to which is adjacent to form a 5-membered heteroaryl, 6-membered heteroaryl, 7-membered heteroaryl, 8-membered heteroaryl, 5-membered heterocyclic, 6-membered heterocyclic, 7-membered heterocyclic or 8-membered heterocyclic; and each of the heteroaryl or heterocyclic contains 1 heteroatom selected from N or O; and each of the ring systems is independently optionally substituted with —F; —Cl; —Br; —$NH_2$; —CN; —OH; —$NO_2$; carboxyl; oxo; =O; —$CONH_2$; methyl; ethyl; propyl; isopropyl; methoxy; ethoxy; propoxy; isopropoxy; —$CH_2OCH_3$; —$CH_2COOH$; —$CH_2NHCONH_2$; —CON($CH_3$)$_2$; —$CH_2NHCOCH_3$; —CO—CON($CH_3$)$_2$; —$COCH_3$; —$C_{1-3}$alkyl substituted with halogen, —$NH_2$, —CN, —OH, —$NO_2$ or carboxyl; or —$C_{1-3}$alkoxy substituted with halogen, —$NH_2$, —CN, —OH, —$NO_2$ or carboxyl.

In some embodiments of Formula I, $R_2$ combines with $R_1$ to which is adjacent to form a 5-membered heterocyclic, and optionally substituted with —F or —$COCH_3$.

In some embodiments of Formula I, $R_2$ and $R_1$ which is adjacent to, together with the aromatic ring they are attached to form

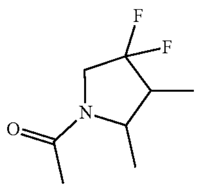 .

In some embodiments of Formula I, each $Y_1$ is independently N or CH.

In some embodiments of Formula I, each of $R_{4a}$ and $R_{4b}$ is independently —H, —F, —Cl, —Br, —I, —$NH_2$, —CN, —OH, —$NO_2$, carboxyl, substituted or unsubstituted —$C_{1-6}$alkoxy, or substituted or unsubstituted —$C_{1-6}$alkyl; or $R_{4a}$ and $R_{4b}$ together with the carbon atom to which they are both attached form C═O, C═NH, or C═N—OH.

In some embodiments of Formula I, each of $R_{4a}$ and $R_{4b}$ is independently —H; —F; —Cl; —Br; —$NH_2$; —CN; —OH; —$NO_2$; carboxyl; —$C_{1-3}$alkyl; —$C_{1-3}$alkoxy; —$C_{1-6}$alkyl substituted with —F, —Cl, —Br, —I, —$NH_2$, —CN, —OH, —$NO_2$, carboxyl, —$C_{1-3}$alkyl or —$C_{1-3}$alkoxy; or $C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy; or $R_{4a}$ and $R_{4b}$ together with the carbon atom to which they are both attached form C═O.

In some embodiments of Formula I, each of $R_{4a}$ or $R_{4b}$ is independently —H; —F; —Cl; —Br; —$NH_2$; —CN; —OH; —$NO_2$; carboxyl; methyl; ethyl; propyl; isopropyl; methoxy; ethoxy; propoxy; isopropoxy; $C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or $C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy; or $R_{4a}$ and $R_{4b}$ together with the carbon atom to which they are both attached form C═O.

In some embodiments of Formula I, each of $R_{4a}$ and $R_{4b}$ is independently —H, —$NH_2$, —OH, methyl, ethyl, methoxy, ethoxy; or $R_{4a}$ and $R_{4b}$ together with the carbon atom to which they are both attached form C═O.

In some embodiments of Formula I, p is 0, 1, 2 or 3.

In some embodiments of Formula I, each of $R_{5a}$ and $R_{5b}$ is independently —H; —F; —Cl; —Br; —I; —$NH_2$; —CN; —OH; —$NO_2$; carboxyl; —$C_{1-3}$alkyl; —$C_{1-3}$alkoxy; —$C_{1-6}$alkyl substituted with —F, —Cl, —Br, —I, —$NH_2$, —CN, —OH, —$NO_2$, carboxyl, —$C_{1-3}$alkyl or —$C_{1-3}$alkoxy; or —$C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy; or $R_{5a}$ and $R_{5b}$ together with the carbon atom to which they are both attached form 3-membered heterocyclic, 4-membered heterocyclic, 5-membered heterocyclic, 6-membered heterocyclic, 7-membered heterocyclic, 8-membered heterocyclic, 9-membered heterocyclic, 5-membered heteroaryl, 6-membered heteroaryl, 7-membered heteroaryl, 8-membered heteroaryl or 9-membered heteroaryl; and each of the heterocyclic or heteroaryl contains 1 or 2 heteroatoms selected from N or O; and each of the ring systems is independently optionally substituted with —H, —F, —Cl, —Br, —I, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula I, each of $R_{5a}$ or $R_{5b}$ is independently —H, —$NH_2$, —OH, methyl, ethyl, methoxy or ethoxy; or $R_{5a}$ and $R_{5b}$ together with the carbon atom to which they are both attached form a 3-membered heterocyclic, 4-membered heterocyclic, 5-membered heterocyclic, 6-membered heterocyclic, 5-membered heteroaryl or 6-membered heteroaryl; and each of the heterocyclic or heteroaryl contains 1 heteroatoms selected from N or O.

In some embodiments of Formula I, each of $R_{5a}$ or $R_{5b}$ is independently —H or —$NH_2$.

In some embodiments of Formula I, W is absent, O, or $NR_w$.

In some embodiments of Formula I, W is NRw, and $R_w$ is —H, —F, —Cl, —Br, —I, —$NH_2$, —CN, —OH, —$NO_2$, carboxyl, —CO—$C_{1-3}$alkyl, —$COOC_{1-3}$alkyl, —$C_{1-3}$alkyl-CO—$C_{1-3}$alkyl, substituted or unsubstituted —$C_{1-3}$alkoxy, or substituted or unsubstituted —$C_{1-3}$alkyl.

In some embodiments of Formula I, W is NRw, and $R_w$ is —H; —F; —Cl; —Br; —$NH_2$; —CN; —OH; —$NO_2$; carboxyl; methyl; ethyl; propyl; isopropyl; methoxy; ethoxy; propoxy; isopropoxy; methyl-CO-methyl; —$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or $C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, ring A is 6-membered aryl, 7-membered aryl, 8-membered aryl, 9-membered aryl, 10-membered aryl; 5-membered heteroaryl, 6-membered heteroaryl, 7-membered heteroaryl, 8-membered heteroaryl, 9-membered heteroaryl, 10-membered heteroaryl; 3-membered heterocyclic, 4-membered heterocyclic, 5-membered heterocyclic, 6-membered heterocyclic, 7-membered heterocyclic, 8-membered heterocyclic, 9-membered heterocyclic, 10-membered heterocyclic; 3-membered carbocyclic, 4-membered carbocyclic, 5-membered carbocyclic, 6-membered carbocyclic, 7-membered carbocyclic, 8-membered carbocyclic, 9-membered carbocyclic or 10-membered carbocyclic; and each of the heteroaryl contains 1, 2 or 3 heteroatoms selected from N, O or S; each of the heterocyclic contains 1, 2 or 3 heteroatoms selected from N or O.

In some embodiments of Formula I, ring A is 6-membered aryl, 7-membered aryl, 8-membered aryl; 5-membered heteroaryl, 6-membered heteroaryl, 7-membered heteroaryl, 8-membered heteroaryl; 3-membered heterocyclic, 4-membered heterocyclic, 5-membered heterocyclic, 6-membered heterocyclic, 7-membered heterocyclic, 8-membered heterocyclic; 3-membered carbocyclic, 4-membered carbocyclic, 5-membered carbocyclic, 6-membered carbocyclic, 7-membered carbocyclic or 8-membered carbocyclic; and each of the heteroaryl contains 1 or 2 heteroatoms selected from N, O or S; each of the heterocyclic contains 1 or 2 heteroatoms selected from N or O.

In some embodiments of Formula I, ring A is

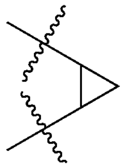 , 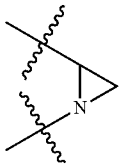 , 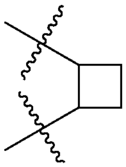 ,

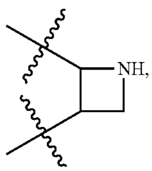 , 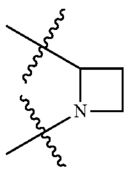 , 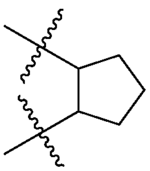 ,

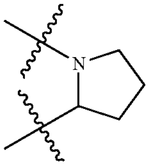 , 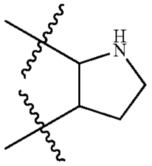 , 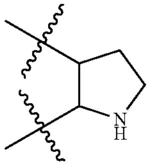 ,

-continued
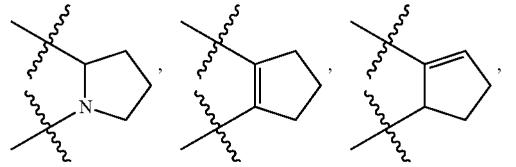
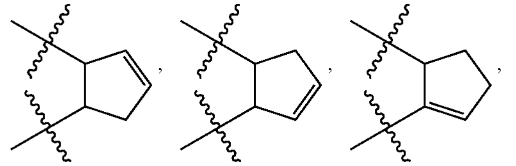
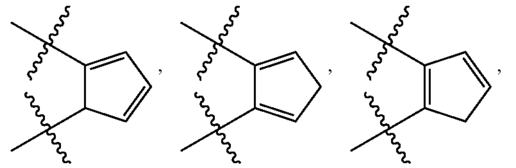
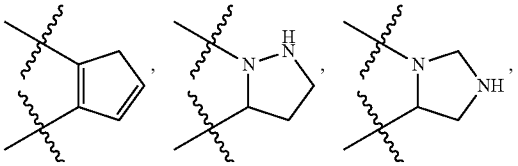
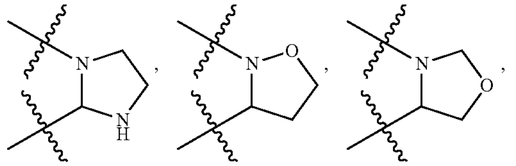
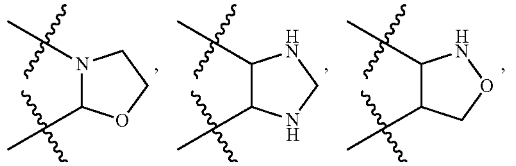
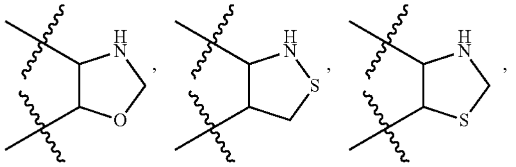
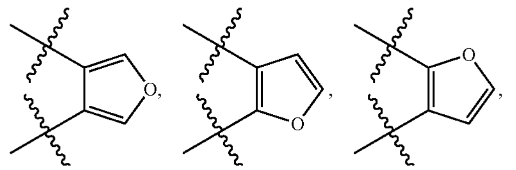
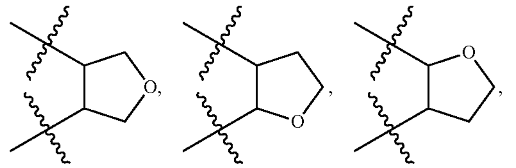
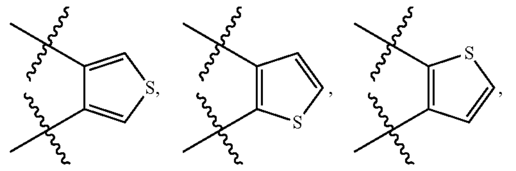
-continued
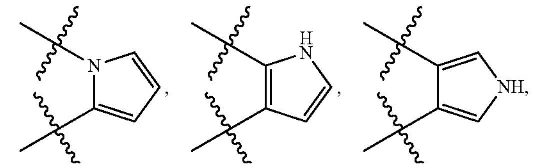
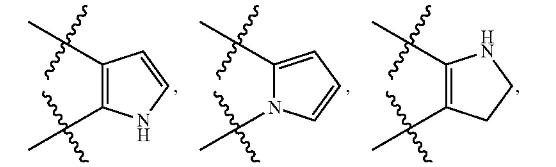
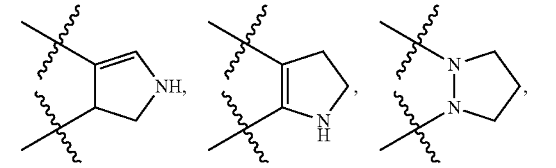
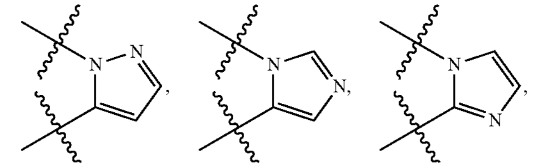
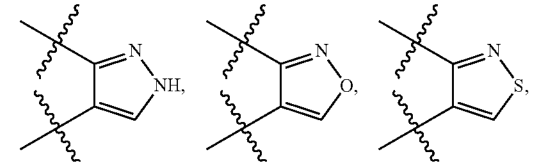
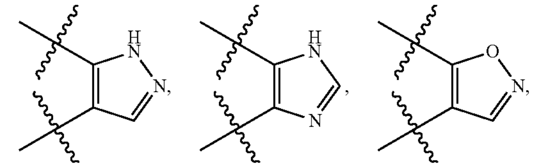
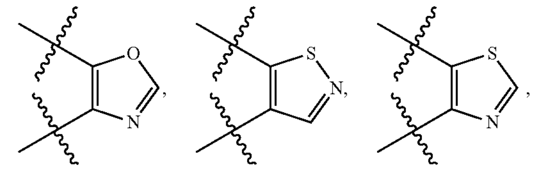
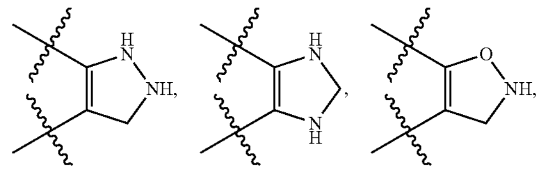
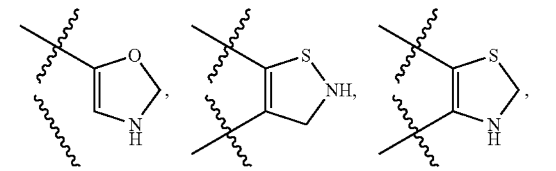
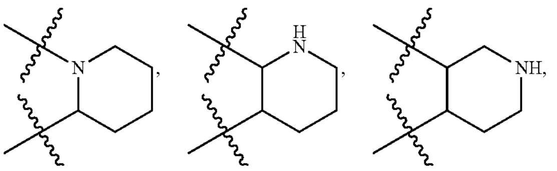

-continued
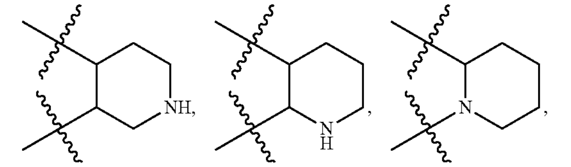
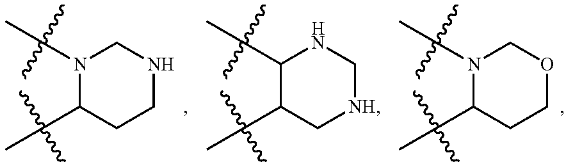
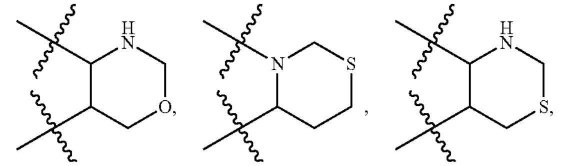
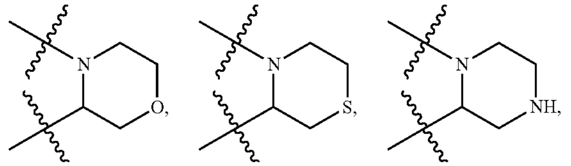
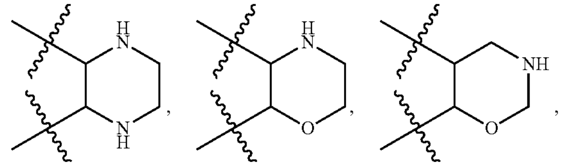
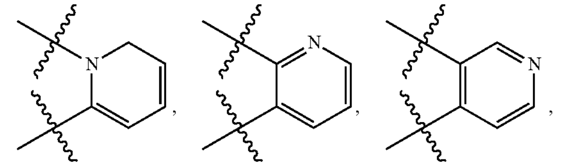
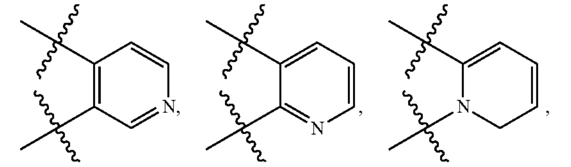
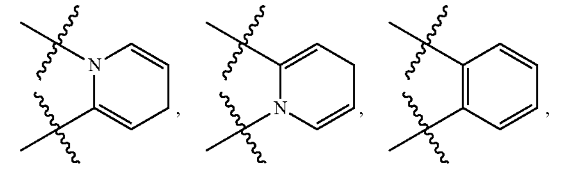
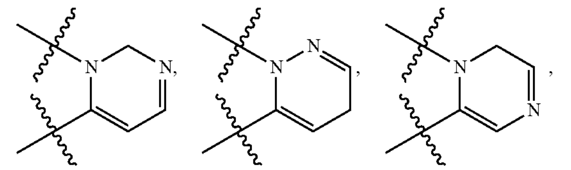
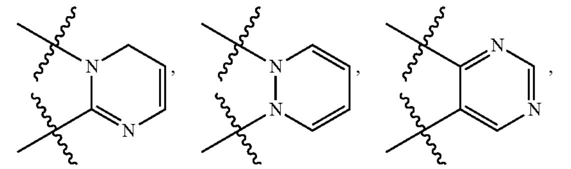
-continued
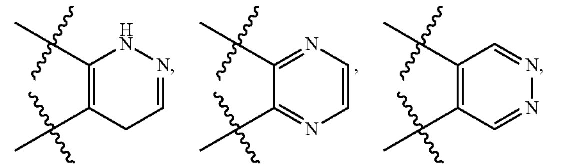
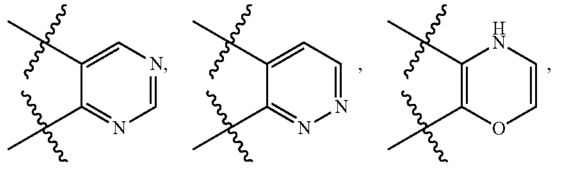
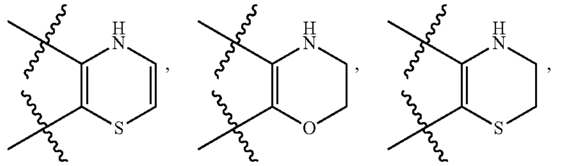
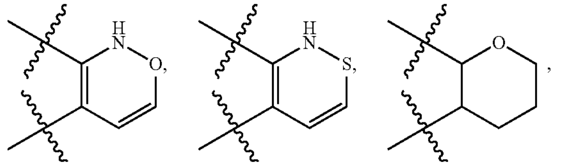
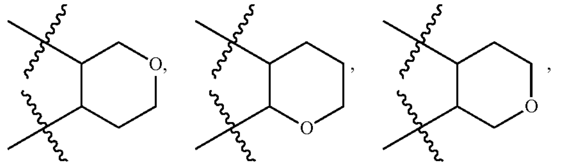
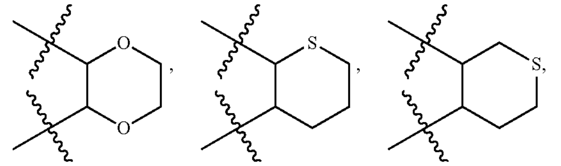
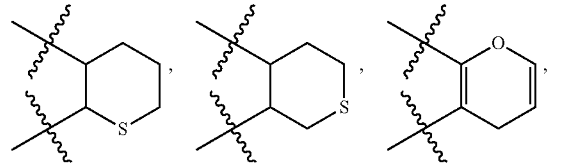
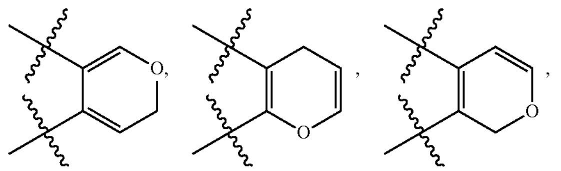
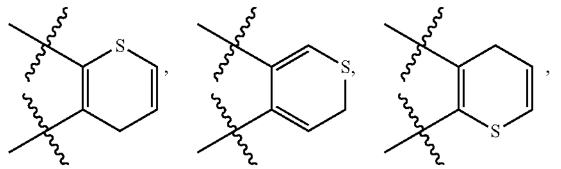
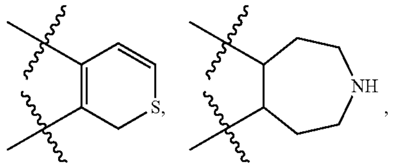

-continued

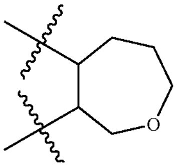, 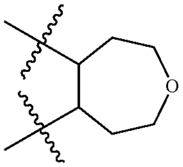 or

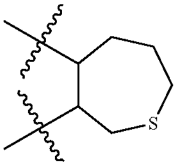.

In some embodiments of Formula I, ring A is

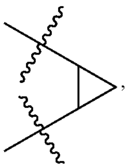, 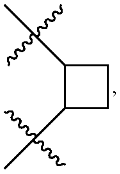, 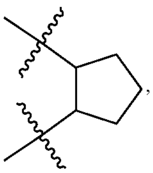,

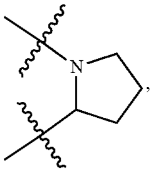, 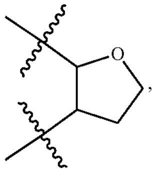, 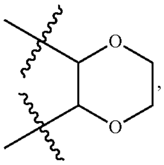,

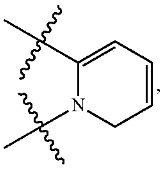, 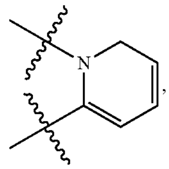, 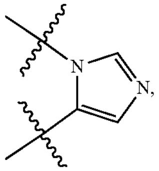,

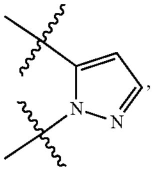, 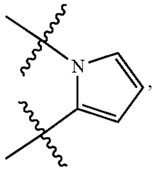, 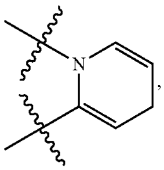,

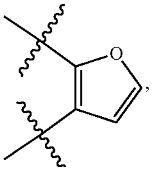, 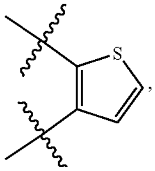, 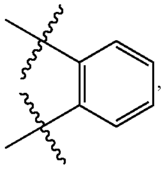,

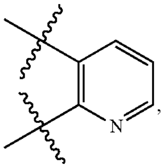, 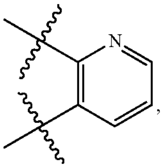, 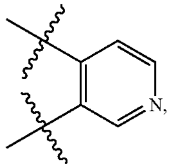,

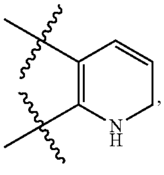, 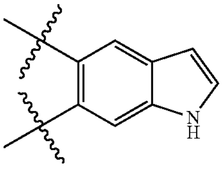 or

-continued

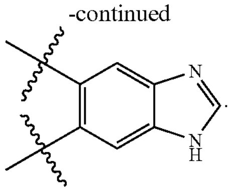.

In some embodiments of Formula I, $Y_2$ is $CR_{2a}$ or N, and $Y_3$ is $CR_{3a}$ or N.

In some embodiments of Formula I, $Y_2$ is $CR_{2a}$ and $Y_3$ is $CR_{3a}$.

In some embodiments of Formula I, each of $R_{2a}$ and $R_{2b}$ is independently —H; —F; —Cl; —Br; —$NH_2$; —CN; —OH; —$NO_2$; carboxyl; —$C_{1-3}$alkyl; —$C_{1-3}$alkoxy; —$C_{1-6}$alkyl substituted with —F, —Cl, —Br, —I, —$NH_2$, —CN, —OH, —$NO_2$, carboxyl, —$C_{1-3}$alkyl or —$C_{1-3}$alkoxy; or —$C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy.

In some embodiments of Formula I, each of $R_{2a}$ and $R_{2b}$ is independently —H; —F; —Cl; —Br; —$NH_2$; —CN; —OH; —$NO_2$; carboxyl; methyl; ethyl; propyl; isopropyl; methoxy; ethoxy; propoxy; isopropoxy; —$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or —$C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula I, each of $R_{2a}$ and $R_{2b}$ is independently —H or methyl.

In some embodiments of Formula I, $R_{2a}$ is —H or methyl, and $R_{2b}$ is —H.

In some embodiments of Formula I, $R_{2a}$ and $R_{2b}$ are both —H.

In some embodiments of Formula I, $Y_2$ is CH or N, and $Y_3$ is CH or N.

In some embodiments of Formula I, $Y_2$ is CH, and $Y_3$ is CH.

In some embodiments of Formula I, $Y_2$ is CH, and $Y_3$ is N.

In some embodiments of Formula I, $Y_2$ is N, and $Y_3$ is CH.

In some embodiments of Formula I, each of $R_{3a}$ and $R_{3b}$ is independently —H, —F, —Cl, —Br, —$NH_2$, —CN, —OH, —$NO_2$, carboxyl, —$C_{1-3}$alkyl, —$C_{1-3}$alkoxy, or —$C_{1-6}$alkyl or —$C_{1-6}$alkoxy substituted with —F, —Cl, —Br, —I, —$NH_2$, —CN, —OH, —$NO_2$, carboxyl, —$C_{1-3}$alkyl or —$C_{1-3}$alkoxy.

In some embodiments of Formula I, each of $R_{3a}$ and $R_{3b}$ is independently —H.

In some embodiments of Formula I, each $R_6$ is independently —H, —F, —Cl, —Br, —I, —$NR_{6a}R_{6b}$, —CN, —OH, oxo, =O, carboxyl, —$C_{1-6}$alkoxy, —$C_{1-6}$alkyl, —$C_{1-6}$alkylene-$NR_{6a}R_{6b}$, —$C_{1-6}$alkylene-O—$C_{1-6}$alkyl, —$C_{1-6}$alkylene-CO—$OR_{6a}$, —$C_{1-6}$alkylene-$C_{5-10}$heterocyclic, —$C_{1-6}$alkylene-$C_{5-10}$heteoaryl, —$C_{1-6}$alkylene-CO—$NR_{6a}R_{6b}$, —$C_{1-6}$alkylene-$NR_{6a}$—CO—$NR_{6a}R_{6b}$, —$C_{1-6}$alkylene-$NR_{6a}$—CO—$C_{1-6}$alkyl, —CO—$NR_{6a}R_{6b}$, —CO—CO—$NR_{6a}R_{6b}$, —CO—$C_{1-6}$alkyl, —CO—$C_{1-6}$alkylene-$NR_{6a}R_{6b}$, —CO—$NR_{6a}$—$C_{5-10}$heterocyclic, —CO—$NR_a$—$C_{5-10}$heterocyclic, —CO—$C_{5-10}$heterocyclic, —O—$C_{1-6}$alkylene-CO—$OR_{6a}$, —O—$C_{1-6}$alkylene-CO—$NR_{6a}R_{6b}$, —O—$C_{1-6}$alkylene-$NR_{6a}R_{6b}$, —O—$C_{5-10}$carbocyclic, —$NR_{6a}$—CO—$C_{1-6}$alkyl, —$NR_{6a}$—CO—$NR_{6a}R_{6b}$, —$NR_{6a}$—CO—$C_{5-10}$heteoaryl, —$NR_{6a}$—$C_{1-6}$alkylene- $NR_{6a}R_{6b}$, —$NR_{6a}$—$C_{1-6}$alkylene-$C_{3-10}$heterocyclic, —$NR_{6a}$—$C_{1-6}$alkylene-$C_{5-10}$heteroaryl, —S—$C_{1-6}$alkyl, —$SO_2NR_{6a}R_{6b}$, —$SO_2C_{1-6}$alkyl, —$PO(CH_3)_2$, —$C_{5-10}$heterocyclic or —$C_{5-10}$heteroaryl, and each of which is independently optionally substituted —F, —Cl, —Br, —I, —$NH_2$, —CN, —OH, —$NO_2$, carboxyl, oxo, =O, substituted or unsubstituted —$C_{1-3}$alkoxy, or substituted or unsubstituted —$C_{1-3}$alkyl; or two adjacent $R_6$ can be joined together to form a 6-membered aryl; 3-membered carbocyclic, 4-membered carbocyclic, 5-membered carbocyclic, 6-membered carbocyclic; 5-membered heteroaryl, 6-membered heteroaryl; 3-membered heterocyclic, 4-membered heterocyclic, 5-membered heterocyclic or 6-membered heterocyclic; and each of heteroaryl or heterocyclic contains 1, 2, 3 or 4 heteroatoms selected from N, O or S; and each of the ring system is independently optionally substituted with halogen, —$NH_2$, —CN, —OH, —$NO_2$, =O, oxo, carboxyl, —$CONH_2$, —$PO(C_{1-6}alkyl)_2$, substituted or unsubstituted —$C_{1-6}$alkoxy or substituted or unsubstituted —$C_{1-6}$alkyl.

In some embodiments of Formula I, each $R_6$ is independently —H, —F, —Cl, —Br, —$NR_{6a}R_{6b}$, —CN, —OH, oxo, =O, carboxyl, —$C_{1-6}$alkoxy, —$C_{1-6}$alkyl, —$C_{1-6}$alkylene-$NR_{6a}R_{6b}$, —$C_{1-6}$alkylene-O—$C_{1-6}$alkyl, —$C_{1-6}$alkylene-CO—$OR_{6a}$, —$C_{1-6}$alkylene-$C_{5-10}$heterocyclic, —$C_{1-6}$alkylene-$C_{5-10}$heteoaryl, —$C_{1-6}$alkylene-CO—$NR_{6a}R_{6b}$, —$C_{1-6}$alkylene-$NR_{6a}$—CO—$NR_{6a}R_{6b}$, —CO—$NR_{6a}R_{6b}$, —CO—CO—$NR_{6a}R_{6b}$, —CO—$C_{1-6}$alkyl, —CO—$NR_{6a}$—$C_{5-10}$heterocyclic, —CO—$C_{5-10}$heterocyclic, —O—$C_{5-10}$carbocyclic, —$NR_{6a}$—CO—$C_{1-6}$alkyl, —$NR_{6a}$—CO—$NR_{6a}R_{6b}$, —$NR_{6a}C_{1-6}$alkylene-$NR_{6a}R_{6b}$, —$NR_{6a}C_{1-6}$alkylene-$C_{3-10}$heterocyclic, —S—$C_{1-6}$alkyl, —$SO_2NR_{6a}R_{6b}$, —$SO_2C_{1-6}$alkyl, —$C_{5-10}$heterocyclic or —$C_{5-10}$heteroaryl, and each of which is independently optionally substituted —F, —Cl, Br, —$NH_2$, —OH, carboxyl, oxo, =O, methyl, ethyl, propyl, isopropyl, methoxy, ethoxy, propoxy or isopropoxy; or two adjacent $R_6$ can be joined together to form a 6-membered aryl; 5-membered carbocyclic, 5-membered heteroaryl or 5-membered heterocyclic; and each of heteroaryl or heterocyclic contains 1, 2 or 3 heteroatoms selected from N, O or S; and each of the ring system is independently optionally substituted with —F, —Cl, —Br, —$NH_2$, —CN, —OH, —$NO_2$, =O, oxo, carboxyl, —$CONH_2$, —$PO(CH_3)_2$, methyl, ethyl, propyl, isopropyl, methoxy, ethoxy, propoxy or isopropoxy.

In some embodiments of Formula I, each $R_6$ is independently —H, —F, —Cl, —Br, —$NR_{6a}R_{6b}$, —CN, —OH, oxo, =O, carboxyl, —$C_{1-3}$alkoxy, —$C_{1-3}$alkyl, —$C_{1-3}$alkylene-$NR_{6a}R_{6b}$, —$C_{1-3}$alkylene-O—$C_{1-3}$alkyl, —$C_{1-3}$alkylene-CO—$OR_{6a}$, —$C_{1-3}$alkylene-$C_{56}$heterocyclic, —$C_{1-3}$alkylene-$C_{5-6}$heteoaryl, —$C_{1-3}$alkylene-CO—$NR_{6a}R_{6b}$, —$C_{1-3}$alkylene-$NR_{6a}$—CO—$NR_{6a}R_{6b}$, —CO—$NR_{6a}R_{6b}$, —CO—CO—$NR_{6a}R_{6b}$, —CO—$C_{1-3}$alkyl, —CO—$NR_{6a}$—$C_{5-6}$heterocyclic, —CO—$C_{5-6}$heterocyclic, —O—$C_{5-6}$carbocyclic, —$NR_{6a}$—CO—$C_{1-6}$alkyl, —$NR_{6a}$—CO—$NR_{6a}R_{6b}$, —$NR_{6a}$—$C_{1-3}$alkylene-$NR_{6a}R_{6b}$, —$NR_{6a}$—$C_{1-6}$alkylene-$C_{3-6}$heterocyclic, —S—$C_{1-3}$alkyl, —$SO_2NR_{6a}R_{6b}$, —$SO_2C_{1-3}$alkyl, —$C_{5-6}$heterocyclic or —$C_{5-6}$heteroaryl, and each of which is independently optionally substituted with one or more substituents each independently selected from —F, —Cl, Br, —$NH_2$, —OH, carboxyl, oxo, =O, methyl, ethyl, propyl, isopropyl, methoxy, ethoxy, propoxy or isopropoxy; or two adjacent $R_6$ can be joined together to form a 6-membered aryl; 5-membered carbocyclic, 5-membered heteroaryl or 5-membered heterocyclic; and each of heteroaryl or heterocyclic contains 1, or 2 heteroatoms selected from N, O or S; and each of the ring system is independently optionally substituted with one or more substituents each independently selected from —F, —Cl, —Br, —$NH_2$, —CN, —OH, —$NO_2$, =O, oxo, carboxyl, —$CONH_2$, —$PO(CH_3)_2$, methyl, ethyl, propyl, isopropyl, methoxy, ethoxy, propoxy or isopropoxy.

In some embodiments of Formula I, each $R_6$ is independently —F, —Cl, —Br, =O, —OH, —CN, —$NH_2$,

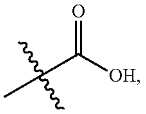 [SMILES: *C(=O)O]

—$CH_3$,

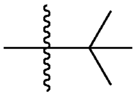

,

—$CF_3$,

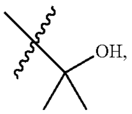 [SMILES: *C(C)(C)O]

—$OCH_3$, —$SCH_3$, —$SOCH_3$, —$SO_2CH_3$, —$PO(CH_3)_2$, —$PO(OC_2H_5)_2$, —$NHSO_2CH_3$, —$C(O)NH_2$,

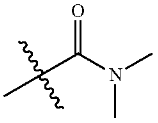

,

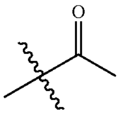

,

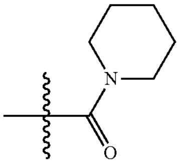

,

—$NHCOCH_3$,

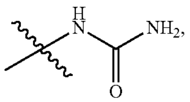 [SMILES: *NC(N)=O]

—$NHCONHCH_3$,

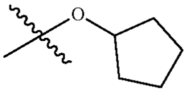

,

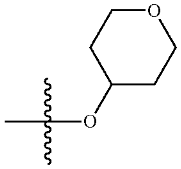

,

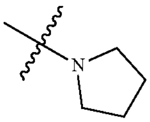

,

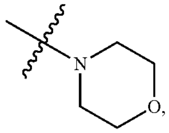

-continued
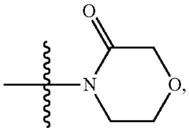 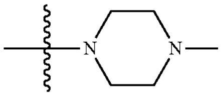,
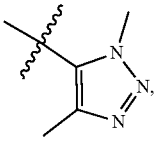, 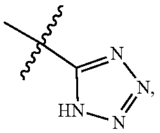,
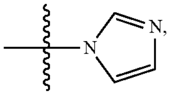, 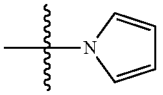,
or two adjacent $R_6$ can be joined together to form
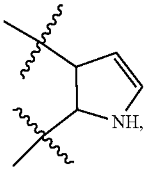, 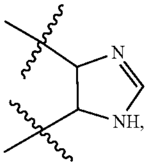 or, 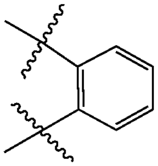.
In some embodiments of Formula I, each $R_6$ is independently methyl, ethyl, isopropyl, methoxy, ethoxy, =O, oxo, —OH, —CN, —$NH_2$, —Cl, —Br, —$CF_3$, —$OCF_3$, —$SO_2NH_2$, —$SO_2CH_3$, —F, —$CH_2NH_2$, —$SCH_3$,
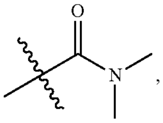, 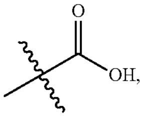 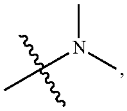,
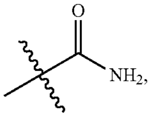 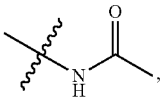,
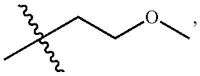, 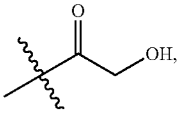
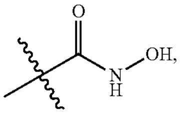 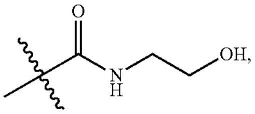
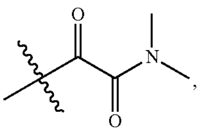, 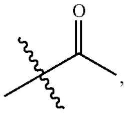, 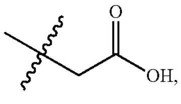
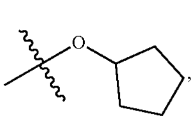, 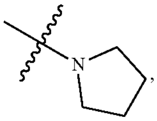, 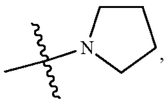,
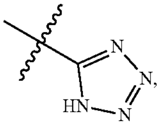 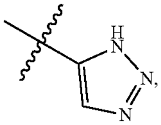 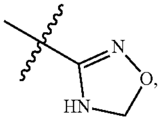
-continued
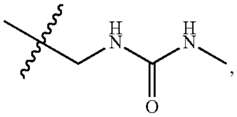, 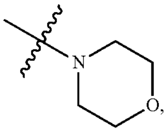
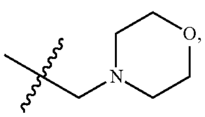 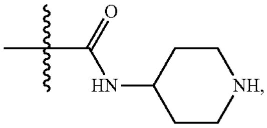
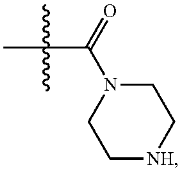 or 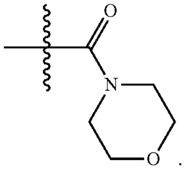.
In some embodiments of Formula I, ring A and the two adjacent $R_6$ taken together to form
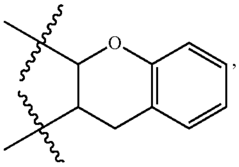, 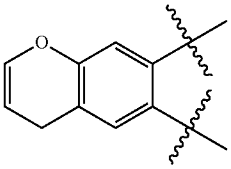,
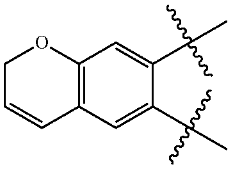, 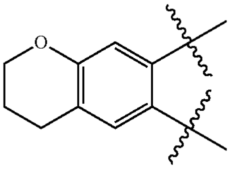,
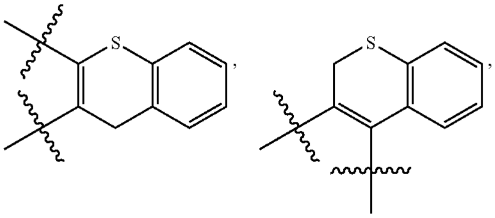,
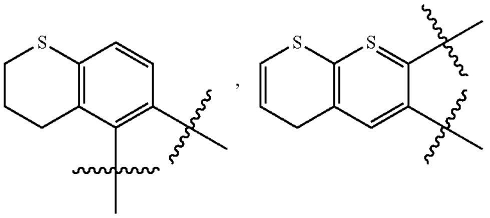,
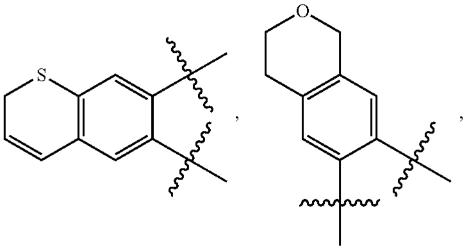, -continued
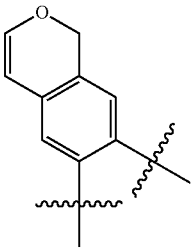 , 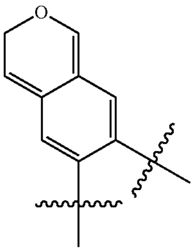 ,
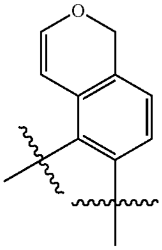 , 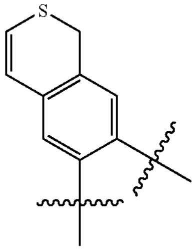 ,
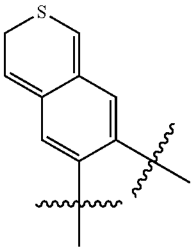 , 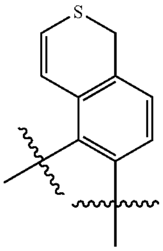 ,
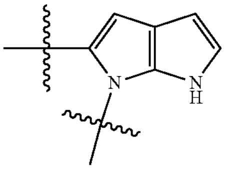 , 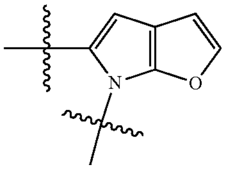 ,
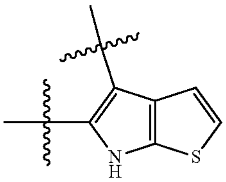 , 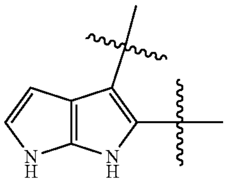 ,
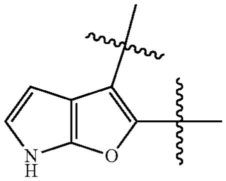 , 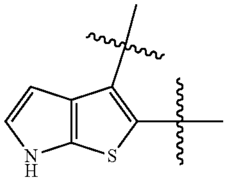 ,
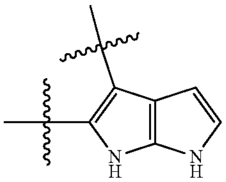 , 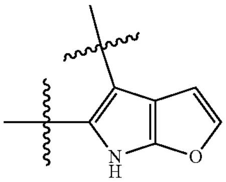 ,
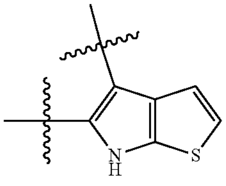 , 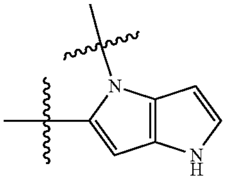 ,
-continued
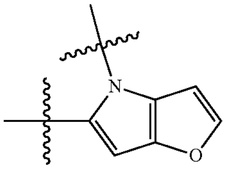 , 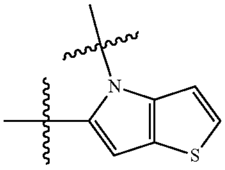 ,
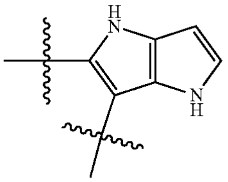 , 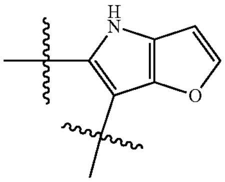 ,
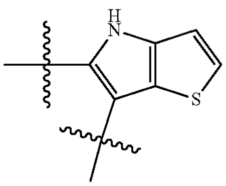 , 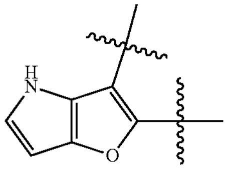 ,
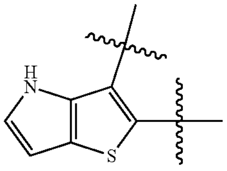 , 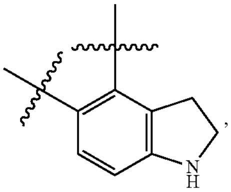 ,
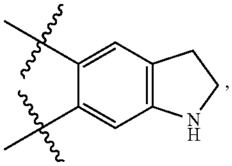 , 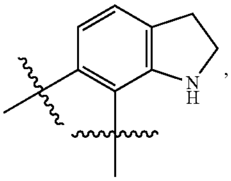 ,
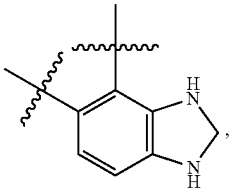 , 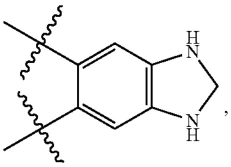 ,
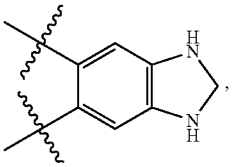 , 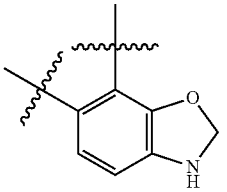 ,
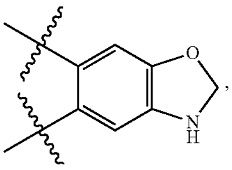 , 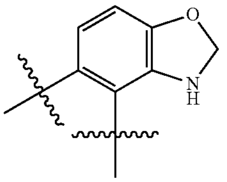 ,
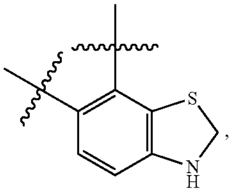 , 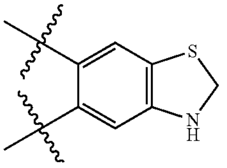 , -continued
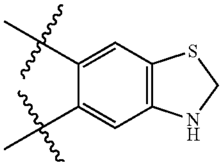,
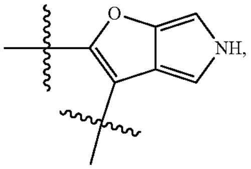,
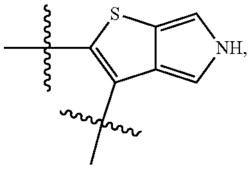,
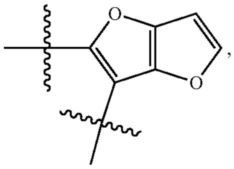,
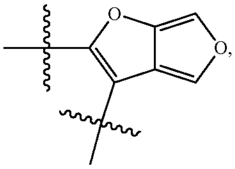,
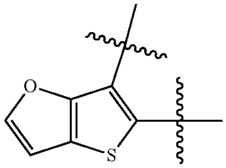,
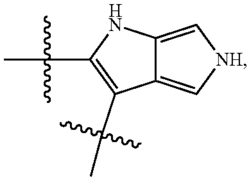,
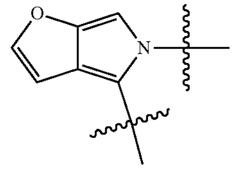,
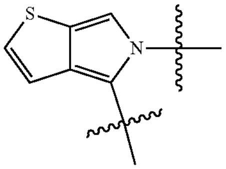,
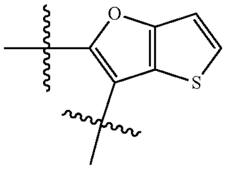,
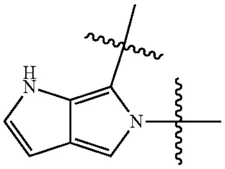,
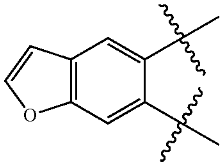,
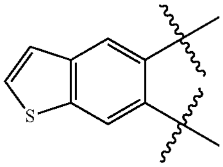,
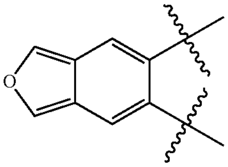,
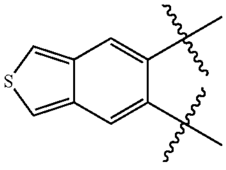,
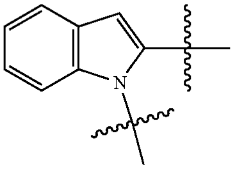,
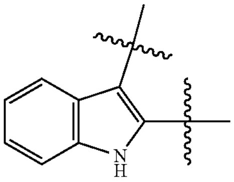,
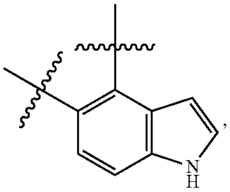,
-continued
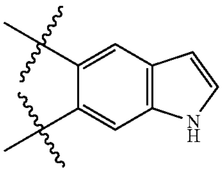,
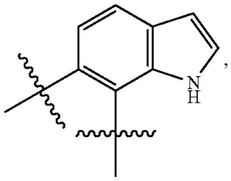,
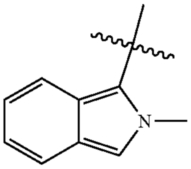,
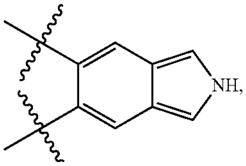,
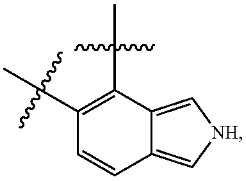,
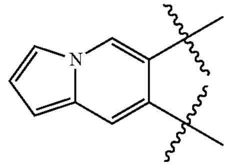,
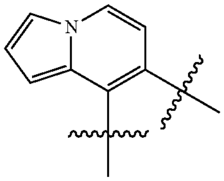,
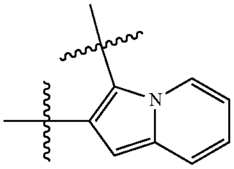,
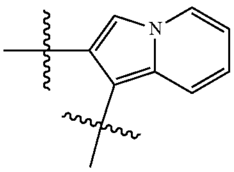,
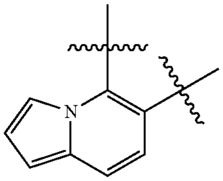,
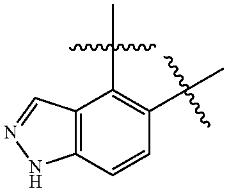,
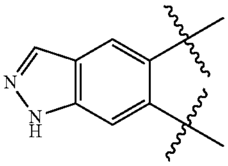,
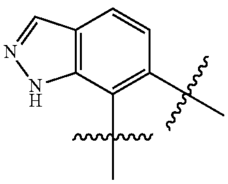,
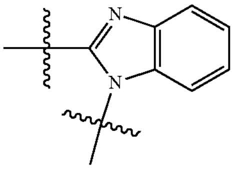,
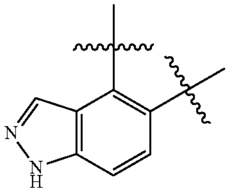,
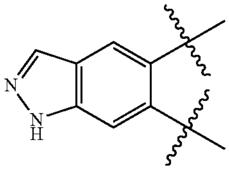,
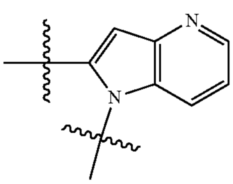,
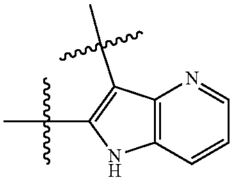, -continued
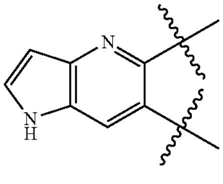,
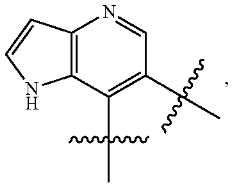,
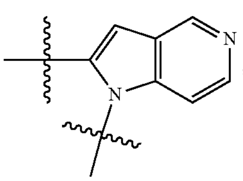,
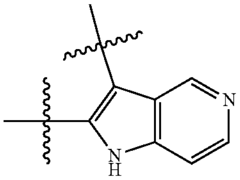,
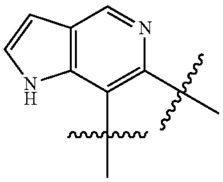,
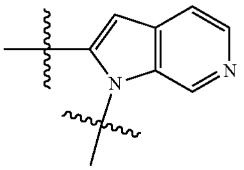,
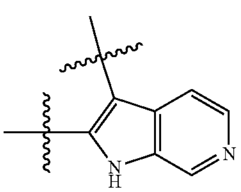,
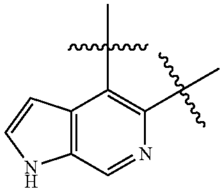,
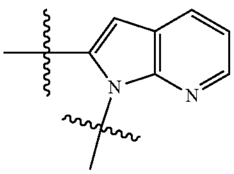,
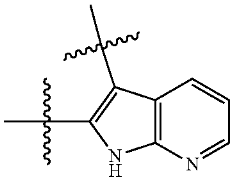,
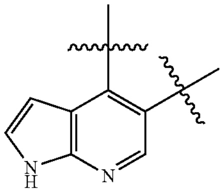,
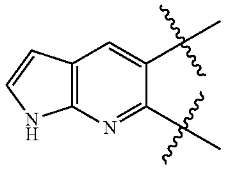,
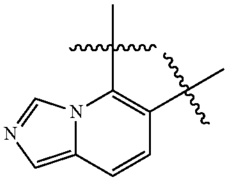,
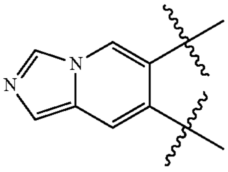,
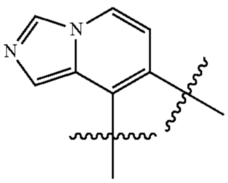,
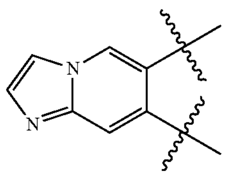,
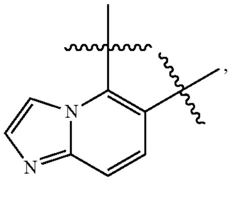,
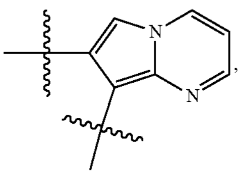,
-continued
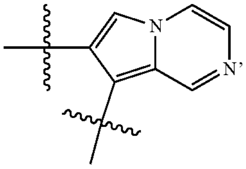,
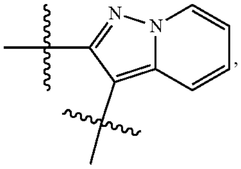,
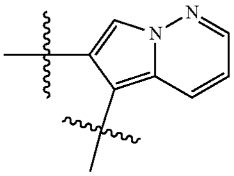,
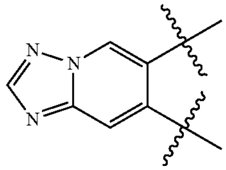,
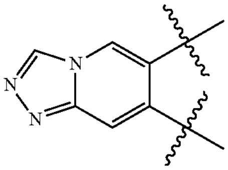,
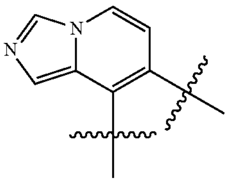,
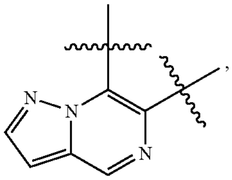,
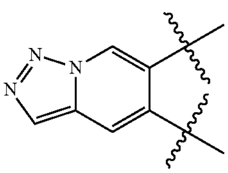,
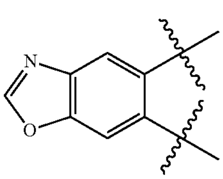,
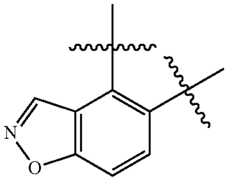,
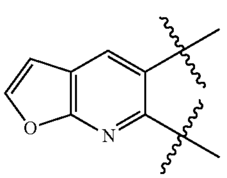,
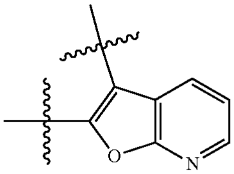,
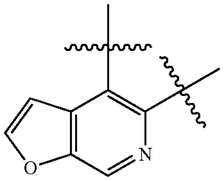,
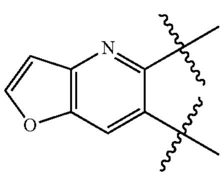,
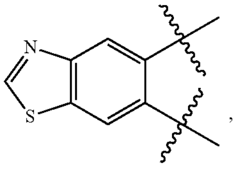,
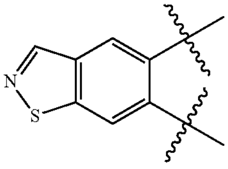,
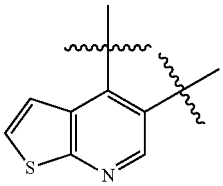,
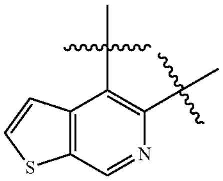, -continued
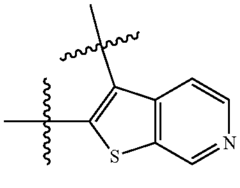,
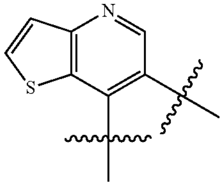,
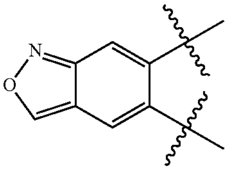,
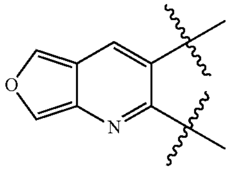,
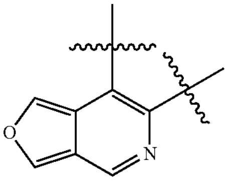,
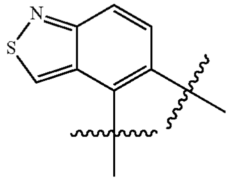,
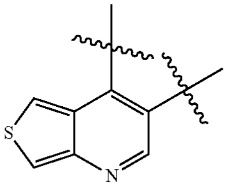,
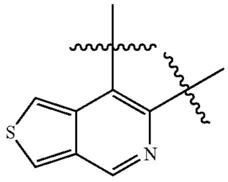,
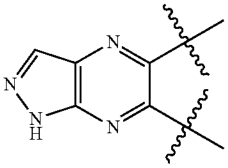,
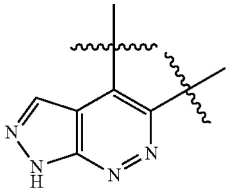,
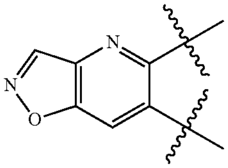,
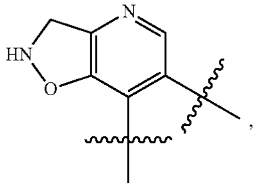,
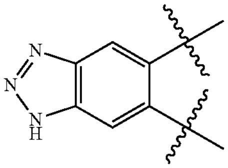,
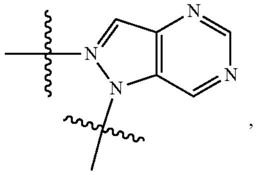,
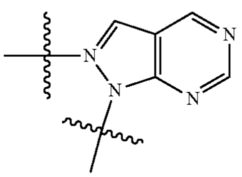,
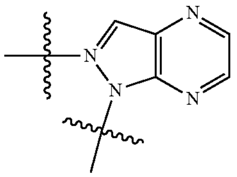,
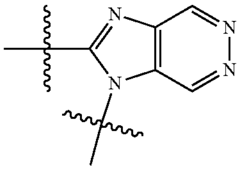,
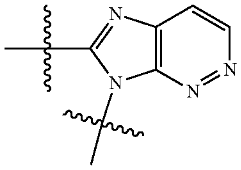,
-continued
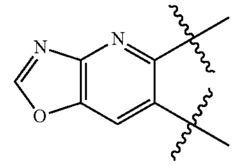,
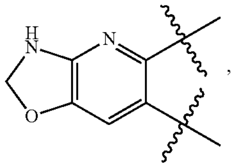,
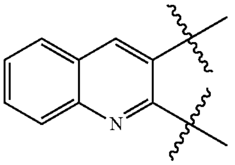,
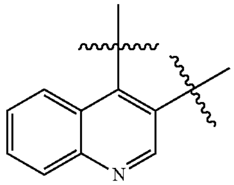,
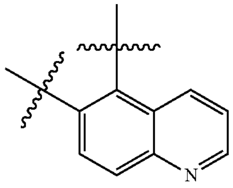,
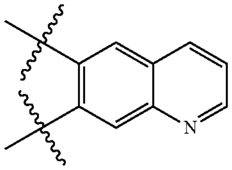,
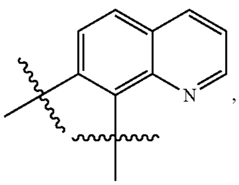,
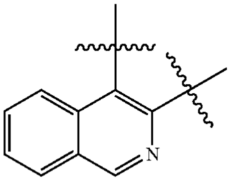,
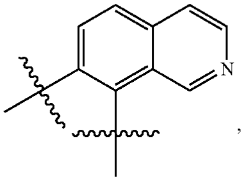,
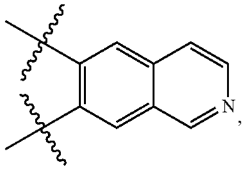,
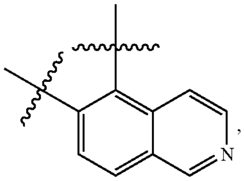,
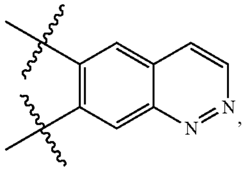,
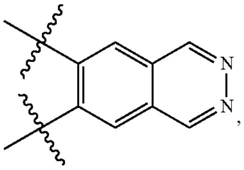,
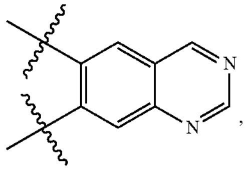,
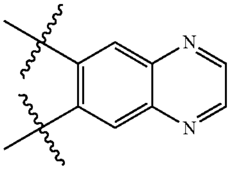,
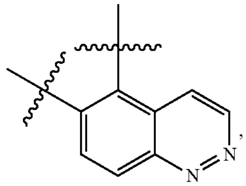,
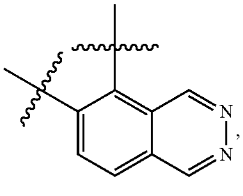,
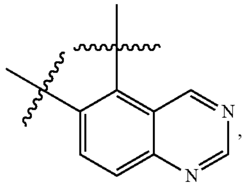, -continued
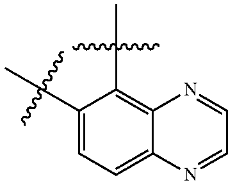,
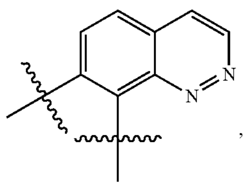,
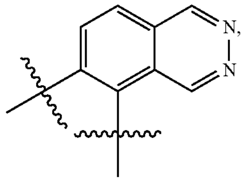
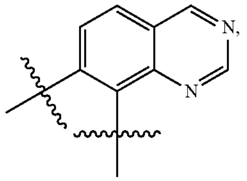
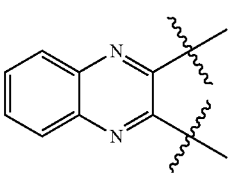,
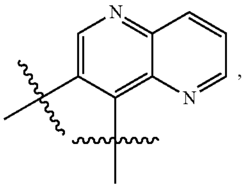,
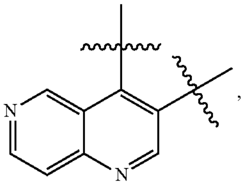,
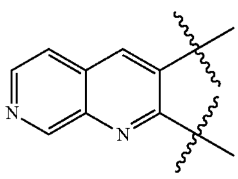,
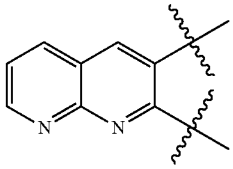,
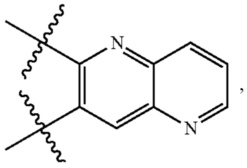,
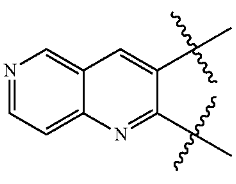,
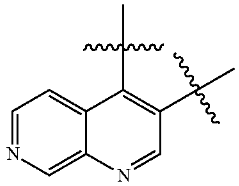,
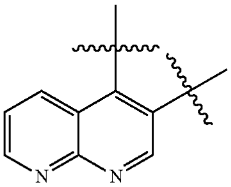,
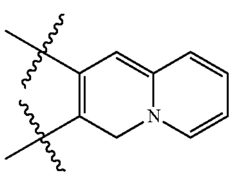,
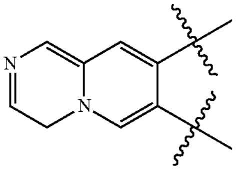,
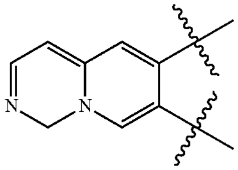,
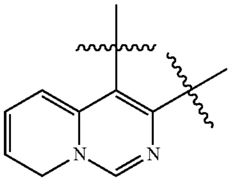,
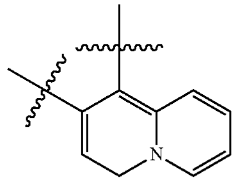,
-continued
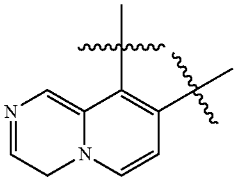,
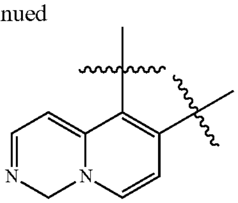,
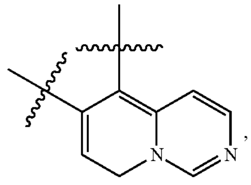,
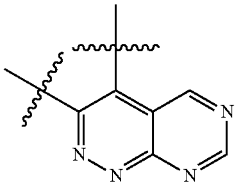,
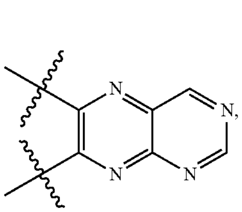
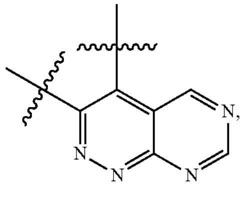
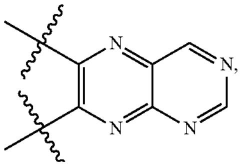
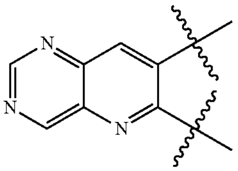,
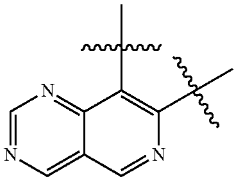,
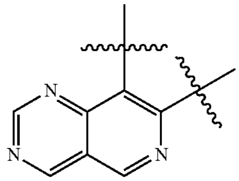,
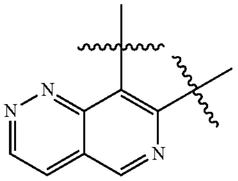,
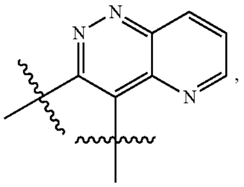,
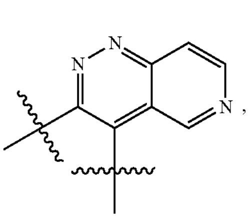,
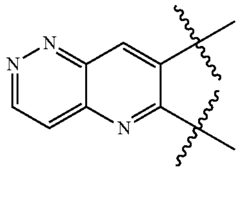,
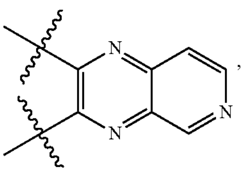,
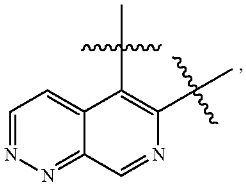,
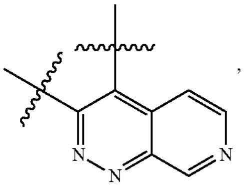,
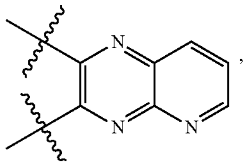, -continued

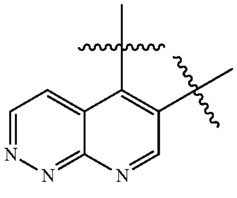
,
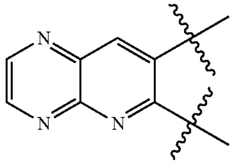
,
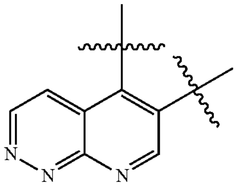
,
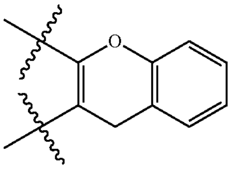
,
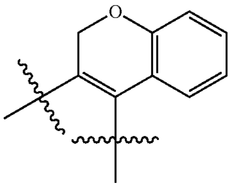
,
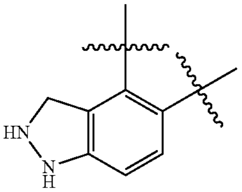
,
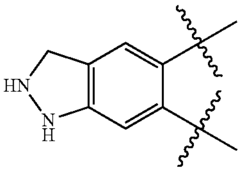
,
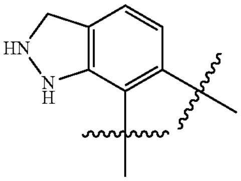
,
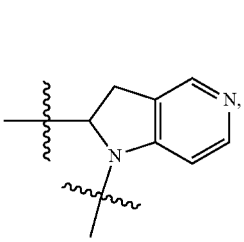
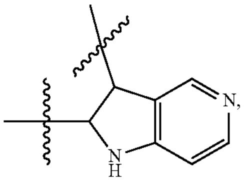
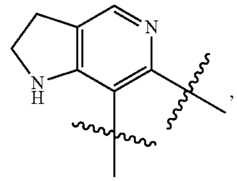
,
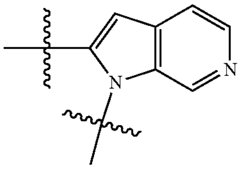
,
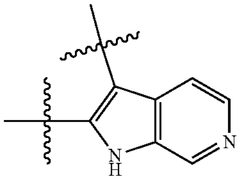
,
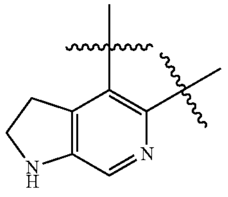
,
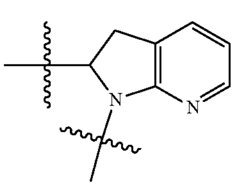
,
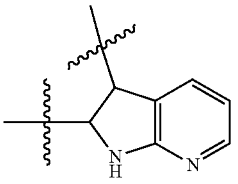
, -continued

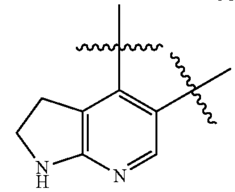
,
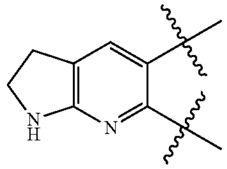
,
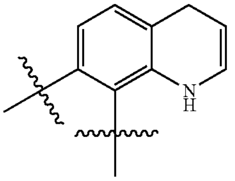
,
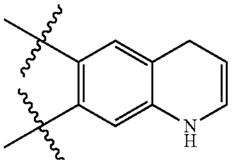
,
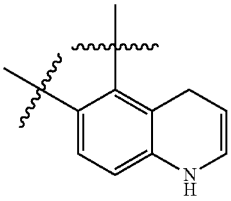
,
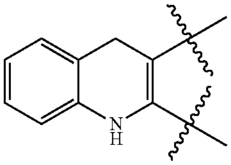
,
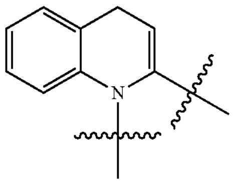
,
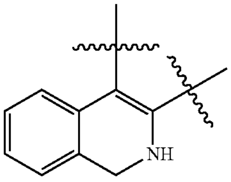
,
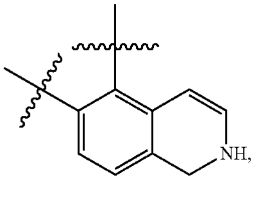
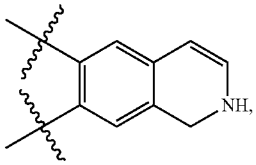
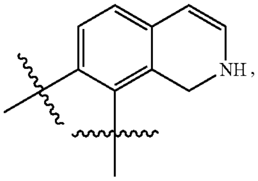
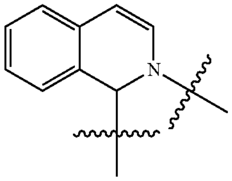
,
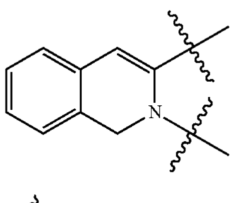
,
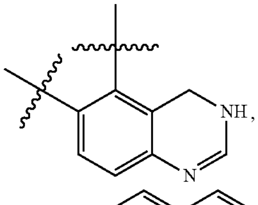
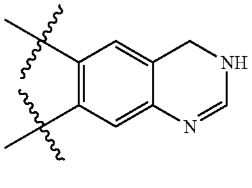
or
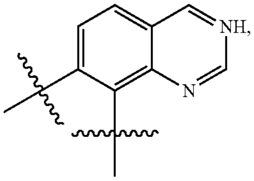

and each of the ring A is independently optionally substituted with another one or more $R_6$.

In some embodiments of Formula I, n is 0, 1, 2 or 3.

In some embodiments of Formula I, each of $R_{6a}$ and $R_{6b}$ is independently —H; —F; —Cl; —Br; —$NH_2$; —CN; —OH; —$NO_2$; carboxyl; —$C_{1-3}$alkyl; —$C_{1-3}$alkoxy; —$C_{1-3}$alkyl substituted with halogen, —$NH_2$, —CN, —OH, —$NO_2$, -carboxyl, —$C_{1-3}$alkyl or —$C_{1-3}$alkoxy; or —$C_{1-3}$alkoxy substituted with halogen, —$NH_2$, —CN, —OH, —$NO_2$, carboxyl, —$C_{1-3}$alkyl or —$C_{1-3}$alkoxy.

In some embodiments of Formula I, each of $R_{6a}$ and $R_{6b}$ is independently —H; —F; —Cl; —Br; —$NH_2$; —CN; —OH; —$NO_2$; carboxyl; methyl; ethyl; propyl; isopropyl; methoxy; ethoxy; propoxy; isopropoxy; —$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or —$C_{1-3}$alkoxy substituted with —F, —Cl, Br, —$NH_2$, —CN, —OH, —$NO_2$, carboxyl, methyl, ethyl, propyl, isopropyl, methoxy, ethoxy, propoxy or isopropoxy.

In some embodiments of Formula I, each of $R_{6a}$ and $R_{6b}$ is independently —H; —F; —Cl; —Br; —$NH_2$; —CN; —OH; carboxyl; methyl; ethyl; isopropyl; methoxy; methyl substituted with —F, —Cl, —$NH_2$, —OH, carboxyl, methyl, ethyl, propyl, isopropyl, methoxy, ethoxy, propoxy or isopropoxy; ethyl substituted with —F, —Cl, —$NH_2$, —OH, carboxyl, methyl, ethyl, propyl, isopropyl, methoxy, ethoxy, propoxy or isopropoxy; or propyl substituted with —F, —Cl, —$NH_2$, —OH, carboxyl, methyl, ethyl, propyl, isopropyl, methoxy, ethoxy, propoxy or isopropoxy.

In some embodiments of Formula I, each of $R_{6a}$ and $R_{6b}$ is independently —H, —$CH_3$, —OH, or —$CH_2CH_2OH$.

In some embodiments of Formula I, the compound is of Formula II:

II

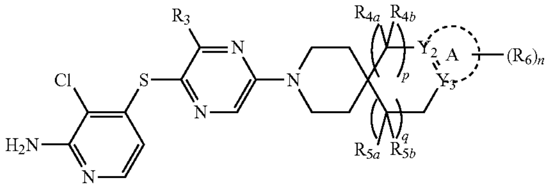

$R_3$ is —H or —$NH_2$;

Each of $R_{4a}$ or $R_{4b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{4a}$ and $R_{4b}$ together with the carbon atom to which they are both attached form C═O, C═NH, or C═N—OH;

p is 0, 1, 2 or 3;

Each of $R_{5a}$ or $R_{5b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{5a}$ and $R_{5b}$ together with the carbon atom to which they are both attached form a 3-10 membered heterocyclic or 5-10 membered heteroaryl; and each of the ring systems is independently optionally substituted;

q is 0, 1, 2, 3 or 4;

Ring A is absent or a 3-10 membered ring;

--- represents a single or double bond;

When ring A is absent, $Y_2$ is $CR_{2a}R_{2b}$, $NR_{2a}$ or O, and $Y_3$ is $CR_{3a}R_{3b}$, $NR_{3a}$ or O;

When ring A is a 3-10 membered ring, and, i) $Y_2$ is $CR_{2a}$ or N, and $Y_3$ is $CR_{3a}$ or N, when --- represents a single bond; or ii) $Y_2$ is C, and $Y_3$ is C, when --- represents a double bond;

Each of $R_{2a}$ and $R_{2b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each of $R_{3a}$ and $R_{3b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

Each $R_6$ is independently —H, halogen, —$NR_{6a}R_{6b}$, —CN, —OH, —$NO_2$, oxo, ═O, carboxyl, —$C_{1-6}$alkoxy, —$C_{1-6}$alkyl, —$C_{1-6}$alkylene-$NR_{6a}R_{6b}$, —$C_{1-6}$alkylene-O—$C_{1-6}$alkyl, —$C_{1-6}$alkylene-CO—$OR_{6a}$, —$C_{1-6}$alkylene-$C_{3-10}$heterocyclic, —$C_{1-6}$alkylene-$C_{5-10}$heteoaryl, —$C_{1-6}$alkylene-CO—$NR_{6a}R_{6b}$, —$C_{1-6}$alkylene-$NR_{6a}$—CO—$NR_{6a}R_{6b}$, —$C_{1-6}$alkylene-$NR_{6a}$—CO—$C_{1-6}$alkyl, —CO—$NR_{6a}R_{6b}$, —CO—CO—$NR_{6a}R_{6b}$, —CO—$C_{1-6}$alkyl, —CO—$C_{1-6}$alkylene-$NR_{6a}R_{6b}$, —CO—$NR_{6a}$—$C_{3-10}$heterocyclic, —CO—$NR_{6a}$—$C_{3-10}$heterocyclic, —CO—$C_{3-10}$heteocyclic, —O—$C_{1-6}$alkylene-CO—$OR_{6a}$, —O—$C_{1-6}$alkylene-CO—$NR_{6a}R_{6b}$, —O—$C_{1-6}$alkylene-$NR_{6a}R_{6b}$, —O—$C_{3-10}$carbocyclic, —$NR_{6a}$—CO—$C_{1-6}$alkyl, —$NR_{6a}$—CO—$NR_{6a}R_{6b}$, —$NR_{6a}$—CO—$C_{5-10}$heteoaryl, —$NR_{6a}$—$C_{1-6}$alkylene-$NR_{6a}R_{6b}$, —$NR_{6a}$ $C_{1-6}$alkylene-$C_{3-10}$heterocyclic, —$NR_{6a}$—$C_{1-6}$alkylene-$C_{5-10}$heteroaryl, —S—$C_{1-6}$alkyl, —$SONR_{6a}R_{6b}$, —$SO_2NR_{6a}R_{6b}$, —SO—$C_{1-6}$alkyl, —$SO_2$—$C_{1-6}$alkyl, —PO($C_{1-6}$alkyl)$_2$, —$C_{3-10}$heterocyclic or —$C_{5-10}$heteroaryl, and each of which is independently optionally substituted; and n is 0, 1, 2 or 3; or two adjacent $R_6$ can be joined together to form a 6-membered aryl, 5-membered heteroaryl, 6-membered heteroaryl, —$C_{3-6}$heterocyclic or —$C_{3-6}$carbocyclic, and each of the ring system is independently optionally substituted;

Each of $R_{6a}$ and $R_{6b}$ is independently —H, halogen, —$NH_2$, —CN, —OH, —$NO_2$, carboxyl, substituted or unsubstituted —$C_{1-6}$alkoxy or substituted or unsubstituted —$C_{1-6}$alkyl.

In some embodiments of Formula II, each of $R_{4a}$ or $R_{4b}$ is independently —H, halogen, —$NH_2$, —CN, —OH, —$NO_2$, carboxyl, substituted or unsubstituted —$C_{1-6}$alkoxy, or substituted or unsubstituted —$C_{1-6}$alkyl; or $R_{4a}$ and $R_{4b}$ together with the carbon atom to which they are both attached form C═O.

In some embodiments of Formula II, each of $R_{4a}$ or $R_{4b}$ is independently —H; —F; —Cl; —Br; —$NH_2$; —CN; —OH; carboxyl; methyl; ethyl; methoxy; ethoxy; methyl substituted with —F, —Cl, —Br, —$NH_2$, —CN, —OH, —$NO_2$, carboxyl, methyl, ethyl, methoxy or ethoxy; ethyl substituted with —F, —Cl, —Br, —$NH_2$, —CN, —OH, —$NO_2$, carboxyl, methyl, ethyl, methoxy or ethoxy; methoxy substituted with —F, —Cl, —Br, —$NH_2$, —CN, —OH, —$NO_2$, carboxyl, methyl, ethyl, methoxy or ethoxy; or ethoxy substituted with —F, —Cl, —Br, —$NH_2$, —CN, —OH, —$NO_2$, carboxyl, methyl, ethyl, methoxy or ethoxy; or $R_{4a}$ and $R_{4b}$ together with the carbon atom to which they are both attached form C═O.

In some embodiments of Formula II, p is 0, 1 or 2.

In some embodiments of Formula II, each of $R_{5a}$ and $R_{5b}$ is independently —H; —F; —Cl; —Br; —$NH_2$; —CN; —OH; carboxyl; —$C_{1-3}$alkyl; —$C_{1-3}$alkoxy; —$C_{1-3}$alkyl substituted with —F, —Cl, —Br, —I, —$NH_2$, —CN, —OH, —$NO_2$, carboxyl, —$C_{1-3}$alkyl or —$C_{1-3}$alkoxy; or —$C_{1-3}$alkoxy substituted with —F, —Cl, —Br, —I, —$NH_2$, —CN, —OH, —$NO_2$, carboxyl, —$C_{1-3}$alkyl or —$C_{1-3}$alkoxy; or $R_{5a}$ and $R_{5b}$ together with the carbon atom to which they are both attached form a 3-membered heterocyclic, 4-membered heterocyclic, 5-membered heterocyclic or 6-membered heterocyclic; and each of the heterocyclic contains 1 or 2 heteroatoms selected from N or O; and each of the ring system is independently optionally substituted with —F, —Cl, —Br, —$NH_2$, —CN, —OH, —$NO_2$, carboxyl, —$C_{1-6}$alkyl, or —$C_{1-6}$alkoxy.

In some embodiments of Formula II, each of $R_{5a}$ or $R_{5b}$ is independently —H; —Cl; —Br; —$NH_2$; —OH; carboxyl; methyl; ethyl; methoxy; ethoxy; methyl substituted with —F, —Cl, —Br, —$NH_2$, —CN, —OH, —$NO_2$, carboxyl, methyl or methoxy; ethyl substituted with —F, —Cl, —Br, —$NH_2$, —CN, —OH, —$NO_2$, carboxyl, methyl or methoxy; methoxy substituted with —F, —Cl, —Br, —$NH_2$, —CN, —OH, —$NO_2$, carboxyl, methyl or methoxy; or ethoxy substituted with —F, —Cl, —Br, —$NH_2$, —CN, —OH, —$NO_2$, carboxyl, methyl or methoxy; or $R_{5a}$ and $R_{5b}$ together with the carbon atom to which they are both attached form

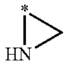 , and *C represents the carbon atom which $R_{5a}$ and $R_{5b}$ attached.

In some embodiments of Formula II, ring A is 6-membered aryl, 7-membered aryl, 8-membered aryl, 9-membered aryl; 5-membered heteroaryl, 6-membered heteroaryl, 7-membered heteroaryl, 8-membered heteroaryl, 9-membered heteroaryl; 3-membered heterocyclic, 4-membered heterocyclic, 5-membered heterocyclic, 6-membered heterocyclic, 7-membered heterocyclic, 8-membered heterocyclic, 9-membered heterocyclic; 3-membered carbocyclic, 4-membered carbocyclic, 5-membered carbocyclic, 6-membered carbocyclic, 7-membered carbocyclic, 8-membered carbocyclic or 9-membered carbocyclic; and each of the heteroaryl contains 1, 2 or 3 heteroatoms selected from N, O or S; each of the heterocyclic contains 1, 2 or 3 heteroatoms selected from N or O.

In some embodiments of Formula II, ring A is 6-membered aryl, 7-membered aryl, 8-membered aryl; 5-membered heteroaryl, 6-membered heteroaryl, 7-membered heteroaryl, 8-membered heteroaryl; 3-membered heterocyclic, 4-membered heterocyclic, 5-membered heterocyclic, 6-membered heterocyclic, 7-membered heterocyclic, 8-membered heterocyclic; 3-membered carbocyclic, 4-membered carbocyclic, 5-membered carbocyclic, 6-membered carbocyclic, 7-membered carbocyclic or 8-membered carbocyclic; and each of the heteroaryl contains 1 or 2 heteroatoms selected from N, O or S; each of the heterocyclic contains 1 or 2 heteroatoms selected from N or O.

In some embodiments of Formula II, ring A is

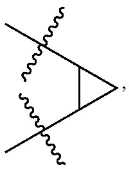, 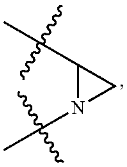, 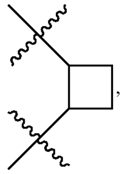,

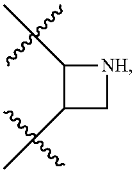, 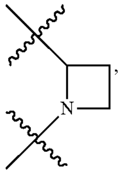, 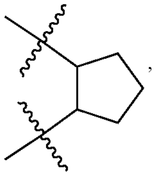,

-continued

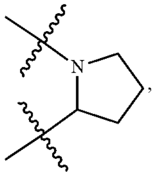, 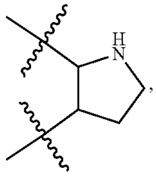, 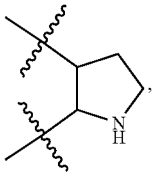,

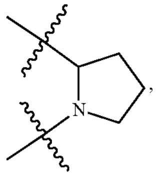, 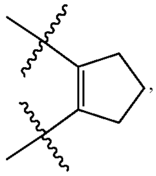, 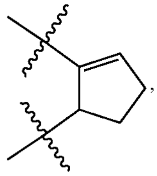,

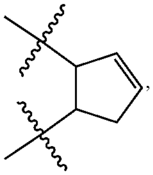, 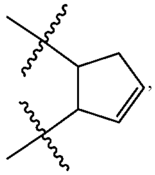, 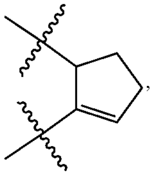,

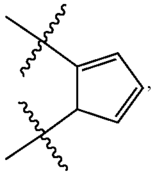, 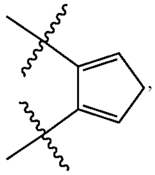, 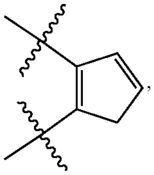,

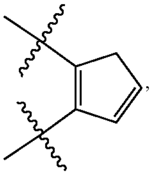, 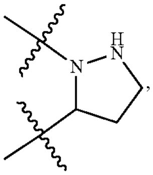, 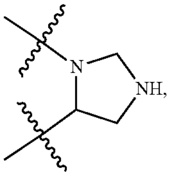,

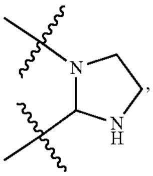, 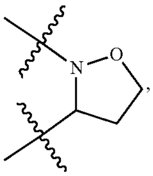, 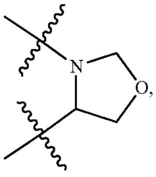,

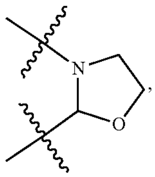, 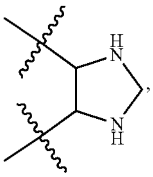, 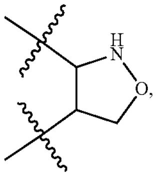,

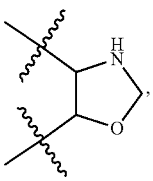, 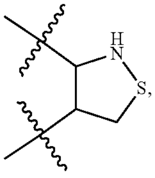, 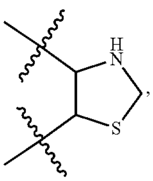,

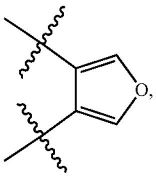, 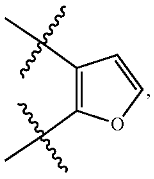, 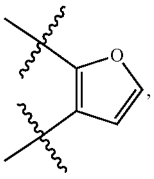,

-continued
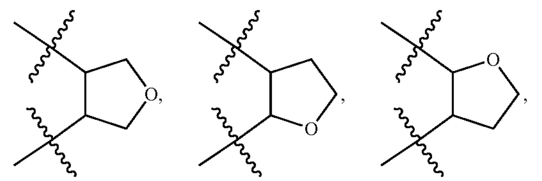
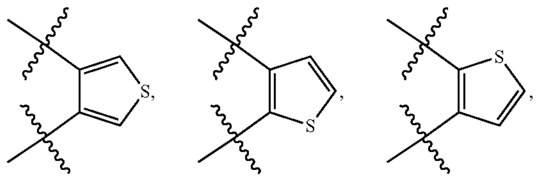
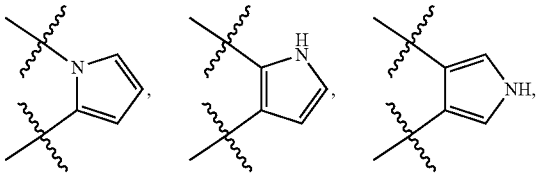
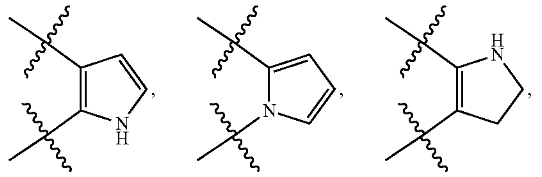
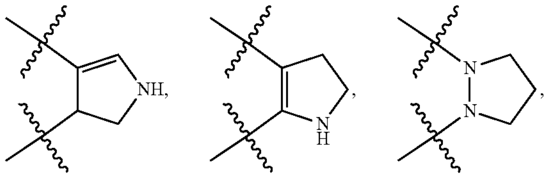
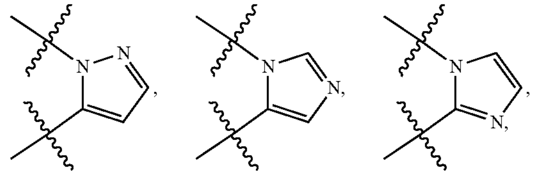
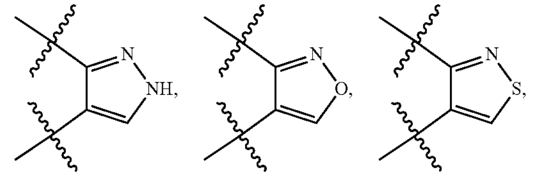
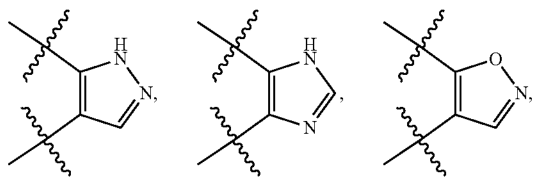
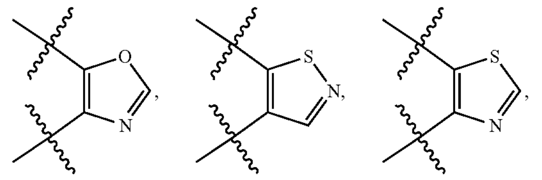
-continued
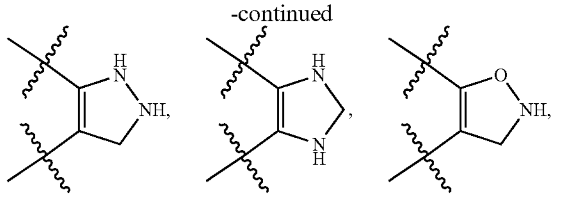
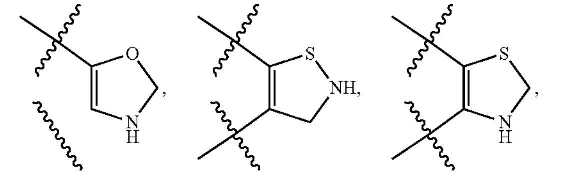
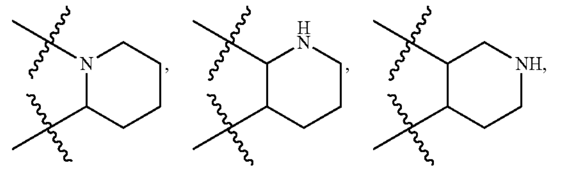
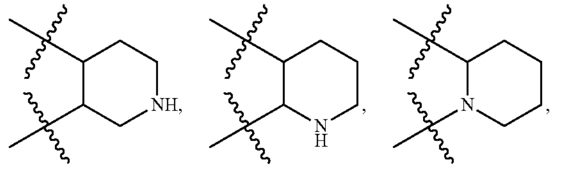
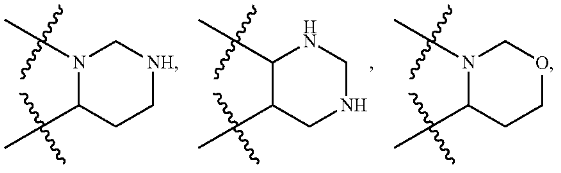
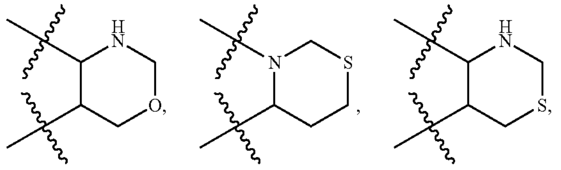
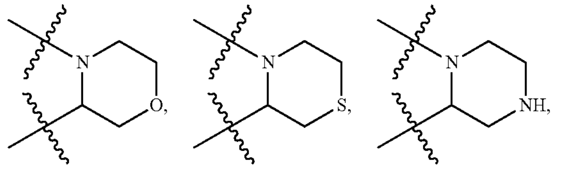
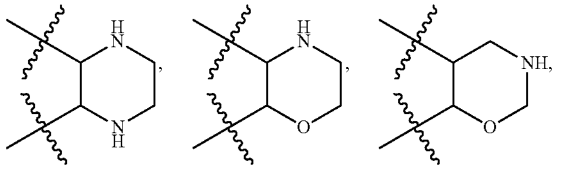
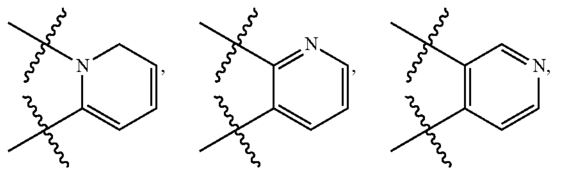
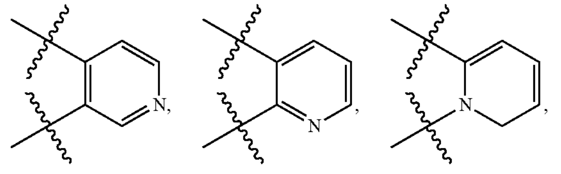

-continued
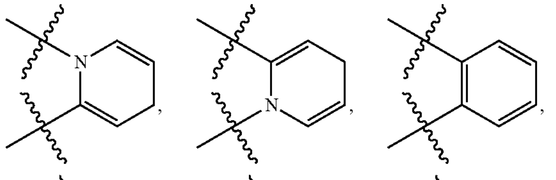
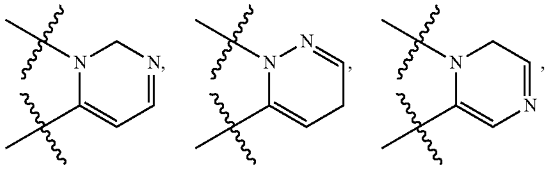
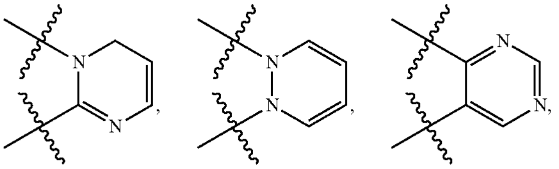
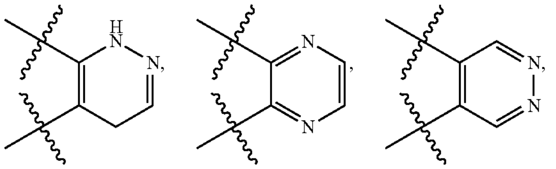
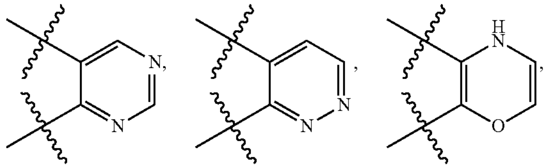
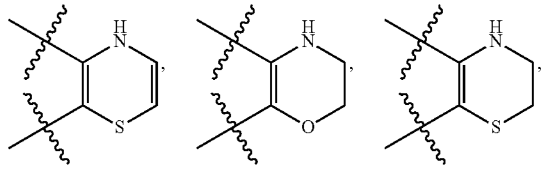
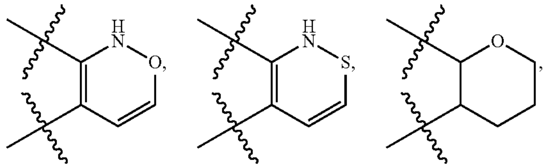
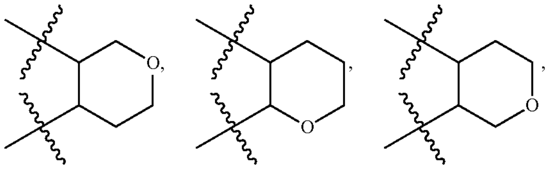
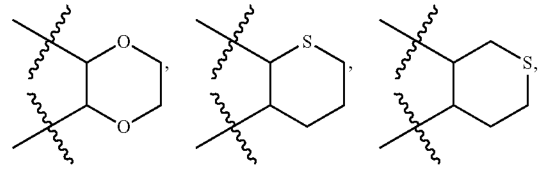
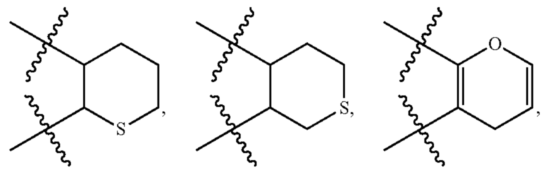
-continued
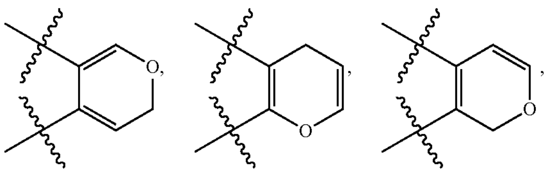
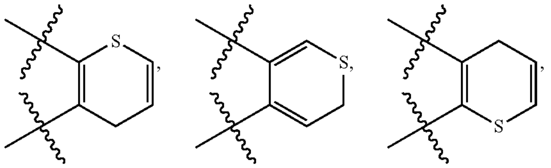
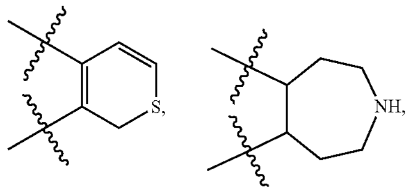
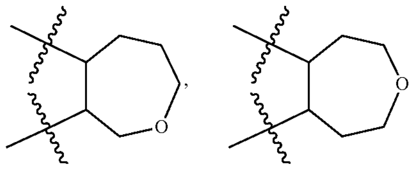
or
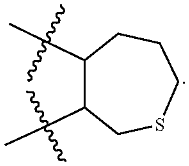
In some embodiments of Formula II, ring A is
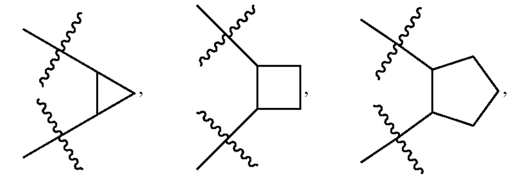
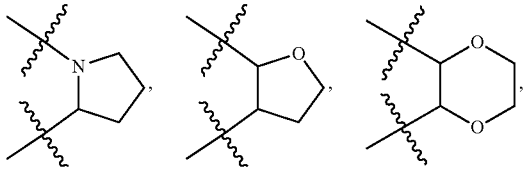
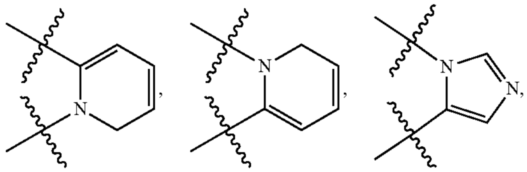
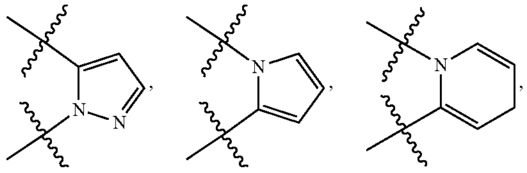

-continued

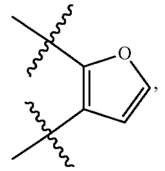,
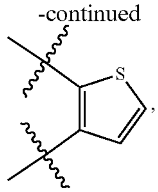,
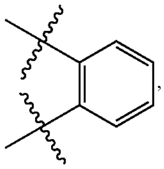,
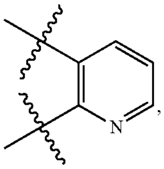,
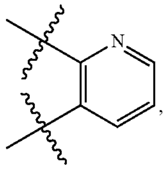,
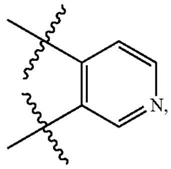,
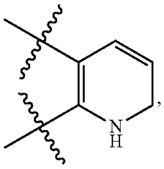,
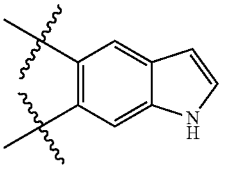 or
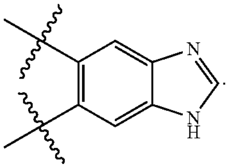.

In some embodiments of Formula II, $Y_2$ is $CR_{2a}$ or N, $Y_3$ is $CR_{3a}$ or N.

In some embodiments of Formula II, each of $R_{2a}$, $R_{2b}$, $R_{3a}$ and $R_{3b}$ is independently —H; —F; —Cl; —Br; —$NH_2$; —CN; —OH; —$NO_2$; carboxyl; methyl; ethyl; propyl; isopropyl; methoxy; ethoxy; propoxy; isopropoxy; —$C_{1-3}$alkyl substituted with —F, —Cl, —Br, —$NH_2$, —CN, —OH, —$NO_2$, carboxyl, methyl, ethyl, propyl, isopropyl, methoxy, ethoxy, propoxy or isopropoxy; or —$C_{1-3}$alkoxy substituted with —F, —Cl, —Br, —$NH_2$, —CN, —OH, —$NO_2$, carboxyl, methyl, ethyl, propyl, isopropyl, methoxy, ethoxy, propoxy or isopropoxy.

In some embodiments of Formula II, each of $R_{2a}$, $R_{2b}$, $R_{3a}$ and $R_{3b}$ is independently —H or methyl.

In some embodiments of Formula II, $R_{2a}$, $R_{2b}$, $R_{3a}$ and $R_{3b}$ are all —H.

In some embodiments of Formula II, $Y_2$ is CH or N, and $Y_3$ is CH or N.

In some embodiments of Formula II, $Y_2$ is C, and $Y_3$ is C.

In some embodiments of Formula II, each $R_6$ is independently —H, —F, —Cl, —Br, —$NH_2$, —$N(CH_3)_2$, —CN, —OH, oxo, =O, carboxyl, —$C_{1-3}$alkoxy, —$C_{1-3}$alkyl, —$CH_2NH_2$, —$C_{1-3}$alkylene-$OCH_3$, —$CH_2$—COOH, —$CH_2$—COO—$C_{1-3}$alkyl, —$CH_2$—$C_{5-10}$heterocyclic, —$C_{1-3}$alkylene-CO—$NR_{6a}R_{6b}$, —$CH_2$NH—CO—$NR_{6a}R_{6b}$, —CO—$NR_{6a}R_{6b}$, —COCO—$NR_{6a}R_{6b}$, —CO—$C_{1-3}$alkyl, —CONH—$C_{5-10}$heteocyclic, —CO-5-membered heteocyclic, —CO-6-membered heteocyclic, —O-5-membered carbocyclic, —O-6-membered carbocyclic, —NH—CO—$C_{1-3}$alkyl, —$NR_{6a}$—CO—$NR_{6a}R_{6b}$, —$NR_{6a}$—$C_{1-3}$alkylene-$NR_{6a}R_{6b}$, —$NR_{6a}$—$C_{1-3}$alkylene-$C_{5-10}$heterocyclic, —S—$C_{1-3}$alkyl, —$SO_2NH_2$, —$SO_2CH_3$, 5-membered heterocyclic, 6-membered heterocyclic, 5-membered heteroaryl, or 6-membered heteroaryl, and each of which is independently optionally substituted with —F, —Cl, —Br, —$NH_2$, —CN, —OH, oxo, =O, substituted or unsubstituted —$C_{1-3}$alkoxy, or substituted or unsubstituted —$C_{1-3}$alkyl; or two adjacent $R_6$ can be joined together to form a 6-membered aryl; 3-membered carbocyclic, 4-membered carbocyclic, 5-membered carbocyclic, 5-membered heteroaryl, 3-membered heterocyclic, 4-membered heterocyclic or 5-membered heterocyclic; and each of heteroaryl or heterocyclic contains 1, 2 or 3 heteroatoms selected from N, O or S; and each of the ring system is independently optionally substituted with —F, —Cl, —Br, —I, —$NH_2$, —CN, —OH, —$NO_2$, =O, oxo, carboxyl, —$CONH_2$, —PO($C_{1-3}$alkyl)$_2$, substituted or unsubstituted —$C_{1-3}$alkoxy, or substituted or unsubstituted —$C_{1-3}$alkyl.

In some embodiments of Formula II, each $R_6$ is independently —F, —Cl, —Br, —$NH_2$, —$N(CH_3)_2$, —CN, —OH, oxo, =O, carboxyl, methoxy, ethoxy, methyl, ethyl, isopropyl, —$CH_2NH_2$, —$CH_2CH_2OCH_3$, —$CH_2$—COOH, —$CH_2$NH—$CONHCH_3$, —$CONH_2$, —$CON(CH_3)_2$, —CONHOH, —$CONHCH_2CH_2OH$, —CO—$CON(CH_3)_2$, —$COCH_3$, —$SO_2NH_2$, —$SO_2CH_3$, —$SCH_3$, —NH—$COCH_3$,

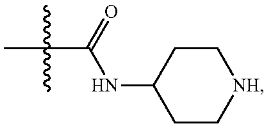,
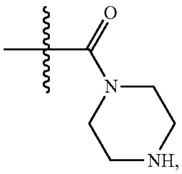,
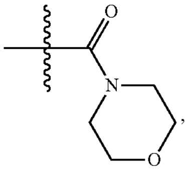,
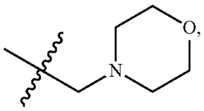,
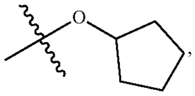,
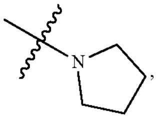,
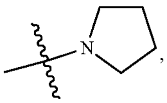,
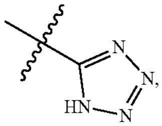,
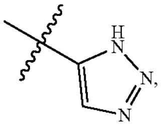,
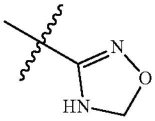 or
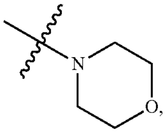, and each of which is independently optionally substituted with —F, —$NH_2$, —OH, oxo, =O, or substituted or unsubstituted —$C_{1-3}$alkyl.

In some embodiments of Formula II, each $R_6$ is independently methyl, methoxy, =O, oxo, —OH, —CN, —$NH_2$, —Cl, —Br, —$CF_3$, —$OCF_3$, —$SO_2NH_2$, —$SO_2CH_3$, —F, —$CH_2NH_2$,

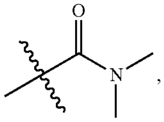,
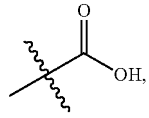,
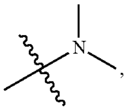,

-continued
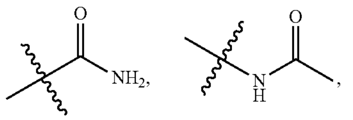
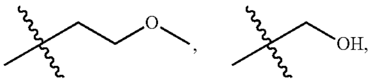
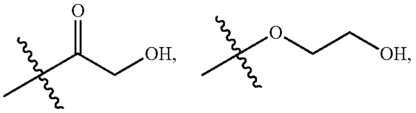
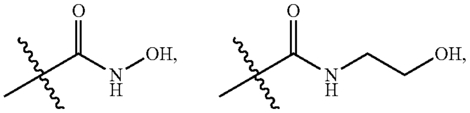
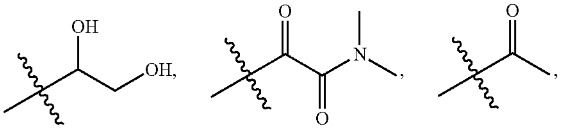
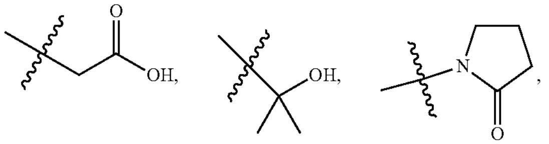
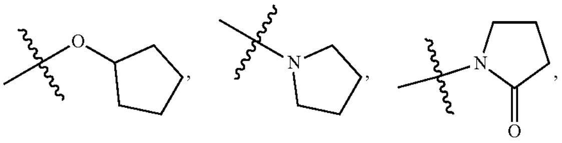
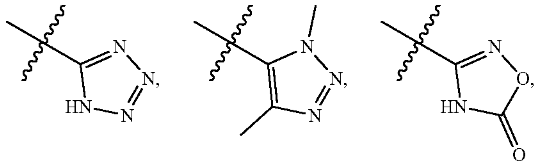
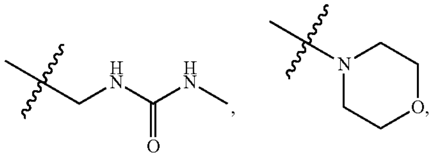
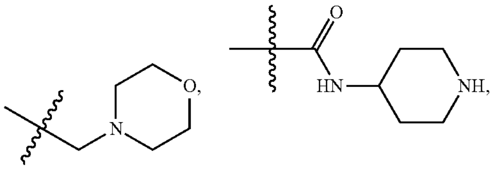
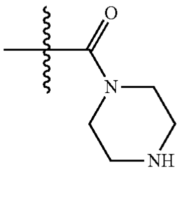
or
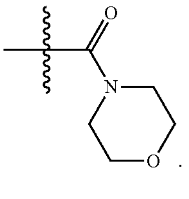
In some embodiments of Formula II, ring A and two adjacent $R_6$ taken together to form
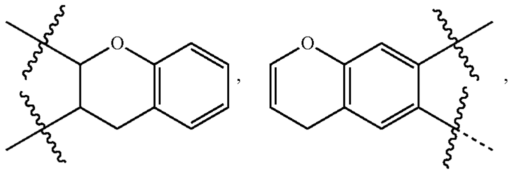
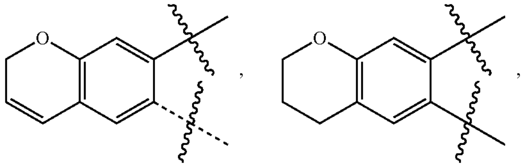
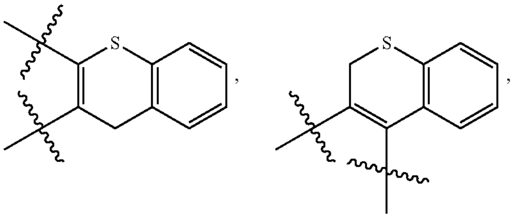
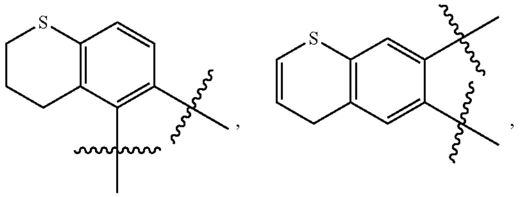
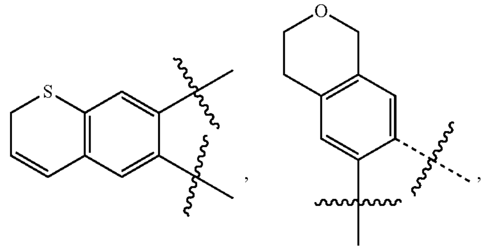
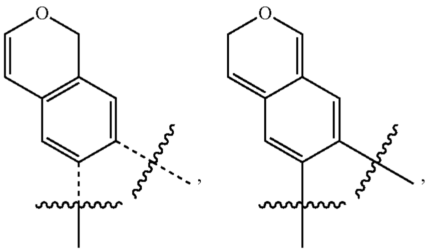
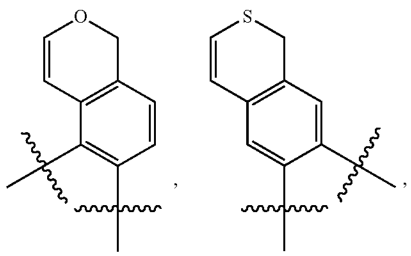

-continued
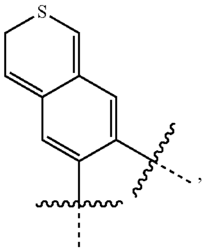,
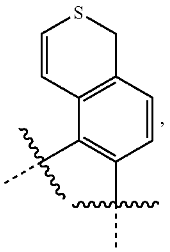,
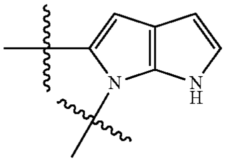,
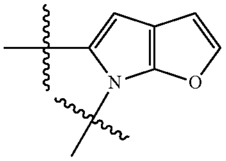,
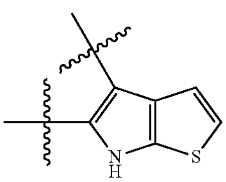,
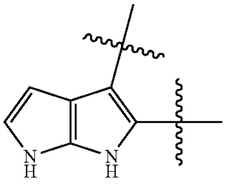,
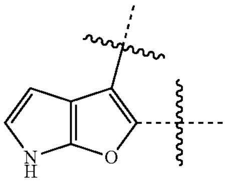,
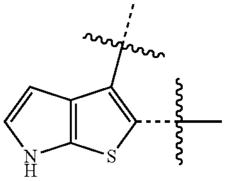,
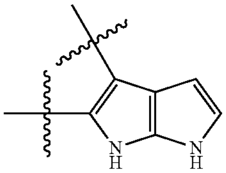,
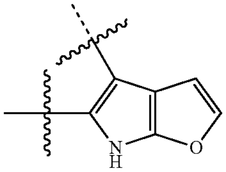,
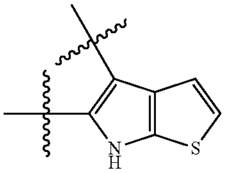,
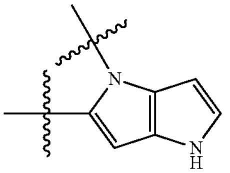,
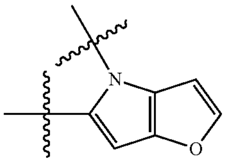,
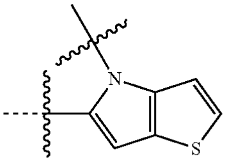,
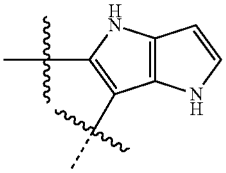,
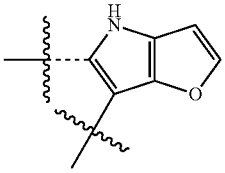,
-continued
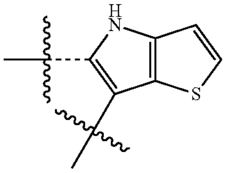,
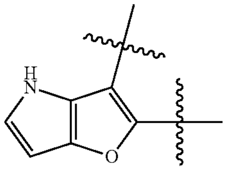,
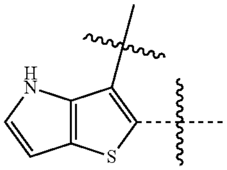,
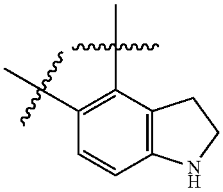,
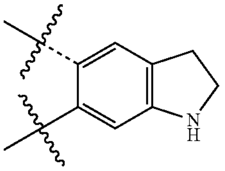,
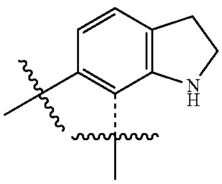,
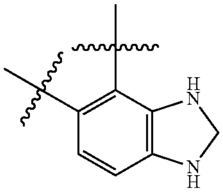,
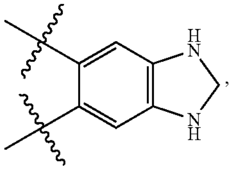,
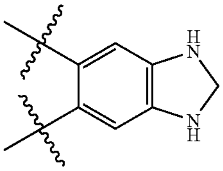,
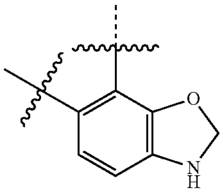,
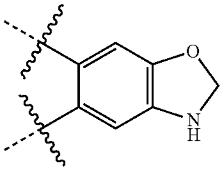,
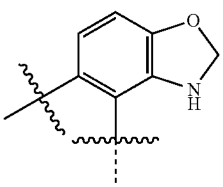,
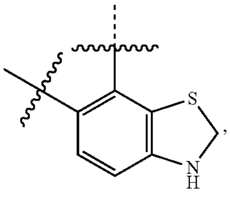,
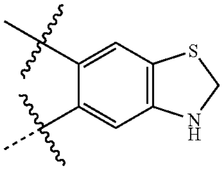,
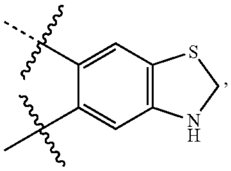,
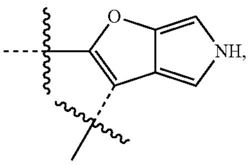, -continued
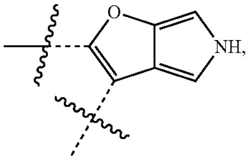,
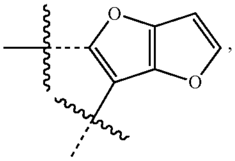,
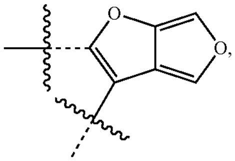,
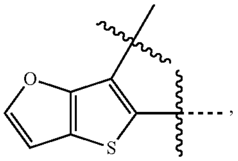,
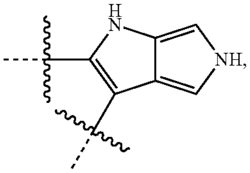,
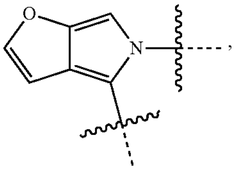,
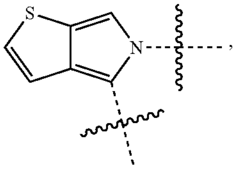,
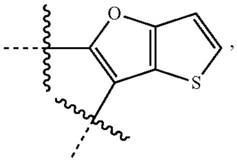,
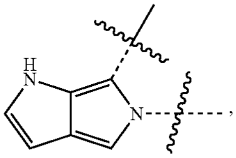,
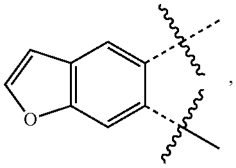,
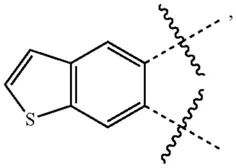,
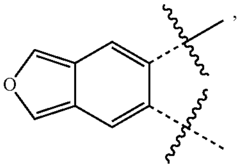,
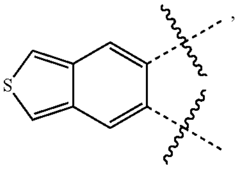,
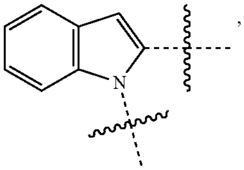,
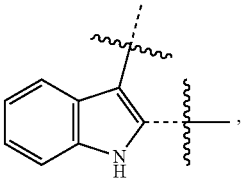,
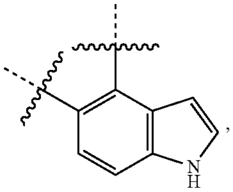,
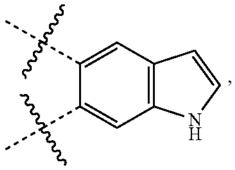,
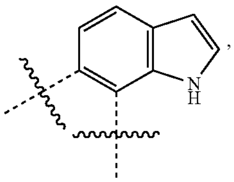,
-continued
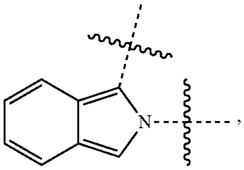,
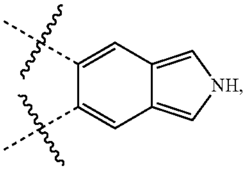,
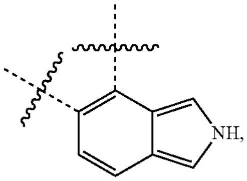,
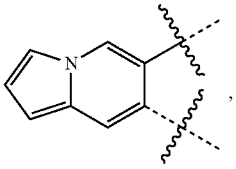,
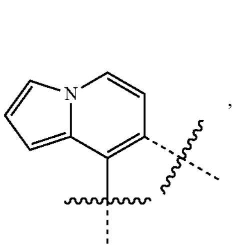,
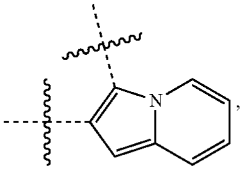,
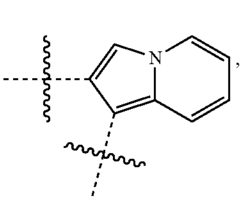,
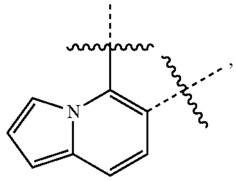,
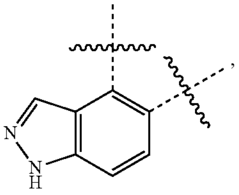,
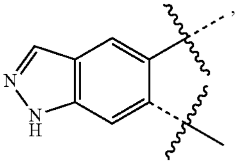,
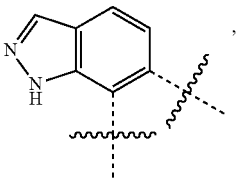,
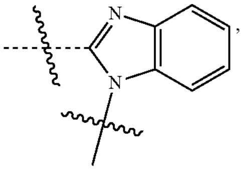,
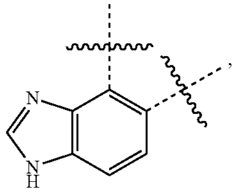,
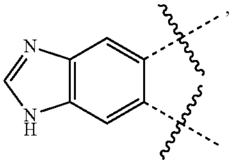,
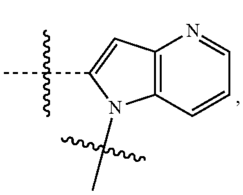,
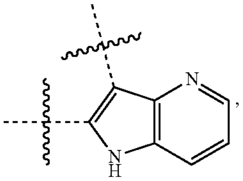, -continued
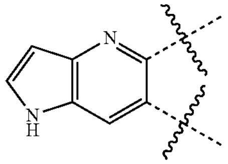
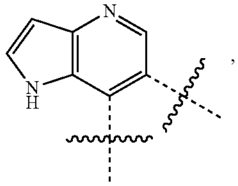
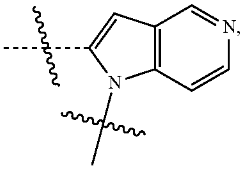
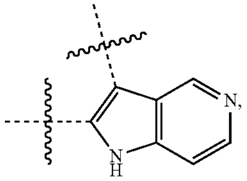
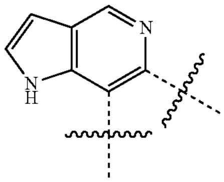
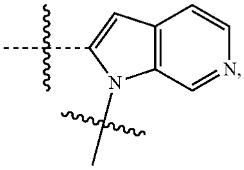
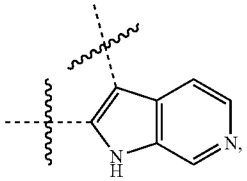
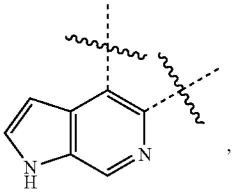
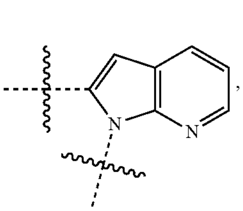
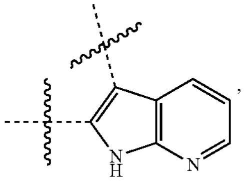
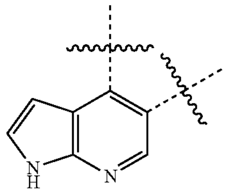
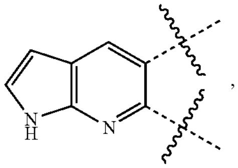
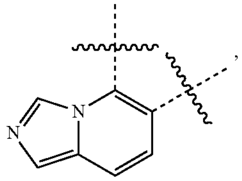
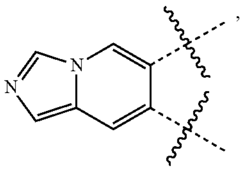
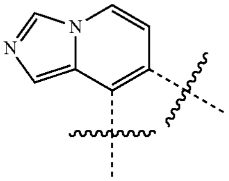
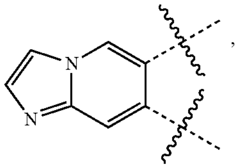
-continued
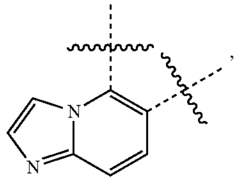
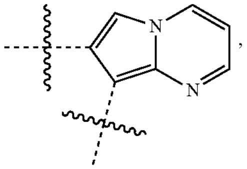
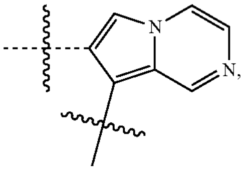
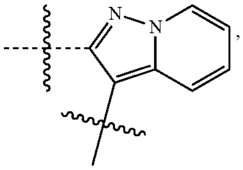
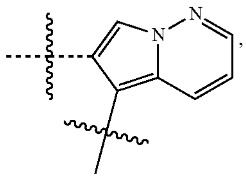
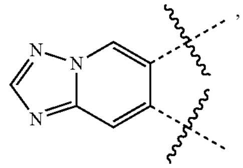
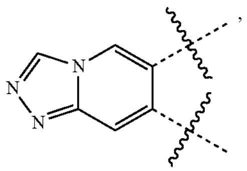
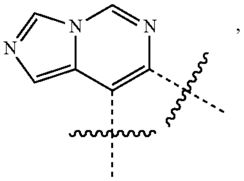
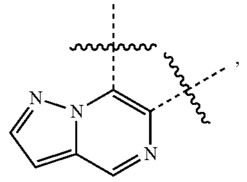
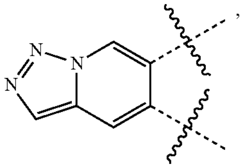
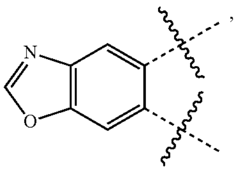
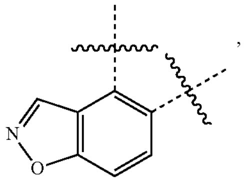
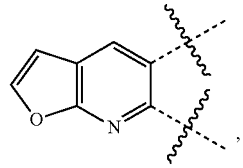
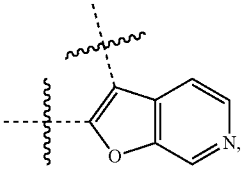
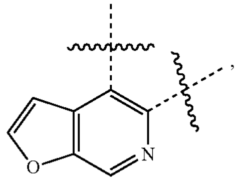
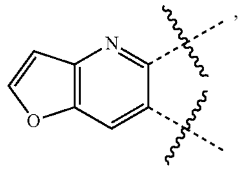

-continued
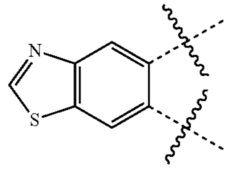,
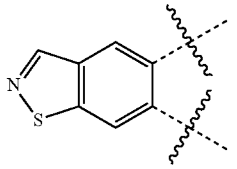,
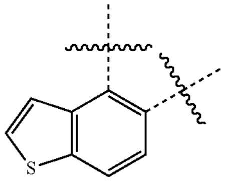,
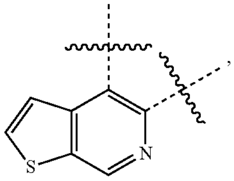,
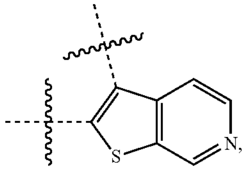,
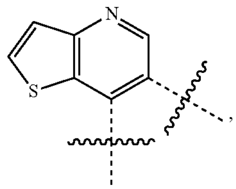,
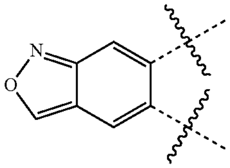,
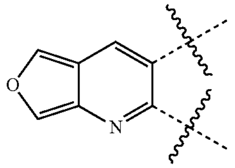,
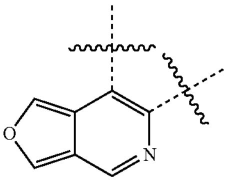,
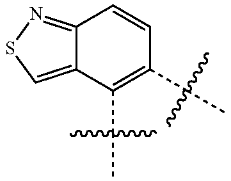,
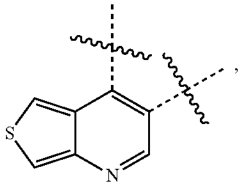,
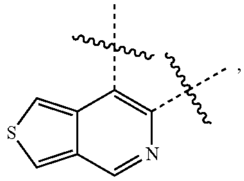,
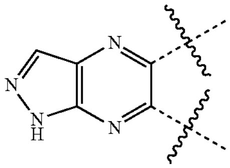,
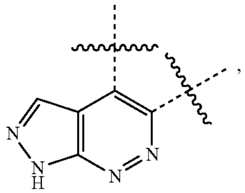,
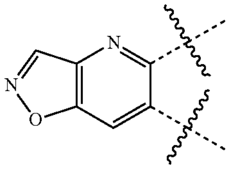,
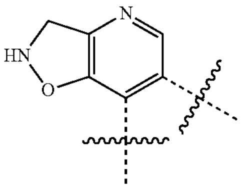,
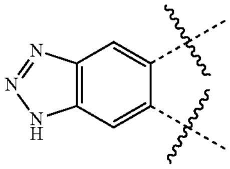,
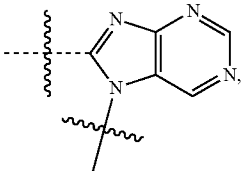,
-continued
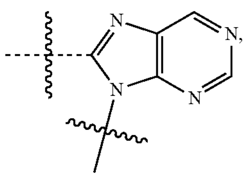,
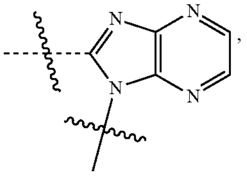,
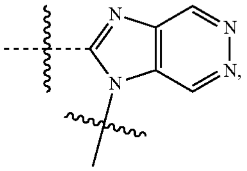,
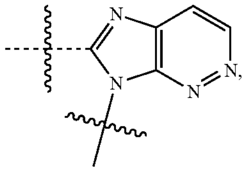,
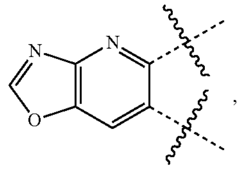,
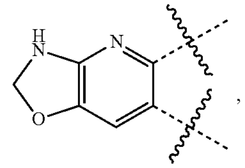,
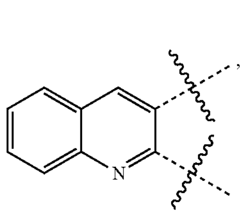,
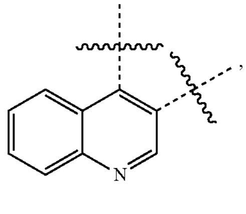,
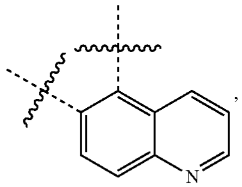,
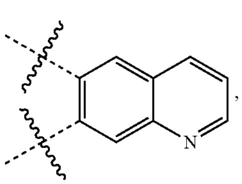,
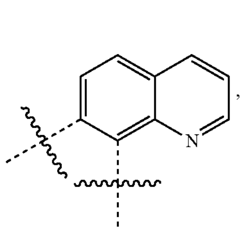,
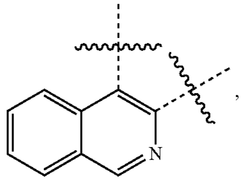,
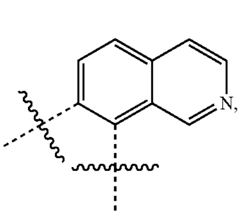,
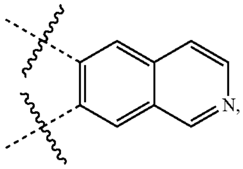,
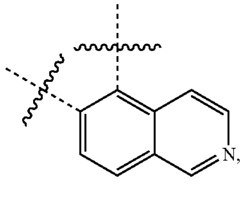,
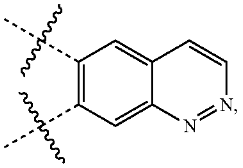

-continued
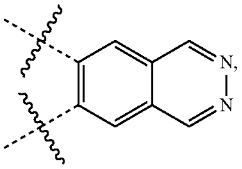
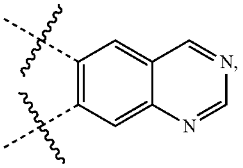
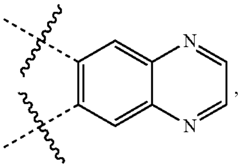
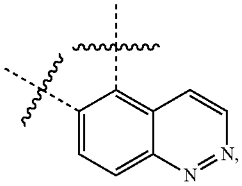
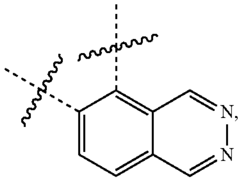
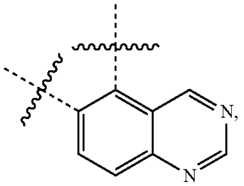
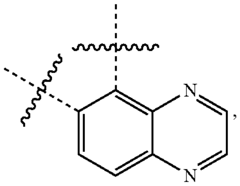
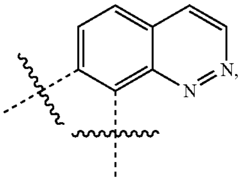
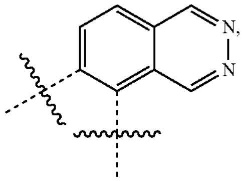
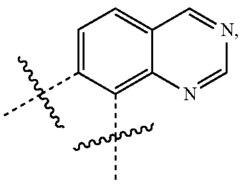
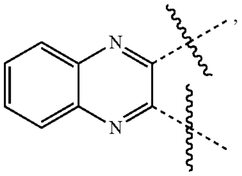
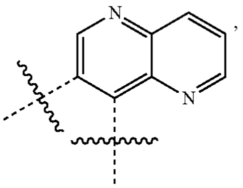
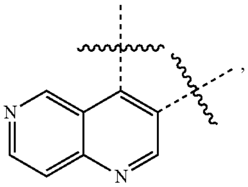
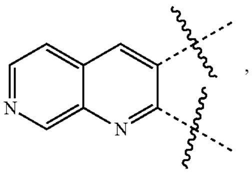
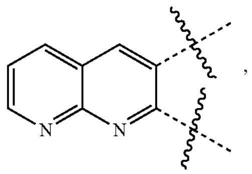
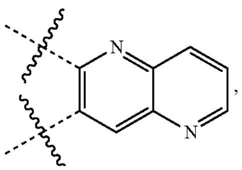
-continued
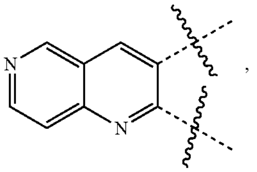
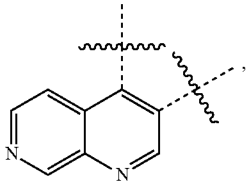
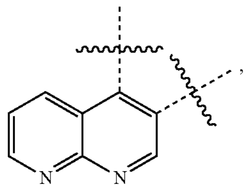
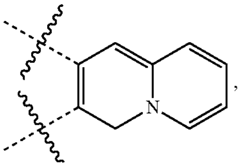
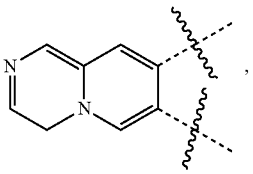
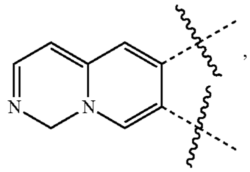
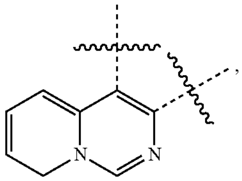
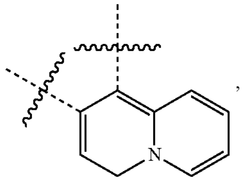
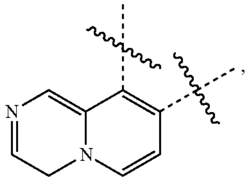
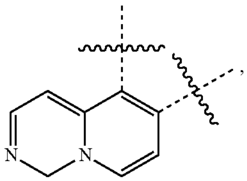
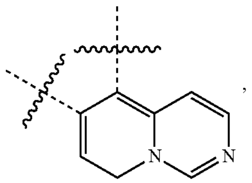
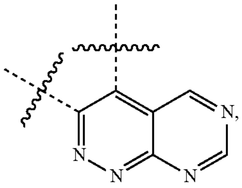
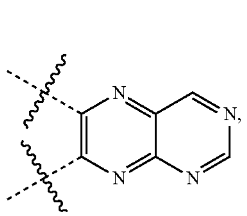
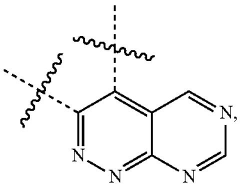
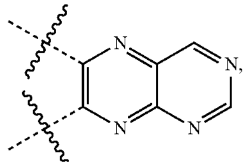
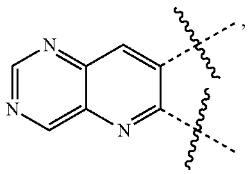

-continued
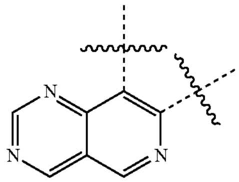,
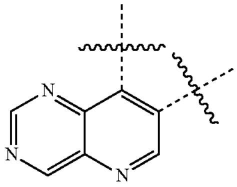,
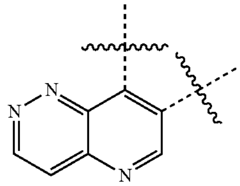,
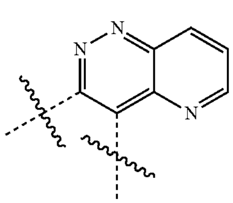,
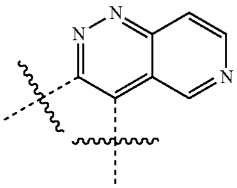,
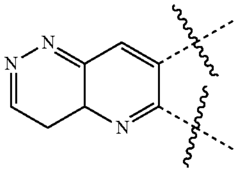,
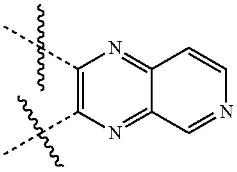,
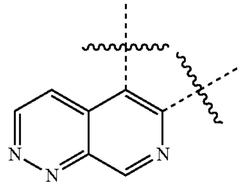,
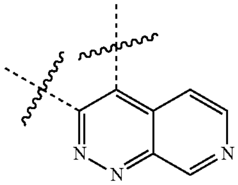,
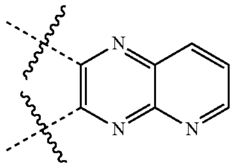,
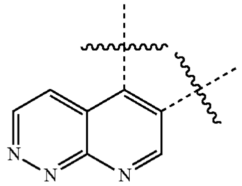,
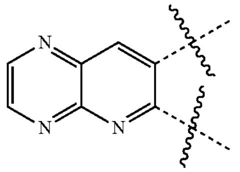,
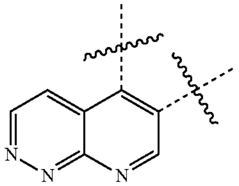,
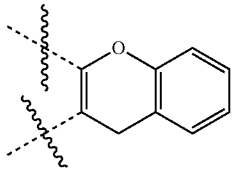,
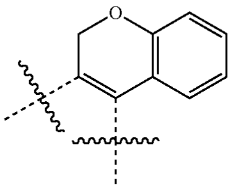,
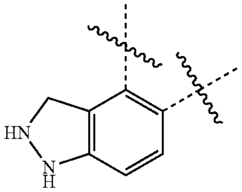,
-continued
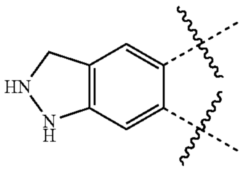,
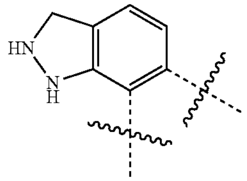,
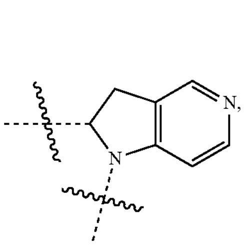,
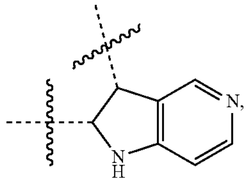,
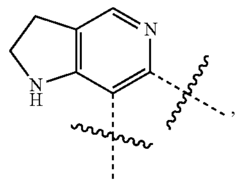,
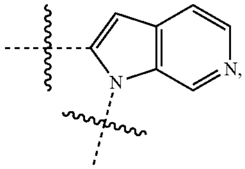,
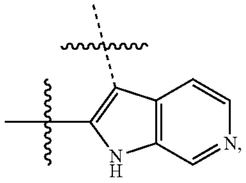,
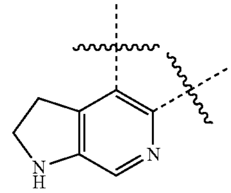,
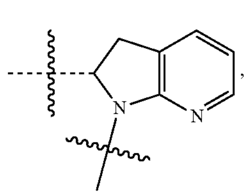,
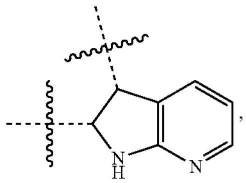,
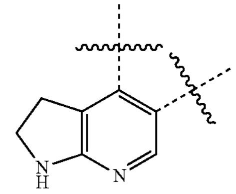,
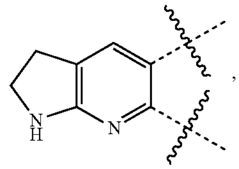,
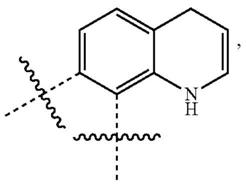,
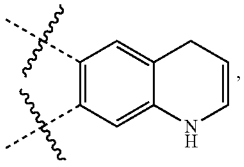,
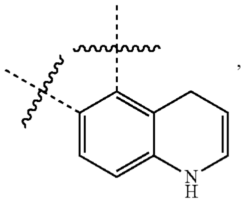,
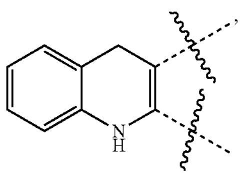, -continued

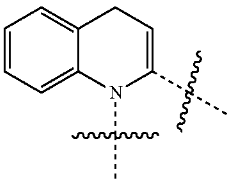,

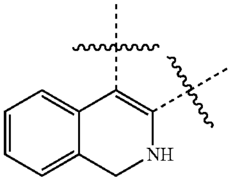,

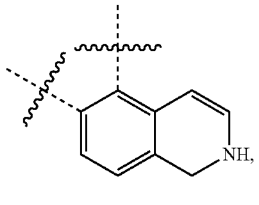

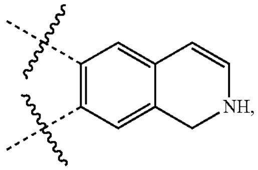

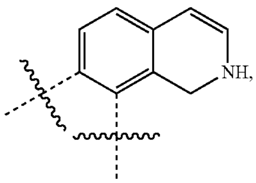

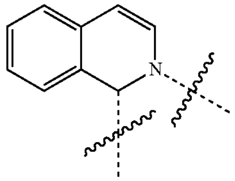,

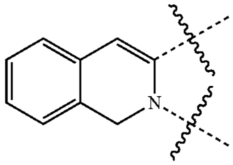,

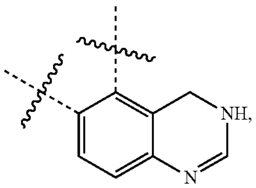

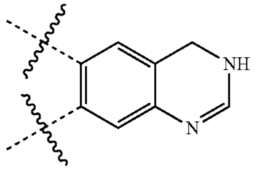

or

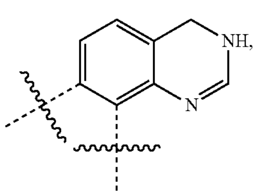

and each of the ring A is independently optionally substituted with one or more $R_6$.

In some embodiments of Formula II, each of $R_{6a}$ and $R_{6b}$ is independently —H, —F, —Cl, —Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula II, each of $R_{6a}$ and $R_{6b}$ is independently —H, —Cl, —Br, —NH, —OH, carboxyl, methyl, ethyl, methoxy, ethoxy propoxy, isopropoxy, methyl substituted with —OH, or ethyl substituted with —OH.

In some embodiments of Formula II, each of $R_{6a}$ and $R_{6b}$ is independently —H, —$CH_3$, —OH, or —$CH_2CH_2OH$.

In some embodiments of Formula II, n is 0, 1 or 2.

In some embodiments of Formula I, the compound is of III:

III

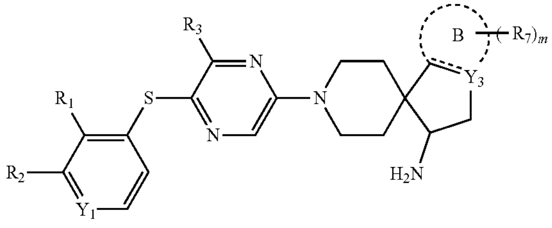

$R_1$ is —H, —F, —Cl, —Br, —$NH_2$, —CN, —OH, —$NO_2$, carboxyl, substituted or unsubstituted —$C_{1-6}$alkoxy, or substituted or unsubstituted —$C_{1-6}$alkyl;

$R_2$ is —H, —F, —Cl, —Br, —$NH_2$, —CN, —OH, —$NO_2$, carboxyl, substituted or unsubstituted —$C_{1-6}$alkoxy, or substituted or unsubstituted —$C_{1-6}$alkyl; or $R_1$ combines with $R_2$ to which is adjacent to form a 5-10 membered heterocyclic ring contains 1, 2 or 3 heteroatoms selected from N or O, and each of the ring systems is independently optionally substituted with halogen, —$NH_2$, —CN, —OH, —$NO_2$, carboxyl, oxo, ═O, —$CONH_2$, substituted or unsubstituted —$C_{1-6}$alkoxy, substituted or unsubstituted —$C_{1-6}$alkyl, or —CO—$C_{1-6}$alkyl;

$Y_1$ is N or CH;

$R_3$ is —H or —$NH_2$;

Ring B is a 6-membered aryl, 5-6 membered heteroaryl, 3-6 membered carbocyclic or 3-6 membered heterocyclic;

$Y_3$ is CH, N or C;

$R_7$ is halogen, —$NH_2$, —CN, —OH, —$NO_2$, carboxyl, oxo, ═O, —$CONH_2$, —NH—$COCH_3$, substituted or unsubstituted —$C_{1-6}$alkoxy, or substituted or unsubstituted —$C_{1-6}$alkyl; and m is 0, 1 or 2.

In some embodiments of Formula III, $R_1$ combines with $R_2$ to which is adjacent to form a 5-membered heterocyclic, 6-membered heterocyclic, 7-membered heterocyclic, 8-membered heterocyclic, 9-membered heterocyclic or 10-membered heterocyclic; and each of the heterocyclic contains 1 or 2 heteroatoms selected from N or O; and each of the ring systems is independently optionally substituted with —F, —Cl, —Br, —$NH_2$, —CN, —OH, oxo, ═O, substituted or unsubstituted —$C_{1-3}$alkoxy, substituted or unsubstituted —$C_{1-3}$alkyl, or —CO—$C_{1-3}$alkyl.

In some embodiments of Formula III, $R_1$ combines with $R_2$ to which is adjacent to form

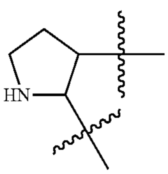;

and the ring systems is independently optionally substituted with —F or —$COCH_3$.

In some embodiments of Formula III, $R_1$ combines with $R_2$ to which is adjacent to form

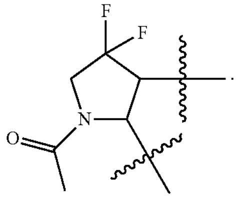 [SMILES: *C1C(*)C(F)(F)CN1C(C)=O]

In some embodiments of Formula III, ring B is 6-membered aryl, 5-membered heteroaryl, 6-membered heteroaryl, 3-membered carbocyclic, 4-membered carbocyclic, 5-membered carbocyclic, 6-membered carbocyclic, 3-membered heterocyclic, 4-membered heterocyclic, 5-membered heterocyclic or 6-membered heterocyclic; and each of the heteroaryl or heterocyclic contains 1, 2 or 3 heteroatoms selected from N, O or S.

In some embodiments of Formula III, ring B is

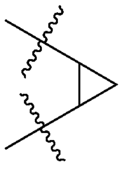 , 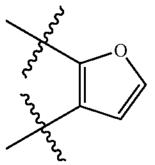 , 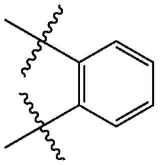 ,

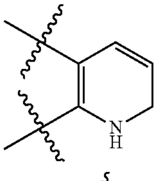 , 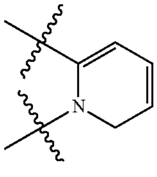 , 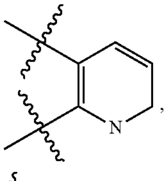 ,

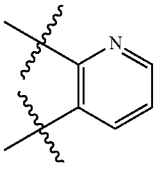 or 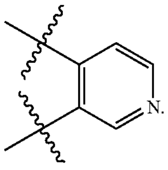

In some embodiments of Formula III, $R_7$ is —$NH_2$, —CN, oxo, =O, —$CONH_2$, —NH—$COCH_3$, methyl or methoxy.

In some embodiments of Formula III, m is 0 or 1.

In some embodiments of Formula I, the compound is of Formula IV:

IV

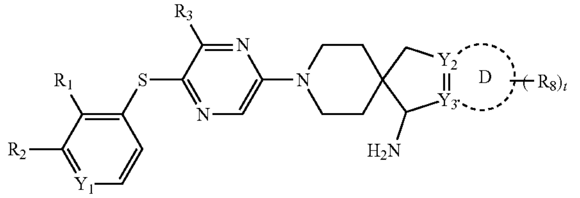

$R_1$ is —H, —F, —Cl, —Br, —$NH_2$, —CN, —OH, —$NO_2$, carboxyl, substituted or unsubstituted —$C_{1-6}$alkoxy, or substituted or unsubstituted-$C_{1-6}$alkyl;

$R_2$ is —H, —F, —Cl, —Br, —$NH_2$, —CN, —OH, —$NO_2$, carboxyl, —$NHC_{1-6}$alkyl, —$N(C_{1-6}alkyl)_2$, substituted or unsubstituted —$C_{1-6}$alkoxy, or substituted or unsubstituted —$C_{1-6}$alkyl; or $R_1$ combines with $R_2$ to which is adjacent to form a 5-12 membered heterocyclic ring contains 1, 2 or 3 heteroatoms selected from N or O, and each of the ring systems is independently optionally substituted with halogen, —$NH_2$, —CN, —OH, —$NO_2$, carboxyl, oxo, =O, —$CONH_2$, substituted or unsubstituted —$C_{1-6}$alkoxy, substituted or unsubstituted —$C_{1-6}$alkyl, or —CO—$C_{1-6}$alkyl;

$Y_1$ is N or CH;

$R_3$ is —H or —$NH_2$;

Ring D is a 6-membered aryl, 5-membered heteroaryl, 6-membered heteroaryl, 3-membered carbocyclic, 4-membered carbocyclic, 5-membered carbocyclic, 6-membered carbocyclic, 3-membered heterocyclic, 4-membered heterocyclic, 5-membered heterocyclic, or 6-membered heterocyclic;

$\overline{\overline{---}}$ represents a single or double bond; and i) $Y_2$ is $CR_{2a}$ or N, and $Y_3$ is $CR_{3a}$ or N, when $\overline{\overline{---}}$ represents a single bond; or ii) $Y_2$ is C, and $Y_3$ is C, when $\overline{\overline{---}}$ represents a double bond;

Each of $R_{2a}$ and $R_{3a}$ is —H, halogen, —$NH_2$, —CN, —OH, —$NO_2$, carboxyl, substituted or unsubstituted —$C_{1-6}$alkoxy, or substituted or unsubstituted —$C_{1-6}$alkyl;

$R_8$ is halogen, —$NH_2$, —CN, —OH, —$NO_2$, carboxyl, oxo, =O, —$SO_2NR_{8a}R_{8b}$, —S—$C_{1-6}$alkyl, —SO—$C_{1-6}$alkyl, —$SO_2$—$C_{1-6}$alkyl, —CO—$NR_{8a}R_{8b}$, —$PO(C_{1-6}alkyl)_2$, —$PO(C_{1-6}alkoxy)_2$, —$NR_{8a}CO$—$C_{1-6}$alkyl, —$NR_{8a}$—CO—$NR_{8a}R_{8b}$, —O—$C_{5-10}$carbocyclic, —O—$C_{5-10}$heterocyclic, —$C_{5-10}$heterocyclic or —$C_{5-10}$heteroaryl, —$C_{5-10}$aryl, —$C_{1-6}$alkoxy, or —$C_{1-6}$alkyl; and each of which is independently optionally substituted; and t is 0, 1, 2 or 3; and Each of $R_{8a}$ and $R_{8b}$ is independently H, halogen, —$NH_2$, —CN, —OH, —$NO_2$, carboxyl, substituted or unsubstituted —$C_{1-6}$alkoxy, or substituted or unsubstituted —$C_{1-6}$alkyl.

In some embodiments of Formula IV, $R_2$ is —H, —F, —Cl, —Br, —$NH_2$, —CN, —OH, —$NO_2$, carboxyl, substituted or unsubstituted —$C_{1-6}$alkoxy, or substituted or unsubstituted —$C_{1-6}$alkyl; or $R_1$ combines with $R_2$ to which is adjacent to form a 5-10 membered heterocyclic ring contains 1, 2 or 3 heteroatoms selected from N or O, and each of the ring systems is independently optionally substituted with halogen, —$NH_2$, —CN, —OH, —$NO_2$, carboxyl, oxo, =O, —$CONH_2$, substituted or unsubstituted —$C_{1-6}$alkoxy, substituted or unsubstituted —$C_{1-6}$alkyl, or —CO—$C_{1-6}$alkyl;

In some embodiments of Formula IV, $R_2$ is —H, —F, —Cl, —Br, —$NH_2$, —CN, —OH, —$NO_2$, carboxyl, —$NHC_{1-3}$alkyl, —$N(C_{1-3}alkyl)_2$, —$C_{1-3}$alkoxy, —$C_{1-3}$alkyl; or $R_1$ combines with $R_2$ to which is adjacent to form a 5-, 6-, or 7-membered heterocyclic ring contains 1, or 2 heteroatoms selected from N or O, and each of the ring systems is independently optionally substituted with —F, —Cl, —Br, —$NH_2$, —CN, —OH, —$NO_2$, carboxyl, oxo, =O, —$CONH_2$, methoxy, ethoxy, methyl, ethyl, —CO-methyl, or —CO-ethyl;

In some embodiments of Formula IV, $R_2$ is —H, —F, —Cl, —Br, —$NH_2$, —CN, —OH, —$NO_2$, carboxyl, —$NHCH_3$, —$N(CH_3)_2$, methoxy, ethoxy, methyl, or ethyl; or $R_1$ combines with $R_2$ to which is adjacent to form a 5-membered heterocyclic contains 1 heteroatoms selected from N or O, or 6-membered heterocyclic ring contains 1 heteroatoms selected from N or O; and each of the ring systems is independently optionally substituted with —F, —Cl, —Br, —$NH_2$, —CN, —OH, —$NO_2$, carboxyl, oxo, ═O, —$CONH_2$, methoxy, ethoxy, methyl, ethyl, —CO-methyl, or —CO-ethyl;

In some embodiments of Formula IV, $R_1$ and $R_2$, together with the aromatic ring they are attached to form to

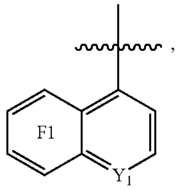

or

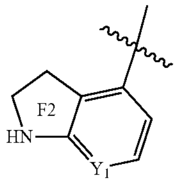

and ring F1 or F2 is independently optionally substituted with —F or —$COCH_3$.

In some embodiments of Formula IV, $R_1$ combines with $R_2$ to which is adjacent to form

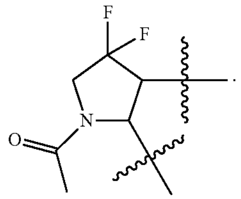 [SMILES: *C1C(*)C(F)(F)CN1C(C)=O]

In some embodiments of Formula IV, $R_2$ is —$NH_2$.

In some embodiments of Formula IV, $R_1$ is —H, —F, —Cl, —Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula IV, $R_1$ is —H, —F, —Cl, —Br, —$NH_2$, —CN, —OH, —$NO_2$, carboxyl, methoxy, ethoxy, methyl, or methyl substituted with one or more substituents selected from halogen.

In some embodiments of Formula IV, $R_1$ is —H; —F; —Cl; —Br; —$NH_2$; —CN; —OH; —$NO_2$; carboxyl; methyl; or methyl substituted with one or more substituents selected from —F, —Cl, or —Br.

In some embodiments of Formula IV, $R_1$ is —Cl.

In some embodiments of Formula IV, ring D is 6-membered aryl, 5-membered heteroaryl, 6-membered heteroaryl, 3-membered carbocyclic, 4-membered carbocyclic, 5-membered carbocyclic, 6-membered carbocyclic, 3-membered heterocyclic, 4-membered heterocyclic, 5-membered heterocyclic or 6-membered heterocyclic; and each of the heteroaryl or heterocyclic contains 1, 2 or 3 heteroatoms selected from N, O or S.

In some embodiments of Formula IV, ring D is 6-membered aryl, 5-membered heteroaryl, 6-membered heteroaryl, 3-membered carbocyclic, 4-membered carbocyclic, 5-membered carbocyclic, 5-membered heterocyclic or 6-membered heterocyclic; and each of the heteroaryl or heterocyclic contains 1 or 2 heteroatoms selected from N, O or S.

In some embodiments of Formula IV, ring D is

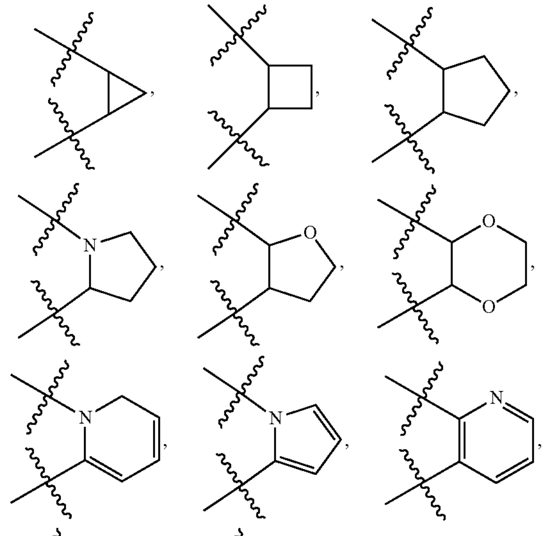

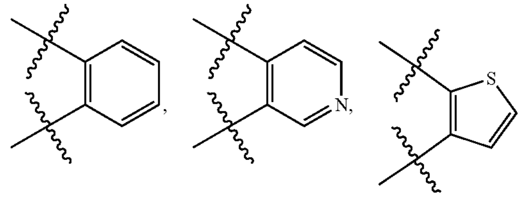

or

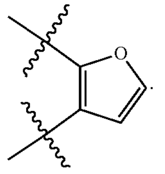

In some embodiments of Formula IV, $Y_2$ is $CR_{2a}$ or N, and $Y_3$ is $CR_{3a}$ or N.

In some embodiments of Formula IV, each of $R_{2a}$ and $R_{3a}$ is —H, —F, —Cl, —Br, —$NH_2$, —CN, —OH, —$NO_2$, carboxyl, substituted or unsubstituted —$C_{1-3}$alkoxy, or substituted or unsubstituted —$C_{1-3}$alkyl.

In some embodiments of Formula IV, each of $R_{2a}$ and $R_{3a}$ is —H, methyl or methoxy.

In some embodiments of Formula IV, $Y_2$ is CH or N, and $Y_3$ is CH or N.

In some embodiments of Formula IV, both $Y_2$ and $Y_3$ are C.

In some embodiments of Formula IV, $R_8$ is —F, —Cl, —Br, —I, —$NH_2$, —CN, —OH, —$NO_2$, carboxyl, oxo, ═O, —$SO_2NR_{8a}R_{8b}$, —S—$C_{1-6}$alkyl, —CO—$NR_{8a}R_{8b}$, —$NR_{8a}$—CO—$C_{1-6}$alkyl, —$NR_{8a}$—CO—$NR_{8a}R_{8b}$, —O—$C_{5-10}$carbocyclic, —$C_{5-10}$heterocyclic or —$C_{5-10}$heteroaryl, —$C_{1-6}$alkoxy, or —$C_{1-6}$alkyl; and each of which is independently optionally substituted with —F, —Cl, —Br, —$NH_2$, —CN, —OH, oxo, ═O, substituted or unsubstituted —$C_{1-3}$alkoxy, or substituted or unsubstituted —$C_{1-3}$alkyl.

In some embodiments of Formula IV, $R_8$ is —F, —Cl, —Br, —$NH_2$, —CN, —OH, —$NO_2$, carboxyl, oxo, ═O, —$SO_2NR_{8a}R_{8b}$, —S—$C_{1-3}$alkyl, —CO—$NR_{8a}R_{8b}$, —NH—CO—$C_{1-3}$alkyl, —NH—CO—$NR_{8a}R_{8b}$, —O—$C_{5-10}$carbocyclic, —$C_{5-10}$heterocyclic, —$C_{5-10}$heteroaryl, —$C_{1-3}$alkoxy, or —$C_{1-3}$alkyl; and each of which is independently optionally substituted with —F, —Cl, —Br, —$NH_2$, —CN, —OH, oxo, =O, —$C_{1-3}$alkoxy, or —$C_{1-3}$alkyl.

In some embodiments of Formula IV, $R_8$ is —F, —Cl, —Br, —$NH_2$, —CN, —OH, —$NO_2$, carboxyl, oxo, =O, methyl, ethyl, proproyl, isopropoyl, methoxy, ethoxy, propoxy, isopropoxy, —$SO_2NR_{8a}R_{8b}$, —S—$C_{1-3}$alkyl, —CO—$NR_{8a}R_{8b}$, —NH—CO—$C_{1-3}$alkyl, —NH—CO—$NR_{8a}R_{8b}$, —O—$C_{5-10}$carbocyclic, —$C_{5-10}$heterocyclic or —$C_{5-10}$heteroaryl; and each of which is independently optionally substituted with —F, —Cl, —Br, —$NH_2$, —CN, —OH, oxo, =O, methoxy, ethoxy, methyl, or ethyl.

In some embodiments of Formula IV, the $C_{5-10}$carbocyclic is 5-membered carbocyclic, 6-membered carbocyclic, 7-membered carbocyclic, 8-membered carbocyclic, 9-membered carbocyclic or 10-membered carbocyclic; the $C_{5-10}$heterocyclic is 5-membered heterocyclic, 6-membered heterocyclic, 7-membered heterocyclic, 8-membered heterocyclic, 9-membered heterocyclic or 10-membered heterocyclic; and the $C_{5-10}$heteroaryl is 5-membered heteroaryl, 6-membered heteroaryl, 7-membered heteroaryl, 8-membered heteroaryl, 9-membered heteroaryl or 10-membered heteroaryl; and each of the heterocyclic or heteroaryl contains 1, 2, 3 or 4 heteroatoms selected from N, O or S.

In some embodiments of Formula IV, $R_8$ is —F, —Cl, —Br, —$NH_2$, —CN, —OH, oxo, =O, methyl, ethyl, isopropoyl, methoxy, —$SO_2CH_3$, —$SCH_3$, —$CONH_2$, —NH—$COCH_3$, —NH—$CONHCH_3$,

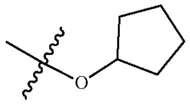,
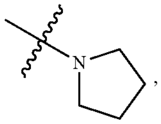,

-continued

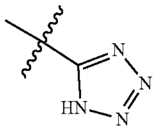
or
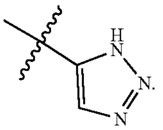.

In some embodiments of Formula IV, $R_8$ is —F, —Cl, —Br, —$NH_2$, —CN, —OH, oxo, =O, methyl, methoxy, —$SO_2CH_3$, —$SCH_3$, —$CONH_2$, —NH—$COCH_3$, —NH—$CONHCH_3$,

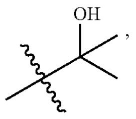,
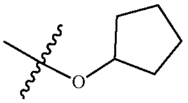,
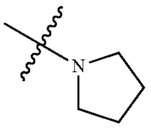,

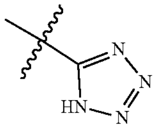
or
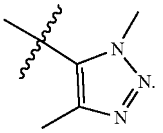.

In some embodiments of Formula IV, t is 0, 1 or 2.

In some embodiments of Formula I, II, III or IV, the compound is

| | |
|---|---|
| 1 | (R)-1'-(6-amino-5-((2-amino-3-chloropyridin-4-yl)thio)pyrazin-2-yl)-2,3-dihydrospiro[indene-1,4'-piperidin]-2-amine |
| 2 | (S)-1'-(6-amino-5-((2-amino-3-chloropyridin-4-yl)thio)pyrazin-2-yl)-1,3-dihydrospiro[indene-2,4'-piperidin]-1-amine |
| 3 | (R)-1'-(6-amino-5-((2-amino-3-chloropyridin-4-yl)thio)pyrazin-2-yl)-3,4-dihydro-2H-spiro[naphthalene-1,4'-piperidin]-2-amine |
| 4 | (R)-1'-(6-amino-5-((2-amino-3-chloropyridin-4-yl)thio)pyrazin-2-yl)-5,6-dihydrospiro[cyclopenta[b]pyridine-7,4'-piperidin]-6-amine |
| 5 | (S)-1'-(6-amino-5-((2-amino-3-chloropyridin-4-yl)thio)pyrazin-2-yl)-6-methoxy-1,3-dihydrospiro[indene-2,4'-piperidin]-1-amine |
| 6 | (R)-1-(4-((3-amino-5-(2-amino-2,3-dihydrospiro[indene-1,4'-piperidin]-1'-yl)pyrazin-2-yl)thio)-3,3-difluoroindolin-1-yl)ethan-1-one |
| 7 | 1-(4-((3-amino-5-((2R)-2-aminospiro[bicyclo[3.1.0]hexane-3,4'-piperidin]-1'-yl)pyrazin-2-yl)thio)-3,3-difluoroindolin-1-yl)ethan-1-one |
| 8 | (S)-1'-(6-amino-5-((2-amino-3-chloropyridin-4-yl)thio)pyrazin-2-yl)-3,4-dihydro-1H-spiro[naphthalene-2,4'-piperidin]-1-amine |
| 9 | (R)-1-(6-amino-5-((2-amino-3-chloropyridin-4-yl)thio)pyrazin-2-yl)-7',8'-dihydro-5'H-spiro[piperidine-4,6'-quinolin]-7'-amine |
| 10 | (S)-1'-(6-amino-5-((2-amino-3-chloropyridin-4-yl)thio)pyrazin-2-yl)-5,7-dihydrospiro[cyclopenta[b]pyridine-6,4'-piperidin]-5-amine |
| 11 | (S)-1'-(6-amino-5-((2-amino-3-chloropyridin-4-yl)thio)pyrazin-2-yl)-5-methoxy-1,3-dihydrospiro[indene-2,4'-piperidin]-1-amine |
| 12 | (S)-1'-(6-amino-5-((2-amino-3-chloropyridin-4-yl)thio)pyrazin-2-yl)-4,6-dihydrospiro[cyclopenta[b]thiophene-5,4'-piperidin]-4-amine |
| 13 | (S)-1-amino-1'-(6-amino-5-((2-amino-3-chloropyridin-4-yl)thio)pyrazin-2-yl)-1,3-dihydrospiro[indene-2,4'-piperidine]-6-carbonitrile |
| 14 | (S)-1'-(6-amino-5-((2-amino-3-chloropyridin-4-yl)thio)pyrazin-2-yl)-4-methoxy-1,3-dihydrospiro[indene-2,4'-piperidin]-1-amine |
| 15 | (S)-1'-(6-amino-5-((2-amino-3-chloropyridin-4-yl)thio)pyrazin-2-yl)-6-chloro-1,3-dihydrospiro[indene-2,4'-piperidin]-1-amine |
| 16 | (S)-1-amino-1'-(6-amino-5-((2-amino-3-chloropyridin-4-yl)thio)pyrazin-2-yl)-1,3-dihydrospiro[indene-2,4'-piperidine]-4-carbonitrile |
| 17 | (S)-1-amino-1'-(6-amino-5-((2-amino-3-chloropyridin-4-yl)thio)pyrazin-2-yl)-1,3-dihydrospiro[indene-2,4'-piperidine]-4-carboxamide |
| 18 | (S)-1'-(6-amino-5-((2-amino-3-chloropyridin-4-yl)thio)pyrazin-2-yl)-1,3-dihydrospiro[indene-2,4'-piperidin]-1-amine |

-continued

| | |
|---|---|
| 19 | (S)-1'-(6-amino-5-((2-amino-3-chloropyridin-4-yl)thio)pyrazin-2-yl)-2-chloro-5,7-dihydrospiro[cyclopenta[b]pyridine-6,4'-piperidin]-5-amine |
| 20 | (S)-1'-(6-amino-5-((2-amino-3-chloropyridin-4-yl)thio)pyrazin-2-yl)-3-methoxy-5,7-dihydrospiro[cyclopenta[c]pyridine-6,4'-piperidin]-7-amine |
| 21 | (S)-1'-(6-amino-5-((2-amino-3-chloropyridin-4-yl)thio)pyrazin-2-yl)-5,7-dihydrospiro[cyclopenta[c]pyridine-6,4'-piperidin]-7-amine |
| 22 | (S)-1'-(6-amino-5-((2-amino-3-chloropyridin-4-yl)thio)pyrazin-2-yl)-5,7-dihydrospiro[cyclopenta[c]pyridine-6,4'-piperidin]-5-amine |
| 23 | (S)-1'-(6-amino-5-((2-amino-3-chloropyridin-4-yl)thio)pyrazin-2-yl)-6-methyl-1,3-dihydrospiro[indene-2,4'-piperidin]-1-amine |
| 24 | (S)-1'-(6-amino-5-((2-amino-3-chloropyridin-4-yl)thio)pyrazin-2-yl)-6-(methylsulfonyl)-1,3-dihydrospiro[indene-2,4'-piperidin]-1-amine |
| 25 | (1S)-1'-(6-amino-5-((2-amino-3-chloropyridin-4-yl)thio)pyrazin-2-yl)-6-(methylsulfinyl)-1,3-dihydrospiro[indene-2,4'-piperidin]-1-amine |
| 26 | (S)-1-amino-1'-(6-amino-5-((2-amino-3-chloropyridin-4-yl)thio)pyrazin-2-yl)-1,3-dihydrospiro[indene-2,4'-piperidine]-6-carboxamide |
| 27 | (S)-1-amino-1'-(6-amino-5-((2-amino-3-chloropyridin-4-yl)thio)pyrazin-2-yl)-N,N-dimethyl-1,3-dihydrospiro[indene-2,4'-piperidine]-6-carboxamide |
| 28 | (S)-1'-(6-amino-5-((2-amino-3-chloropyridin-4-yl)thio)pyrazin-2-yl)-6-bromo-1,3-dihydrospiro[indene-2,4'-piperidin]-1-amine |
| 29 | (S)-1'-(6-amino-5-((2-amino-3-chloropyridin-4-yl)thio)pyrazin-2-yl)-4-bromo-1,3-dihydrospiro[indene-2,4'-piperidin]-1-amine |
| 30 | (S)-1'-(5-((2-amino-3-chloropyridin-4-yl)thio)pyrazin-2-yl)-5,7-dihydrospiro[cyclopenta[b]pyridine-6,4'-piperidin]-5-amine |
| 31 | (S)-1'-(6-amino-5-((2-amino-3-chloropyridin-4-yl)thio)pyrazin-2-yl)-1,3-dihydrospiro[cyclopenta[a]naphthalene-2,4'-piperidin]-3-amine |
| 32 | (S)-1'-(6-amino-5-((2-amino-3-chloropyridin-4-yl)thio)pyrazin-2-yl)-6-chloro-5-methoxy-1,3-dihydrospiro[indene-2,4'-piperidin]-1-amine |
| 33 | (S)-1'-(6-amino-5-((2-amino-3-chloropyridin-4-yl)thio)pyrazin-2-yl)-1,3-dihydrospiro[indene-2,4'-piperidine]-1,6-diamine |
| 34 | (S)-(1-amino-1'-(6-amino-5-((2-amino-3-chloropyridin-4-yl)thio)pyrazin-2-yl)-1,3 -dihydrospiro[indene-2,4'-piperidin]-4-yl)dimethylphosphine oxide |
| 35 | (S)-1'-(6-amino-5-((2-amino-3-chloropyridin-4-yl)thio)pyrazin-2-yl)-6-(trifluoromethyl)-1,3-dihydrospiro[indene-2,4'-piperidin]-1-amine |
| 36 | (S)-1'-(6-amino-5-((2-amino-3-chloropyridin-4-yl)thio)pyrazin-2-yl)-6-(1H-imidazol-1-yl)-1,3-dihydrospiro[indene-2,4'-piperidin]-1-amine |
| 37 | (S)-1'-(6-amino-5-((2-amino-3-chloropyridin-4-yl)thio)pyrazin-2-yl)-6-(1H-pyrrol-1-yl)-1,3-dihydrospiro[indene-2,4'-piperidin]-1-amine |
| 38 | (S)-1'-(6-amino-5-((2-amino-3-chloropyridin-4-yl)thio)pyrazin-2-yl)-6-bromo-5-fluoro-1,3-dihydrospiro[indene-2,4'-piperidin]-1-amine |
| 39 | (S)-1'-(6-amino-5-((2-amino-3-chloropyridin-4-yl)thio)pyrazin-2-yl)-5,6-difluoro-1,3-dihydrospiro[indene-2,4'-piperidin]-1-amine |
| 40 | (S)-1'-(6-amino-5-((2-amino-3-chloropyridin-4-yl)thio)pyrazin-2-yl)-6,7-difluoro-1,3-dihydrospiro[indene-2,4'-piperidin]-1-amine |
| 41 | (S)-(1-amino-1'-(6-amino-5-((2-amino-3-chloropyridin-4-yl)thio)pyrazin-2-yl)-5-fluoro-1,3-dihydrospiro[indene-2,4'-piperidin]-6-yl)dimethylphosphine oxide |
| 42 | (S)-1-amino-1'-(6-amino-5-((2-amino-3-chloropyridin-4-yl)thio)pyrazin-2-yl)-5-fluoro-1,3-dihydrospiro[indene-2,4'-piperidine]-6-carbonitrile |
| 43 | (S)-1-amino-1'-(6-amino-5-((2-amino-3-chloropyridin-4-yl)thio)pyrazin-2-yl)-5-fluoro-1,3-dihydrospiro[indene-2,4'-piperidine]-6-carboxamide |
| 44 | (S)-1'-(6-amino-5-((2-amino-3-chloropyridin-4-yl)thio)pyrazin-2-yl)-2-chloro-4,6-dihydrospiro[cyclopenta[d]thiazole-5,4'-piperidin]-4-amine |
| 45 | (R)-1'-(6-amino-5-((2-amino-3-chloropyridin-4-yl)thio)pyrazin-2-yl)-3H-spiro[benzofuran-2,4'-piperidin]-3-amine |
| 46 | (S)-1-(1-amino-1'-(6-amino-5-((2-amino-3-chloropyridin-4-yl)thio)pyrazin-2-yl)-1,3-dihydrospiro[indene-2,4'-piperidin]-6-yl)urea |
| 47 | (S)-1'-(6-amino-5-((2-amino-3-chloropyridin-4-yl)thio)pyrazin-2-yl)-5-bromo-1,3-dihydrospiro[indene-2,4'-piperidin]-1-amine |
| 48 | (S)-1'-(5-((2-amino-3-chloropyridin-4-yl)thio)pyrazin-2-yl)-1,3-dihydrospiro[indene-2,4'-piperidin]-1-amine |
| 49 | (S)-1'-(5-((3-chloro-2-(dimethylamino)pyridin-4-yl)thio)pyrazin-2-yl)-1,3-dihydrospiro[indene-2,4'-piperidin]-1-amine |
| 50 | (S)-1'-(5-((3-amino-2-chlorophenyl)thio)pyrazin-2-yl)-1,3-dihydrospiro[indene-2,4'-piperidin]-1-amine |
| 51 | (S)-1'-(5-((3-chloro-2-methoxypyridin-4-yl)thio)pyrazin-2-yl)-1,3-dihydrospiro[indene-2,4'-piperidin]-1-amine |
| 52 | (S)-1'-(6-amino-5-((3-chloro-2-(dimethylamino)pyridin-4-yl)thio)pyrazin-2-yl)-1,3-dihydrospiro[indene-2,4'-piperidin]-1-amine |
| 53 | (S)-1'-(6-amino-5-((3-amino-2-chlorophenyl)thio)pyrazin-2-yl)-1,3-dihydrospiro[indene-2,4'-piperidin]-1-amine |
| 54 | (S)-1'-(6-amino-5-((3-chloro-2-methoxypyridin-4-yl)thio)pyrazin-2-yl)-1,3-dihydrospiro[indene-2,4'-piperidin]-1-amine |
| 55 | (S)-1'-(6-amino-5-((2,3-dichlorophenyl)thio)pyrazin-2-yl)-1,3-dihydrospiro[indene-2,4'-piperidin]-1-amine |
| 56 | (R)-1'-(5-((2-amino-3-chloropyridin-4-yl)thio)pyrazin-2-yl)-3H-spiro[benzofuran-2,4'-piperidin]-3-amine |
| 57 | (S)-(1-amino-1'-(6-amino-5-((2-amino-3-chloropyridin-4-yl)thio)pyrazin-2-yl)-1,3-dihydrospiro[indene-2,4'-piperidin]-6-yl)dimethylphosphine oxide |
| 58 | (S)-1'-(6-amino-5-((2-amino-3-chloropyridin-4-yl)thio)pyrazin-2-yl)-6-((tetrahydro-2H-pyran-4-yl)oxy)-1,3-dihydrospiro[indene-2,4'-piperidin]-1-amine |

-continued

| | |
|---|---|
| 59 | (S)-(1-amino-1'-(6-amino-5-((2-amino-3-chloropyridin-4-yl)thio)pyrazin-2-yl)-1,3-dihydrospiro[indene-2,4'-piperidin]-6-yl)(piperidin-1-yl)methanone |
| 60 | (S)-1'-(6-amino-5-((2-amino-3-chloropyridin-4-yl)thio)pyrazin-2-yl)-6-morpholino-1,3-dihydrospiro[indene-2,4'-piperidin]-1-amine |
| 61 | (S)-1'-(6-amino-5-((2-amino-3-chloropyridin-4-yl)thio)pyrazin-2-yl)-5,6,7-trifluoro-1,3-dihydrospiro[indene-2,4'-piperidin]-1-amine |
| 62 | (S)-4-(1-amino-1'-(6-amino-5-((2-amino-3-chloropyridin-4-yl)thio)pyrazin-2-yl)-1,3-dihydrospiro[indene-2,4'-piperidin]-6-yl)morpholin-3-one |
| 63 | (S)-N-(1-amino-1'-(6-amino-5-((2-amino-3-chloropyridin-4-yl)thio)pyrazin-2-yl)-1,3-dihydrospiro[indene-2,4'-piperidin]-6-yl)methanesulfonamide |
| 64 | (S)-1'-(6-amino-5-((2-amino-3-chloropyridin-4-yl)thio)pyrazin-2-yl)-1,3-dihydrospiro[cyclopenta[b]quinoline-2,4'-piperidin]-1-amine |
| 65 | (R)-1'-(6-amino-5-((2-amino-3-chloropyridin-4-yl)thio)pyrazin-2-yl)-5,7-dihydrospiro[cyclopenta[c]pyridine-6,4'-piperidin]-5-amine |
| 66 | (S)-1'-(6-amino-5-((2,3-dichloropyridin-4-yl)thio)pyrazin-2-yl)-1,3-dihydrospiro[indene-2,4'-piperidin]-1-amine |
| 67 | (1R,3R)-1'-(6-amino-5-((2-amino-3-chloropyridin-4-yl)thio)pyrazin-2-yl)-1,3-dihydrospiro[indene-2,4'-piperidine]-1,3-diamine |
| 68 | (S)-1'-(5-((2-amino-3-chloropyridin-4-yl)thio)pyrazin-2-yl)-2-chloro-4,6-dihydrospiro[cyclopenta[d]thiazole-5,4'-piperidin]-6-amine |
| 69 | (S)-1'-(6-amino-5-((2-amino-3-chloropyridin-4-yl)thio)pyrazin-2-yl)-2-chloro-4,6-dihydrospiro[cyclopenta[d]thiazole-5,4'-piperidin-6-amine |
| 70 | (S)-1-amino-1'-(6-amino-5-((2-amino-3-chloropyridin-4-yl)thio)pyrazin-2-yl)-3H-spiro[indolizine-2,4'-piperidin]-5(1H)-one |
| 71 | (R)-1'-(5-((2-amino-3-chloropyridin-4-yl)thio)pyrazin-2-yl)spiro[indoline-2,4'-piperidin]-3-amine |
| 72 | (R)-1'-(6-amino-5-((2-amino-3-chloropyridin-4-yl)thio)pyrazin-2-yl)-6,7-dihydrospiro[cyclopenta[b]pyridine-5,4'-piperidin]-6-amine |
| 73 | (S)-1'-(6-amino-5-((2-amino-3-chloropyridin-4-yl)thio)pyrazin-2-yl)-3-chloro-5,7-dihydrospiro[cyclopenta[b]pyridine-6,4'-piperidin]-5-amine |
| 74 | (S)-1'-(6-amino-5-((2-amino-3-chloropyridin-4-yl)thio)pyrazin-2-yl)-6-(methylthio)-1,3-dihydrospiro[indene-2,4'-piperidin]-1-amine |
| 75 | (S)-1'-(6-amino-5-((2-amino-3-chloropyridin-4-yl)thio)pyrazin-2-yl)-6-(4-methylpiperazin-1-yl)-1,3-dihydrospiro[indene-2,4'-piperidin]-1-amine |
| 76 | (S)-1'-(5-((2,3-dichloropyridin-4-yl)thio)pyrazin-2-yl)-1,3-dihydrospiro[indene-2,4'-piperidin]-1-amine |
| 77 | (S)-1'-(6-amino-5-((2-(trifluoromethyl)pyridin-3-yl)thio)pyrazin-2-yl)-1,3-dihydrospiro[indene-2,4'-piperidin]-1-amine |
| 78 | (S)-1-(4-((3-amino-5-(1-amino-1,3-dihydrospiro[indene-2,4'-piperidin]-1'-yl)pyrazin-2-yl)thio)-3,3-difluoroindolin-1-yl)ethan-1-one |
| 79 | (S)-1'-(6-amino-5-((2-amino-3-chloropyridin-4-yl)thio)pyrazin-2-yl)-2-(tert-butyl)-4,6-dihydrospiro[cyclopenta[b]thiophene-5,4'-piperidin]-4-amine |
| 80 | (S)-1-amino-1'-(6-amino-5-((2-amino-3-chloropyridin-4-yl)thio)pyrazin-2-yl)-1,3-dihydrospiro[indene-2,4'-piperidine]-6-carboxylic acid |
| 81 | (2R)-1'-(6-amino-5-((2-amino-3-chloropyridin-4-yl)thio)pyrazin-2-yl)spiro[bicyclo[3.1.0]hexane-3,4'-piperidin]-2-amine |
| 82 | (S)-1'-(6-amino-5-((2-amino-3-chloropyridin-4-yl)thio)pyrazin-2-yl)-5,7-dihydrospiro[cyclopenta[b]pyridine-6,4'-piperidin]-7-amine |
| 83 | (S)-1'-(5-(quinolin-4-ylthio)pyrazin-2-yl)-5,7-dihydrospiro[cyclopenta[b]pyridine-6,4'-piperidin]-5-amine |
| 84 | (S)-1'-(6-amino-5-((2,3-dichlorophenyl)thio)pyrazin-2-yl)-5,7-dihydrospiro[cyclopenta[b]pyridine-6,4'-piperidin]-5-amine |
| 85 | (S)-1'-(5-((3-chloro-2-(dimethylamino)pyridin-4-yl)thio)pyrazin-2-yl)-5,7-dihydrospiro[cyclopenta[b]pyridine-6,4'-piperidin]-5-amine |
| 86 | (S)-1'-(5-(pyridin-4-ylthio)pyrazin-2-yl)-5,7-dihydrospiro[cyclopenta[b]pyridine-6,4'-piperidin]-5-amine |
| 87 | (S)-1'-(6-amino-5-((3-fluoropyridin-4-yl)thio)pyrazin-2-yl)-5,7-dihydrospiro[cyclopenta[b]pyridine-6,4'-piperidin]-5-amine |
| 88 | (S)-1'-(6-amino-5-((3-fluoropyridin-4-yl)thio)pyrazin-2-yl)-4,6-dihydrospiro[cyclopenta[d]thiazole-5,4'-piperidin]-4-amine |
| 89 | (S)-1'-(6-amino-5-((3-chloro-2-(methylamino)pyridin-4-yl)thio)pyrazin-2-yl)-5,7-dihydrospiro[cyclopenta[b]pyridine-6,4'-piperidin]-5-amine |
| 90 | diethyl(S)-(1-amino-1'-(6-amino-5-((2-amino-3-chloropyridin-4-yl)thio)pyrazin-2-yl)-1,3-dihydrospiro[indene-2,4'-piperidin]-6-yl)phosphonate |
| 91 | (S)-1'-(6-amino-5-((2-amino-3-fluoropyridin-4-yl)thio)pyrazin-2-yl)-5,7-dihydrospiro[cyclopenta[b]pyridine-6,4'-piperidin]-5-amine |
| 92 | (S)-1'-(5-((2-amino-3-fluoropyridin-4-yl)thio)pyrazin-2-yl)-5,7-dihydrospiro[cyclopenta[b]pyridine-6,4'-piperidin]-5-amine |
| 93 | (S)-1'-(6-amino-5-((3-chloropyridin-4-yl)thio)pyrazin-2-yl)-5,7-dihydrospiro[cyclopenta[b]pyridine-6,4'-piperidin]-5-amine |
| 94 | (S)-1'-(6-amino-5-((3-chloro-2-(dimethylamino)pyridin-4-yl)thio)pyrazin-2-yl)-5,7-dihydrospiro[cyclopenta[b]pyridine-6,4'-piperidin]-5-amine |
| 95 | (S)-1'-(5-((2-amino-3-chloropyridin-4-yl)thio)pyrazin-2-yl)-2-chloro-4,6-dihydrospiro[cyclopenta[d]thiazole-5,4'-piperidin]-4-amine |
| 96 | (R)-1'-(6-amino-5-((2-amino-3-chloropyridin-4-yl)thio)pyrazin-2-yl)-3H-spiro[furo[2,3-b]pyridine-2,4'-piperidin]-3-amine |
| 97 | (S)-1'-(5-((3-amino-2-chlorophenyl)thio)pyrazin-2-yl)-5,7-dihydrospiro[cyclopenta[b]pyridine-6,4'-piperidin]-5-amine |

-continued

| | |
|---|---|
| 98 | (S)-1'-(6-amino-5-((3-amino-2-chlorophenyl)thio)pyrazin-2-yl)-5,7-dihydrospiro[cyclopenta[b]pyridine-6,4'-piperidin]-5-amine |
| 99 | (S)-1'-(5-((3-chloro-2-methoxypyridin-4-yl)thio)pyrazin-2-yl)-5,7-dihydrospiro[cyclopenta[b]pyridine-6,4'-piperidin]-5-amine |
| 100 | (S)-1'-(6-amino-5-((3-chloro-2-methoxypyridin-4-yl)thio)pyrazin-2-yl)-5,7-dihydrospiro[cyclopenta[b]pyridine-6,4'-piperidin]-5-amine |
| 101 | (S)-1'-(5-((5-chloro-2-fluoropyridin-4-yl)thio)pyrazin-2-yl)-5,7-dihydrospiro[cyclopenta[b]pyridine-6,4'-piperidin]-5-amine |
| 102 | (S)-1'-(6-amino-5-((5-chloro-2-fluoropyridin-4-yl)thio)pyrazin-2-yl)-5,7-dihydrospiro[cyclopenta[b]pyridine-6,4'-piperidin]-5-amine |
| 103 | (S)-1-(4-((3-amino-5-(5-amino-5,7-dihydrospiro[cyclopenta[b]pyridine-6,4'-piperidin]-1'-yl)pyrazin-2-yl)thio)-3,3-difluoroindolin-1-yl)ethan-1-one |
| 104 | (S)-1'-(5-((2,3-dichloropyridin-4-yl)thio)pyrazin-2-yl)-5,7-dihydrospiro[cyclopenta[b]pyridine-6,4'-piperidin]-5-amine |
| 105 | (S)-1'-(6-amino-5-((2,3-dichloropyridin-4-yl)thio)pyrazin-2-yl)-5,7-dihydrospiro[cyclopenta[b]pyridine-6,4'-piperidin]-5-amine |
| 106 | (S)-1'-(5-((4-chloropyridin-3-yl)thio)pyrazin-2-yl)-5,7-dihydrospiro[cyclopenta[b]pyridine-6,4'-piperidin]-5-amine |
| 107 | (S)-1'-(6-amino-5-((4-chloropyridin-3-yl)thio)pyrazin-2-yl)-5,7-dihydrospiro[cyclopenta[b]pyridine-6,4'-piperidin]-5-amine |
| 108 | (S)-1'-(5-((3-aminopyridin-4-yl)thio)pyrazin-2-yl)-5,7-dihydrospiro[cyclopenta[b]pyridine-6,4'-piperidin]-5-amine |
| 109 | (S)-1'-(6-amino-5-((3-aminopyridin-4-yl)thio)pyrazin-2-yl)-5,7-dihydrospiro[cyclopenta[b]pyridine-6,4'-piperidin]-5-amine |
| 110 | (S)-1'-(5-((3,5-dichloropyridin-4-yl)thio)pyrazin-2-yl)-5,7-dihydrospiro[cyclopenta[b]pyridine-6,4'-piperidin]-5-amine |
| 111 | (S)-1'-(6-amino-5-((3,5-dichloropyridin-4-yl)thio)pyrazin-2-yl)-5,7-dihydrospiro[cyclopenta[b]pyridine-6,4'-piperidin]-5-amine |
| 112 | (S)-1'-(5-((2-amino-5-chloropyridin-4-yl)thio)pyrazin-2-yl)-5,7-dihydrospiro[cyclopenta[b]pyridine-6,4'-piperidin]-5-amine |
| 113 | (S)-1'-(6-amino-5-((2-amino-5-chloropyridin-4-yl)thio)pyrazin-2-yl)-5,7-dihydrospiro[cyclopenta[b]pyridine-6,4'-piperidin]-5-amine |
| 114 | (S)-1'-(6-amino-5-((2-(trifluoromethyl)pyridin-3-yl)thio)pyrazin-2-yl)-5,7-dihydrospiro[cyclopenta[b]pyridine-6,4'-piperidin]-5-amine |
| 115 | (S)-1'-(5-((3-chloro-2-fluoropyridin-4-yl)thio)pyrazin-2-yl)-5,7-dihydrospiro[cyclopenta[b]pyridine-6,4'-piperidin]-5-amine |
| 116 | (S)-1'-(6-amino-5-((3-chloro-2-fluoropyridin-4-yl)thio)pyrazin-2-yl)-5,7-dihydrospiro[cyclopenta[b]pyridine-6,4'-piperidin]-5-amine |
| 117 | (S)-3-((5-(5-amino-5,7-dihydrospiro[cyclopenta[b]pyridine-6,4'-piperidin]-1'-yl)pyrazin-2-yl)thio)picolinonitrile |
| 118 | (S)-3-((3-amino-5-(5-amino-5,7-dihydrospiro[cyclopenta[b]pyridine-6,4'-piperidin]-1'-yl)pyrazin-2-yl)thio)picolinonitrile |
| 119 | (S)-1'-(5-((2-chloro-5-(trifluoromethyl)pyridin-4-yl)thio)pyrazin-2-yl)-5,7-dihydrospiro[cyclopenta[b]pyridine-6,4'-piperidin]-5-amine |
| 120 | (S)-1'-(6-amino-5-((2-chloro-5-(trifluoromethyl)pyridin-4-yl)thio)pyrazin-2-yl)-5,7-dihydrospiro[cyclopenta[b]pyridine-6,4'-piperidin]-5-amine |
| 121 | 1'-(6-amino-5-((2-amino-3-chloropyridin-4-yl)thio)pyrazin-2-yl)-5,7-dihydrospiro[cyclopenta[b]pyridine-6,4'-piperidin]-5-amine |
| 122 | 1'-(5-((2-amino-3-chloropyridin-4-yl)thio)pyrazin-2-yl)-5,7-dihydrospiro[cyclopenta[b]pyridine-6,4'-piperidin]-5-amine |
| 123 | 1'-(6-amino-5-((3-chloropyridin-4-yl)thio)pyrazin-2-yl)-5,7-dihydrospiro[cyclopenta[b]pyridine-6,4'-piperidin]-5-amine |
| 124 | 1'-(6-amino-5-((2-amino-3-chloropyridin-4-yl)thio)pyrazin-2-yl)-1,3-dihydrospiro[indene-2,4'-piperidin]-1-amine |
| 125 | 1'-(5-((2-amino-3-chloropyridin-4-yl)thio)pyrazin-2-yl)-1,3-dihydrospiro[indene-2,4'-piperidin]-1-amine |
| 126 | 1'-(6-amino-5-((3-amino-2-chlorophenyl)thio)pyrazin-2-yl)-5,7-dihydrospiro[cyclopenta[b]pyridine-6,4'-piperidin]-5-amine |
| 127 | 1'-(6-amino-5-((2-amino-3-chloropyridin-4-yl)thio)pyrazin-2-yl)-5,7-dihydrospiro[cyclopenta[c]pyridine-6,4'-piperidin]-5-amine |
| 128 | 1'-(5-((3-amino-2-chlorophenyl)thio)pyrazin-2-yl)-5,7-dihydrospiro[cyclopenta[b]pyridine-6,4'-piperidin]-5-amine |
| 129 | 1'-(6-amino-5-((2-amino-3-chloropyridin-4-yl)thio)pyrazin-2-yl)-5-bromo-1,3-dihydrospiro[indene-2,4'-piperidin]-1-amine |
| 130 | 1'-(6-amino-5-((2-amino-3-chloropyridin-4-yl)thio)pyrazin-2-yl)-2-chloro-4,6-dihydrospiro[cyclopenta[d]thiazole-5,4'-piperidin]-4-amine |
| 131 | 1'-(5-((2-amino-3-chloropyridin-4-yl)thio)pyrazin-2-yl)-2-chloro-4,6-dihydrospiro[cyclopenta[d]thiazole-5,4'-piperidin]-4-amine |
| 132 | 1'-(5-((2-amino-3-chloropyridin-4-yl)thio)pyrazin-2-yl)-2,3-dihydrospiro[indene-1,4'-piperidin]-2-amine |
| 133 | (S)-4-((5-(1-amino-1,3-dihydrospiro[indene-2,4'-piperidin]-1'-yl)pyrazin-2-yl)thio)-3-chloropyridin-2-ol |
| 134 | (S)-4-((3-amino-5-(1-amino-1,3-dihydrospiro[indene-2,4'-piperidin]-1'-yl)pyrazin-2-yl)thio)-3-chloropyridin-2-ol |
| 135 | (S)-4-((5-(5-amino-5,7-dihydrospiro[cyclopenta[b]pyridine-6,4'-piperidin]-1'-yl)pyrazin-2-yl)thio)-3-chloropyridin-2-ol |
| 136 | (S)-4-((3-amino-5-(5-amino-5,7-dihydrospiro[cyclopenta[b]pyridine-6,4'-piperidin]-1'-yl)pyrazin-2-yl)thio)-3-chloropyridin-2-ol |

-continued

| | |
|---|---|
| 137 | (S)-1-amino-1'-(6-amino-5-((2-amino-3-chloropyridin-4-yl)thio)pyrazin-2-yl)-1,3-dihydrospiro[indene-2,4'-piperidin]-6-ol |
| 138 | (S)-1-amino-1'-(6-amino-5-((2-amino-3-chloropyridin-4-yl)thio)pyrazin-2-yl)-1,3-dihydrospiro[indene-2,4'-piperidin]-4-ol |
| 139 | 1'-(6-amino-5-((2-amino-3-chloropyridin-4-yl)thio)pyrazin-2-yl)-5-methyl-5,7-dihydrospiro[cyclopenta[b]pyridine-6,4'-piperidin]-5-amine |
| 140 | 1-amino-1'-(6-amino-5-((2-amino-3-chloropyridin-4-yl)thio)pyrazin-2-yl)-3H-spiro[indolizine-2,4'-piperidin]-7(1H)-one (2 mg) |
| 141 | 1-amino-1'-(6-amino-5-((2-amino-3-chloropyridin-4-yl)thio)pyrazin-2-yl)-3H-spiro[indolizine-2,4'-piperidin]-5(1H)-one |
| 142 | 3-((2-amino-3-chloropyridin-4-yl)thio)-6-(1-imino-1,3-dihydrospiro[indene-2,4'-piperidin]-1'-yl)pyrazin-2-amine |
| 143 | 3-((2-amino-3-chloropyridin-4-yl)thio)-6-(1-imino-5-methoxy-1,3-dihydrospiro[indene-2,4'-piperidin]-1'-yl)pyrazin-2-amine |
| 144 | 3-((2-amino-3-chloropyridin-4-yl)thio)-6-(4-imino-4,6-dihydrospiro[cyclopenta[b]thiophene-5,4'-piperidin]-1'-yl)pyrazin-2-amine |
| 145 | 3-((2-amino-3-chloropyridin-4-yl)thio)-6-(1-bromo-4-imino-4H,6H-spiro[cyclopenta[c]thiophene-5,4'-piperidin]-1'-yl)pyrazin-2-amine |
| 146 | 3-((2-amino-3-chloropyridin-4-yl)thio)-6-(4-imino-4H,6H-spiro[cyclopenta[c]thiophene-5,4'-piperidin]-1'-yl)pyrazin-2-amine |
| 147 | 3-((2-amino-3-chloropyridin-4-yl)thio)-6-(2-bromo-4-imino-4,6-dihydrospiro[cyclopenta[b]thiophene-5,4'-piperidin]-1'-yl)pyrazin-2-amine |
| 148 | 1'-(6-amino-5-((2-amino-3-chloropyridin-4-yl)thio)pyrazin-2-yl)-7-methoxy-1,3-dihydrospiro[indene-2,4'-piperidin]-1-amine |
| 149 | (Z)-1'-(6-amino-5-((2-amino-3-chloropyridin-4-yl)thio)pyrazin-2-yl)spiro[indene-2,4'-piperidin]-1(3H)-one oxime |
| 150 | (S)-1'-(6-amino-5-((2-amino-3-chloropyridin-4-yl)thio)pyrazin-2-yl)-2-methoxy-4,6-dihydrospiro[cyclopenta[d]thiazole-5,4'-piperidin]-4-amine |
| 151 | (S)-1'-(6-amino-5-((2-amino-3-chloropyridin-4-yl)thio)pyrazin-2-yl)-4,6-dihydrospiro[cyclopenta[d]thiazole-5,4'-piperidin]-4-amine |
| 152 | (S)-1'-(5-((2-amino-3-chloropyridin-4-yl)thio)pyrazin-2-yl)-4,6-dihydrospiro[cyclopenta[d]thiazole-5,4'-piperidin]-4-amine |
| 153 | 1'-(6-amino-5-((2-amino-3-chloropyridin-4-yl)thio)pyrazin-2-yl)-4,6-dihydrospiro[cyclopenta[d]thiazole-5,4'-piperidin]-4-amine |
| 154 | 1'-(5-((2-amino-3-chloropyridin-4-yl)thio)pyrazin-2-yl)-4,6-dihydrospiro[cyclopenta[d]thiazole-5,4'-piperidin]-4-amine |
| 155 | (S)-1'-(6-amino-5-((2-amino-3-chloropyridin-4-yl)thio)pyrazin-2-yl)-4,6-dihydrospiro[cyclopenta[d]thiazole-5,4'-piperidin]-6-amine |
| 156 | (S)-1'-(5-((2-amino-3-chloropyridin-4-yl)thio)pyrazin-2-yl)-4,6-dihydrospiro[clyclopenta[d]thiazole-5,4'-piperidin]-6-amine |
| 157 | (S)-1'-(6-amino-5-((3-fluoro-1H-indol-4-yl)thio)pyrazin-2-yl)-1,3-dihydrospiro[indene-2,4'-piperidin]-1-amine |
| 158 | (S)-1-(1-amino-1'-(6-amino-5-((2-amino-3-chloropyridin-4-yl)thio)pyrazin-2-yl)-1,3-dihydrospiro[indene-2,4'-piperidin]-6-yl)ethan-1-one |
| 159 | (S)-1-(1-amino-1'-(6-amino-5-((2-amino-3-chloropyridin-4-yl)thio)pyrazin-2-yl)-1,3-dihydrospiro[indene-2,4'-piperidin]-4-yl)ethan-1-one |
| 160 | (R)-1'-(5-((2-amino-3-chloropyridin-4-yl)thio)pyrazin-2-yl)-1-methylspiro[indoline-2,4'-piperidin]-3-amine |
| 161 | 1'-(6-amino-5-((2-amino-3-chloropyridin-4-yl)thio)pyrazin-2-yl)-2,3-dihydrospiro[indene-1,4'-piperidin]-2-amine |
| 162 | 1'-(6-amino-5-((2-amino-3-chloropyridin-4-yl)thio)pyrazin-2-yl)-3,4-dihydro-2H-spiro[naphthalene-1,4'-piperidin]-2-amine |
| 163 | 1'-(6-amino-5-((2-amino-3-chloropyridin-4-yl)thio)pyrazin-2-yl)-5,6-dihydrospiro[cyclopenta[b]pyridine-7,4'-piperidin]-6-amine |
| 164 | 1-(6-amino-5-((2-amino-3-chloropyridin-4-yl)thio)pyrazin-2-yl)tetrahydro-1'H,3'H-spiro[piperidine-4,2'-pyrrolizin]-1'-amine |
| 165 | (1'S)-1-(6-amino-5-((2-amino-3-chloropyridin-4-yl)thio)pyrazin-2-yl)tetrahydro-1'H,3'H-spiro[piperidine-4,2'-pyrrolizin]-1'-amine |
| 166 | 1'-(6-amino-5-((2-amino-3-chloropyridin-4-yl)thio)pyrazin-2-yl)-4,6-dihydrospiro[cyclopenta[b]furan-5,4'-piperidin]-4-amine |
| 167 | (S)-1'-(6-amino-5-((2-amino-3-chloropyridin-4-yl)thio)pyrazin-2-yl)-4,6-dihydrospiro[cyclopenta[b]furan-5,4'-piperidin]-4-amine |
| 168 | 1'-(6-amino-5-((2-amino-3-chloropyridin-4-yl)thio)pyrazin-2-yl)-6,7-dihydrospiro[cyclopenta[b]pyridine-5,4'-piperidin]-6-amine |
| 169 | 1'-(6-amino-5-((2-amino-3-chloropyridin-4-yl)thio)pyrazin-2-yl)hexahydrospiro[cyclopenta[b]furan-5,4'-piperidin]-4-amine |
| 170 | (4R)-1'-(6-amino-5-((2-amino-3-chloropyridin-4-yl)thio)pyrazin-2-yl)hexahydrospiro[cyclopenta[b]furan-5,4'-piperidin]-4-amine |
| 171 | 1'-(6-amino-5-((2-amino-3-chloropyridin-4-yl)thio)pyrazin-2-yl)spiro[bicyclo[3.1.0]hexane-3,4'-piperidin]-2-amine |
| 172 | 1'-amino-1-(6-amino-5-((2-amino-3-chloropyridin-4-yl)thio)pyrazin-2-yl)tetrahydro-1'H,3'H-spiro[piperidine-4,2'-pyrrolizin]-3'-one |
| 173 | (1'S)-1'-amino-1-(6-amino-5-((2-amino-3-chloropyridin-4-yl)thio)pyrazin-2-yl)tetrahydro-1'H,3'H-spiro[piperidine-4,2'-pyrrolizin]-3'-one |
| 174 | 1'-(6-amino-5-((2-amino-3-chloropyridin-4-yl)thio)pyrazin-2-yl)spiro[bicyclo[3.1.0]hexane-2,4'-piperidin]-3-amine |
| 175 | (3R)-1'-(6-amino-5-((2-amino-3-chloropyridin-4-yl)thio)pyrazin-2-yl)spiro[bicyclo[3.1.0]hexane-2,4'-piperidin]-3-amine |

-continued

| | |
|---|---|
| 176 | 3-((2-amino-3-chloropyridin-4-yl)thio)-6-(11-oxa-1,7-diazadispiro[2.0.5$^4$.3$^3$]dodecan-7-yl)pyrazin-2-amine |
| 177 | 1-(4-((3-amino-5-(2-aminospiro[bicyclo[3.1.0]hexane-3,4'-piperidin]-1'-yl)pyrazin-2-yl)thio)-3,3-difluoroindolin-1-yl)ethan-1-one |
| 178 | 1'-(6-amino-5-((2-amino-3-chloropyridin-4-yl)thio)pyrazin-2-yl)-1-methylspiro[bicyclo[3.1.0]hexane-3,4'-piperidin]-4-amine |
| 179 | (4R)-1'-(6-amino-5-((2-amino-3-chloropyridin-4-yl)thio)pyrazin-2-yl)-l-methylspiro[bicyclo[3.1.0]hexane-3,4'-piperidin]-4-amine |
| 180 | 1'-(6-amino-5-((2-amino-3-chloropyridin-4-yl)thio)pyrazin-2-yl)spiro[bicyclo[3.2.0]heptane-3,4'-piperidin]-2-amine |
| 181 | (2R)-1'-(6-amino-5-((2-amino-3-chloropyridin-4-yl)thio)pyrazin-2-yl)spiro[bicyclo[3.2.0]heptane-3,4'-piperidin]-2-amine |
| 182 | 1'-(6-amino-5-((2-amino-3-chloropyridin-4-yl)thio)pyrazin-2-yl)hexahydro-1H-spiro[pentalene-2,4'-piperidin]-1-amine |
| 183 | (1R)-1'-(6-amino-5-((2-amino-3-chloropyridin-4-yl)thio)pyrazin-2-yl)hexahydro-1H-spiro[pentalene-2,4'-piperidin]-1-amine |
| 184 | 1-(4-((3-amino-5-(2-amino-2,3-dihydrospiro[indene-1,4'-piperidin]-1'-yl)pyrazin-2-yl)thio)-3,3-difluoroindolin-1-yl)ethan-1-one |
| 185 | 1'-(6-amino-5-((2-amino-3-chloropyridin-4-yl)thio)pyrazin-2-yl)-4-methoxy-2,3-dihydrospiro[indene-1,4'-piperidin]-2-amine |
| 186 | (R)-1'-(6-amino-5-((2-amino-3-chloropyridin-4-yl)thio)pyrazin-2-yl)-4-methoxy-2,3-dihydrospiro[indene-1,4'-piperidin]-2-amine |
| 187 | 1'-(6-amino-5-((2-amino-3-chloropyridin-4-yl)thio)pyrazin-2-yl)-4,5-dihydrospiro[cyclopenta[b]furan-6,4'-piperidin]-5-amine |
| 188 | (R)-1'-(6-amino-5-((2-amino-3-chloropyridin-4-yl)thio)pyrazin-2-yl)-4,5-dihydrospiro[cyclopenta[b]furan-6,4'-piperidin]-5-amine |
| 189 | 1-(4-((3-amino-5-(11-oxa-1,7-diazadispiro[2.0.5$^4$.3$^3$]dodecan-7-yl)pyrazin-2-yl)thio)-3,3-difluoroindolin-1-yl)ethan-1-one |
| 190 | 1'-(6-amino-5-((2-amino-3-chloropyridin-4-yl)thio)pyrazin-2-yl)hexahydrospiro[cyclopenta[b][1,4]dioxine-6,4'-piperidin]-5-amine |
| 191 | (5S)-1'-(6-amino-5-((2-amino-3-chloropyridin-4-yl)thio)pyrazin-2-yl)hexahydrospiro[cyclopenta[b][1,4]dioxine-6,4'-piperidin]-5-amine |
| 192 | 6-amino-1'-(6-amino-5-((2-amino-3-chloropyridin-4-yl)thio)pyrazin-2-yl)-6,7-dihydrospiro[cyclopenta[b]pyridine-5,4'-piperidin]-2(1H)-one |
| 193 | (R)-6-amino-1'-(6-amino-5-((2-amino-3-chloropyridin-4-yl)thio)pyrazin-2-yl)-6,7-dihydrospiro[cyclopenta[b]pyridine-5,4'-piperidin]-2(1H)-one |
| 194 | 2-amino-1'-(6-amino-5-((2-amino-3-chloropyridin-4-yl)thio)pyrazin-2-yl)-2,3-dihydro-5H-spiro[indolizine-1,4'-piperidin]-5-one |
| 195 | (S)-2-amino-1'-(6-amino-5-((2-amino-3-chloropyridin-4-yl)thio)pyrazin-2-yl)-2,3-dihydro-5H-spiro[indolizine-1,4'-piperidin]-5-one |
| 196 | 1'-(6-amino-5-((2-amino-3-chloropyridin-4-yl)thio)pyrazin-2-yl)spiro[chromane-4,4'-piperidin]-3-amine |
| 197 | (S)-1'-(6-amino-5-((2-amino-3-chloropyridin-4-yl)thio)pyrazin-2-yl)spiro[chromane-4,4'-piperidin]-3-amine |
| 198 | 1'-(6-amino-5-((2-amino-3-chloropyridin-4-yl)thio)pyrazin-2-yl)-6-methoxy-1,3-dihydrospiro[indene-2,4'-piperidin]-1-amine |
| 199 | 1'-(6-amino-5-((2-amino-3-chloropyridin-4-yl)thio)pyrazin-2-yl)-3,4-dihydro-1H-spiro[naphthalene-2,4'-piperidin]-1-amine |
| 200 | 1-(6-amino-5-((2-amino-3-chloropyridin-4-yl)thio)pyrazin-2-yl)-7',8'-dihydro-5'H-spiro[piperidine-4,6'-quinolin]-7'-amine |
| 201 | 1'-(6-amino-5-((2-amino-3-chloropyridin-4-yl)thio)pyrazin-2-yl)-6,7-dihydrospiro[cyclopenta[c]pyridine-5,4'-piperidin]-6-amine |
| 202 | (R)-1'-(6-amino-5-((2-amino-3-chloropyridin-4-yl)thio)pyrazin-2-yl)-6,7-dihydrospiro[clyclopenta[c]pyridine-5,4'-piperidin]-6-amine |
| 203 | 1'-(6-amino-5-((2-amino-3-chloropyridin-4-yl)thio)pyrazin-2-yl)-6-methoxy-3,4-dihydro-1H-spiro[naphthalene-2,4'-piperidin]-1-amine |
| 204 | (S)-1'-(6-amino-5-((2-amino-3-chloropyridin-4-yl)thio)pyrazin-2-yl)-6-methoxy-3,4-dihydro-1H-spiro[naphthalene-2,4'-piperidin]-1-amine |
| 205 | 1'-(6-amino-5-((2-amino-3-chloropyridin-4-yl)thio)pyrazin-2-yl)-5,6-dimethoxy-1,3-dihydrospiro[indene-2,4'-piperidin]-1-amine |
| 206 | (S)-1'-(6-amino-5-((2-amino-3-chloropyridin-4-yl)thio)pyrazin-2-yl)-5,6-dimethoxy-1,3-dihydrospiro[indene-2,4'-piperidin]-1-amine |
| 207 | 1-amino-1'-(6-amino-5-((2-amino-3-chloropyridin-4-yl)thio)pyrazin-2-yl)-1,3-dihydrospiro[indene-2,4'-piperidin]-6-ol |
| 208 | 1'-(6-amino-5-((2-amino-3-chloropyridin-4-yl)thio)pyrazin-2-yl)-5-methoxy-1,3-dihydrospiro[indene-2,4'-piperidin]-1-amine |
| 209 | 1'-(6-amino-5-((2-amino-3-chloropyridin-4-yl)thio)pyrazin-2-yl)-4,6-dihydrospiro[cyclopenta[b]thiophene-5,4'-piperidin]-4-amine |
| 210 | 1-amino-1'-(6-amino-5-((2-amino-3-chloropyridin-4-yl)thio)pyrazin-2-yl)-1,3-dihydrospiro[indene-2,4'-piperidine]-6-carbonitrile |
| 211 | 1'-(6-amino-5-((2-amino-3-chloropyridin-4-yl)thio)pyrazin-2-yl)-4-methoxy-1,3-dihydrospiro[indene-2,4'-piperidin]-1-amine |
| 212 | 1'-(6-amino-5-((2-amino-3-chloropyridin-4-yl)thio)pyrazin-2-yl)-1,3-dihydrospiro[indene-2,4'-piperidine]-1,6-diamine |
| 213 | 1-amino-1'-(6-amino-5-((2-amino-3-chloropyridin-4-yl)thio)pyrazin-2-yl)-1,3-dihydrospiro[indene-2,4'-piperidin]-4-ol |
| 214 | 1'-(6-amino-5-((2-amino-3-chloropyridin-4-yl)thio)pyrazin-2-yl)-6-chloro-1,3-dihydrospiro[indene-2,4'-piperidin]-1-amine |

-continued

| | |
|---|---|
| 215 | 1'-(6-amino-5-((2-amino-3-chloropyridin-4-yl)thio)pyrazin-2-yl)-6-bromo-1,3-dihydrospiro[indene-2,4'-piperidin]-1-amine |
| 216 | 1'-(6-amino-5-((2-amino-3-chloropyridin-4-yl)thio)pyrazin-2-yl)-2,3-dihydrospiro[indene-1,4'-piperidine]-2,5-diamine |
| 217 | (R)-1'-(6-amino-5-((2-amino-3-chloropyridin-4-yl)thio)pyrazin-2-yl)-2,3-dihydrospiro[indene-1,4'-piperidine]-2,5-diamine |
| 218 | 1'-(6-amino-5-((2-amino-3-chloropyridin-4-yl)thio)pyrazin-2-yl)-6-methoxy-2,3-dihydrospiro[indene-1,4'-piperidin]-2-amine |
| 219 | (R)-1'-(6-amino-5-((2-amino-3-chloropyridin-4-yl)thio)pyrazin-2-yl)-6-methoxy-2,3-dihydrospiro[indene-1,4'-piperidin]-2-amine |
| 220 | 1-(6-amino-5-((2-amino-3-chloropyridin-4-yl)thio)pyrazin-2-yl)-1'H,3'H-spiro [piperidine-4,2'-pyrrolizin]-1'-amine |
| 221 | (S)-1-(6-amino-5-((2-amino-3-chloropyridin-4-yl)thio)pyrazin-2-yl)-1'H,3'H-spiro [piperidine-4,2'-pyrrolizin]-1'-amine |
| 222 | 1'-(6-amino-5-((2-amino-3-chloropyridin-4-yl)thio)pyrazin-2-yl)-5,7-dihydrospiro[cyclopenta[c]pyridine-6,4'-piperidin]-7-amine |
| 223 | 2-amino-1'-(6-amino-5-((2-amino-3-chloropyridin-4-yl)thio)pyrazin-2-yl)-2,3-dihydrospiro[indene-1,4'-piperidine]-4-carboxamide |
| 224 | (R)-2-amino-1'-(6-amino-5-((2-amino-3-chloropyridin-4-yl)thio)pyrazin-2-yl)-2,3-dihydrospiro[indene-1,4'-piperidine]-4-carboxamide |
| 225 | 2-amino-1'-(6-amino-5-((2-amino-3-chloropyridin-4-yl)thio)pyrazin-2-yl)-2,3-dihydrospiro[indene-1,4'-piperidine]-4-carbonitrile |
| 226 | (R)-2-amino-1'-(6-amino-5-((2-amino-3-chloropyridin-4-yl)thio)pyrazin-2-yl)-2,3-dihydrospiro[indene-1,4'-piperidine]-4-carbonitrile |
| 227 | N-(2-amino-1'-(6-amino-5-((2-amino-3-chloropyridin-4-yl)thio)pyrazin-2-yl)-2,3-dihydrospiro[indene-1,4'-piperidin]-4-yl)acetamide |
| 228 | (R)-N-(2-amino-1'-(6-amino-5-((2-amino-3-chloropyridin-4-yl)thio)pyrazin-2-yl)-2,3-dihydrospiro[indene-1,4'-piperidin]-4-yl)acetamide |
| 229 | 1'-(6-amino-5-((2-amino-3-chloropyridin-4-yl)thio)pyrazin-2-yl)-6-(pyrrolidin-1-yl)-1,3-dihydrospiro[indene-2,4'-piperidin]-1-amine |
| 230 | (S)-1'-(6-amino-5-((2-amino-3-chloropyridin-4-yl)thio)pyrazin-2-yl)-6-(pyrrolidin-1-yl)-1,3-dihydrospiro[indene-2,4'-piperidin]-1-amine |
| 231 | 1'-(6-amino-5-((2-amino-3-chloropyridin-4-yl)thio)pyrazin-2-yl)-6-(1,4-dimethyl-1H-1,2,3-triazol-5-yl)-1,3-dihydrospiro[indene-2,4'-piperidin]-1-amine |
| 232 | (S)-1'-(6-amino-5-((2-amino-3-chloropyridin-4-yl)thio)pyrazin-2-yl)-6-(1,4-dimethyl-1H-1,2,3-triazol-5 -yl)-1,3-dihydrospiro[indene-2,4'-piperidin]-1-amine |
| 233 | 1'-(6-amino-5-((2-amino-3-chloropyridin-4-yl)thio)pyrazin-2-yl)-6-(methylthio)-1,3-dihydrospiro[indene-2,4'-piperidin]-1-amine |
| 234 | 2-(1-amino-1'-(6-amino-5-((2-amino-3-chloropyridin-4-yl)thio)pyrazin-2-yl)-1,3-dihydrospiro[indene-2,4'-piperidin]-6-yl)propan-2-ol |
| 235 | (S)-2-(1-amino-1'-(6-amino-5-((2-amino-3-chloropyridin-4-yl)thio)pyrazin-2-yl)-1,3-dihydrospiro[indene-2,4'-piperidin]-6-yl)propan-2-ol |
| 236 | 1'-(6-amino-5-((2-amino-3-chloropyridin-4-yl)thio)pyrazin-2-yl)-6-(methylsulfonyl)-1,3-dihydrospiro[indene-2,4'-piperidin]-1-amine |
| 237 | N-(1-amino-1'-(6-amino-5-((2-amino-3-chloropyridin-4-yl)thio)pyrazin-2-yl)-1,3-dihydrospiro[indene-2,4'-piperidin]-6-yl)acetamide |
| 238 | (S)-N-(1-amino-1'-(6-amino-5-((2-amino-3-chloropyridin-4-yl)thio)pyrazin-2-yl)-1,3-dihydrospiro[indene-2,4'-piperidin]-6-yl)acetamide |
| 239 | 1-amino-1'-(6-amino-5-((2-amino-3-chloropyridin-4-yl)thio)pyrazin-2-yl)-1,3-dihydrospiro[indene-2,4'-piperidine]-6-carboxamide |
| 240 | 1'-(6-amino-5-((2-amino-3-chloropyridin-4-yl)thio)pyrazin-2-yl)-6-(cyclopentyloxy)-1,3-dihydrospiro[indene-2,4'-piperidin]-1-amine |
| 241 | (S)-1'-(6-amino-5-((2-amino-3-chloropyridin-4-yl)thio)pyrazin-2-yl)-6-(cyclopentyloxy)-1,3-dihydrospiro[indene-2,4'-piperidin]-1-amine |
| 242 | 1-amino-1'-(6-amino-5-((2-amino-3-chloropyridin-4-yl)thio)pyrazin-2-yl)-3H-spiro[indolizine-2,4'-piperidin]-7(1H)-one |
| 243 | 1-amino-1'-(6-amino-5-((2-amino-3-chloropyridin-4-yl)thio)pyrazin-2-yl)-5-fluoro-1,3-dihydrospiro[indene-2,4'-piperidin]-6-ol |
| 244 | (S)-1-amino-1'-(6-amino-5-((2-amino-3-chloropyridin-4-yl)thio)pyrazin-2-yl)-5-fluoro-1,3-dihydrospiro[indene-2,4'-piperidin]-6-ol |
| 245 | 1'-(6-amino-5-((2-amino-3-chloropyridin-4-yl)thio)pyrazin-2-yl)-5,7-dihydro-1H-spiro[clyclopenta[f]indole-6,4'-piperidin]-7-amine |
| 246 | (S)-1'-(6-amino-5-((2-amino-3-chloropyridin-4-yl)thio)pyrazin-2-yl)-5,7-dihydro-1H-spiro[cyclopenta[f]indole-6,4'-piperidin]-7-amine |
| 247 | 1'-(6-amino-5-((2-amino-3-chloropyridin-4-yl)thio)pyrazin-2-yl)-5,7-dihydro-1H-spiro[indeno[5,6-d]imidazole-6,4'-piperidin]-7-amine |
| 248 | (S)-1'-(6-amino-5-((2-amino-3-chloropyridin-4-yl)thio)pyrazin-2-yl)-5,7-dihydro-1H-spiro[indeno[5,6-d]imidazole-6,4'-piperidin]-7-amine |
| 249 | 1'-(6-amino-5-((2-amino-3-chloropyridin-4-yl)thio)pyrazin-2-yl)-6-(1H-tetrazol-5-yl)-1,3-dihydrospiro[indene-2,4'-piperidin]-1-amine |
| 250 | (S)-1'-(6-amino-5-((2-amino-3-chloropyridin-4-yl)thio)pyrazin-2-yl)-6-(1H-tetrazol-5-yl)-1,3-dihydrospiro[indene-2,4'-piperidin]-1-amine |
| 251 | 1-(1-amino-1'-(6-amino-5-((2-amino-3-chloropyridin-4-yl)thio)pyrazin-2-yl)-1,3-dihydrospiro[indene-2,4'-piperidin]-6-yl)-3-methylurea |
| 252 | (S)-1-(1-amino-1'-(6-amino-5-((2-amino-3-chloropyridin-4-yl)thio)pyrazin-2-yl)-1,3-dihydrospio[indene-2,4'-piperidin]-6-yl)-3-methylurea |
| 253 | 1'-(5-((2-amino-3-chloropyridin-4-yl)thio)pyrazin-2-yl)-2,3-dihydrospiro[indene-1,4'-piperidin]-2-amine |

The present invention also provides a pharmaceutical composition comprising at least one compound or pharmaceutically acceptable salt thereof of Formula I, II, III or IV and at least one pharmaceutically acceptable excipient. Furthermore, in the composition, the said compound or pharmaceutically acceptable salt thereof of Formula I, II, III or IV in a weight ratio to the said excipient within the range from about 0.0001 to about 10.

The present invention additionally provided a use of aboved said pharmaceutical composition for the preparation of a medicament.

In some embodiments, the medicament is for treatment or prevention a disease or disorder mediated by the activity of SHP2.

In some embodiments, the disease or disorder mediated by the activity of SHP2 is cancer, cancer metastasis, cardiovascular disease, an immunological disorder, fibrosis, or an ocular disorder.

In some embodiments, the disease or disorder mediated by the activity of SHP2 is one or more selected from Noonan Syndrome, Leopard Syndrome, juvenile myelomonocytic leukemias, neuroblastoma, melanoma, head and neck squamous-cell carcinoma, acute myeloid leukemia, breast cancer, esophageal tumor, lung cancer, colon cancer, head cancer, gastric carcinoma, lymphoma, glioblastoma, gastric cancer, pancreatic cancer, and combination thereof.

The present invention additionally provided a use of at least one compound or pharmaceutically acceptable salt thereof of Formula I, II, III or IV for the preparation of a medicament.

In some embodiments, the medicament is for treatment or prevention a disease or disorder mediated by the activity of SHP2.

In some embodiments, the disease or disorder mediated by the activity of SHP2 is cancer, cancer metastasis, cardiovascular disease, an immunological disorder, fibrosis, or an ocular disorder.

In some embodiments, the disease or disorder mediated by the activity of SHP2 is one or more selected from Noonan Syndrome, Leopard Syndrome, juvenile myelomonocytic leukemias, neuroblastoma, melanoma, head and neck squamous-cell carcinoma, acute myeloid leukemia, breast cancer, esophageal tumor, lung cancer, colon cancer, head cancer, gastric carcinoma, lymphoma, glioblastoma, gastric cancer, pancreatic cancer, and combination thereof.

The present invention additionally provided using at least one compound or pharmaceutically acceptable salt thereof of Formula I, II, III or IV, or pharmaceutical composition described above, which is for the preparation of a medicament.

In some embodiments, the medicament is for treatment or prevention a disease or disorder mediated by the activity of SHP2.

In some embodiments, the disease or disorder mediated by the activity of SHP2 is cancer, cancer metastasis, cardiovascular disease, an immunological disorder, fibrosis, or an ocular disorder.

In some embodiments, the disease or disorder mediated by the activity of SHP2 is one or more selected from Noonan Syndrome, Leopard Syndrome, juvenile myelomonocytic leukemias, neuroblastoma, melanoma, head and neck squamous-cell carcinoma, acute myeloid leukemia, breast cancer, esophageal tumor, lung cancer, colon cancer, head cancer, gastric carcinoma, lymphoma, glioblastoma, gastric cancer, pancreatic cancer, and combination thereof.

The present invention additionally provided a method of treating a patient having a condition which is mediated by the activity of SHP2, said method comprising administering to the patient a therapeutically effective amount of at least one compound or pharmaceutically acceptable salt thereof of Formula I, II, III or IV, or the pharmaceutical composition described above.

In some embodiments, the condition mediated by the activity of SHP2 is cancer, cancer metastasis, cardiovascular disease, an immunological disorder, fibrosis, or an ocular disorder.

In some embodiments, the condition mediated by the activity of SHP2 is noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, lymphoma, glioblastoma, gastric cancer, pancreatic cancer, and combination thereof.

The present invention additionally provided a method of treating cancer selected from the group consisting of noonan syndrome, leopard syndrome, juvenile myelomonocytic leukemias, liver cancer, neuroblastoma, melanoma, squamous-cell carcinoma of the head and neck, acute myeloid leukemia, breast cancer, esophageal cancer, lung cancer, colon cancer, head cancer, gastric carcinoma, neuroblastoma, lymphoma, glioblastoma, gastric cancer, pancreatic cancer, and combinations thereof, comprising administering to a mammal in need of such treatment an effective amount of at least one compound or pharmaceutically acceptable salt thereof of Formula I, II, III or IV, or the pharmaceutical composition described above.

The term "halogen", as used herein, unless otherwise indicated, means fluoro, chloro, bromo or iodo. The preferred halogen groups include F, Cl and Br. The terms "halo$C_{1-6}$alkyl", "halo$C_{2-6}$alkenyl", "halo$C_{2-6}$alkynyl" and "halo$C_{1-6}$alkoxy" mean a $C_{1-6}$alkyl, $C_{2-6}$alkenyl, $C_{2-6}$alkynyl or $C_{1-6}$alkoxy in which one or more (in particular, 1, 2 or 3) hydrogen atoms have been replaced by halogen atoms, especially fluorine or chlorine atoms. In some embodiment, preferred are fluoro$C_{1-6}$alkyl, fluoro$C_{2-6}$alkenyl, fluoro $C_{2-6}$alkynyl and fluoro$C_{1-6}$alkoxy groups, in particular fluoro$C_{1-3}$alkyl, for example, $CF_3$, $CHF_2$, $CH_2F$, $CH_2CH_2F$, $CH_2CHF_2$, $CH_2CF_3$ and fluoro$C_{1-3}$alkoxy groups, for example, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl) butyl, 2-pentyl, 2-methylbutyl, neopentyl, cyclcopentyl, n-hexyl, 2-hexyl, 2-methylpentyl and cyclohexyl. Similarly, $C_{1-8}$, as in $C_{1-8}$alkyl is defined to identify the group as having 1, 2, 3, 4, 5, 6, 7 or 8 carbon atoms in a linear or branched arrangement.

Alkylene means a difunctional group obtained by removal of a hydrogen atom from an alkyl group that is defined above. For example, methylene (i.e., $—CH_2—$), ethylene (i.e., $—CH_2—CH_2—$ or $—CH(CH_3)—$) and propylene (i.e., $—CH_2—CH_2—$ $CH_2—$, $—CH(—CH_2—CH_3)—$ or $—CH_2—CH(CH_3)—$).

Alkoxy radicals are oxygen ethers formed from the previously described straight, branched chain or cyclic alkyl groups.

The term "aryl", as used herein, unless otherwise indicated, by itself or as part of another substituent refers to a monocyclic or polycyclic aromatic hydrocarbon. Phenyl and naphthyl are preferred aryls. The most preferred aryl is phenyl.

The term "heterocyclic", as used herein, unless otherwise indicated, by itself or as part of another substituent refers to unsubstituted and substituted mono- or polycyclic non-aromatic, partially unsaturated or fully saturated ring system containing one or more heteroatoms. Preferred heteroatoms include N, O, and S, including N-oxides, sulfur oxides, and dioxides. Preferably the ring is three to eight membered and is either fully saturated or has one or more degrees of unsaturation. Multiple degrees of substitution, preferably one, two or three, are included within the present definition.

Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, by itself or as part of another substituent refers to an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "cycloalkyl" as used herein, unless otherwise indicated, by itself or as part of another substituent refers to a substituted or unsubstituted monocyclic, bicyclic or polycyclic non-aromatic saturated or partially unsaturated hydrocarbon group, which optionally includes an alkylene linker through which the cycloalkyl may be attached. Exemplary "cycloalkyl" groups includes but not limited to, cyclopropyl, cyclobutyl, cyclopentyl, cyclohexyl and so on.

The term "carbonyl", "—C=O", "C=O", "—CO", "—C(O)", and "CO" refer to the group

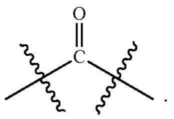 [SMILES: *C(*)=O]

The term "oxo" refers to the radical =O.

Whenever the term "alkyl" or "aryl" or either of their prefix roots appear in a name of a substituent (e.g., aralky or dialkylamino), unless otherwise indicated, by itself or as part of another substituent, it shall be interpreted as including those limitations given above for "alkyl" and "aryl". Designated numbers of carbon atoms (e.g., $C_{1-6}$) shall refer independently to the number of carbon atoms in an alkyl moiety or to the alkyl portion of a larger substituent in which alkyl appears as its prefix root.

The substituents the two "$R_1$" of Formula I, II, III or IV can be the same or different. Similar to "$R_1$", and the two "$Y_1$" of Formula I, II, III or IV can be the same or different.

Compounds described herein, such as certain compounds of Formula I, II, III or IV may contain asymmetrically substituted carbon atoms (or chiral centers) in the R or S configuration. The present invention includes racemic mixtures, relative and absolute stereoisomers, and mixtures of relative and absolute stereoisomers.

The compounds described herein, when specifically designated as the R- or S-isomer, either in a chemical name or in a drawing, should be understood as an enriched R-isomer or S-isomer, respectively. For example, in any of the embodiments described herein, such enriched R- or S-designated isomer can be substantially free (e.g., with less than 5%, less than 1%, or non-detectable, as determined by chiral HPLC) of the other isomer for the respective chiral center. The enriched R- or S-isomers can be prepared by methods exemplified in this application, such as by using a chiral auxiliary such as R- or S-tert-butylsulfinamide in the synthetic process. Other methods for prepaing the enriched R- or S-isomers herein include, but are not limited to, chiral HPLC purifications of a stereoisomeric mixture, such as a racemic mixture. General methods for separating stereoisomers (such as enantiomers and/or diastereomers) using HPLC are known in the art.

Compounds described herein can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention. In some embodiments, one or more hydrogen atoms of any of the compounds described herein can be substituted with deuterium to provide the corresponding deterium-labeled or -enriched compounds.

The term "subject" (alternatively referred to herein as "patient") as used herein refers to an animal, preferably a mammal, most preferably a human, who has been the object of treatment, observation or experiment.

The term "ring systems" as used herein, unless otherwise indicated, include but not limited to a carbocyclic ring, a heterocyclic ring, a heteroaromatic ring, etc., may also include only a heterocyclic ring, and/or a heteroaromatic ring, and the like, specifically includes which rings need to be determined according to the context, but anyway the "ring systems" do not include the cycloalkyl based on a $C_{1-6}$ alkyl or $C_{1-3}$ alkyl group, and do not include the cycloalkoxy based on a $C_{1-6}$ alkoxy or $C_{1-3}$ alkoxy group.

Compounds of Formula I, II, III or IV may have different isomeric forms. For example, any asymmetric carbon atom may be present in the (R)-, (S)- or (R,S)-configuration, preferably in the (R)- or (S)-configuration. Substituents at a double bond or especially a ring may be present m cis-(=Z-) or trans (=E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the Formula I, II, III or IV (or a salt thereof) is present, the "a" merely representing the indefinite article. "A" can thus preferably be read as "one or more", less preferably alternatively as "one".

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y, D61Y, V; E69K; A72V, T, D; E76G, Q, K (ALL); G60A: D61Y; E69V; F71K; A72V; T731; E76G, K; R289G; G503V (AML); G60R, D61Y, V, N; Y62D; E69K; A72T, V; T731; E76K, V, G, A, Q; E139D; G503A, R; Q506P (JMML); G60V; D61V; E69K; F71L; A72V; E76A (MDS), Y63C (CMML); Y62C; E69K; T507K (neuroblastoma); V46L; N58S; E76V (Lung cancer), R138Q (melanoma); E76G (colon cancer)

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I, II, III or IV is shown without a definitive stereochemistry at certain positions. The present invention includes all stereoisomers of Formula I, II, III or IV and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula I, II, III or IV exists, the present invention includes any possible tautomers and pharmaceutically acceptable salts thereof, and mixtures thereof, except where specifically stated otherwise.

When the compound of Formula I, II, III or IV and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula I, II, III or IV are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I, II, III or IV (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, II, III or IV, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, II, III or IV, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I, II, III or IV. The compounds of Formula I, II, III or IV, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I, II, III or IV of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration and the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, II, III or IV, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following Examples are provided to better illustrate the present invention. All parts and percentages are by weight and all temperatures are degrees Celsius, unless explicitly stated otherwise. The following abbreviations have been used in the examples:

| | | | |
|---|---|---|---|
| DMF | N,N-Dimethylformamide | THF | Tetrahydrofuran |
| EA | Ethyl acetate | $Ti(OEt)_4$ | Titanium ethoxide |
| Hex | Hexane | NMP | 1-Methyl-2-pyrrolidinone |
| MeOH | Methanol | DMSO | Dimethyl sulfoxide |
| DCM | Dichloromethane | DIEA | N,N-Diisopropylethylamine |
| DCE | 1,2-Dichloroethane | $(Boc)_2O$ | Di-tert-butyl dicarbonate |
| EtOH | Ethanol | LDA | Lithium diisopropylamide |
| t-BuOH | tert-Butanol | PPA | Polyphosphoric acids |
| AcOH | Acetic acid glacial | $Pd(PPh_3)_4$ | Tetrakis(triphenylphosphine)palladium |
| AcONa | Sodium acetate | n-BuLi | n-Butyllithium |
| DBU | 1,8-Diazabicyclo[5.4.0]undec-7-ene | LAH | Lithium aluminium hydride |
| XantPhos | 4,5-Bis(diphenylphosphino)-9,9-dimethylxanthene | t-BuOK | Potassium tert-butoxide |
| | | NaOEt | Sodium ethoxide |
| TEA | Triethylamine | TFA | Triethylamine |
| $CH_3I$ | Iodomethane | HCl | Hydrochloric acid |
| $Pd(OAc)_2$ | Palladium diacetate | RT | Room temperature |
| $Pd_2(dba)_3$ | Tris(dibenzylideneacetone)dipalladium(0) | min | minute(s) |
| HATU | 2-(7-Azabenzotriazol-1-yl)-N,N,N',N'-tetramethyluronium hexafluorophosphate | h | hour(s) |
| | | aq | aqueous |
| $Cy_3PH•BF_4$ | Tricyclohexylphosphonium tetrafluoroborate | sat | saturated |
| | | TLC | Thin layer chromatography |
| MsCl | Methanesulfonyl chloride | Pre-TLC | Preparative thin layer chromatography |

Intermediate A1

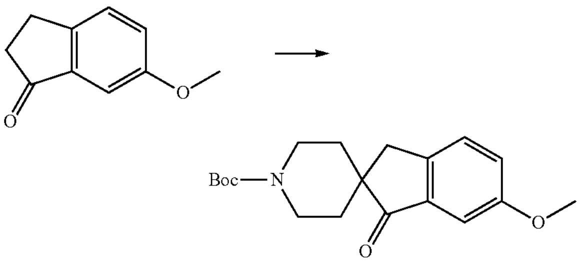

To a solution of 6-methoxy-2,3-dihydro-1H-inden-1-one (1.50 g, 9.25 mmol) in DMF (10 mL) under nitrogen atmosphere was added NaH (60% dispersion in mineral oil, 1.11 g, 27.75 mmol) in portions. The mixture was heated to 60° C., stirred for 20 min at this temperature. Tert-butyl bis(2-chloroethyl)carbamate (2.46 g, 10.17 mmol) was added dropwise, and the mixture was stirred for 85 min. After cooling to RT, the reaction mixture was diluted with EA (200 mL), washed with brine (3×200 mL), dried over anhydrous $Na_2SO_4$, filtered and concentrated under reduced pressure. The residue was purified by silica chromatography (eluting with EA:Hex=1:12, v/v) to give tert-butyl 6-methoxy-1-oxo-1,3-dihydrospiro[indene-2,4'-piperidine]-1'-carboxylate (557 mg) as a yellow solid. MS: m/z 332 $(M+H)^+$.

The following compounds were synthesized using the above procedure with the corresponding starting materials.

TABLE 1

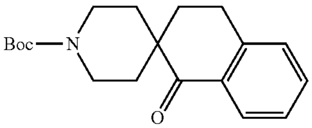 [SMILES: CC(C)(C)OC(=O)N1CCC2(CCc3ccccc3C2=O)CC1]

TABLE 1-continued

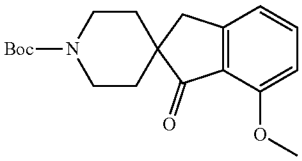 [SMILES: COc1cccc2c1C(=O)C1(CCN(C(=O)OC(C)(C)C)CC1)C2]

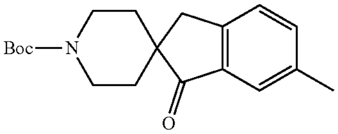 [SMILES: Cc1ccc2c(c1)C(=O)C1(CCN(C(=O)OC(C)(C)C)CC1)C2]

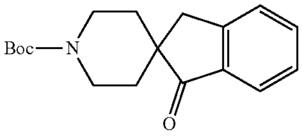 [SMILES: CC(C)(C)OC(=O)N1CCC2(CC1)Cc1ccccc1C2=O]

TABLE 1-continued

| |
|---|
| 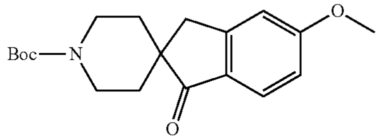 [SMILES: COc1ccc2c(c1)CC1(CCN(C(=O)OC(C)(C)C)CC1)C2=O] |
| 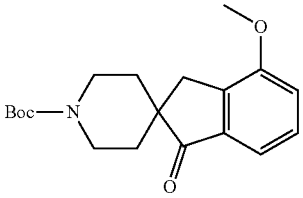 [SMILES: COc1cccc2c1CC1(CCN(C(=O)OC(C)(C)C)CC1)C2=O] |

Intermediate A2

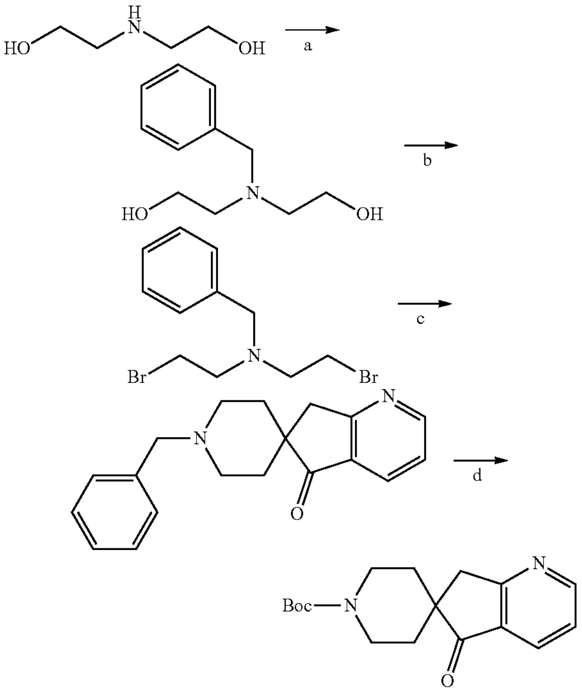

Step a: A solution of 2,2'-azanediylbis(ethan-1-ol) (198.15 g, 1.88 mol), $K_2CO_3$ (520.95 g, 3.77 mol) and (bromomethyl)benzene (386.79 g, 2.26 mol) in acetonitrile (2000 mL) was stirred at 90° C. for 2.5 h. After cooling to RT, the reaction mixture was filtered followed by EA (2×100 mL) wash. The filtrate was concentrated under reduced pressure. The residue was purified by silica chromatography (eluting with MeOH:DCM=1:10, v/v) to give 2,2'-(benzylazanediyl)bis(ethan-1-ol) (89.44 g) as a colorless oil. MS: m/z 196 $(M+H)^+$.

Step b: To a 0° C. solution of 2,2'-(benzylazanediyl)bis(ethan-1-ol) (30.66 g, 0.16 mol) in toluene (300 mL) was added tribromophosphane (69.13 g, 0.26 mol) dropwise. The resulting mixture was stirred at 105° C. for 16 h. After cooling to RT, the volatiles were removed under reduce pressure. The residue was diluted with water (300 mL), and the pH value was adjusted to 9 with NaOH. The resulting mixture was extracted with EA (3×150 mL), the organic layers combined, dried over anhydrous $Na_2SO_4$ and filtered. The filtrate was concentrated under reduced pressure to give N-benzyl-2-bromo-N-(2-bromoethyl) ethan-1-amine (41.58 g) which was used in next step without any further purification. MS: m/z 320 $(M+H)^+$.

Step c: To a 0° C. solution of 6,7-dihydro-5H-cyclopenta[b]pyridin-5-one (1.70 g, 12.77 mmol) in DMF (20 mL) under nitrogen atmosphere was added NaH (60% dispersion in mineral oil, 982 mg, 24.55 mmol) in three portions, and the mixture was heated to 60° C., stirred for 1 h at this temperature. Then N-benzyl-2-bromo-N-(2-bromoethyl) ethan-1-amine (4.54 g, 14.14 mmol) was added and stirred at 60° C. for another 1 h. After cooling to RT, the reaction mixture was quenched with water (80 mL), extracted with EA (3×80 mL). The combined organic layers were washed with water (3×80 mL), dried over anhydrous $Na_2SO_4$, filtered and concentrated under reduced pressure. The residue was purified by silica chromatography (eluting with EA) to give 1'-benzylspiro[cyclopenta[b]pyridine-6,4'-piperidin]-5(7H)-one (1.14 g). MS: m/z 293 $(M+H)^+$.

Step d: To a 0° C. solution of 1'-benzylspiro[cyclopenta[b]pyridine-6,4'-piperidin]-5(7H)-one (1.05 g, 3.59 mmol) in DCE (10 mL) was added 1-chloroethyl carbonochloridate (903 mg, 6.32 mmol) dropwise. The resulting mixture was stirred at RT for 1.5 h. The volatiles were removed under reduced pressure and the residue was dissolved in MeOH (20 mL), stirred at 80° C. for 4 h. The volatiles were removed under reduced pressure and dissolved in DCM (20 mL). DIEA (1.33 g, 10.32 mmol) and $(Boc)_2O$ (1.38 g, 6.32 mmol) were added. The resulting solution was stirred for 16 h at RT. The reaction mixture was concentrated under reduced pressure. The residue was purified by silica chromatography (eluting with EA:Hex=1:1, v/v) to give tert-butyl 5-oxo-5,7-dihydrospiro[cyclopenta[b]pyridine-6,4'-piperidine]-1'-carboxylate (438 mg). MS: m/z 303 $(M+H)^+$.

Intermediate A3

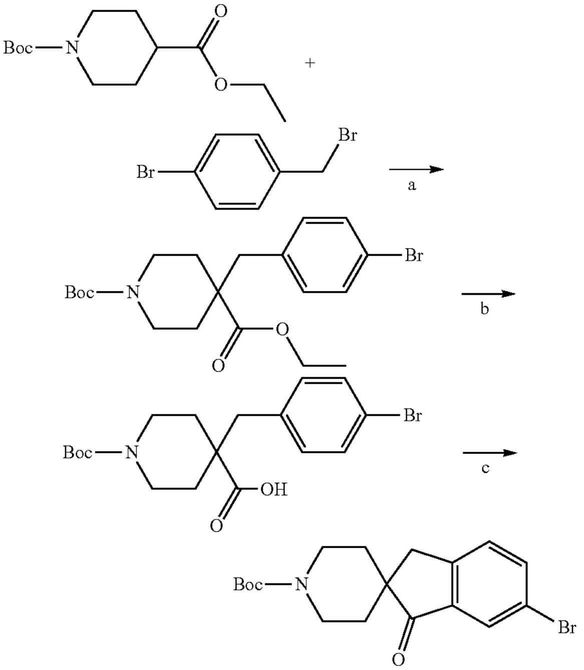

Step a: To a −70° C. solution of 1-(tert-butyl) 4-ethyl piperidine-1,4-dicarboxylate (8.14 g, 31.64 mmol) in THF (80 mL) under nitrogen atmosphere was added LDA (2 M solution in THF/Hex, 24 mL, 48.00 mmol) dropwise. After stirred for 70 min at this temperature, 1-bromo-4-(bromomethyl)benzene (7.91 g, 31.64 mmol) was added in portions. The resulting solution was stirred for 3 h at −70° C., and carefully quenched with sat. aq. $NH_4Cl$ (50 mL). The aqueous layer was separated, and extracted with EA (1×80 mL), the organic layers combined, dried over anhydrous $Na_2SO_4$, filtered and concentrated under reduced pressure to give 1-(tert-butyl) 4-ethyl 4-(4-bromobenzyl)piperidine-1,4-dicarboxylate (14.55 g) as a brown oil which was used in next step without any further purification. MS: m/z 426 $(M+H)^+$.

Step b: A solution of 1-(tert-butyl) 4-ethyl 4-(4-bromobenzyl)piperidine-1,4-dicarboxylate (14.55 g, 34.13 mmol) and NaOH (8.12 g, 203.00 mmol) in MeOH (80 mL) and water (80 mL) was stirred for 16.5 h at 75° C. After cooling to RT, the volatiles were removed under reduced pressure. The resulting mixture was extracted with EA (3×80 mL). The combined organic layers were dried over anhydrous $Na_2SO_4$, filtered and concentrated under reduced pressure to give 4-(4-bromobenzyl)-1-(tert-butoxycarbonyl)piperidine-4-carboxylic acid (16.87 g) which was used in next step without any further purification. MS: m/z 398 $(M+H)^+$.

Step c: A mixture of 4-(4-bromobenzyl)-1-(tert-butoxycarbonyl)piperidine-4-carboxylic acid (16.87 g, 42.36 mmol) and PPA (60 mL) was stirred for 30 min at 120° C. The reaction mixture was poured into ice/water (300 mL), the pH value was adjusted to 10 with NaOH. Then $(Boc)_2O$ (13.86 g, 63.53 mmol) was added and stirred for 18 h at RT. The reaction mixture was extracted with EA (3>×150 mL). The combined organic layers were dried over anhydrous $Na_2SO_4$, filtered and concentrated under reduced pressure to give tert-butyl 6-bromo-1-oxo-1,3-dihydrospiro [indene-2,4'-piperidine]-1'-carboxylate (16.87 g) which was used in next step without any further purification. MS: m/z 380 $(M+H)^+$.

The following compounds were synthesized using the above procedure or modifications procedure with the corresponding starting materials.

TABLE 2

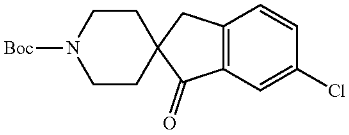 [SMILES: CC(C)(C)OC(=O)N1CCC2(CC1)Cc1ccc(Cl)cc1C2=O]

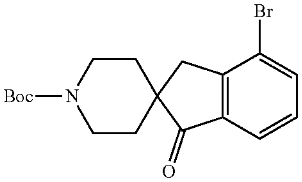 [SMILES: CC(C)(C)OC(=O)N1CCC2(CC1)Cc1c(Br)cccc1C2=O]

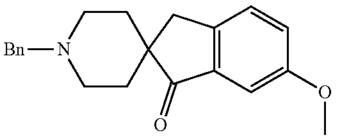 [SMILES: COc1ccc2c(c1)C(=O)C1(CCN(Cc3ccccc3)CC1)C2]

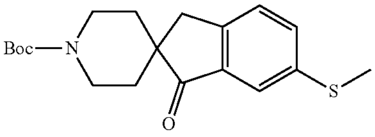 [SMILES: CSc1ccc2c(c1)C(=O)C1(CCN(C(=O)OC(C)(C)C)CC1)C2]

TABLE 2-continued

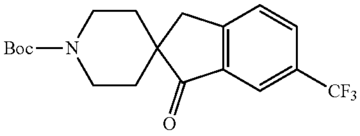 [SMILES: CC(C)(C)OC(=O)N1CCC2(CC1)Cc1ccc(C(F)(F)F)cc1C2=O]

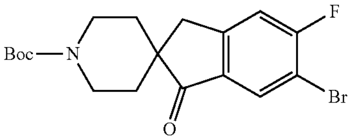 [SMILES: CC(C)(C)OC(=O)N1CCC2(CC1)Cc1cc(F)c(Br)cc1C2=O]

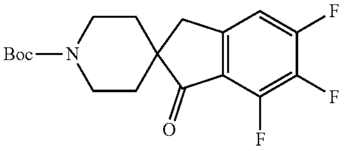 [SMILES: CC(C)(C)OC(=O)N1CCC2(CC1)Cc1cc(F)c(F)c(F)c1C2=O]

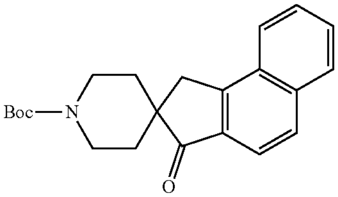 [SMILES: CC(C)(C)OC(=O)N1CCC2(CC1)Cc1c(ccc3ccccc13)C2=O]

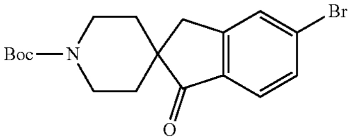 [SMILES: CC(C)(C)OC(=O)N1CCC2(CC1)Cc1cc(Br)ccc1C2=O]

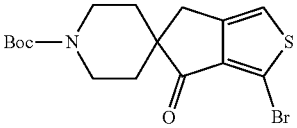 [SMILES: CC(C)(C)OC(=O)N1CCC2(CC1)Cc1csc(Br)c1C2=O]

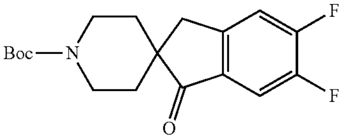 [SMILES: CC(C)(C)OC(=O)N1CCC2(CC1)Cc1cc(F)c(F)cc1C2=O]

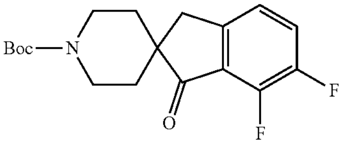 [SMILES: CC(C)(C)OC(=O)N1CCC2(CC1)Cc1ccc(F)c(F)c1C2=O]

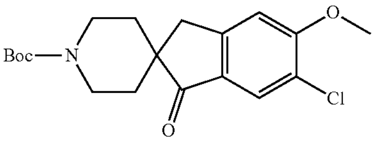 [SMILES: COc1cc2c(cc1Cl)C(=O)C1(CCN(C(=O)OC(C)(C)C)CC1)C2]

Intermediate A4

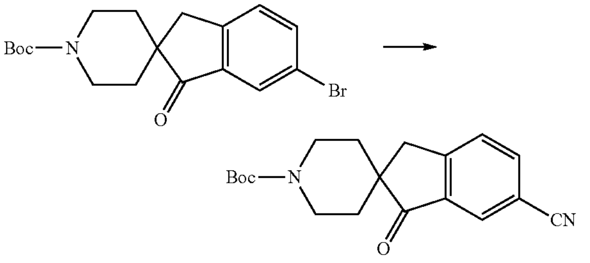

A mixture of tert-butyl 6-bromo-1-oxo-1,3-dihydrospiro [indene-2,4'-piperidine]-1'-carboxylate (2.06 g, 5.42 mmol), $Pd(PPh_3)_4$ (626 mg, 0.54 mmol), DBU (252 mg, 1.66 mmol), t-BuOH (15 mL), water (15 mL) and potassium ferrocyanide trihyrate (1.16 g, 2.75 mmol) was stirred for 22.5 h at 90° C. under nitrogen atmosphere. After cooling to RT, the mixture was diluted with EA (30 mL), filtered followed by EA (15 mL) wash. The filtrate was washed with brine (1×30 mL), dried over anhydrous $Na_2SO_4$, filtered and concentrated under reduced pressure. The residue was purified by silica chromatography (eluting with EA:Hex=1:10, v/v) to give tert-butyl 6-cyano-1-oxo-1,3-dihydrospiro[indene-2,4'-piperidine]-1'-carboxylate (1.86 g). MS: m/z 327 $(M+H)^+$.

The following compounds were synthesized using the above procedure with the corresponding starting materials.

TABLE 3

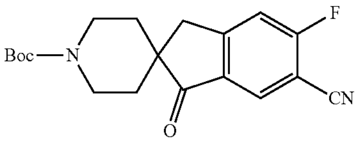 [SMILES: CC(C)(C)OC(=O)N1CCC2(CC1)Cc1cc(F)c(C#N)cc1C2=O]

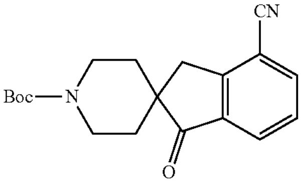 [SMILES: CC(C)(C)OC(=O)N1CCC2(CC1)Cc1c(C#N)cccc1C2=O]

Intermediate A5

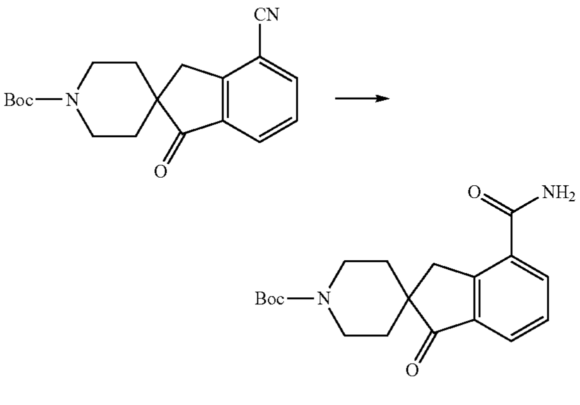

A solution of tert-butyl 4-cyano-1-oxo-1,3-dihydrospiro [indene-2,4'-piperidine]-1'-carboxylate (0.93 g, 2.85 mmol) and KOH (1.60 g, 28.50 mmol) in MeOH (15 mL) and water (15 mL) was stirred for 2 h at 100° C. After cooling to RT, the reaction mixture was diluted with water (30 mL), extracted with EA (60 mL, 30 mL). The combined organic layers were washed with brine (1×80 mL), dried over anhydrous $Na_2SO_4$, filtered and concentrated under reduced pressure to give tert-butyl 4-carbamoyl-1-oxo-1,3-dihydrospiro[indene-2,4'-piperidine]-1'-carboxylate (1.04 g) which was used in next step without any further purification. MS: m/z 345 $(M+H)^+$.

The following compounds were synthesized using the above procedure with the corresponding starting materials.

TABLE 4

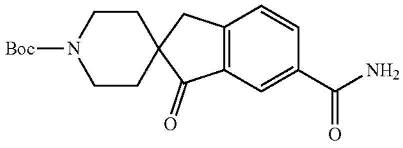 [SMILES: CC(C)(C)OC(=O)N1CCC2(CC1)Cc1ccc(C(N)=O)cc1C2=O]

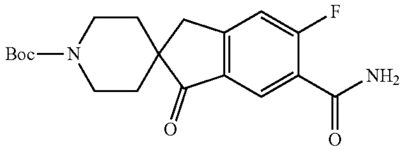 [SMILES: CC(C)(C)OC(=O)N1CCC2(CC1)Cc1cc(F)c(C(N)=O)cc1C2=O]

Intermediate A6

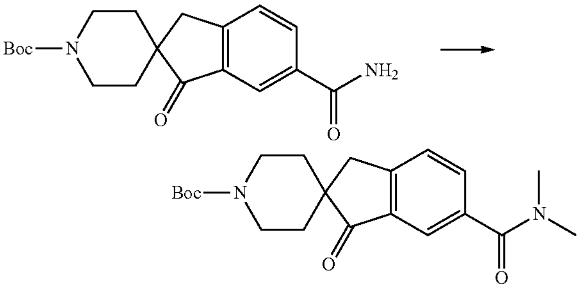

To a solution of tert-butyl 6-carbamoyl-1-oxo-1,3-dihydrospiro[indene-2,4'-piperidine]-1'-carboxylate (1.57 g, 4.56 mmol) in DMF (15 mL) was added NaH (60% dispersion in mineral oil, 0.91 g, 22.79 mmol) followed by the addition of $CH_3I$ (1 mL, 16.06 mmol). The resulting mixture was stirred for 17 h at RT. The reaction was quenched with brine (50 mL), extracted with EA (2×50 mL). The combined organic layers were washed with brine (1×100 mL), dried over anhydrous $Na_2SO_4$, filtered and concentrated under reduced pressure. The residue was purified by silica chromatography (eluting with EA:Hex=1:3, v/v) to give tert-butyl 6-(dimethylcarbamoyl)-1-oxo-1,3-dihydrospiro[indene-2,4'-piperidine]-1'-carboxylate (0.82 g). MS: m/z 373 $(M+H)^+$.

Intermediate A7

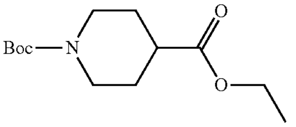

+

-continued

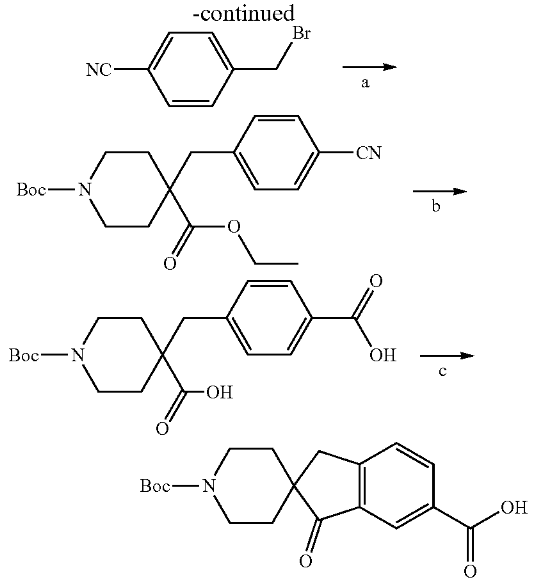

Step a-c: Step (a-c) of Intermediate A3 was applied to provide 1'-(tert-butoxycarbonyl)-1-oxo-1,3-dihydrospiro [indene-2,4'-piperidine]-6-carboxylic acid. MS: m/z 346 $(M+H)^+$.

Intermediate A8

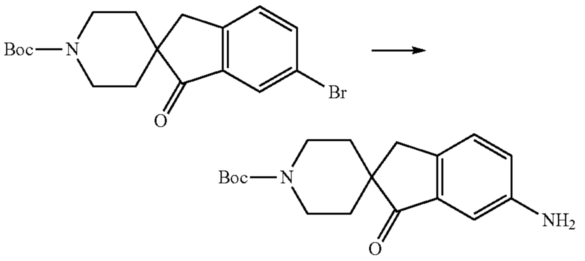

A 50 mL sealed tube was charged with tert-butyl 6-bromo-1-oxo-1,3-dihydrospiro [indene-2,4'-piperidine]-1'-carboxylate (998 mg, 2.62 mmol), DMSO (8 mL), water (4 mL), CuI (217 mg, 1.14 mmol) and ammonium hydroxide (25%, 4 mL). The resulting mixture was stirred for 5 days at 100° C. After cooling to RT, the reaction mixture was diluted with brine (20 mL) and EA (30 mL). The organic layer was separated, dried over anhydrous $Na_2SO_4$, filtered and concentrated under reduced pressure to give tert-butyl 6-amino-1-oxo-1,3-dihydrospiro [indene-2,4'-piperidine]-1'-carboxylate (750 mg). MS: m/z 317 $(M+H)^+$.

Intermediate A9

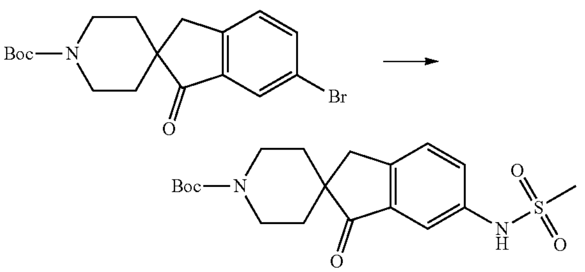

A mixture of tert-butyl 6-bromo-1-oxo-1,3-dihydrospiro [indene-2,4'-piperidine]-1'-carboxylate (534 mg, 1.40 mmol), methanesulfonamide (371 mg, 3.90 mmol), $K_2CO_3$ (1.10 g, 7.95 mmol), N,N'-dimethyl-1,2-ethanediamine (85 mg, 0.96 mmol), CuI (72 mg, 0.38 mmol) in 1,4-dioxane (20 mL) under nitrogen atmosphere was stirred for 23 h at 110° C. An additional portion of methanesulfonamide (370 mg, 3.89 mmol), N,N'-dimethyl-1,2-ethanediamine (85 mg, 0.96 mmol), CuI (75 mg, 0.39 mmol) was added, and stirred for another 7 h at the same temperature. After cooling to RT, the reaction was quenched with water (30 mL), extracted with EA (3×50 mL). The combined organic layers were dried over anhydrous $Na_2SO_4$, filtered and concentrated under reduced pressure. The residue was purified by silica chromatography (eluting with EA:Hex=2:3, v/v) to give tert-butyl 6-(methylsulfonamido)-1-oxo-1,3-dihydrospiro [indene-2,4'-piperidine]-1'-carboxylate (562 mg). MS: m/z 395 $(M+H)^+$.

The following compound was synthesized using the above procedure with the corresponding starting materials.

TABLE 5

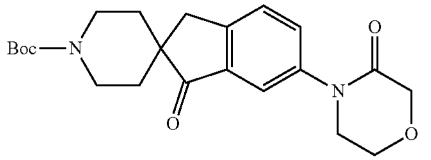 [SMILES: CC(C)(C)OC(=O)N1CCC2(CC1)Cc1ccc(N3CCOCC3=O)cc1C2=O]

Intermediate A10

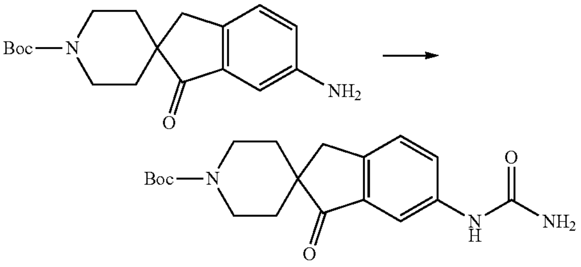

To a solution of tert-butyl 6-amino-1-oxo-1,3-dihydrospiro[indene-2,4'-piperidine]-1'-carboxylate (0.66 g, 2.09 mmol) in AcOH (5 mL) and water (10 mL) was added a solution of sodium cyanate (0.28 g, 4.31 mmol) in water (2 mL) dropwise. The resulting mixture was stirred for 4 h at 50° C. After cooling to RT, the pH value of the reaction mixture was adjusted to 12 with ammonium hydroxide (25%) and extracted with DCM (60 mL, 30 mL). The combined organic layers were washed with brine (1×60 mL), dried over anhydrous $Na_2SO_4$, filtered and concentrated under reduced pressure. The residue was purified by silica chromatography (eluting with EA:Hex=2:1, v/v) to give tert-butyl 1-oxo-6-ureido-1,3-dihydrospiro[indene-2, 4'-piperidine]-1'-carboxylate (0.39 g). MS: m/z 360 $(M+H)^+$.

Intermediate A11

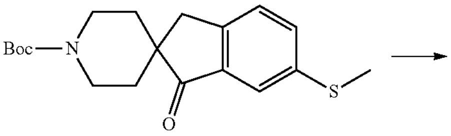

-continued

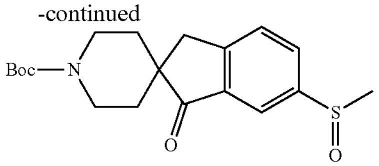

To a 0° C. solution of tert-butyl 6-(methylthio)-1-oxo-1,3-dihydrospiro[indene-2,4'-piperidine]-1'-carboxylate (336 mg, 0.97 mmol) in MeOH (20 mL) and water (20 mL) was added potassium peroxymonosulfate (296 mg, 1.76 mmol). The resulting mixture was stirred for 1 h at 0° C. The reaction mixture was quenched with sat. aq. $Na_2S_2O_3$ (10 mL), the volatiles were removed under reduced pressure. The resulting mixture was extracted with EA (3×40 mL), the combined organic layers were dried over anhydrous $Na_2SO_4$, filtered and concentrated under reduced pressure. The residue was purified by silica chromatography (eluting with EA:Hex=4:1, v/v) to give tert-butyl 6-(methylsulfinyl)-1-oxo-1,3-dihydrospiro[indene-2,4'-piperidine]-1'-carboxylate (285 mg). MS: m/z 364 $(M+H)^+$.

The following compound was synthesized using the above procedure with the corresponding starting materials.

TABLE 6

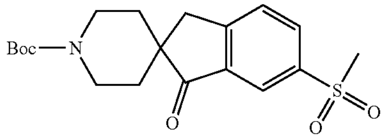 [SMILES: CC(C)(C)OC(=O)N1CCC2(CC1)Cc1ccc(S(C)(=O)=O)cc1C2=O]

Intermediate A12

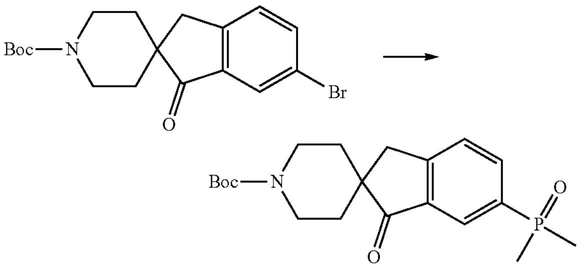

A mixture of tert-butyl 6-bromo-1-oxo-1,3-dihydrospiro[indene-2,4'-piperidine]-1'-carboxylate (1.51 g, 3.97 mmol), dimethyl(oxo)phosphanium (503 mg, 6.44 mmol), $Pd(OAc)_2$ (92 mg, 0.41 mmol), Xantphos (457 mg, 0.79 mmol), $K_3PO_4$ (1.57 g, 7.40 mmol) and DMF (30 mL) was stirred for 16.5 h at 130° C. under nitrogen atmosphere. After cooling to RT, the reaction mixture was quenched with water (120 mL), extracted with EA (3×80 mL). The combined organic layers were washed with brine (1×120 mL), dried over anhydrous $Na_2SO_4$, filtered and concentrated under reduced pressure. The residue was purified by silica chromatography (eluting with MeOH:DCM=1:30, v/v) to give tert-butyl 6-(dimethylphosphoryl)-1-oxo-1,3-dihydrospiro[indene-2,4'-piperidine]-1'-carboxylate (0.81 g) as a white solid. MS: m/z 378 $(M+H)^+$.

The following compounds were synthesized using the above procedure with the corresponding starting materials.

TABLE 7

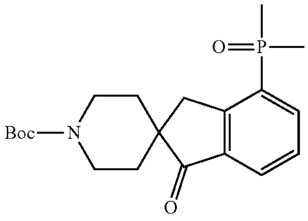 [SMILES: CC(C)(C)OC(=O)N1CCC2(CC1)Cc1c(cccc1P(C)(C)=O)C2=O]

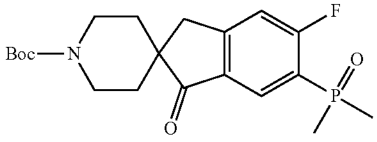 [SMILES: CC(C)(C)OC(=O)N1CCC2(CC1)Cc1cc(F)c(P(C)(C)=O)cc1C2=O]

Intermediate A13

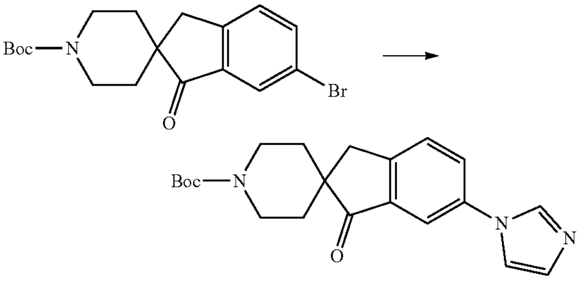

A mixture of tert-butyl 6-bromo-1-oxo-1,3-dihydrospiro[indene-2,4'-piperidine]-1'-carboxylate (1.09 g, 2.87 mmol), 1H-imidazole (180 mg, 2.64 mmol), CuBr (34 mg, 0.24 mmol), $Cs_2CO_3$ (851 mg, 2.61 mmol), 1,2,3,4-tetrahydro-8-hydroxyquinoline (74 mg, 0.49 mmol) and DMSO (10 mL) was stirred for 23 h at 110° C. under nitrogen atmosphere. After cooling to RT, the reaction mixture was quenched with water (30 mL), extracted with EA (1×40 mL). The organic layer was dried over anhydrous $Na_2SO_4$, filtered and concentrated under reduced pressure. The residue was purified by silica chromatography (eluting with EA) to give tert-butyl 6-(1H-imidazol-1-yl)-1-oxo-1,3-dihydrospiro[indene-2,4'-piperidine]-1'-carboxylate (142 mg) as a yellow solid. MS: m/z 368 $(M+H)^+$.

The following compound was synthesized using the above procedure with the corresponding starting materials.

TABLE 8

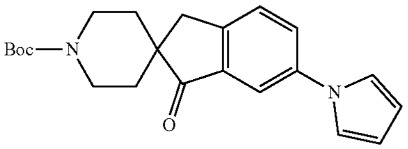 [SMILES: CC(C)(C)OC(=O)N1CCC2(CC1)Cc1ccc(-n3cccc3)cc1C2=O]

Intermediate A14

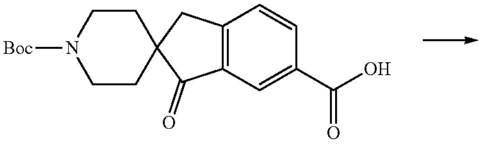

-continued

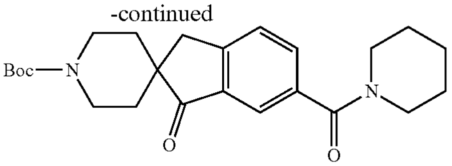

A mixture of 1'-(tert-butoxycarbonyl)-1-oxo-1,3-dihydrospiro[indene-2,4'-piperidine]-6-carboxylic acid (345 mg, 1.00 mmol), piperidine (129 mg, 1.51 mmol) and HATU (422 mg, 1.11 mmol) in DMF was stirred for 1 h at RT. The reaction mixture was diluted with water (30 mL) and EA (30 mL). The organic layer was separated, washed with brine (1×30 mL), dried over anhydrous $Na_2SO_4$, filtered and concentrated under reduced pressure to give tert-butyl 1-oxo-6-(piperidine-1-carbonyl)-1,3-dihydrospiro[indene-2,4'-piperidine]-1'-carboxylate (380 mg). MS: m/z 413 $(M+H)^+$.

Intermediate A15

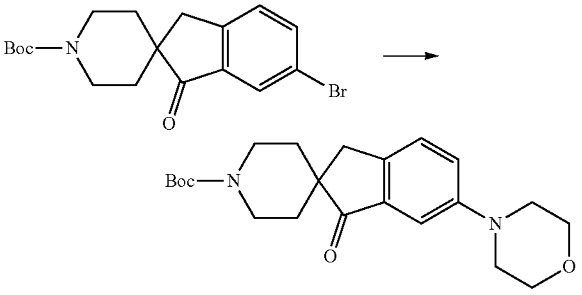

A mixture of tert-butyl 6-bromo-1-oxo-1,3-dihydrospiro [indene-2,4'-piperidine]-1'-carboxylate (1.02 g, 2.68 mmol), morpholine (0.67 g, 7.69 mmol), $Cu(OAc)_2$ (0.51 g, 2.81 mmol), DBU (1.03 g, 6.77 mmol) in DMSO (10 mL) was stirred for 23 h at 130° C. under nitrogen atmosphere. After cooling to RT, the reaction mixture was diluted with water (70 mL), extracted with EA (3×50 mL). The combined organic layers were dried over anhydrous $Na_2SO_4$, filtered and concentrated under reduced pressure. The residue was purified by silica chromatography (eluting with EA:Hex=1:1, v/v) to give tert-butyl 6-morpholino-1-oxo-1,3-dihydrospiro [indene-2,4'-piperidine]-1'-carboxylate (467 mg). MS: m/z 387 $(M+H)^+$.

Intermediate A16

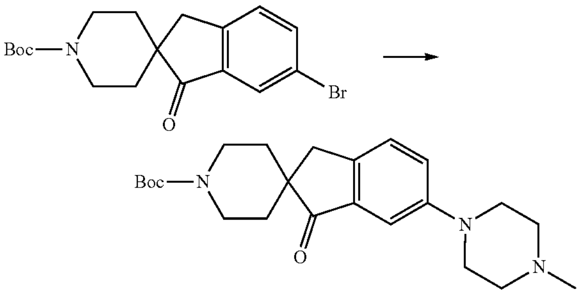

A mixture of tert-butyl 6-bromo-1-oxo-1,3-dihydrospiro [indene-2,4'-piperidine]-1'-carboxylate (500 mg, 1.31 mmol), 1-methylpiperazine (270 mg, 2.70 mmol), $Cs_2CO_3$ (1306 mg, 4.01 mmol), $Pd_2(dba)_3$ (66 mg, 0.07 mmol) and XantPhos (75 mg, 0.13 mmol) in 1,4-dioxane (18 mL) was stirred for 0.5 h at 100° C. under nitrogen atmosphere. After cooling to RT, the reaction mixture was quenched with water, extracted with EA (2×100 mL). The combined organic layers were washed with brine (1×100 mL), dried over anhydrous $Na_2SO_4$, filtered and concentrated under reduced pressure to give tert-butyl 6-(4-methylpiperazin-1-yl)-1-oxo-1,3-dihydrospiro [indene-2,4'-piperidine]-1'-carboxylate (0.87 g, crude) which was used in next step without any further purification. MS: m/z 400 $(M+H)^+$.

Intermediate A17

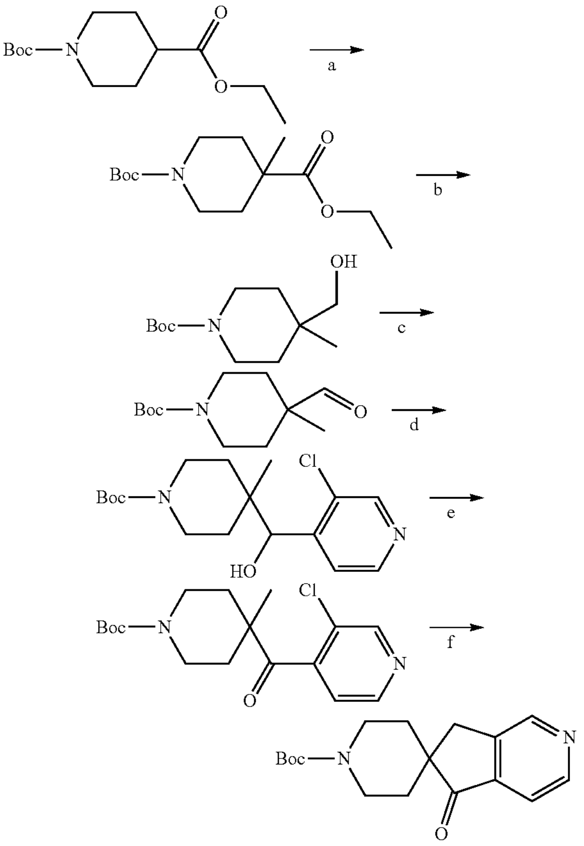

Step a: To a −60° C. solution of 1-(tert-butyl) 4-ethyl piperidine-1,4-dicarboxylate (15.52 g, 60.31 mmol) in THF (100 ml) was added LDA (2 M solution in THF/Hex, 45.00 mL, 90.00 mmol) dropwise under nitrogen atmosphere. The resulting mixture was allowed to warm to −20° C. and stirred for 50 min. The mixture was cooled to −50° C., and a solution of $CH_3I$ (8.56 g, 60.31 mmol) in THF (20 mL) was added dropwise. The resulting mixture was stirred for 50 min at this temperature. The reaction mixture was carefully quenched with sat. aq. $NH_4Cl$ (80 mL), extracted with EA (100 mL, 50 mL). The combined organic layers were dried over anhydrous $Na_2SO_4$, filtered and concentrated under reduced pressure to give 1-(tert-butyl) 4-ethyl 4-methylpiperidine-1,4-dicarboxylate (17.70 g) which was used without any further purification. MS: m/z 216 (M+H−56)+.

Step b: To a 0° C. solution of 1-(tert-butyl) 4-ethyl 4-methylpiperidine-1,4-dicarboxylate (17.70 g, 65.23 mmol) in THF (150 mL) was added a $LiBH_4$ (2 M solution in THF, 98.00 mL, 196.00 mmol). The resulting mixture was stirred for 18 h at 70° C. After cooling to RT, water (100 mL)

was added dropwise. The resulting mixture was extracted with EA (200 mL, 100 mL), the combined organic layers were washed with brine (1×200 mL), dried over anhydrous $Na_2SO_4$, filtered and concentrated under reduced pressure to give tert-butyl 4-(hydroxymethyl)-4-methylpiperidine-1-carboxylate (12.90 g) which was used in next step without any further purification. MS: m/z 174 (M+H−56)+.

Step c: To a −78° C. solution of oxalyl chloride (10.71 g, 84.38 mmol) in DCM (150 mL) was added a solution of DMSO (10.99 g, 140.63 mmol) in DCM (30 mL) dropwise, stirred for 30 min at this temperature. A solution of tert-butyl 4-(hydroxymethyl)-4-methylpiperidine-1-carboxylate (12.90 g, 56.25 mmol) in DCM (30 mL) was added dropwise, stirred for 30 min at −78° C. Triethylamine (22.77 g, 225.02 mmol) was added dropwise, the resulting mixture was allowed to warm to −20° C., and stirred for 40 min. The reaction mixture was quenched with water (80 mL). The aqueous layer was separated and extracted with DCM (1×80 mL). The combined organic layers were washed with brine (1×200 mL), dried over anhydrous $Na_2SO_4$, filtered and concentrated under reduced pressure. The residue was purified by silica chromatography (eluting with EA:Hex=1:20, v/v) to give tert-butyl 4-formyl-4-methylpiperidine-1-carboxylate (11.82 g). MS: m/z 172 (M+H−56)+.

Step d: To a −70° C. solution of 3-chloropyridine (2.25 g, 17.64 mmol) in THF (50 mL) was added LDA (2 M solution in THF/Hex, 11.00 mL, 22.00 mmol) dropwise. The resulting mixture was allowed to warm to −60° C. and stirred for 1.5 h. A solution of tert-butyl 4-formyl-4-methylpiperidine-1-carboxylate (3.95 g, 17.37 mmol) in THF (10 mL) was added dropwise at −70° C. After stirring for 1 h, the mixture was quenched with water (50 mL). The aqueous layer was separated and extracted with EA (60 mL, 30 mL). The combined organic layers were washed with brine (1×80 mL), dried over anhydrous $Na_2SO_4$, filtered and concentrated under reduced pressure to give tert-butyl 4-((3-chloropyridin-4-yl)(hydroxy)methyl)-4-methylpiperidine-1-carboxylate (8.10 g) which was used in next step without any further purification. MS: m/z 341 $(M+H)^+$.

Step e: To a solution of tert-butyl 4-((3-chloropyridin-4-yl)(hydroxy)methyl)-4-methylpiperidine-1-carboxylate (8.10 g, 23.76 mmol) in DCM (50 ml) was added Dess-Martin periodinane (20.12 g, 47.44 mmol). The resulting mixture was stirred for 16 h at RT. The reaction mixture was diluted with DCM (100 mL), washed with aq. $Na_2S_2O_3$ (25%, 1×80 mL), sat. aq. $NaHCO_3$ (1×80 mL) and brine (1×100 mL). The organic layer was dried over anhydrous $Na_2SO_4$, filtered and concentrated under reduced pressure. The residue was purified by silica chromatography (eluting with EA:Hex=1:3, v/v) to give tert-butyl 4-(3-chloroisonicotinoyl)-4-methylpiperidine-1-carboxylate (4.81 g). MS: m/z 339 $(M+H)^+$.

Step f: A mixture of tert-butyl 4-(3-chloroisonicotinoyl)-4-methylpiperidine-1-carboxylate (6.31 g, 18.62 mmol), $Cs_2CO_3$ (6.72 g, 21.90 mmol), pivalic_acid (571 mg, 5.60 mmol), $Pd(OAc)_2$ (0.22 g, 0.98 mmol) and $Cy_3PH.BF_4$ (0.70 g, 1.90 mmol) in 1,3,5-mesitylene (40 mL) was stirred for 72 h at 140° C. under nitrogen atmosphere. After cooling to RT, the mixture was filtered followed by EA (3×40 mL) wash. The filtrate was concentrated under reduced pressure. The residue was purified by silica chromatography (eluting with EA:Hex=1:1, v/v) to give tert-butyl 5-oxo-5,7-dihydrospiro[cyclopenta[c]pyridine-6,4'-piperidine]-1'-carboxylate (2.82 g). MS: m/z 303 $(M+H)^+$.

The following compounds were synthesized using the above procedure with the corresponding starting materials.

TABLE 9

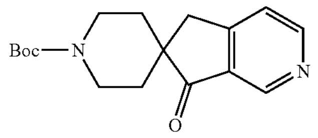 [SMILES: CC(C)(C)OC(=O)N1CCC2(CC1)Cc1ccncc1C2=O]

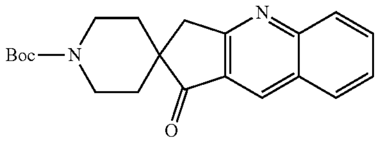 [SMILES: CC(C)(C)OC(=O)N1CCC2(CC1)Cc1nc3ccccc3cc1C2=O]

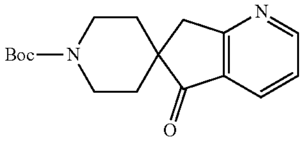 [SMILES: CC(C)(C)OC(=O)N1CCC2(CC1)Cc1ncccc1C2=O]

Intermediate A18

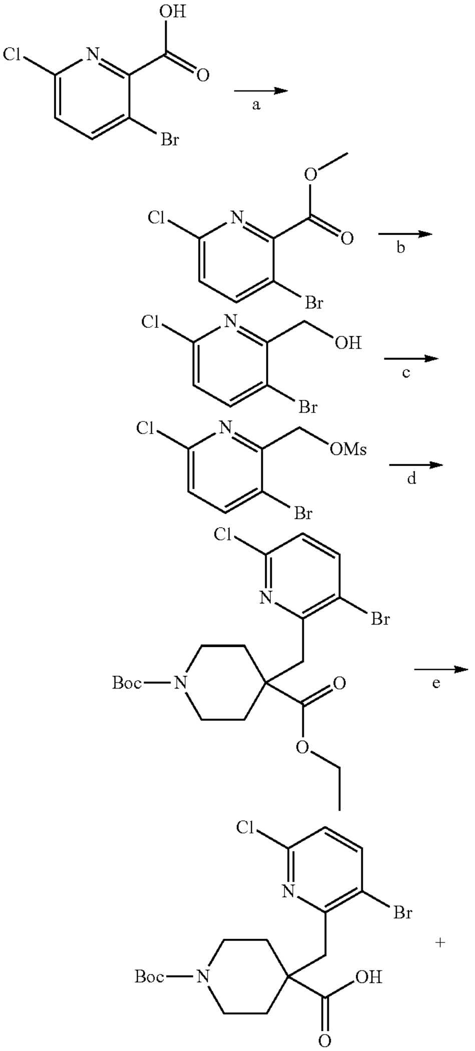

-continued

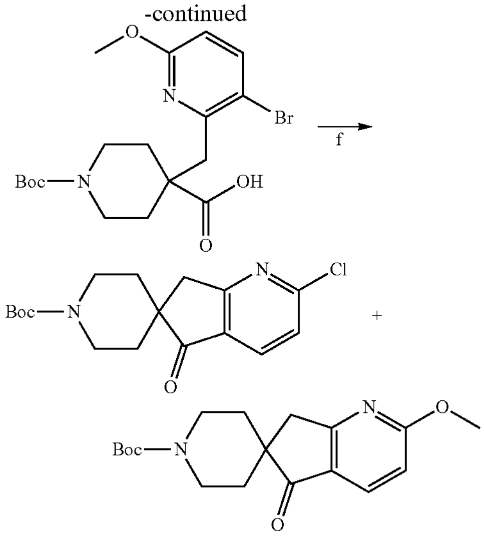

Step a: To a solution of 3-bromo-6-chloropicolinic acid (9.98 g, 42.21 mmol) in MeOH (100 mL) was added $H_2SO_4$ (98%, 10.00 mL) dropwise. The mixture was stirred for 3 h at 70° C. After cooling to RT, the pH value of the reaction mixture was adjusted to 9 by ammonium hydroxide (25%). The volatiles were removed under reduced pressure. The mixture was diluted with water (60 mL), extracted with EA (1×100 mL). The organic layer was washed with brine (1×60 mL), dried over anhydrous $Na_2SO_4$, filtered and concentrated under reduced pressure to give methyl 3-bromo-6-chloropicolinate (10.14 g) as an off-white solid. MS: m/z 250 $(M+H)^+$.

Step b: To a 0° C. solution of methyl 3-bromo-6-chloropicolinate (10.14 g, 40.48 mmol) in MeOH (150 mL) was added $NaBH_4$ (4.62 g, 122.13 mmol) in portions. The resulting mixture was allowed to warm to RT and stirred for 16 h. The reaction mixture was diluted with brine (110 mL) and MeOH was removed under reduced pressure. The resulting mixture was extracted with EA (100 mL, 80 mL), the organic layers combined, dried over anhydrous $Na_2SO_4$, filtered and concentrated under reduced pressure to give (3-bromo-6-chloropyridin-2-yl)methanol (8.31 g). MS: m/z 222 $(M+H)^+$.

Step c: To a −15° C. solution of (3-bromo-6-chloropyridin-2-yl)methanol (8.31 g, 37.35 mmol) and triethylamine (7.63 g, 75.40 mmol) in DCM (100 mL) was added MsCl (4.71 g, 41.12 mmol) dropwise. The resulting mixture was allowed to warm to RT and stirred for 2 h. The reaction mixture was quenched with water (50 mL) and the aqueous layer was separated. The organic layer was washed with brine (1×50 mL), dried over anhydrous $Na_2SO_4$, filtered and concentrated under reduced pressure to give (3-bromo-6-chloropyridin-2-yl)methyl methanesulfonate (8.54 g). MS: m/z 300 $(M+H)^+$.

Step d: To a −50° C. solution of 1-(tert-butyl) 4-ethyl piperidine-1,4-dicarboxylate (9.66 g, 37.54 mmol) in THF (30 mL) was added LDA (2 M solution in THF/Hex, 23.00 mL, 46.00 mmol) dropwise under nitrogen atmosphere. The resulting mixture was stirred for 1 h at this temperature. A solution of (3-bromo-6-chloropyridin-2-yl)methyl methanesulfonate (8.54 g, 28.41 mmol) in THF (15 mL) was added dropwise, the resulting mixture was allowed to warmed to RT and stirred for 1 h. The reaction mixture was quenched with brine (60 mL) and extracted with EA (1×30 mL). The organic layer was dried over anhydrous $Na_2SO_4$, filtered and concentrated under reduced pressure to give 1-(tert-butyl) 4-ethyl 4-((3-bromo-6-chloropyridin-2-yl)methyl)piperidine-1,4-dicarboxylate (17.73 g) which was used in next step without any further purification. MS: m/z 461 $(M+H)^+$.

Step e: A solution of 1-(tert-butyl) 4-ethyl 4-((3-bromo-6-chloropyridin-2-yl)methyl) piperidine-1,4-dicarboxylate (17.73 g, 38.39 mmol) and NaOH (8.03 g, 200.75 mmol) in MeOH (100 mL) and water (20 mL) was stirred for 16 h at 65° C. After cooling to RT, the volatiles were removed under reduced pressure and the resulting mixture was diluted with water (150 mL). The pH value was adjusted to 6 with sat. aq. citric acid. The mixture was extracted with EA (2×100 mL), the combined organic layers were washed with brine (1×100 mL), dried over anhydrous $Na_2SO_4$, filtered and concentrated under reduced pressure. The residue was purified by silica chromatography (eluting with EA:Hex=1:10, v/v) to give the mixture of 4-((3-bromo-6-chloropyridin-2-yl)methyl)-1-(tert-butoxycarbonyl)piperidine-4-carboxylic acid and 4-((3-bromo-6-methoxypyridin-2-yl)methyl)-1-(tert-butoxycarbonyl)piperidine-4-carboxylic acid (18.24 g). MS: m/z 433 (M+H)+, MS: m/z 429 $(M+H)^+$.

Step f: To a −15° C. solution of 4-((3-bromo-6-chloropyridin-2-yl)methyl)-1-(tert-butoxycarbonyl)piperidine-4-carboxylic acid and 4-((3-bromo-6-methoxypyridin-2-yl)methyl)-1-(tert-butoxycarbonyl)piperidine-4-carboxylic acid (3.80 g, 8.76 mmol) in THF (20 mL) was added NaH (60% dispersion in mineral oil, 0.42 g, 10.50 mmol) in portions under nitrogen atmosphere. After stirring for 1 h at this temperature, the mixture was cooled to −60° C. To the mixture was added n-BuLi (2.5M solution in Hex, 5 mL, 12.50 mmol) dropwise, stirred for 1 h. The reaction mixture was quenched with water (20 mL), extracted with EA (1×40 mL). The organic layer was washed with brine (1×30 mL), dried over anhydrous $Na_2SO_4$, filtered and concentrated under reduced pressure. The residue was purified by silica chromatography (EA:Hex=1:10, v/v) to give the mixture of tert-butyl 2-chloro-5-oxo-5,7-dihydrospiro[cyclopenta[b]pyridine-6,4'-piperidine]-1'-carboxylate and tert-butyl 2-methoxy-5-oxo-5,7-dihydrospiro[cyclopenta[b]pyridine-6,4'-piperidine]-1'-carboxylate (1.48 g). MS: m/z 337 $(M+H)^+$. MS: m/z 333 $(M+H)^+$.

The following compounds were synthesized using the above procedure or modification procedure with the corresponding starting materials.

TABLE 10

| |
|---|
| 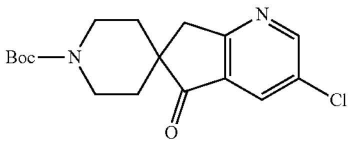 [SMILES: CC(C)(C)OC(=O)N1CCC2(CC1)Cc1ncc(Cl)cc1C2=O] |
| 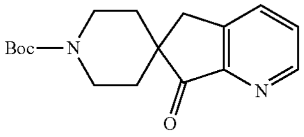 [SMILES: CC(C)(C)OC(=O)N1CCC2(CC1)Cc1cccnc1C2=O] |

Intermediate A19

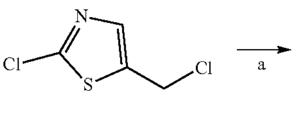

-continued

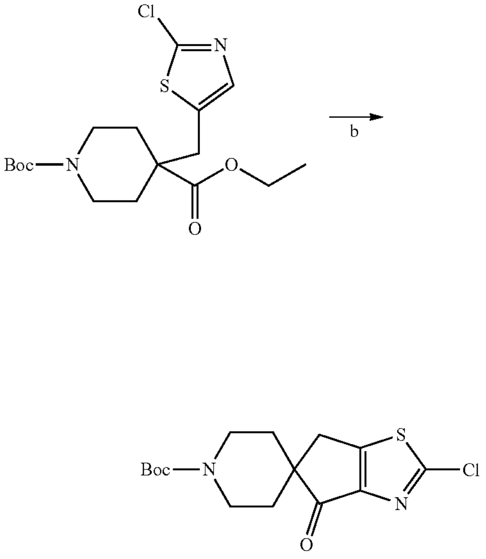

Step a: To a −78° C. solution of 1-(tert-butyl) 4-ethyl piperidine-1,4-dicarboxylate (2.83 g, 11.00 mmol) in THF (50 mL) was added LDA (2 M solution in THF/Hex, 6.00 mL, 12.00 mmol) dropwise under nitrogen atmosphere. The resulting mixture was stirred for 1 h at this temperature. 2-Chloro-5-(chloromethyl)thiazole (in 3 mL THF, 1.69 g, 10.06 mmol) was added dropwise at −78° C., and stirred for 1 h. The reaction mixture was quenched with brine (50 mL), extracted with EA (2×30 mL). The combined organic layers were dried over anhydrous $Na_2SO_4$, filtered and concentrated under reduced pressure. The residue was purified by silica chromatography (eluting with EA:Hex=1:20, v/v) to give 1-(tert-butyl) 4-ethyl 4-((2-chlorothiazol-5-yl)methyl) piperidine-1,4-dicarboxylate (1.15 g). MS: m/z 389 $(M+H)^+$.

Step b: To a −78° C. solution of 1-(tert-butyl) 4-ethyl 4-((2-chlorothiazol-5-yl)methyl) piperidine-1,4-dicarboxylate (900 mg, 2.31 mmol) in THF (50 mL) was added LDA (2 M solution in THF/Hex, 3.00 mL, 6.00 mmol) dropwise under nitrogen atmosphere. The resulting mixture was stirred for 30 min at this temperature, quenched with brine (30 mL). The resulting mixture was extracted with EA (2×30 mL), the organic layers combined, dried over anhydrous $Na_2SO_4$, filtered and concentrated under reduced pressure to give tert-butyl 2-chloro-4-oxo-4,6-dihydrospiro[cyclopenta[d]thiazole-5,4'-piperidine]-1'-carboxylate (832 mg). MS: m/z 343 $(M+H)^+$.

Intermediate A20

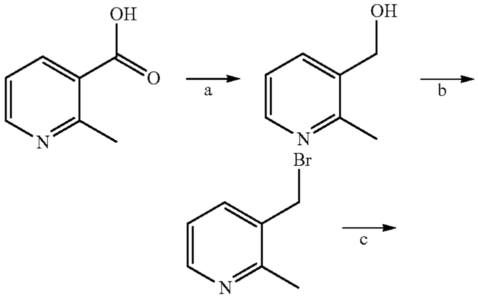

-continued

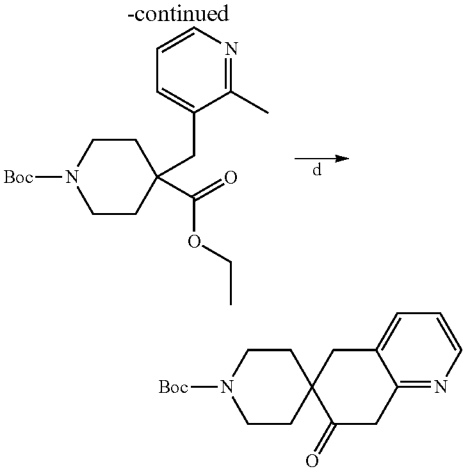

Step a: To a 0° C. solution of 2-methylnicotinic acid (4.56 g, 33.25 mmol) in THF (50 mL) was added LAH (1.51 g, 39.90 mmol). The resulting mixture was allowed to warm to RT and stirred for 4 h. The reaction mixture was diluted carefully with sat. aq. $NH_4Cl$ (50 mL). The resulting mixture was filtered, the organic extract was collected and dried over anhydrous $Na_2SO_4$, filtered and concentrated under reduced pressure to give (2-methylpyridin-3-yl) methanol as a yellow oil (1.42 g). MS: m/z 124 $(M+H)^+$.

Step b: To a 0° C. mixture of (2-methylpyridin-3-yl) methanol (1.41 g, 11.45 mmol) in DCM (20 mL) was added $PBr_3$ (1.86 g, 6.87 mmol) dropwise. The resulting mixture was allowed to warm to RT and stirred for 1.5 h. The reaction mixture was taken to pH 8 using aq. NaOH (5 M, 10 mL). The aqueous layer was separated and the organic layer was washed with brine (1×20 mL), dried over anhydrous $Na_2SO_4$ and concentrated under reduced pressure to give 3-(bromomethyl)-2-methylpyridine as a yellow oil (3.52 g) which was used in next step without any further purification. MS: m/z 186 $(M+H)^+$.

Step c: To a −50° C. solution of 1-tert-butyl 4-ethyl piperidine-1,4-dicarboxylate (4.63 g, 18.00 mmol) in THF (30 mL) was added LDA (2 M solution in THF/Hex, 12.00 mL, 24.00 mmol) dropwise, stirred for 1 h at this temperature. 3-(Bromomethyl)-2-methylpyridine (3.25 g, 18.00 mmol) was added, the resulting mixture was allowed to warm to RT and stirred for 16 h. The reaction mixture was diluted carefully with sat. aq. $NH_4Cl$ (50 mL). The aqueous layer was separated and the organic layer was washed with brine (1×50 mL), dried over anhydrous $Na_2SO_4$, filtered and concentrated under reduced pressure to give 1-(tert-butyl) 4-ethyl 4-((2-methylpyridin-3-yl)methyl)piperidine-1,4-dicarboxylate as a red oil (4.87 g) which was used in next step without any further purification. MS: m/z 363 $(M+H)^+$.

Step d: To a −20° C. solution of 1-(tert-butyl) 4-ethyl 4-((2-methylpyridin-3-yl)methyl) piperidine-1,4-dicarboxylate (4.23 g, 11.67 mmol) in THF (40 mL) was added LDA (2 M solution in THF/Hex, 12.00 mL, 24.00 mmol) dropwise, the resulting mixture was allowed to warm to RT and stirred for 2 h. The reaction mixture was diluted carefully with brine (50 mL). The aqueous layer was separated and the organic layer was dried over anhydrous $Na_2SO_4$, filtered and concentrated under reduced pressure. The residue was purified by silica chromatography (eluting with EA:Hex=1:1, v/v) to give tert-butyl 7'-oxo-7',8'-dihydro-5'H-spiro[piperidine-4,6'-quinoline]-1-carboxylate (1.23 g) as a yellow oil. MS: m/z 317 $(M+H)^+$.

Intermediate A21

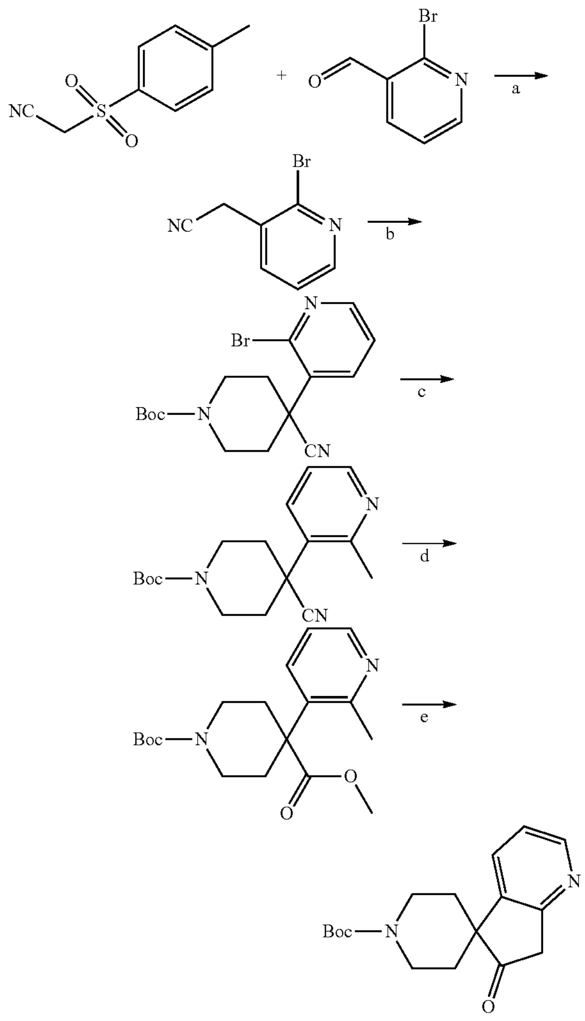

Step a: To a −60° C. mixture of t-BuOK (5.92 g, 52.76 mmol) in 1,2-dimethoxyethane (50 mL) was added a solution of 2-tosylacetonitrile (5.08 g, 26.02 mmol) in 1,2-dimethoxyethane (20 mL) dropwise. To the resulting mixture was added a solution of 2-bromonicotinaldehyde (4.81 g, 25.86 mmol) in 1,2-dimethoxyethane (20 mL) dropwise at −60° C. After stirring for 1 h at this temperature, MeOH was added (50 mL), the resulting mixture was allowed to warm to RT, stirred for 1 h and warmed to 85° C., stirred for another 1 h. After cooling to RT, the volatiles was removed under reduced pressure, diluted with brine (200 mL) and extracted with EA (3×150 mL). The combined organic layers were dried over anhydrous $Na_2SO_4$, filtered and concentrated under reduced pressure. The residue was purified by silica chromatography (eluting with EA:Hex=1:10, v/v) to give 2-(2-bromopyridin-3-yl)acetonitrile (2.21 g). MS: m/z 197 $(M+H)^+$.

Step b: To a 0° C. solution of 2-(2-bromopyridin-3-yl) acetonitrile (2.21 g, 11.21 mmol) in DMF (20 mL) was added NaH (60% dispersion in mineral oil, 1.12 g, 28.03 mmol) in portions. The resulting mixture was warmed to 60° C. and stirred for 1.5 h. Tert-butyl bis(2-chloroethyl)carbamate (3.26 g, 13.46 mmol) was added to the mixture and stirred for 2 h at 60° C. After cooling to RT, the reaction mixture was quenched with brine (50 mL), extracted with EA (3×100 mL). The combined organic layers were washed with brine (3×80 mL), dried over anhydrous $Na_2SO_4$, filtered and concentrated under reduced pressure. The residue was purified by silica chromatography (eluting with EA:Hex=1:3, v/v) to give tert-butyl 4-(2-bromopyridin-3-yl)-4-cyanopiperidine-1-carboxylate (1.56 g). MS: m/z 366 $(M+H)^+$.

Step c: A mixture of tert-butyl 4-(2-bromopyridin-3-yl)-4-cyanopiperidine-1-carboxylate (1.56 g, 4.26 mmol), $K_2CO_3$ (2.35 g, 17.04 mmol), 2,4,6-trimethyl-1,3,5,2,4,6-trioxatriborinane (1.07 g, 8.52 mmol) and $Pd(PPh_3)_4$ (47 mg, 0.041 mmol) in 1,4-dioxane (40 mL) and water (8 mL) was stirred for 2 h at 110° C. under nitrogen atmosphere. An additional portion of 2,4,6-trimethyl-1,3,5,2,4,6-trioxatriborinane (2.15 g, 17.13 mmol) and $Pd(PPh_3)_4$ (45 mg, 0.039 mmol) was added and stirred for another 3 h at 110° C. After cooling to RT, the reaction mixture was diluted with brine (100 mL), extracted with EA (3×100 mL), the organic layers combined, dried over anhydrous $Na_2SO_4$, filtered and concentrated under reduced pressure. The residue was purified by silica chromatography (eluting with EA:Hex=2:1, v/v) to give tert-butyl 4-cyano-4-(2-methylpyridin-3-yl)piperidine-1-carboxylate (1.08 g). MS: m/z 302 $(M+H)^+$.

Step d: To a 0° C. solution of tert-butyl 4-cyano-4-(2-methylpyridin-3-yl)piperidine-1-carboxylate (1.08 g, 3.58 mmol) in MeOH (50 mL) was added $H_2SO_4$ (98%, 45 mL) dropwise. The resulting mixture was stirred for 18 h at reflux temperature. After cooling to RT, the reaction mixture was poured into ice/water (200 mL), the pH value was adjusted to 9 with sat. aq. NaOH. To the mixture was added $(Boc)_2O$ (11.00 g, 50.40 mmol) and stirred for 2 h at RT. The reaction mixture was extracted with EA (3×100 mL), the organic layers combined, dried over anhydrous $Na_2SO_4$, filtered and concentrated under reduced pressure. The residue was purified by silica chromatography (eluting with EA) to give 1-(tert-butyl) 4-methyl 4-(2-methylpyridin-3-yl)piperidine-1,4-dicarboxylate (467 mg). MS: m/z 335 $(M+H)^+$.

Step e: To a 0° C. solution of 1-(tert-butyl) 4-methyl 4-(2-methylpyridin-3-yl)piperidine-1,4-dicarboxylate (467 mg, 1.40 mmol) in THF (10.50 mL) was potassium bis (trimethylsilyl)amide (1 M solution in THF, 7.00 mL, 7.00 mmol) dropwise under nitrogen atmosphere. The resulting mixture was allowed to warm to RT and stirred for 3.5 h, then quenched with $sat.aq.NH_4Cl$ (10 mL) and extracted with EA (3×40 mL). The combined organic layers were dried over anhydrous $Na_2SO_4$, filtered and concentrated under reduced pressure. The residue was purified by silica chromatography (eluting with EA) to give tert-butyl 6-oxo-6,7-dihydrospiro[cyclopenta[b]pyridine-5,4'-piperidine]-1'-carboxylate (170 mg). MS: m/z 303 $(M+H)^+$.

Intermediate A22

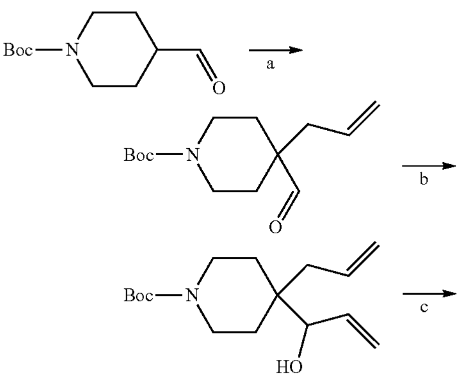

-continued

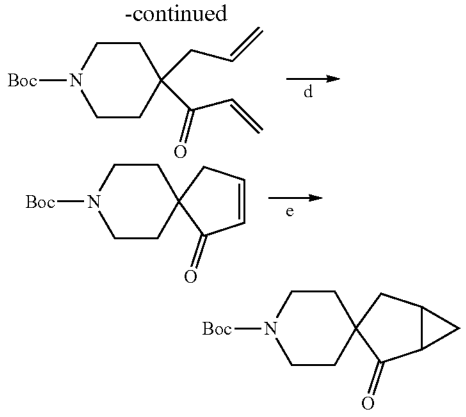

Step a: To a 0° C. mixture of tert-butyl 4-formylpiperidine-1-carboxylate (15.00 g, 70.33 mmol) in DMF (60 mL) was added lithium 2-methylpropan-2-olate (6.75 g, 84.44 mmol) in portions. The resulting mixture was stirred for 30 min at 0° C. To the mixture was added 3-bromoprop-1-ene (9.73 g, 80.44 mmol) dropwise at 0° C. and stirred for 1 h at this temperature. The reaction mixture was diluted with brine (100 mL), extracted with EA (3×200 mL). The organic layers were combined, dried over anhydrous $Na_2SO_4$, filtered and concentrated under reduced pressure. The residue was purified by silica chromatography (eluting with EA:Hex=1:20, v/v) to give tert-butyl 4-allyl-4-formylpiperidine-1-carboxylate (7.01 g). MS: m/z 254 $(M+H)^+$.

Step b: To a −78° C. solution of tert-butyl 4-allyl-4-formylpiperidine-1-carboxylate (7.01 g, 27.63 mmol) in THF (30 mL) was added allylmagnesium bromide (1 M solution in THF, 63.55 mL, 63.55 mmol) dropwise. The resulting mixture was allowed to warm to RT and stirred for 1.5 h. The reaction mixture was quenched with sat. aq. $NH_4Cl$, extracted with EA (3×200 mL). The combined organic layers were washed with brine (1×200 mL), dried over anhydrous $Na_2SO_4$, filtered and concentrated under reduced pressure to give tert-butyl 4-allyl-4-(1-hydroxyallyl)piperidine-1-carboxylate (7.01 g). MS: m/z 282 $(M+H)^+$.

Step c: To a solution of tert-butyl 4-allyl-4-(1-hydroxyallyl)piperidine-1-carboxylate (7.00 g, 24.88 mmol) in DCM (50 mL) was added Dess-Martin periodinane (12.66 g, 29.85 mmol) in portions. After stirring for 1.5 h at RT, the reaction mixture was diluted with brine (150 mL) and extracted with EA (3×200 mL). The combined organic layers were dried over anhydrous $Na_2SO_4$, filtered and concentrated under reduced pressure. The residue was purified by silica chromatography (EA:Hex=1:30, v/v) to give tert-butyl 4-acryloyl-4-allylpiperidine-1-carboxylate (5.63 g). MS: m/z 280 $(M+H)^+$.

Step d: A mixture of tert-butyl 4-acryloyl-4-allylpiperidine-1-carboxylate (5.63 g, 20.15 mmol), Grubbs II (428 mg, 0.50 mmol) and toluene (30 mL) was stirred for 3.5 h at 85° C. under nitrogen atmosphere. After cooling to RT, the mixture was concentrated under reduced pressure. The residue was purified by silica chromatography (eluting with EA:Hex=1:5, v/v) to give tert-butyl 1-oxo-8-azaspiro[4.5]dec-2-ene-8-carboxylate (3.61 g). MS: m/z 252 $(M+H)^+$.

Step e: To a solution of trimethylsulfoxonium iodide (3.79 g, 17.22 mmol) in DMSO (50 mL) was added NaH (60% dispersion in mineral oil, 730 mg, 18.25 mmol) in portions. After stirring for 30 min, tert-butyl 1-oxo-8-azaspiro[4.5]dec-2-ene-8-carboxylate (a DMSO solution, 3.61 g, 14.36 mmol) was added dropwise. The resulting mixture was stirred for 1.5 h at RT. The reaction mixture was diluted with brine (200 mL), extracted with EA (3×200 mL). The combined organic layers were washed with brine (3×200 mL), dried over anhydrous $Na_2SO_4$, filtered and concentrated under reduced pressure to give tert-butyl 2-oxospiro[bicyclo[3.1.0]hexane-3,4'-piperidine]-1'-carboxylate (3.60 g). MS: m/z 266 $(M+H)^+$.

Intermediate A23

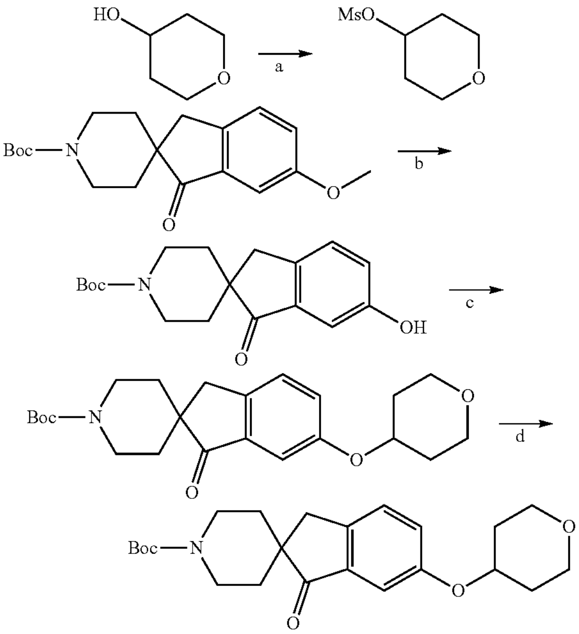

Step a: To a −10° C. solution of tetrahydro-2H-pyran-4-ol (3.54 g, 34.66 mmol), triethylamine (4.65 g, 45.95 mmol) in DCM (100 mL) was added MsCl (4.61 g, 40.24 mmol) dropwise. After stirring for 30 min, the reaction mixture was diluted with water (100 mL), extracted with DCM (100 mL, 50 mL). The combined organic layers were washed with brine (1×50 mL), dried over anhydrous $Na_2SO_4$, filtered and concentrated under reduced pressure to give tetrahydro-2H-pyran-4-yl methanesulfonate (6.74 g). MS: m/z 181 $(M+H)^+$.

Step b: To a solution of 1'-benzyl-6-methoxyspiro[indene-2,4'-piperidin]-1(3H)-one (4.35 g, 13.53 mmol) in DCM (200 mL) was added $BBr_3$ (1 M solution in DCM, 15.00 mL, 15.00 mmol), stirred for 13 h at 45° C. An additional portion of $BBr_3$ (1 M solution in DCM, 5.00 mL, 5.00 mmol) was added and stirred for 24 h at 45° C. After cooling to RT, the reaction mixture was diluted with water (150 mL), $NaHCO_3$ (20.00 g) was added in portions. The resulting mixture was extracted with DCM (2×100 mL), the organic layers combined, dried over anhydrous $Na_2SO_4$, filtered and concentrated under reduced pressure to give 1'-benzyl-6-hydroxyspiro[indene-2,4'-piperidin]-1(3H)-one (2.80 g) which was used in next step without any further purification. MS: m/z 308 $(M+H)^+$.

Step c: A mixture of 1'-benzyl-6-hydroxyspiro[indene-2,4'-piperidin]-1(3H)-one (2.80 g, 9.11 mmol), tetrahydro-2H-pyran-4-yl methanesulfonate (3.40 g, 18.87 mmol) and $K_2CO_3$ (8.23 g, 59.55 mmol) in DMF (60 mL) was stirred for 5.5 h at 110° C. An additional portion of tetrahydro-2H-pyran-4-yl methanesulfonate (1.10 g, 6.10 mmol) and $K_2CO_3$ (4.55 g, 32.92 mmol) was added and stirred for 1.5 h at 110° C. After cooling to RT, the mixture was diluted with water (300 mL) and EA (600 mL). The aqueous layer was separated and extracted with EA (1×200 mL), the organic layers combined, washed with water (2×300 mL) and brine (1×300 mL), dried over anhydrous $Na_2SO_4$, filtered and concentrated under reduced pressure. The residue was purified by silica chromatography (eluting with MeOH:DCM=1:40, v/v) to give 1'-benzyl-6-((tetrahydro-2H-pyran-4-yl)oxy)spiro[indene-2,4'-piperidin]-1(3H)-one (1.70 g). MS: m/z 392 $(M+H)^+$.

Step d: A mixture of 1'-benzyl-6-((tetrahydro-2H-pyran-4-yl)oxy)spiro[indene-2,4'-piperidin]-1(3H)-one (1.70 g, 4.34 mmol) and $Pd(OH)_2$ (10% on carbon, 1.21 g) in MeOH was stirred for 3 h at RT under hydrogen atmosphere. The reaction mixture was filtered. To the filtration was added $(Boc)_2O$ (1.10 g, 5.04 mmol) and stirred for 40 h at RT. The reaction mixture was concentrated under reduced pressure. The residue was purified by silica chromatography (eluting with EA:Hex=1:5, v/v) to give tert-butyl 1-oxo-6-((tetrahydro-2H-pyran-4-yl)oxy)-1,3-dihydrospiro[indene-2,4'-piperidine]-1'-carboxylate (1.45 g). MS: m/z 402 $(M+H)^+$.

Intermediate A24

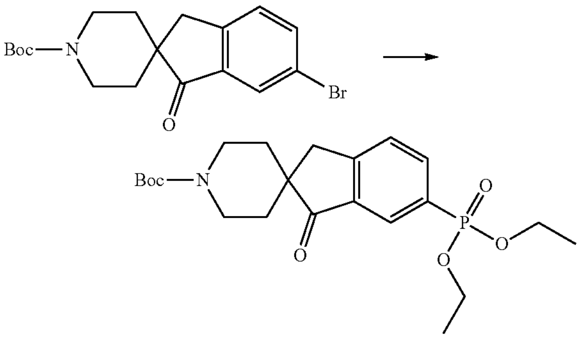

A mixture of tert-butyl 6-bromo-1-oxo-1,3-dihydrospiro[indene-2,4'-piperidine]-1'-carboxylate (1017 mg, 2.67 mmol), diethyl phosphonate (564 mg, 4.08 mmol), potassium phosphate (1156 mg, 5.45 mmol), $Pd(OAc)_2$ (63 mg, 0.28 mmol) and XantPhos (307 mg, 0.53 mmol) in DMF (10 mL) was stirred for 21 h at 130° C. under nitrogen atmosphere. After cooling to RT, the reaction mixture was quenched with water (60 mL), filtered followed by EA (2×30 mL) wash. The layers of the filtration was separated, the aqueous layer was extracted with EA (2×60 mL). The combined organic layers were dried over anhydrous $Na_2SO_4$, filtered and concentrated under reduced pressure. The residue was purified by silica chromatography (eluting with EA) to give tert-butyl 6-(diethoxyphosphoryl)-1-oxo-1,3-dihydrospiro[indene-2,4'-piperidine]-1'-carboxylate (134 mg) which was used in next step without any further purification. MS: m/z 438 $(M+H)^+$.

Intermediate A25

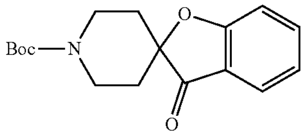 [SMILES: CC(C)(C)OC(=O)N1CCC2(CC1)Oc1ccccc1C2=O]

Following procedures of Y. Uto et al./*Bioorg. Med. Chem. Lett.* 20 (2010) 746-754, intermediate A25 was prepared.

The following compound was synthesized using the above procedure with the corresponding starting materials.

TABLE 11

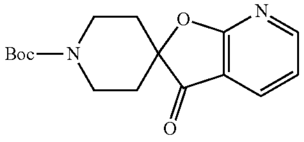 [SMILES: CC(C)(C)OC(=O)N1CCC2(CC1)Oc1ncccc1C2=O]

Intermediate A26

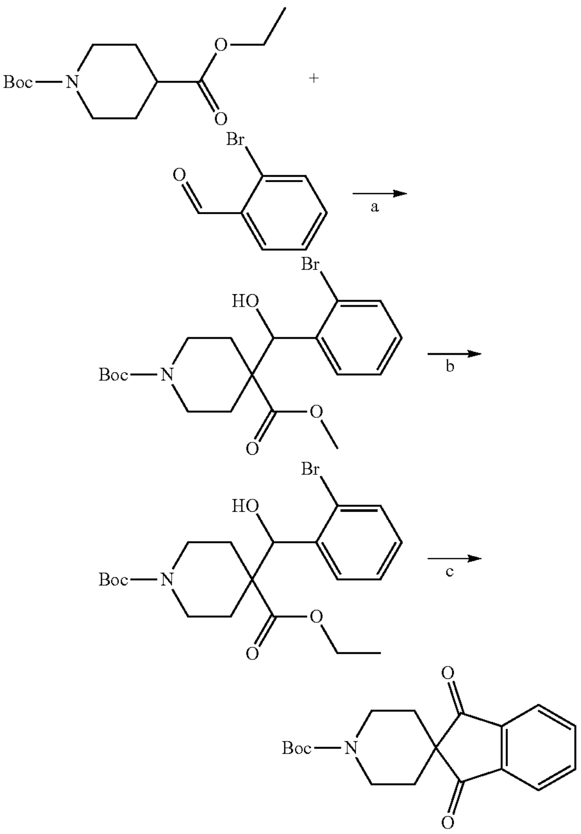

Step a: To a −65° C. solution of 1-(tert-butyl) 4-ethyl piperidine-1,4-dicarboxylate (5.23 g, 20.32 mmol) in THF (30 ml) was added LDA (2 M solution in THF/Hex, 12.00 mL, 24.00 mmol) dropwise. The resulting mixture was stirred for 1.0 h at this temperature. 2-Bromobenzaldehyde (3.44 g, 18.59 mmol) was added dropwise at −70° C. After stirring for 1 h, the mixture was quenched with brine (40 mL). The organic layer was separated, dried over anhydrous $Na_2SO_4$, filtered and concentrated under reduced pressure to give 1-(tert-butyl) 4-ethyl 4-((2-bromophenyl)(hydroxy)methyl)piperidine-1,4-dicarboxylate (9.15 g) which was used in next step without any further purification. MS: m/z 442 $(M+H)^+$.

Step b: To a −5° C. solution of 1-(tert-butyl) 4-ethyl 4-((2-bromophenyl)(hydroxy)methyl) piperidine-1,4-dicarboxylate (9.15 g, 20.68 mmol) in DCM (70 ml) was added Dess-Martin periodinane (18.02 g, 42.49 mmol). The resulting mixture was stirred for 2.5 h at RT. The reaction mixture was washed with aq. $Na_2S_2O_3$ (25%, 1×80 mL), sat. aq. $NaHCO_3$ (1×80 mL) and brine (1×100 mL). The organic layer was dried over anhydrous $Na_2SO_4$, filtered and concentrated under reduced pressure. The residue was purified by silica chromatography (eluting with EA:Hex 25=1:5, v/v) to give 1-(tert-butyl) 4-ethyl 4-(2-bromobenzoyl)piperidine-1,4-dicarboxylate (7.16 g). MS: m/z 440 $(M+H)^+$.

Step d: To a −80° C. solution of 1-(tert-butyl) 4-ethyl 4-(2-bromobenzoyl)piperidine-1,4-dicarboxylate (2.00 g, 4.54 mmol) in THF (20 mL) was added n-BuLi (2.5 M solution in THF/Hex, 1.80 mL, 4.50 mmol) dropwise under nitrogen atmosphere. The resulting mixture was allowed to warm to RT and stirred for 1 h. The reaction mixture was quenched with brine (30 mL) and extracted with EA (1×20 mL). The organic layer was dried over anhydrous $Na_2SO_4$, filtered and concentrated under reduced pressure. The residue was purified by silica chromatography (eluting with EA:Hex=1:10, v/v) to give tert-butyl 1,3-dioxo-1,3-dihydrospiro[indene-2,4'-piperidine]-1'-carboxylate (500 mg). MS: m/z 316 $(M+H)^+$.

Intermediate A27

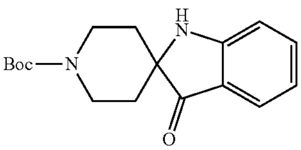 [SMILES: CC(C)(C)OC(=O)N1CCC2(CC1)Nc1ccccc1C2=O]

Following procedures of *J. Org. Chem.* 1999, 64, 5504-5510, intermediate A27 was prepared.

Intermediate A28

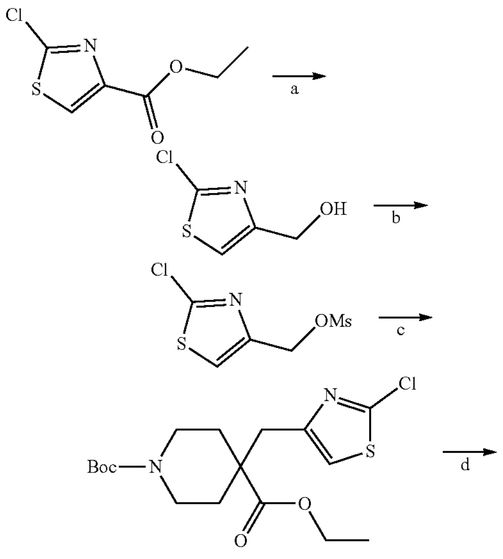

-continued

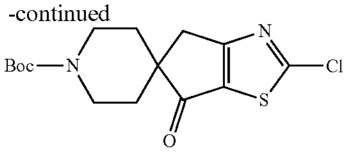

Step a: To a 0° C. solution of ethyl 2-chlorothiazole-4-carboxylate (24.95 g, 130.19 mmol) in MeOH (250 mL) was added $NaBH_4$ (17.29 g, 456.97 mmol) in portions. The resulting mixture was allowed to warm to RT and stirred for 2 h. The reaction mixture was diluted with water (200 mL) and the volatiles were removed under reduced pressure. The resulting mixture was extracted with EA (2×200 mL), the combined organic layers were washed with brine (1×400 mL), dried over anhydrous $Na_2SO_4$, filtered and concentrated under reduced pressure to give (2-chlorothiazol-4-yl) methanol (18.88 g). MS: m/z 150 $(M+H)^+$.

Step b: To a solution of (2-chlorothiazol-4-yl)methanol (18.88 g, 130.19 mmol) and triethylamine (25.56 g, 252.57 mmol) in DCM (200 mL) was added MsCl (15.96 g, 139.30 mmol) dropwise over 15 min. The resulting mixture was stirred for 25 min at RT. The reaction mixture was quenched with brine (200 mL) and the aqueous layer was separated. The organic layer was dried over anhydrous $Na_2SO_4$, filtered and concentrated under reduced pressure to give (2-chlorothiazol-4-yl)methyl methanesulfonate which was used in next step without any further purification. MS: m/z 228 $(M+H)^+$.

Step c: To a −60° C. solution of 1-(tert-butyl) 4-ethyl piperidine-1,4-dicarboxylate (35.67 g, 138.62 mmol) in THF (200 mL) was added LDA (2 M solution in THF/Hex, 75.00 mL, 150.00 mmol) dropwise over 30 min under nitrogen atmosphere. A solution of (2-chlorothiazol-4-yl) methyl methanesulfonate in THF (50 mL) was added dropwise, the resulting mixture was allowed to warmed to RT and stirred for 2 h. The reaction mixture was quenched with brine (300 mL). The organic layer was separated, dried over anhydrous $Na_2SO_4$, filtered and concentrated under reduced pressure. The residue was purified by silica chromatography (eluting with EA:Hex=1:10, v/v) to give 1-(tert-butyl) 4-ethyl 4-((2-chlorothiazol-4-yl)methyl) piperidine-1,4-dicarboxylate (38.12 g). MS: m/z 389 $(M+H)^+$.

Step d: To a −60° C. solution of 1-(tert-butyl) 4-ethyl 4-((2-chlorothiazol-4-yl)methyl) piperidine-1,4-dicarboxylate (8.51 g, 21.88 mmol) in THF (80 mL) was added LDA (2 M solution in THF/Hex, 11.00 mL, 22.00 mmol) dropwise under nitrogen atmosphere. Once finished, the reaction mixture was quenched with brine (50 mL). The organic layer was separated, dried over anhydrous $Na_2SO_4$, filtered and concentrated under reduced pressure. The residue was purified by silica chromatography (eluting with EA:Hex=1:10, v/v) to give tert-butyl 2-chloro-6-oxo-4,6-dihydrospiro[cyclopenta[d]thiazole-5,4'-piperidine]-1'-carboxylate (1.93 g). MS: m/z 343 (M+H).

Intermediate A29

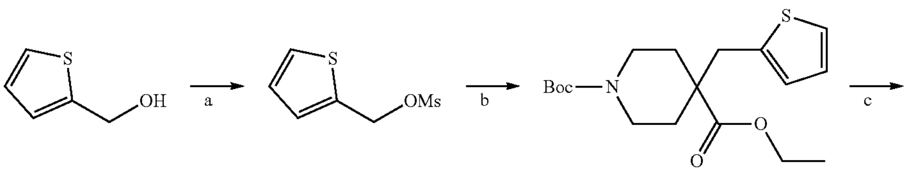

-continued

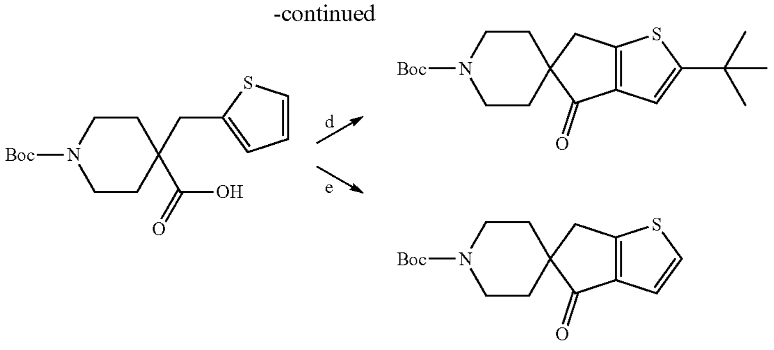

Step (a-c): Step (b-c) of Intermediate A28 and step (b) of Intermediate A3 were applied to provide 1-(tert-butoxycarbonyl)-4-(thiophen-2-ylmethyl)piperidine-4-carboxylic acid.

Step d: A mixture of 1-(tert-butoxycarbonyl)-4-(thiophen-2-ylmethyl)piperidine-4-carboxylic acid (4.92 g, 15.12 mmol) and PPA (30.12 g) was stirred for 5 h at 110° C. The reaction mixture was poured into ice/water (100 mL), the pH value was adjusted to 10 with NaOH. Then $(Boc)_2O$ (5.05 g, 23.14 mmol) was added and stirred for 18 h at RT. The reaction mixture was extracted with EA (2×50 mL). The combined organic layers were washed with brine (1×50 mL), dried over anhydrous $Na_2SO_4$, filtered and concentrated under reduced pressure to give tert-butyl 2-(tert-butyl)-4-oxo-4,6-dihydrospiro[cyclopenta[b]thiophene-5,4'-piperidine]-1'-carboxylate (1.70 g). MS: m/z 364 $(M+H)^+$.

Step e: A mixture of 1-(tert-butoxycarbonyl)-4-(thiophen-2-ylmethyl)piperidine-4-carboxylic acid (4.88 g, 15.12 mmol) and HCl (4M solution in 1,4-dioxane, 8 mL) in DCM (50 mL) was stirred for 1 h at RT. The reaction mixture was concentrated under reduced pressure. PPA (21.15 g) was added and the resulting mixture was stirred for 1.5 h at 110° C. The reaction mixture was poured into ice/water (100 mL), the pH value was adjusted to 10 with NaOH. Then $(Boc)_2O$ (5.12 g, 23.46 mmol) was added and stirred for 18 h at RT. The reaction mixture was extracted with EA (2×50 mL). The combined organic layers were washed with brine (1×100 mL), dried over anhydrous $Na_2SO_4$, filtered and concentrated under reduced pressure. The residue was purified by silica chromatography (eluting with EA:Hex=1:10, v/v) to give tert-butyl4-oxo-4,6-dihydrospiro[cyclopenta[b]thiophene-5,4'-piperidine]-1'-carboxylate (2.71 g). MS: m/z 308 $(M+H)^+$.

Intermediate A30

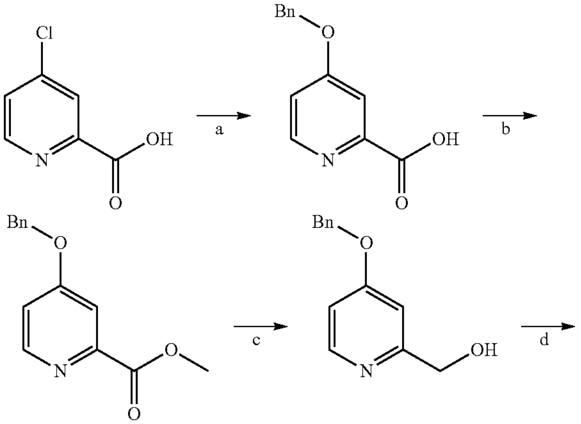

-continued

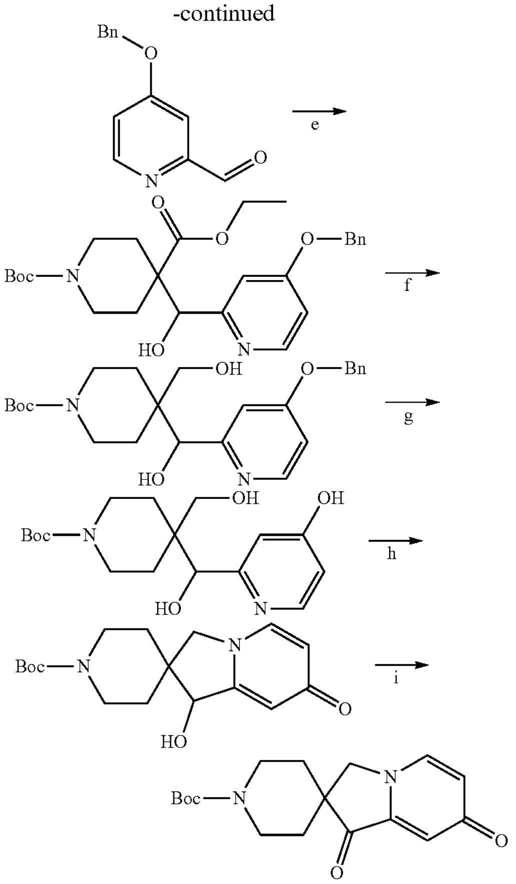

Step a: To a solution of phenylmethanol (5.15 g, 47.62 mmol) in DMF (50 mL) was added NaH (60% dispersion in mineral oil, 3.01 g, 75.25 mmol) in portions, stirred for 20 min. 4-Chloropicolinic acid (2.68 g, 17.01 mmol) was added and stirred for 3.5 h at 85° C. After cooling to RT, HCl (4 M solution in 1,4-dioxane, 10 mL) was added. The resulting mixture was used in next step. MS: m/z 230 $(M+H)^+$.

Step b: The mixture was mixed with $NaHCO_3$ (7.51 g, 89.39 mmol), $CH_3I$ (1.5 mL) and DMF (10 mL). After stirring for 0.5 h, an additional portion of $CH_3I$ (1.5 mL) was added and stirred for 16 h. The reaction mixture was diluted with EA (250 mL), filtered and the filtration was washed with brine (2×150 mL). The organic layer was dried over anhydrous $Na_2SO_4$, filtered and concentrated under reduced pressure. The residue was purified by silica chromatography (eluting with EA:Hex=1:1, v/v) to give methyl 4-(benzyloxy)picolinate (1.50 g). MS: m/z 244 $(M+H)^+$.

Step c: A mixture of methyl 4-(benzyloxy)picolinate (1.50 g, 6.17 mmol), $LiBH_4$ (2M solution in THF, 9.00 mL, 18.00 mmol) in THF (40 mL) was stirred for 1 h at 50° C. The reaction mixture was diluted with MeOH (15 mL) and water (150 mL), extracted with EA (200 mL, 50 mL). The combined organic layers were washed with brine (2×100 mL), dried over anhydrous $Na_2SO_4$, filtrated and concentrated under reduced pressure. The residue was purified by silica chromatography (eluting with EA) to give (4-(benzyloxy)pyridin-2-yl)methanol (0.50 g). MS: m/z 216 $(M+H)^+$.

Step d: A mixture of (4-(benzyloxy)pyridin-2-yl)methanol (0.50 g, 2.32 mmol), dess-martin periodinane (1.25 g, 2.95 mmol) in DCM (20 mL) was stirred for 1.5 h. The reaction mixture was diluted with sat.aq.$NaHSO_3$, sat.aq.$NaHCO_3$ and DCM (50 mL). The aqueous layer was separated and extracted with DCM (50 mL). The combined organic layers were dried over anhydrous $Na_2SO_4$, filtrated and concentrated under reduced pressure. The residue was purified by silica chromatography to give 4-(benzyloxy)picolinaldehyde (0.40 g). MS: m/z 214 $(M+H)^+$.

Step e: To a 0° C. solution of 1-(tert-butyl) 4-ethyl piperidine-1,4-dicarboxylate (0.52 g, 2.02 mmol) in THF (15 mL) was added LDA (2 M solution in THF/Hex, 1.30 mL, 2.60 mmol) dropwise. The resulting mixture was cooled to −70° C., a solution of 4-(benzyloxy)picolinaldehyde (0.40 g, 1.88 mmol) in THF (5 mL) was added. The resulting mixture was allowed to warm to −15° C. and stirred for 30 min, then quenched with sat.aq.$NH_4Cl$ (10 mL), diluted with water (50 mL) and extracted with EA (1×100 mL). The organic layer was washed with brine (2×50 mL), dried over anhydrous $Na_2SO_4$, filtered and concentrated under reduced pressure. The residue was purified by silica chromatography (eluting with EA:Hex=1:1) to give 1-(tert-butyl) 4-ethyl 4-((4-(benzyloxy)pyridin-2-yl)(hydroxy)methyl)piperidine-1,4-dicarboxylate (0.25 g). MS: m/z 471 $(M+H)^+$.

Step f: A mixture of 1-(tert-butyl) 4-ethyl 4-((4-(benzyloxy)pyridin-2-yl)(hydroxy) methyl)piperidine-1,4-dicarboxylate (0.25 g, 0.53 mmol), $LiBH_4$ (2 M solution in THF, 1.00 mL, 2.00 mmol) in THF (10 mL) was stirred for 40 min at 55° C. The reaction mixture was quenched with MeOH (10 mL), the volatiles were removed under reduced pressure. The residue was diluted with water (150 mL), extracted with EA (1×50 mL). The organic layer was washed with brine (1×30 mL), dried over anhydrous $Na_2SO_4$, filtrated and concentrated under reduced pressure to give tert-butyl 4-((4-(benzyloxy)pyridin-2-yl)(hydroxy)methyl)-4-(hydroxymethyl)piperidine-1-carboxylate (0.22 g). MS: m/z 429 $(M+H)^+$.

Step g: A mixture of tert-butyl 4-((4-(benzyloxy)pyridin-2-yl)(hydroxy)methyl)-4-(hydroxymethyl)piperidine-1-carboxylate (0.22 g, 0.51 mmol), Pd (10% on carbon, 0.12 g) in MeOH (20 mL) was stirred for 1.5 h under hydrogen atmosphere. The reaction mixture filtrated follow by MeOH wash and the filtration was concentrated under reduced pressure to give tert-butyl 4-(hydroxy(4-hydroxypyridin-2-yl)methyl)-4-(hydroxymethyl)piperidine-1-carboxylate (154 mg). MS: m/z 339 $(M+H)^+$.

Step h: To a mixture of tert-butyl 4-(hydroxy(4-hydroxypyridin-2-yl)methyl)-4-(hydroxymethyl)piperidine-1-carboxylate (120 mg, 0.36 mmol) and triphenyl phosphate (175 mg, 0.67 mmol) in THF (10 mL) was added N,N,N',N'-tetramethylazodicarboxamide (158 mg, 0.68 mmol). The mixture was stirred for 30 min at RT. The reaction was purified by silica chromatography (eluting with MeOH:DCM=1:7, v/v) to give tert-butyl 1-hydroxy-7-oxo-1,7-dihydro-3H-spiro[indolizine-2,4'-piperidine]-1'-carboxylate (100 mg). MS: m/z 321 $(M+H)^+$.

Step i: A mixture of tert-butyl1-hydroxy-7-oxo-1,7-dihydro-3H-spiro[indolizine-2,4'-piperidine]-1'-carboxylate (0.35 g, 1.09 mmol), Dess-Martin periodinane (0.72 g, 1.70 mmol) and DCM (35 mL) was stirred for 2 h at RT. The resulting mixture was washed with sat.aq.$Na_2SO_3$ (1×20 mL) and sat.aq.$NaHCO_3$ (1×20 mL). The organic layer was dried over anhydrous $Na_2SO_4$, filtered and concentrated under reduced pressure to give tert-butyl 1,7-dioxo-1,7-dihydro-3H-spiro[indolizine-2,4'-piperidine]-1'-carboxylate (0.33 g). MS: m/z 319 $(M+H)^+$.

The following compounds were synthesized using the above procedure with the corresponding starting materials.

TABLE 12

| |
|---|
| 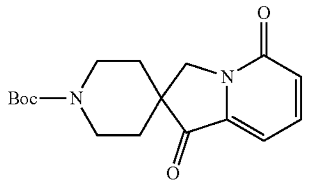 [SMILES: CC(C)(C)OC(=O)N1CCC2(CC1)Cn1c(cccc1=O)C2=O] |
| 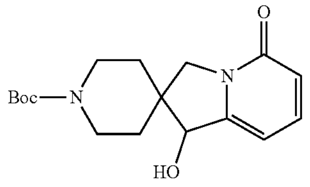 [SMILES: CC(C)(C)OC(=O)N1CCC2(CC1)Cn1c(cccc1=O)C2O] |

Intermediate B1

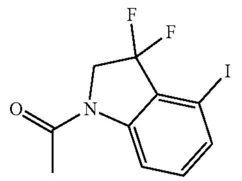

Following procedures of WO2017211303 A1, intermediate B1 was prepared from 4-iodoindoline-2,3-dione in 3 steps.

Intermediate B2

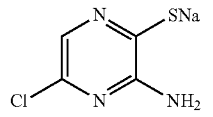

Following procedures of WO2017211303 A1, intermediate B2 was prepared from 3-bromo-6-chloropyrazin-2-amine in 2 steps.

The following compounds were synthesized using the above procedure or modifications procedure with the corresponding starting materials.

TABLE 13

| |
|---|
| 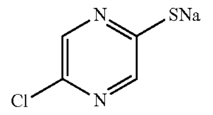 |

TABLE 13-continued

| |
|---|
| 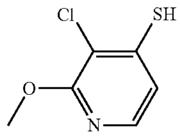 |
| 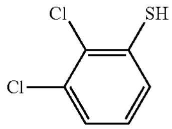 |

Intermediate B3

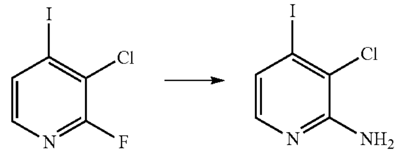 [SMILES: Fc1nccc(I)c1Cl ; Nc1nccc(I)c1Cl]

3-Chloro-2-fluoro-4-iodopyridine (10.10 g, 39.23 mmol) and DMSO (50 mL) was added to a sealed tube, ammonium hydroxide (25%, 50 mL) was added dropwise. The resulting mixture was stirred for 16 h at 80° C. After cooling to RT, the reaction mixture was poured into water (250 mL), the resulting precipitate was collected, dissolved in DCM (280 mL), washed with brine (1×100 mL), dried over anhydrous $Na_2SO_4$, filtered and concentrated under reduced pressure to give 3-chloro-4-iodopyridin-2-amine (7.01 g). MS: m/z 255 $(M+H)^+$.

The following compounds were synthesized using the above procedure or modification procedure with the corresponding starting materials.

TABLE 14

| |
|---|
| 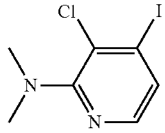 |
| 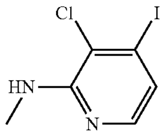 |

Intermediate B4

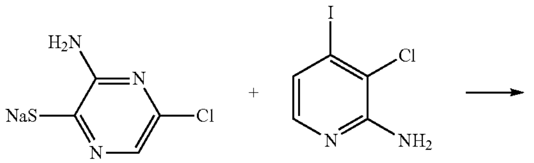

-continued

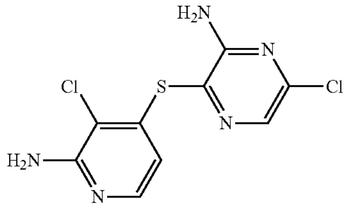

A mixture of 3-chloro-4-iodopyridin-2-amine (25.53 g, 100.33 mmol), sodium 3-amino-5-chloropyrazine-2-thiolate (20.18 g, 109.92 mmol), $Pd_2(dba)_3$ (4.47 g, 4.88 mmol), XantPhos (5.81 g, 10.04 mmol) and DIEA (26.12 g, 202.10 mmol) in 1,4-dioxane (10 mL) was stirred for 1.5 h at 70° C. under nitrogen atmosphere. After cooling to RT, the reaction mixture was filtered through a pad of Celite followed by 1,4-dioxane (30 mL) wash and the filtrate was concentrated under reduced pressure. DCM (100 mL) and EA (100 mL) were added and the resulting mixture was stirred for 40 min. The precipitate was collected, dried in a vacuum oven to give 3-((2-amino-3-chloropyridin-4-yl)thio)-6-chloropyrazin-2-amine (13.86 g). MS: m/z 288 $(M+H)^+$.

The following compounds were synthesized using the above procedure or modification procedure with the corresponding starting materials.

TABLE 15

| |
|---|
| 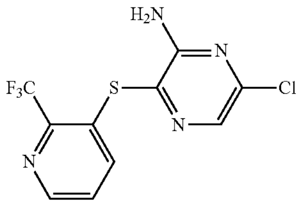 [SMILES: Nc1nc(Cl)cnc1Sc1cccnc1C(F)(F)F] |
| 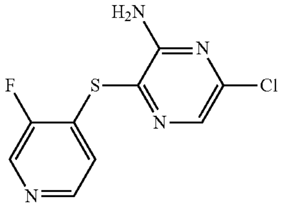 [SMILES: Nc1nc(Cl)cnc1Sc1ccncc1F] |
| 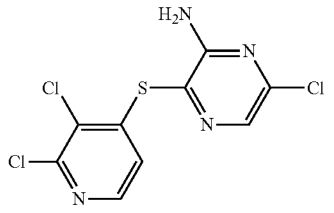 [SMILES: Nc1nc(Cl)cnc1Sc1ccnc(Cl)c1Cl] |
| 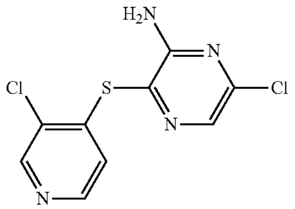 [SMILES: Nc1nc(Cl)cnc1Sc1ccncc1Cl] |

TABLE 15-continued
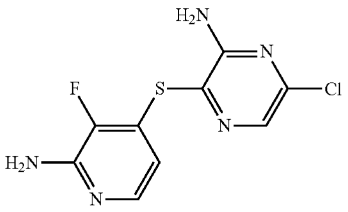 [SMILES: Nc1nc(Cl)cnc1Sc1ccnc(N)c1F]
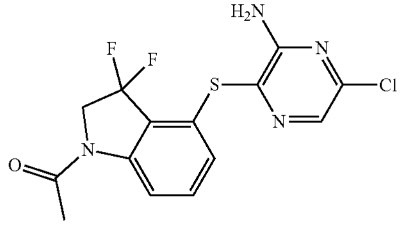 [SMILES: CC(=O)N1CC(F)(F)c2c(Sc3ncc(Cl)nc3N)cccc21]
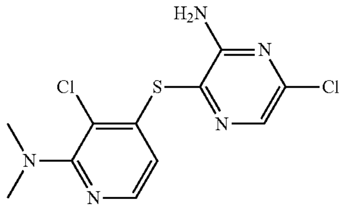 [SMILES: CN(C)c1nccc(Sc2ncc(Cl)nc2N)c1Cl]
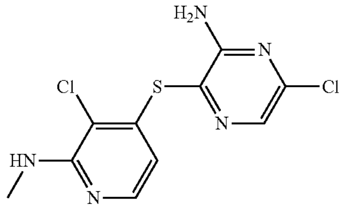
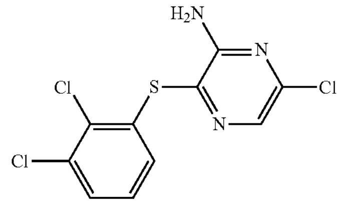 [SMILES: Nc1nc(Cl)cnc1Sc1cccc(Cl)c1Cl]
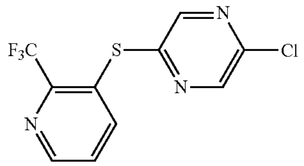 [SMILES: FC(F)(F)c1ncccc1Sc1cnc(Cl)cn1]
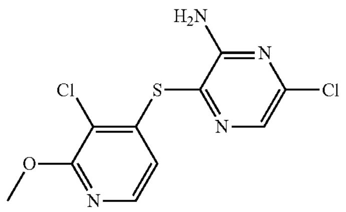 [SMILES: COc1nccc(Sc2ncc(Cl)nc2N)c1Cl]
TABLE 15-continued
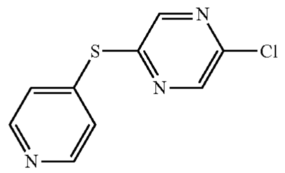 [SMILES: Clc1cnc(Sc2ccncc2)cn1]
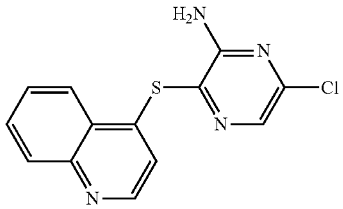 [SMILES: Nc1nc(Cl)cnc1Sc1ccnc2ccccc12]
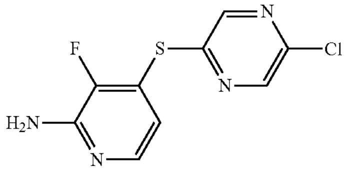 [SMILES: Nc1nccc(Sc2cnc(Cl)cn2)c1F]
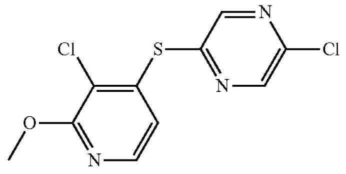 [SMILES: COc1nccc(Sc2cnc(Cl)cn2)c1Cl]
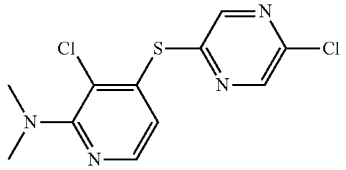 [SMILES: CN(C)c1nccc(Sc2cnc(Cl)cn2)c1Cl]
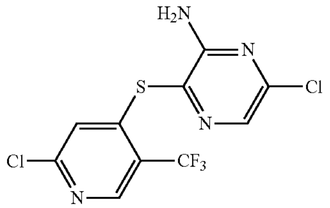
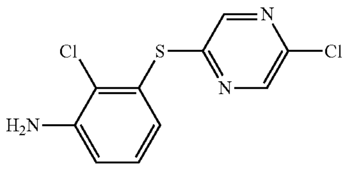 [SMILES: Nc1cccc(Sc2cnc(Cl)cn2)c1Cl]
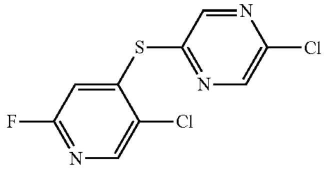 [SMILES: Fc1cc(Sc2cnc(Cl)cn2)c(Cl)cn1]

TABLE 15-continued
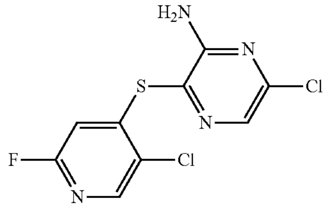 [SMILES: Nc1nc(Cl)cnc1Sc1cc(F)ncc1Cl]
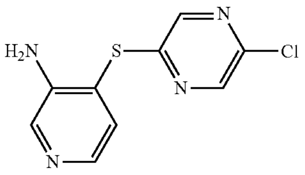 [SMILES: Nc1cnccc1Sc1cnc(Cl)cn1]
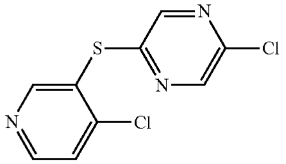 [SMILES: Clc1cnc(Sc2cnccc2Cl)cn1]
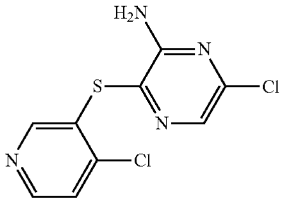 [SMILES: Nc1nc(Cl)cnc1Sc1cnccc1Cl]
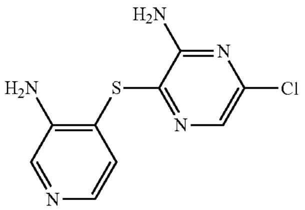 [SMILES: Nc1cnccc1Sc1ncc(Cl)nc1N]
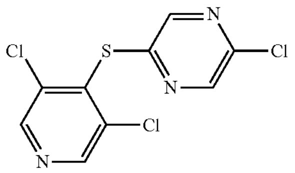 [SMILES: Clc1cnc(Sc2c(Cl)cncc2Cl)cn1]
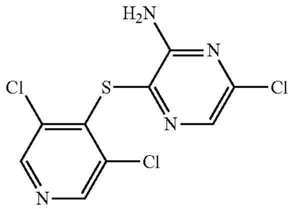 [SMILES: Nc1nc(Cl)cnc1Sc1c(Cl)cncc1Cl]
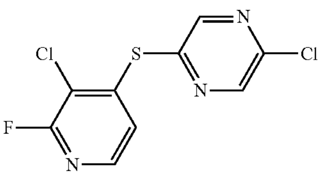 [SMILES: Fc1nccc(Sc2cnc(Cl)cn2)c1Cl]
TABLE 15-continued
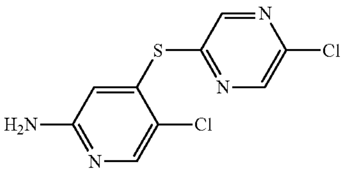 [SMILES: Nc1cc(Sc2cnc(Cl)cn2)c(Cl)cn1]
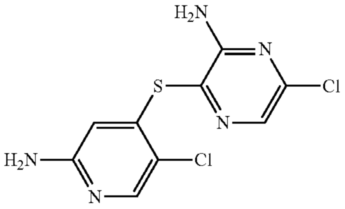 [SMILES: Nc1cc(Sc2ncc(Cl)nc2N)c(Cl)cn1]
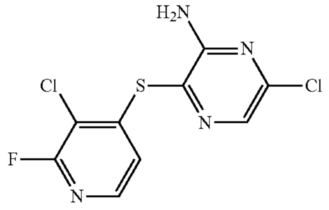 [SMILES: Nc1nc(Cl)cnc1Sc1ccnc(F)c1Cl]
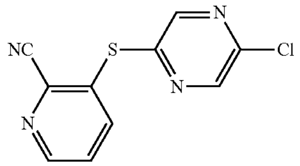 [SMILES: N#Cc1ncccc1Sc1cnc(Cl)cn1]
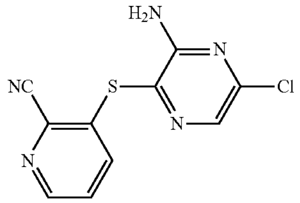 [SMILES: N#Cc1ncccc1Sc1ncc(Cl)nc1N]
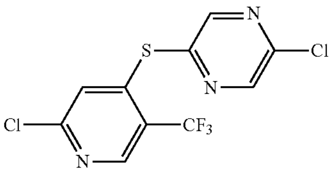 [SMILES: FC(F)(F)c1cnc(Cl)cc1Sc1cnc(Cl)cn1]
Example 1
(R)-1'-(6-amino-5-((2-amino-3-chloropyridin-4-yl)thio)pyrazin-2-yl)-2,3-dihydrospiro[indene-1,4'-piperidin]-2-amine
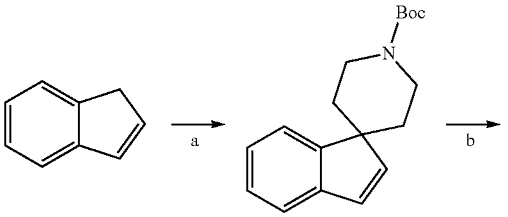

-continued

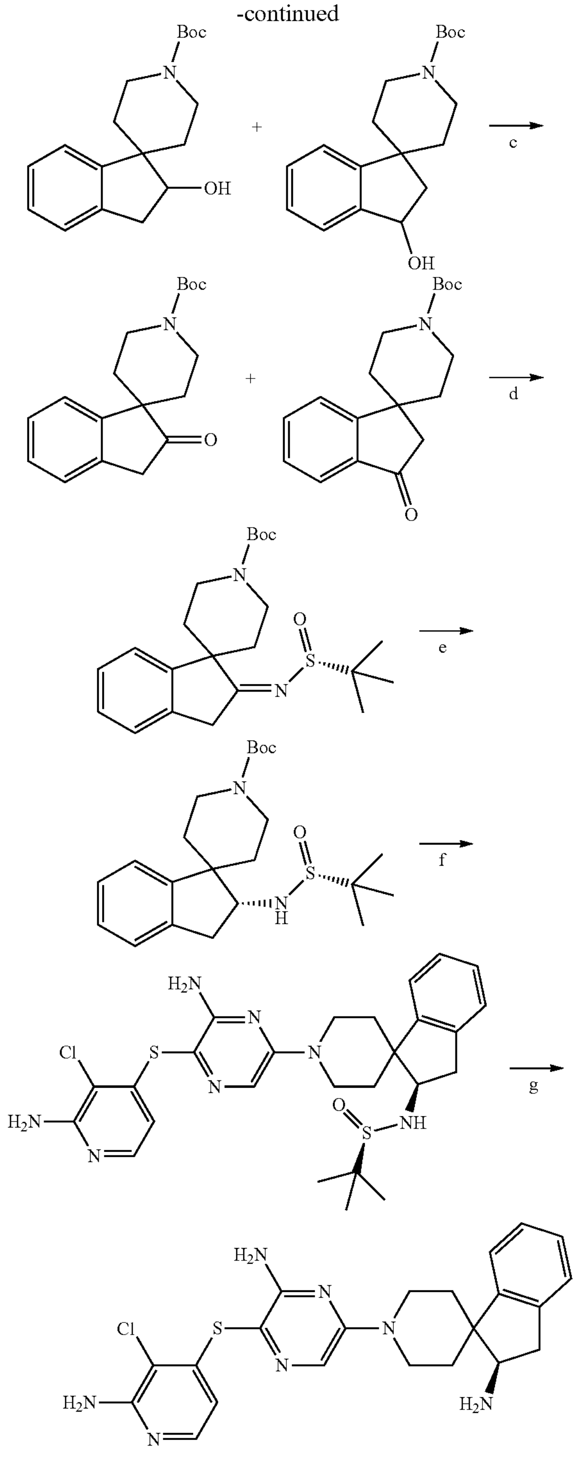

Step a: A mixture of Compound 1H-indene (11.62 g, 0.10 mol) and LiHMDS (220 mL, 1 mol/L in THF) in THF (120 mL) was stirred at −50° C. for 1 hour. Tert-butyl bis(2-chloroethyl)carbamate (24.21 g, 0.10 mol) was added to the reaction mixture and stirred at −50° C. for 1 hr. The reaction was quenched with brine (300 mL). The organic extracts were dried with anhydrous $Na_2SO_4$, and concentrated under reduced pressure in vacuo. The residue was purified by column chromatography to afford Compound tert-butyl spiro[indene-1,4'-piperidine]-1'-carboxylate as a yellow solid (10.36 g, 36%). MS: 286 $(M+H)^+$.

Step b: A mixture of Compound tert-butyl spiro[indene-1,4'-piperidine]-1'-carboxylate (117.02 g, 0.41 mol) and borane-methyl sulfide complex (10 mol/L, 220 mL) in THF (800 mL) was stirred at 0° C. for 3 hours. NaOH (2 mol/L, 1.2 L) and $H_2O_2$ (300 mL) was added and stirred at 0° C. for 1 hour. The organic extracts were collected, dried over anhydrous $Na_2SO_4$ and concentrated under reduced pressure in vacuo to afford the mixture of tert-butyl 2-hydroxy-2,3-dihydrospiro[indene-1,4'-piperidine]-1'-carboxylate and tert-butyl 3-hydroxy-2,3-dihydrospiro[indene-1,4'-piperidine]-1'-carboxylate as a yellow oil (130.33 g, crude). MS: 304 $(M+H)^+$.

Step c: A mixture of tert-butyl 2-hydroxy-2,3-dihydrospiro[indene-1,4'-piperidine]-1'-carboxylate and tert-butyl 3-hydroxy-2,3-dihydrospiro[indene-1,4'-piperidine]-1'-carboxylate (130.02 g, 0.43 mol) and Dess-Martin periodinane (364.76 g, 0.86 mol) in DCM (2 L) was stirred at 25° C. for 12 hours. The reaction mixture was filtered and the filtrate was washed by saturated sodium bicarbonate solution (1 L) and brine (1 L). The organic extracts were dried over anhydrous $Na_2SO_4$ and concentrated under reduced pressure in vacuo. The residue was purified by column chromatography to afford Compound tert-butyl 3-oxo-2,3-dihydrospiro[indene-1,4'-piperidine]-1'-carboxylate as a white solid (41.75 g, 34%, 2 steps). MS: 302 $(M+H)^+$.

Step d: To a solution of Compound tert-butyl 3-oxo-2,3-dihydrospiro[indene-1,4'-piperidine]-1'-carboxylate (41.01 g, 0.14 mol) in Titanium(IV) ethoxide (80 mL) was added R-(+)-tert-Butylsulfinamide (49.46 g, 0.41 mol). The resulting mixture was stirred at 85° C. for 2 hours. EA (0.5 L) and water (0.5 L) was added to the reaction mixture. The reaction mixture was filtered and organic extracts were collected. The aqueous solution was extracted with EA (200 mL×2). The combined organic extracts were washed with brine (500 mL), dried over anhydrous $Na_2SO_4$, and concentrated under reduced pressure in vacuo to afford Compound tert-butyl 3-oxo-2,3-dihydrospiro[indene-1,4'-piperidine]-1'-carboxylate (132.05 g crude). MS: 405 $(M+H)^+$. Without purification to next step.

Step e: A mixture of Compound tert-butyl 3-oxo-2,3-dihydrospiro[indene-1,4'-piperidine]-1'-carboxylate (132.02 g, 0.33 mol) in THF (200 mL) was stirred at −50° C. $NaBH_4$ (7.71 g, 0.51 mol) was added to the reaction mixture and allowed to return to room temperature. Reaction was quenched with saturated ammonium chloride solution (100 mL). The organic extracts were collected, dried over anhydrous $Na_2SO_4$, and concentrated under reduced pressure in vacuo. The residue was purified by column chromatography to afford Compound tert-butyl (R)-2-(((R)-tert-butylsulfinyl)amino)-2,3-dihydrospiro[indene-1,4'-piperidine]-1'-carboxylate as a white solid (27.25 g, 49%, 2 steps). MS: 407 $(M+H)^+$.

Step f: A mixture of Compound tert-butyl (R)-2-(((R)-tert-butylsulfinyl)amino)-2,3-dihydrospiro[indene-1,4'-piperidine]-1'-carboxylate (1.16 g, 3.98 mmol), $CF_3COOH$ (3.6 mL) in DCM (20 mL) was stirred at 25° C. for 1.5 hours. The reaction mixture was concentrated under reduced pressure, The residue was dissolved in NMP (15 mL), then 3-((2-amino-3-chloropyridin-4-yl)thio)-6-chloropyrazin-2-amine (1.03 g, 3.59 mmol) and $K_2CO_3$ (6.60 g, 47.76 mmol) was added to mixture and stirred at 90° C. for 16 hours. $H_2O$ (30 mL) was added to the reaction mixture and the precipitate was filtered. The filter cake dissolved in DCM (40 mL) and washed with brine (40 mL). The organic extracts were dried over anhydrous $Na_2SO_4$ and concentrated under reduced pressure in vacuo to afford the Compound (R)—N—((R)-

1'-(6-amino-5-((2-amino-3-chloropyridin-4-yl)thio)pyrazin-2-yl)-2,3-dihydrospiro[indene-1,4'-piperidin]-2-yl)-2-methylpropane-2-sulfinamide (1.55 g, 70%) as a yellow solid.

Step g: To a solution of Compound (R)—N—((R)-1'-(6-amino-5-((2-amino-3-chloropyridin-4-yl)thio)pyrazin-2-yl)-2,3-dihydrospiro[indene-1,4'-piperidin]-2-yl)-2-methylpropane-2-sulfinamide (1.52 g, 2.72 mmol) in DCM (20 mL) was added HCl/Dixoane (2 mL, 4 mol/L). The resulting mixture was stirred at 25° C. for 1 hour and the precipitate was filtered. The filter cake dispersed in DCM (30 mL) and Ammonium hydroxide (5 mL) was added to adjust pH>10. The mixture was washed with brine (40 mL), dried over anhydrous Na2SO4 and concentrated under reduced pressure in vacuo. The residue was purified by column chromatography to afford Compound (R)-1'-(6-amino-5-((2-amino-3-chloropyridin-4-yl)thio)pyrazin-2-yl)-2,3-dihydrospiro[indene-1,4'-piperidin]-2-amine as a yellow solid (530 mg, 42%). MS: 454 $(M+H)^+$. H NMR (400 MHz, DMSO-d6) δ 7.64-7.66 (m, 2H), 7.30 (d, 1H), 7.20 (d, 1H), 7.13-7.15 (m, 2H), 6.78 (d, 1H), 4.05-4.09 (m, 1H), 3.91-3.95 (m, 1H), 3.54-3.60 (m, 3H), 3.12-3.18 (m, 1H), 2.57-2.63 (m, 1H), 1.91-2.09 (m, 2H), 1.66-1.76 (m, 1H), 1.49-1.58 (m, 1H).

Example 2

(S)-1'-(6-amino-5-((2-amino-3-chloropyridin-4-yl)thio)pyrazin-2-yl)-1,3-dihydrospiro[indene-2,4'-piperidin]-1-amine

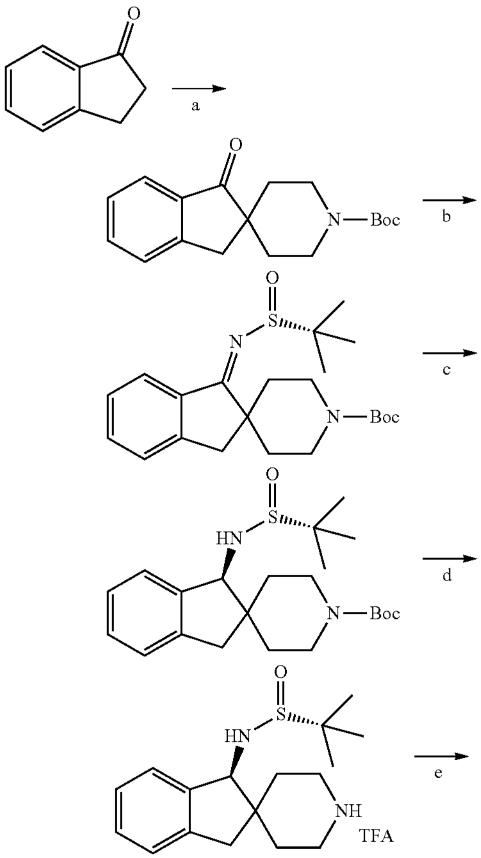

-continued

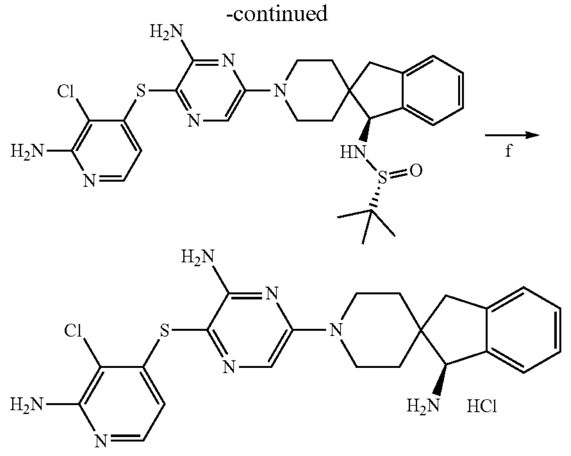

Step a: NaH (60%) (3.63 g, 90.80 mmol) was added into the solution of Compound 2,3-dihydro-1H-inden-1-one (4.00 g, 30.27 mmol) in DMF (80 mL). The mixture was stirred for 30 min at 16° C. Tert-butyl bis(2-chloroethyl) carbamate (8.06 g, 33.29 mmol) was added dropwise. And then the mixture was stirred for 16 hours at 60° C. The mixture was quenched with brine (200 mL), extracted with EA (100 mL×2). The organic layers were combined and washed with brine (100 mL×2), dried over anhydrous $Na_2SO_4$. After concentrated, the residue was purified by column chromatography to afford the Compound tert-butyl 1-oxo-1,3-dihydrospiro[indene-2,4'-piperidine]-1'-carboxylate (1.21 g, 13%) as a dark red oil. MS: 302 $(M+H)^+$.

Step b: After the Titanium(IV) ethoxide (12.00 g) was warmed into 90° C., the compound tert-butyl 1-oxo-1,3-dihydrospiro[indene-2,4'-piperidine]-1'-carboxylate (1.21 g, 4.01 mmol) and (R)-2-methylpropane-2-sulfinamide (1.22 g, 12.04 mmol) were added. After stirred for 19 hrs at 90° C. The mixture was poured into EA (200 mL), and brine (200 mL) was added. After stirred for 15 mins, the solids were filtrated out. The liquid was separated. The organic layer was washed with brine (200 mL×2), and dried over anhydrous $Na_2SO_4$. The solids were filtrated out, and the filtration was concentrated under reduced pressure in vacuo. The residue was purified by column chromatography to afford the compound tert-butyl (R,E)-1-((tert-butylsulfinyl)imino)-1,3-dihydrospiro[indene-2,4'-piperidine]-1'-carboxylate (1.01 g, 62%) as a black solid. MS: 405 $(M+H)^+$.

Step c: The solution of the compound tert-butyl (R,E)-1-((tert-butylsulfinyl)imino)-1,3-dihydrospiro[indene-2,4'-piperidine]-1'-carboxylate (1.01 g, 2.50 mmol) in THF (10 mL) was cooled in −50° C. $NaBH_4$ (142 mg, 3.74 mmol) was added in portionwise. The mixture was stirred for 15.5 hours with natural warming to room temperature, and then poured into EA (100 mL). The mixture was washed with brine (100 mL×3). The organic layer was dried over anhydrous Na2SO4 and concentrated under reduced pressure in vacuo. The residue was purified by column chromatography to afford the Compound tert-butyl (S)-1-(((R)-tert-butylsulfinyl)amino)-1,3-dihydrospiro[indene-2,4'-piperidine]-1'-carboxylate (580 mg, 57%) as a yellow oil. MS: 407 $(M+H)^+$.

Step d: The mixture of the compound tert-butyl (S)-1-(((R)-tert-butylsulfinyl)amino)-1,3-dihydrospiro[indene-2,4'-piperidine]-1'-carboxylate (580 mg, 1.43 mmol) and TFA (1 mL) in DCM (5 mL) was stirred for 40 mins at 20° C. The solution was concentrated to afford the compound (R)—

N—((S)-1,3-dihydrospiro[indene-2,4'-piperidin]-1-yl)-2-methylpropane-2-sulfinamide (520 mg, 90%) as a yellow oil. MS: 307 $(M+H)^+$.

Step e: The mixture of (R)—N—((S)-1,3-dihydrospiro[indene-2,4'-piperidin]-1-yl)-2-methylpropane-2-sulfinamide (260 mg, 0.62 mmol), 3-((2-amino-3-chloropyridin-4-yl) thio)-6-chloropyrazin-2-amine (196 mg, 0.68 mmol) and $K_2CO3$ (427 mg, 3.09 mmol) in NMP (8 mL) were stirred for 16 hours at 100° C. The mixture poured into EA (200 mL) and washed with brine (200 mL×3). The organic layer was dried over anhydrous Na2SO4 and concentrated under reduced pressure in vacuo. The residue was purified by column chromatography to afford the Compound (R)—N—((S)-1'-(6-amino-5-((2-amino-3-chloropyridin-4-yl)thio)pyrazin-2-yl)-1,3-dihydrospiro[indene-2,4'-piperidin]-1-yl)-2-methylpropane-2-sulfinamide (260 mg, 65%) as a yellow solid. MS: 558 $(M+H)^+$.

Step f: The compound (R)—N—((S)-1'-(6-amino-5-((2-amino-3-chloropyridin-4-yl)thio)pyrazin-2-yl)-1,3-dihydrospiro[indene-2,4'-piperidin]-1-yl)-2-methylpropane-2-sulfinamide (260 mg, 0.47 mmol) was dissolved in DCM (5 mL) and HCl/Dixoane (4 mol/L, 5 mL) was added dropwise. The mixture was stirred for 30 mins at 20° C. The mixture was concentrated and the residue was dissolved in methanol (2 mL). And EA (5 mL) was added. The solids were collected by filtration to afford the compound (S)-1'-(6-amino-5-((2-amino-3-chloropyridin-4-yl)thio)pyrazin-2-yl)-1,3-dihydrospiro[indene-2,4'-piperidin]-1-amine (123 mg, 54%) as an off-white solid. MS: 454 $(M+H)^+$. H NMR (400 MHz, DMSO-d6) δ 7.81 (d, 1H), 7.72 (s, 1H), 7.62 (d, 1H), 7.27-7.36 (m, 3H), 6.12 (d, 1H), 4.21-4.35 (m, 3H), 2.97-3.24 (m, 4H), 1.77-1.91 (m, 2H), 1.49-1.59 (m, 2H).

Example 3

(R)-1'-(6-amino-5-((2-amino-3-chloropyridin-4-yl)thio)pyrazin-2-yl)-3,4-dihydro-2H-spiro[naphthalene-1,4'-piperidin]-2-amine

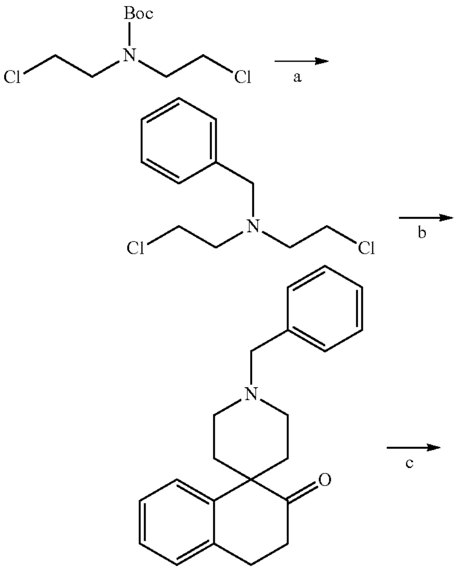

-continued

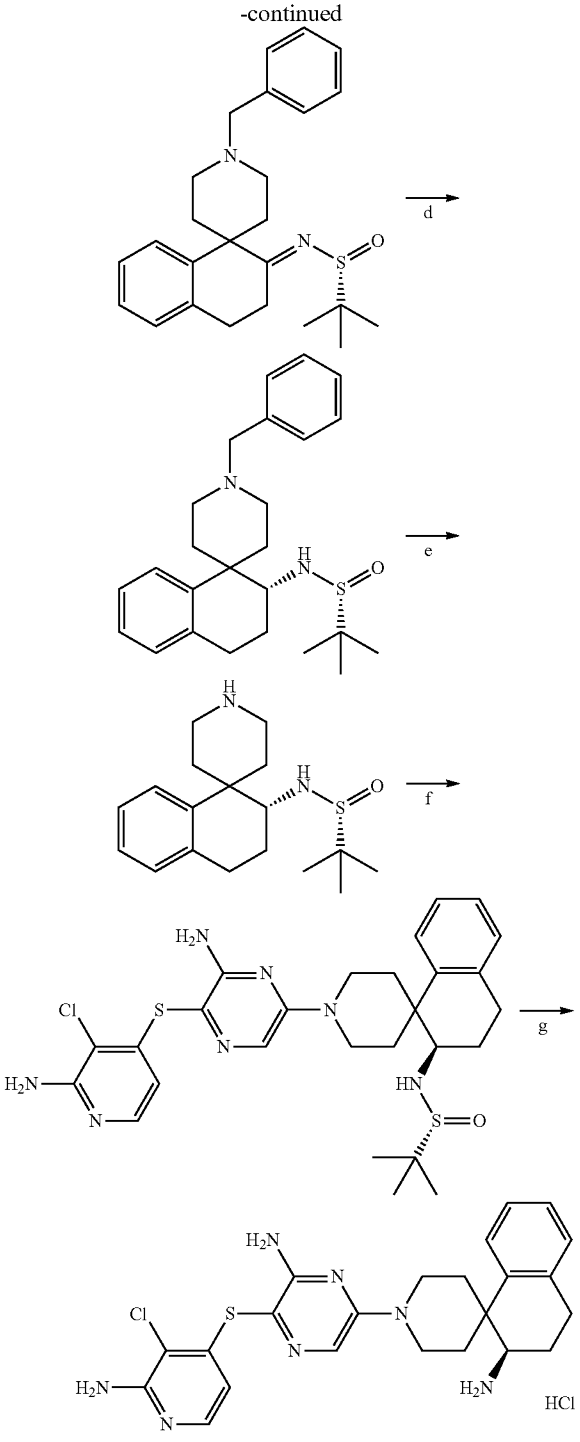

Step a: The solution of the compound tert-butyl bis(2-chloroethyl)carbamate (11.00 g, 45.43 mmol) in HCl/Dixoane (4 mol/L, 200 mL) was stirred for 1h at 20° C. The solution was concentrated and the residue was dissolved in DCE (200 mL). Triethylamine (22.95 g, 227.14 mmol) and benzaldehyde (7.23 g, 68.14 mmol) was added to the mixture. And then $NaBH(OAc)_3$ (24.07 g, 113.57 mmol) was added in portionwise. The mixture was stirred for 54 hours at 20° C., and then EA (300 mL) and brine (200 mL) was added. The organic layer was concentrated under reduced pressure in vacuo. The residue was dissolved in HCl solution (2 mol/L, 200 mL) and extracted with EA (100 mL). The pH value of the aqueous layer was adjusted to 9 with saturated $Na_2CO_3$ solution. The mixture was extracted with EA (200 mL). The organic layer was dried over anhydrous $Na_2SO_4$ and concentrated to afford the compound N-benzyl-2-chloro-N-(2-chloroethyl)ethan-1-amine (8.52 g, 81%) as a colorless oil.

Step b: Into the solution of the compound N-benzyl-2-chloro-N-(2-chloroethyl)ethan-1-amine (8.52 g, 36.70 mmol) and 3,4-dihydronaphthalen-2(1H)-one (4.88 g, 33.36 mmol) in THF (80 mL) and DMSO (50 mL) was added Potassium tert-butylate (9.36 g, 83.14 mmol). The mixture was stirred for 20 hours at 20° C. The mixture was concentrated and diluted with EA (200 mL). And then the mixture was washed with brine (200 mL×3). The organic layer was dried over anhydrous $Na_2SO_4$ and concentrated. The residue was purified by column chromatography to afford 1'-benzyl-3,4-dihydro-2H-spiro[naphthalene-1,4'-piperidin]-2-one (2.32 g, 21%) as a black oil. MS: 306 $(M+H)^+$.

Step c: Into Titanium(IV) ethoxide was added the compound 1'-benzyl-3,4-dihydro-2H-spiro[naphthalene-1,4'-piperidin]-2-one (2.32 g, 7.60 mmol) and (R)-2-methylpropane-2-sulfinamide (2.76 g, 22.79 mmol). The mixture was stirred for 19h at 100° C. EA (200 mL) and water (200 mL) was added. The solids were filtrated out. The liquid mixture was separated. The organic layer was washed with brine (100 mL×5), dried over anhydrous $Na_2SO_4$, and concentrated under reduced pressure in vacuo. The residue was purified by column chromatography to afford the compound (R,E)-N-(1'-benzyl-3,4-dihydro-2H-spiro[naphthalene-1,4'-piperidin]-2-ylidene)-2-methylpropan e-2-sulfinamide (660 mg, 21%) as a yellow oil. MS: 409 $(M+H)^+$.

Step d: The solution of the compound (R,E)-N-(1'-benzyl-3,4-dihydro-2H-spiro[naphthalene-1,4'-piperidin]-2-ylidene)-2-methylpropane-2-sulfinamide (660 mg, 1.62 mmol) in THF (10 mL) was cooled into −50° C. And then NaBH4 (122 mg, 3.23 mmol) was added in portionwise. The mixture was stirred for 18h with natural warming to room temperature. The mixture was quenched with water (50 mL) and extracted with EA (50 mL×2). The organic layers were combined and washed with brine (50 mL×2), dried over anhydrous Na2SO4 and concentrated under reduced pressure in vacuo. The residue was purified by column chromatography to afford the compound (R)—N—((R)-1'-benzyl-3,4-dihydro-2H-spiro[naphthalene-1,4'-piperidin]-2-yl)-2-methylpropane-2-sulfinamide (195 mg, 29%) as a yellow oil. MS: 411 $(M+H)^+$.

Step e: Into the solution of the compound (R)—N—((R)-1'-benzyl-3,4-dihydro-2H-spiro[naphthalene-1,4'-piperidin]-2-yl)-2-methylpropane-2-sulfinamide (195 mg, 0.47 mmol) in methanol (5 mL) was added palladium hydroxide (20%, 120 mg). The mixture was stirred for 18h at 40° C. under hydrogen atmosphere. The mixture was filtrated and the filtration was concentrated to afford the compound (R)—N—((R)-3,4-dihydro-2H-spiro[naphthalene-1,4'-piperidin]-2-yl)-2-methylpropane-2-sulfinamide (92 mg, 60%). MS: 321 $(M+H)^+$.

Step f: The compound (R)—N—((R)-3,4-dihydro-2H-spiro[naphthalene-1,4'-piperidin]-2-yl)-2-methylpropane-2-sulfinamide (92 mg, 0.29 mmol) was dissolved in NMP (3 mL). 3-((2-amino-3-chloropyridin-4-yl)thio)-6-chloropyrazin-2-amine (91 mg, 0.32 mmol) and $K_2CO_3$ (198 mg, 1.44 mmol) were added into. The mixture was stirred for 3 hours at 100° C., and diluted with EA (30 mL), washed with brine (30 mL×3). The organic layer was dried with anhydrous $Na_2SO_4$. The residue was purified with Pre-TLC to afford the compound (R)—N—((R)-1'-(6-amino-5-((2-amino-3-chloropyridin-4-yl)thio)pyrazin-2-yl)-3,4-dihydro-2H-spiro[naphthalene-1,4'-piperidin]-2-yl)-2-methylpropane-2-sulfinamide (18 mg, 11%) as an off-white solid.

Step g: In to the solution of the compound (R)—N—((R)-1'-(6-amino-5-((2-amino-3-chloropyridin-4-yl)thio)pyrazin-2-yl)-3,4-dihydro-2H-spiro[naphthalene-1,4'-piperidin]-2-yl)-2-methylpropane-2-sulfinamide (18 mg, 0.03 mmol) in 1,4-dioxane (2 mL) was added HCl/Dixoane (4 mol/L, 2 mL). The mixture was stirred for 30 mins. The resulted mixture was concentrated and washed with EA for twice. The solid was dried in high vacuum to afford the compound (R)-1'-(6-amino-5-((2-amino-3-chloropyridin-4-yl)thio) pyrazin-2-yl)-3,4-dihydro-2H-spiro[naphthalene-1,4'-piperidin]-2-amine (14 mg, 88%) as an off-white solid. MS: 468 $(M+H)^+$.

Example 4

(R)-1'-(6-amino-5-((2-amino-3-chloropyridin-4-yl) thio)pyrazin-2-yl)-5,6-dihydrospiro[cyclopenta[b] pyridine-7,4'-piperidin]-6-amine

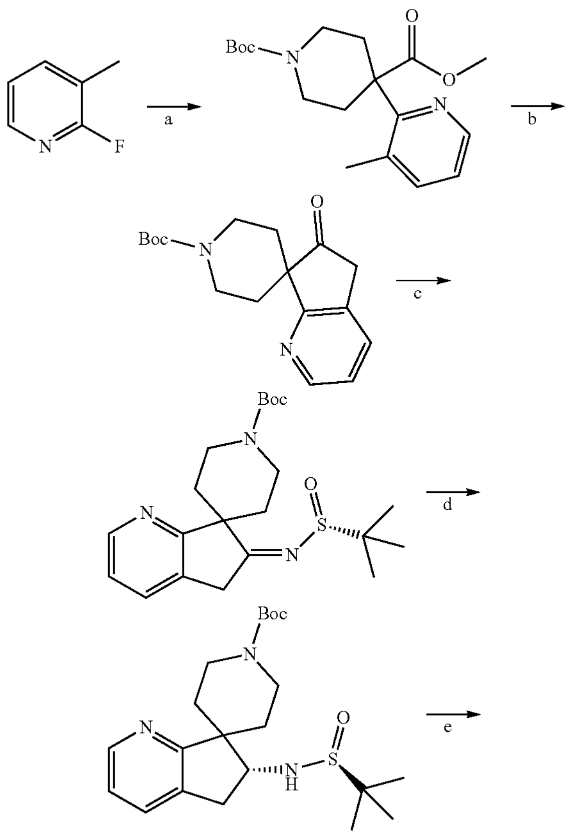

-continued

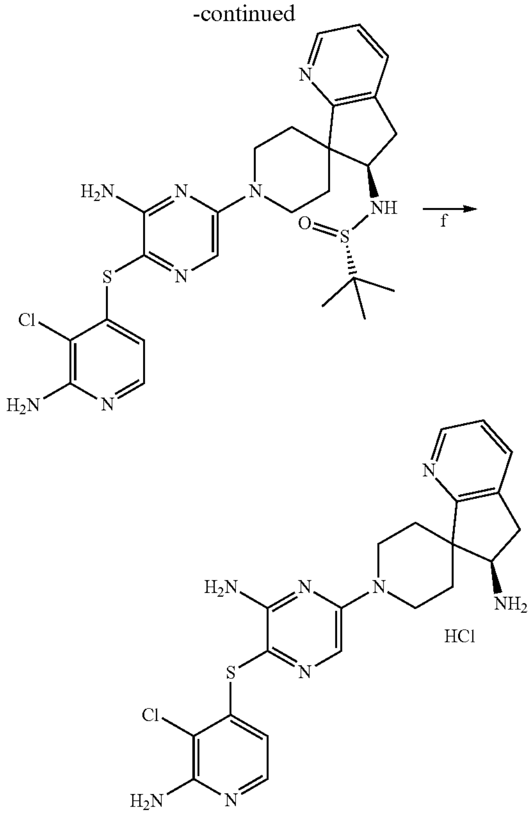

Step a: NaHMDS (38 ml, 2 mol/L in THF) was added to the mixture of the compound 2-fluoro-3-methylpyridine (5.56 g, 50.00 mmol), 1-tert-butyl 4-ethyl piperidine-1,4-dicarboxylate (14.15 g, 55.00 mmol) in toluene (50 mL) dropwise at 0° C., then naturally warmed to 20° C. and stirred for 24 hours. Reaction mixture was quenched with brine (100 mL). The organic extracts were dried over $Na_2SO_4$ and concentrated under reduced pressure in vacuo. The residue was purified by column chromatography to afford the compound 1-(tert-butyl) 4-ethyl 4-(3-methylpyridin-2-yl)piperidine-1,4-dicarboxylate (6.32 g, 36%) as a yellow oil. MS: 349 $(M+H)^+$.

Step b: A mixture of the compound 1-(tert-butyl) 4-ethyl 4-(3-methylpyridin-2-yl)piperidine-1,4-dicarboxylate (4.80 g, 13.78 mmol), LDA (2 mol/L, 17 mL) in THF (48 mL) was stirred at 0° C. for 0.5 hour. The mixture was removed under reduced pressure in vacuo. The residue was purified by column chromatography to afford the compound tert-butyl 6-oxo-5,6-dihydrospiro[cyclopenta[b]pyridine-7,4'-piperidine]-1'-carboxylate (0.95 g, 23%) as a red oil. MS: 303 $(M+H)^+$.

Step c: To a solution of the compound tert-butyl 6-oxo-5,6-dihydrospiro[cyclopenta[b]pyridine-7,4'-piperidine]-1'-carboxylate (0.94 g, 3.11 mol) in Titanium(IV) ethoxide (5 mL) was added R-(+)-tert-Butylsulfinamide (1.13 g, 9.33 mmol). The resulting mixture was stirred at 80° C. for 1 hour. EA (30 mL) and water (20 mL) was added to the reaction mixture. The reaction mixture was filtered and organic extracts were collected. The aqueous solution was extracted with EA (10 mL×2). The combined organic extracts were washed with brine (50 mL), dried over $Na_2SO_4$ and concentrated under reduced pressure in vacuo to afford the compound tert-butyl (R,Z)-6-((tert-butylsulfinyl)imino)-5,6-dihydrospiro[cyclopenta[b]pyridine-7,4'-piperidine]-1'-carboxylate (2.51 g, crude) as a red oil. Without purification to next step. MS: 406 $(M+H)^+$.

Step d: A solution of the compound tert-butyl (R,Z)-6-((tert-butylsulfinyl)imino)-5,6-dihydrospiro[cyclopenta[b]pyridine-7,4'-piperidine]-1'-carboxylate (2.12 g, crude) in THF (20 mL) was stirred at −50° C. $NaBH_4$ (176 mg, 4.66 mmol) was added to the reaction mixture and naturally warmed to room temperature. Reaction was quenched with saturated ammonium chloride solution (30 mL). The organic extracts were collected and dried over anhydrous $Na_2SO_4$ and concentrated under reduced pressure in vacuo. The residue was purified by column chromatography to afford the compound tert-butyl (R)-6-(((S)-tert-butylsulfinyl)amino)-5,6-dihydrospiro[cyclopenta[b]pyridine-7,4'-piperidine]-1'-carboxylate (0.21 g, 17%, 2 steps) as a yellow solid. MS: 408 $(M+H)^+$.

Step e: A mixture of the compound tert-butyl (R)-6-(((S)-tert-butylsulfinyl)amino)-5,6-dihydrospiro[cyclopenta[b]pyridine-7,4'-piperidine]-1'-carboxylate (204 mg, 0.50 mmol), $CF_3COOH$ (1 mL) in DCM (10 mL) was stirred at 25° C. for 1.5 hours. The reaction mixture was concentrated under reduced pressure. The residue was dissolved in NMP (10 mL), then 3-((2-amino-3-chloropyridin-4-yl)thio)-6-chloropyrazin-2-amine (144 mg, 0.50 mmol) and $K_2CO_3$ (0.82 g, 6.00 mmol) was added to mixture and stirred at 95° C. for 16 hours. $H_2O$ (50 mL) was added to the reaction mixture. The aqueous solution was extracted with EA (30 mL×2). The combined organic extracts were washed with brine (50 mL), dried over anhydrous $Na_2SO_4$ and concentrated under reduced pressure in vacuo to afford the compound (S)—N—((R)-1'-(6-amino-5-((2-amino-3-chloropyridin-4-yl)thio)pyrazin-2-yl)-5,6-dihydrospiro[cyclopenta[b]pyridine-7,4'-piperidin]-6-yl)-2-methylpropane-2-sulfinamide (302 mg, crude). Without purification to next step. MS: 559 $(M+H)^+$.

Step f: To a solution of the compound (S)—N—((R)-1'-(6-amino-5-((2-amino-3-chloropyridin-4-yl)thio)pyrazin-2-yl)-5,6-dihydrospiro[cyclopenta[b]pyridine-7,4'-piperidin]-6-yl)-2-methylpropane-2-sulfinamide (302 mg, 0.54 mmol) in DCM (10 mL) was added HCl/Dixoane (4 mol/L, 1 mL). The resulting mixture was stirred at 25° C. for 1 hour and the precipitate was filtered. The filter cake dissolved in MeOH (2 mL), then DCM (15 mL) was added into. The mixture was stirred for 0.5 hour and filtered to afford the compound (R)-1'-(6-amino-5-((2-amino-3-chloropyridin-4-yl)thio)pyrazin-2-yl)-5,6-dihydrospiro[cyclopenta[b]pyridine-7,4'-piperidin]-6-amine (163 mg, 71%, 2 steps) as a yellow solid. MS: 455 $(M+H)^+$. $^1H$ NMR (600 MHz, MeOH-d4) δ 8.69 (d, 1H), 8.54 (d, 1H), 7.92-7.96 (m, 1H), 7.88 (s, 1H), 7.75 (d, 1H), 6.58 (d, 1H), 4.54-4.67 (m, 3H), 3.89-3.95 (m, 1H), 3.37-3.61 (m, 3H), 2.79-2.86 (m, 1H), 1.93-2.20 (m, 3H).

Example 5

(S)-1'-(6-amino-5-((2-amino-3-chloropyridin-4-yl)thio)pyrazin-2-yl)-6-methoxy-1,3-dihydro spiro[indene-2,4'-piperidin]-1-amine

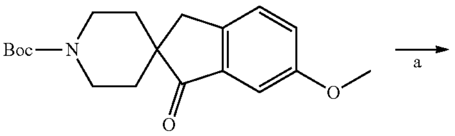

-continued

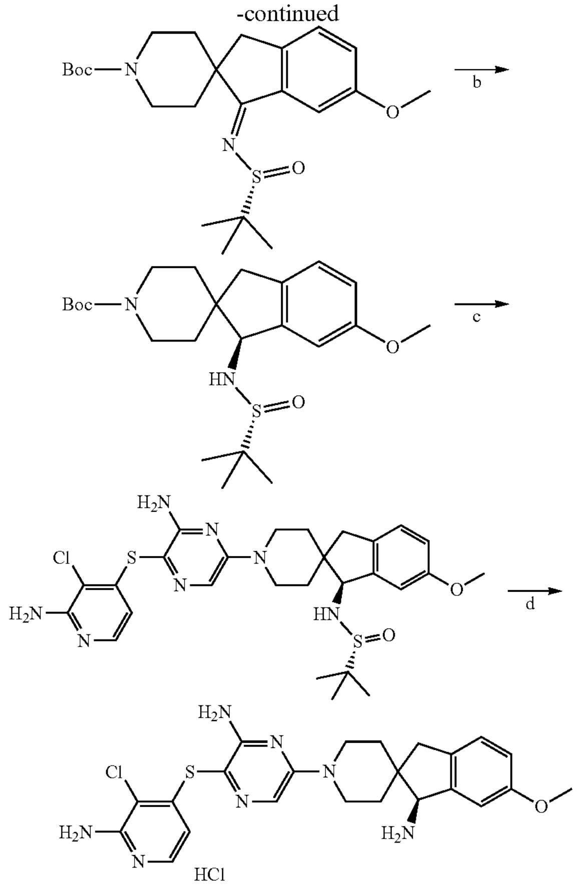

Step a: A mixture of tert-butyl 6-methoxy-1-oxo-1,3-dihydrospiro[indene-2,4'-piperidine]-1'-carboxylate (557 mg, 1.68 mmol) and (R)-(+)-2-Methyl-2-propanesulfinamide (610 mg, 5.04 mmol) in $Ti(OEt)_4$ (5 mL) was stirred for 16 h at 100° C. After cooling to RT, the reaction mixture was diluted with EA (20 mL) and water (30 mL). The resulting mixture was filtered through a pad of Celite followed by EA wash. The filtrate was washed with brine (1×50 mL), dried over anhydrous $Na_2SO_4$, filtered and concentrated under reduced pressure to give tert-butyl (R,Z)-1-((tert-butylsulfinyl)imino)-6-methoxy-1,3-dihydrospiro[indene-2,4'-piperidine]-1'-carboxylate (0.98 g) which was used in next step without any further purification. MS: m/z 435 (M+H).

Step b: To a −50° C. solution of tert-butyl (R,Z)-1-((tert-butylsulfinyl)imino)-6-methoxy-1,3-dihydrospiro[indene-2,4'-piperidine]-1'-carboxylate (0.98 g, 2.25 mmol) in THF (10 mL) was added $NaBH_4$ (0.17 g, 4.51 mmol). The resulting mixture was allowed to warm to RT and stirred for 24 h. The reaction mixture was diluted with EA (50 mL) and water (50 mL), the organic layer was separated, washed with brine (1×50 mL), dried over anhydrous $Na_2SO_4$, filtered and concentrated under reduced pressure. The residue was purified by silica chromatography (eluting with EA:Hex=1:5, v/v) to give tert-butyl (S)-1-(((R)-tert-butylsulfinyl)amino)-6-methoxy-1,3-dihydrospiro[indene-2,4'-piperidine]-1'-carboxylate (380 mg). MS: m/z 437 (M+H).

Step c: To solution of tert-butyl (S)-1-(((R)-tert-butylsulfinyl)amino)-6-methoxy-1,3-dihydrospiro[indene-2,4'-piperidine]-1'-carboxylate (380 mg, 0.87 mmol) in DCM (10 mL) was added TFA (2 mL), and stirred for 1.5 h at RT. The resulting mixture was concentrated under reduced pressure. The residue was dissolved in NMP (10 mL), 3-((2-amino-3-chloropyridin-4-yl)thio)-6-chloropyrazin-2-amine (301 mg, 1.04 mmol) and $K_2CO_3$ (601 mg, 4.35 mmol) was added. The resulting mixture was stirred for 16 h at 100° C. After cooling to RT, the reaction mixture was diluted with water (50 mL) and EA (50 mL). The aqueous layer was separated, the organic layer was washed with brine (2×50 mL), dried over anhydrous $Na_2SO_4$, filtered and concentrated under reduced pressure. The residue was purified by silica chromatography (eluting with MeOH:DCM=1:20, v/v) to give (R)—N—((S)-1'-(6-amino-5-((2-amino-3-chloropyridin-4-yl)thio)pyrazin-2-yl)-5-methoxy-1,3-dihydrospiro[indene-2,4'-piperidin]-3-yl)-2-methylpropane-2-sulfinamide (254 mg). MS: m/z 588 $(M+H)^+$.

Step d: To a solution of (R)—N—((S)-1'-(6-amino-5-((2-amino-3-chloropyridin-4-yl)thio)pyrazin-2-yl)-5-methoxy-1,3-dihydrospiro[indene-2,4'-piperidin]-3-yl)-2-methylpropane-2-sulfinamide (254 mg, 0.43 mmol) in 1,4-dioxane (3 mL) was added HCl (4M solution in 1,4-dioxane, 3 mL) dropwise and stirred for 30 min at RT. The reaction mixture was filtered and the collected precipitate was dried in a vacuum oven to give (S)-1'-(6-amino-5-((2-amino-3-chloropyridin-4-yl)thio)pyrazin-2-yl)-6-methoxy-1,3-dihydrospiro[indene-2,4'-piperidin]-1-amine (221 mg) as a HCl salt. MS: m/z 484 $(M+H)^+$. H NMR (600 MHz, MeOH-d4) δ 7.90 (s, 1H), 7.76 (d, 1H), 7.28 (d, 1H), 7.12 (d, 1H), 6.95-6.89 (m, 1H), 6.58 (d, 1H), 4.50-4.35 (m, 3H), 3.82 (s, 3H), 3.49-3.40 (m, 2H), 3.16-3.08 (m, 2H), 2.01-1.66 (m, 4H).

The following examples were synthesized using the above procedure or modification procedure using the corresponding Intermediate A and Intermediate B.

The following examples are compounds with free base, or a pharmaceutically acceptable salt.

TABLE 16

| EX No | Chemical Name | Structure | $^1$HNMR & MS: $(M + H)^+$ |
|---|---|---|---|
| 6 | (R)-1-(4-((3-amino-5-(2-amino-2,3-dihydrospiro[indene-1,4'-piperidin]-1'-yl) pyrazin-2-yl)thio)-3,3-difluoroindolin-1-yl)ethan-1-one | 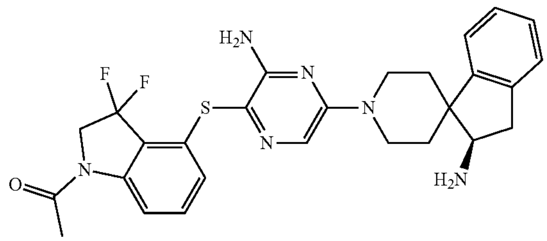 [SMILES: CC(=O)N1CC(F)(F)c2c(Sc3ncc(N4CCC5(CC4)c4ccccc4C[C@H]5N)nc3N)cccc21] | $^1$H NMR (600 MHz, MeOH-d4) δ 8.07 (d, 1H), 7.60 (s, 1H), 7.39-7.30 (m, 5H), 6.64 (d, 1H), 4.52 (t, 2H), 4.28-4.12 (m, 3H), 3.57-3.53 (m, 3H), 3.00 (d, 1H), 2.28 (s, 3H), 2.01-1.65 (m, 4H). MS: 523 $(M + H)^+$. |

TABLE 16-continued

| EX No | Chemical Name | Structure | $^1$HNMR & MS: $(M + H)^+$ |
|---|---|---|---|
| 7 | 1-(4-((3-amino-5-((2R)-2-aminospiro[bicyclo[3.1.0]hexane-3,4'-piperidin]-1'-yl)pyrazin-2-yl)thio)-3,3-difluoro-indolin-1-yl)ethan-1-one | 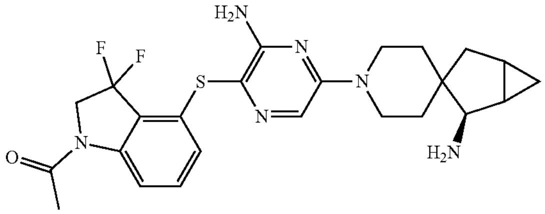 [SMILES: CC(=O)N1CC(F)(F)c2c(Sc3ncc(N4CCC5(CC4)CC4CC4[C@H]5N)nc3N)cccc21] | $^1$H NMR (600 MHz, MeOH-d4) δ 8.05 (d, 1H), 7.51 (s, 1H), 7.30 (t, 1H), 6.51 (d, 1H), 4.51 (t, 2H), 4.25-4.10 (m, 2H), 3.32 (d, 1H), 3.24 (d, 1H), 3.05-2.97 (m, 2H), 2.27 (s, 3H), 1.91 (d, 1H), 1.71-1.39 (m, 8H). MS: 487 $(M + H)^+$. |
| 8 | (S)-1'-(6-amino-5-((2-amino-3-chloro pyridin-4-yl)thio) pyrazin-2-yl)-3,4-dihydro-1H-spiro [naphthalene-2,4'-piperidin]-1-amine | 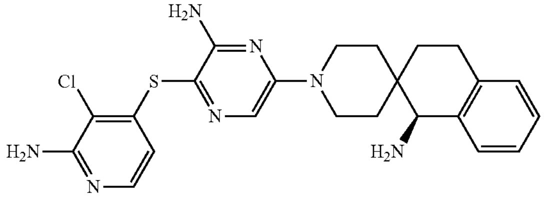 [SMILES: Nc1nc(N2CCC3(CCc4ccccc4[C@H]3N)CC2)cnc1Sc1ccnc(N)c1Cl] | $^1$H NMR (600 MHz, MeOH-d4) δ 7.89 (s, 1H), 7.76 (d, 1H), 7.43 (d, 1H), 7.39-7.28 (m, 3H), 6.57 (d, 1H), 4.33 (s, 1H), 4.26 (d, 1H), 4.08 (d, 1H), 3.74-3.56 (m, 2H), 3.07-2.92 (m, 2H), 2.24-2.19 (m, 1H), 1.97-1.90 (m, 2H), 1.81-1.52 (m, 3H). MS: 468 $(M + H)^+$. |
| 9 | (R)-1-(6-amino-5-((2-amino-3-chloro pyridin-4-yl)thio) pyrazin-2-yl)-7,8'-dihydro-5'H-spiro [piperidine-4,6'-quinolin]-7'-amine | 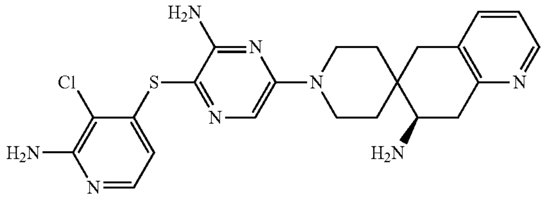 [SMILES: Nc1nc(N2CCC3(CC2)Cc2cccnc2C[C@H]3N)cnc1Sc1ccnc(N)c1Cl] | $^1$H NMR (400 MHz, MeOH-d4) δ 8.75 (d, 1H), 8.52 (d, 1H), 7.98-7.95 (m, 1H), 7.91 (s, 1H), 7.77 (d, 1H), 6.59 (d, 1H), 4.34 (t, 2H), 3.93 (t, 1H), 3.83-3.76 (m, 2H), 3.53-3.35 (m, 4H), 2.01-1.94 (m, 2H), 1.83 (d, 1H), 1.71 (d, 1H). MS: 469 $(M + H)^+$. |
| 10 | (S)-1'-(6-amino-5-((2-amino-3-chloro pyridin-4-yl)thio) pyrazin-2-yl)-5,7-dihydrospiro [cyclopenta[b]pyridine-6,4'-piperidin]-5-amine | 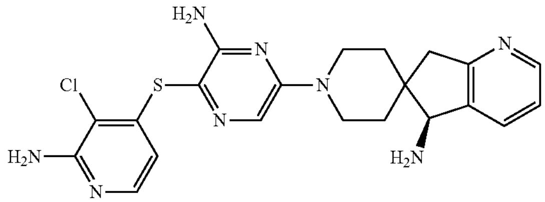 | $^1$H NMR (400 MHz, DMSO-d6) δ 8.31 (d, 1H), 7.67-7.63 (m, 3H), 7.17 (m, 1H), 5.76 (d, 1H), 4.22 (d, 2H), 3.90 (s, 1H), 3.20-3.08 (m, 3H), 2.75 (d, 1H), 1.80-1.66 (m, 2H), 1.53 (d, 1H), 1.13 (d, 1H). MS: 455 $(M + H)^+$. |
| 11 | (S)-1'-(6-amino-5-((2-amino-3-chloro pyridin-4-yl)thio) pyrazin-2-yl)-5-methoxy-1,3-dihydrospiro [indene-2,4'-piperidin]-1-amine | 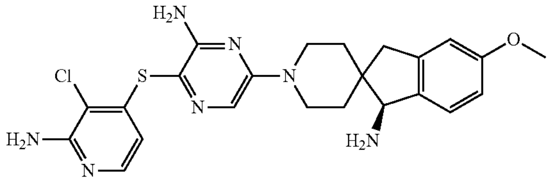 | $^1$H NMR (400 MHz, DMSO-d6) δ 7.80 (d, 1H), 7.72 (s, 1H), 7.50 (d, 1H), 6.92-6.79 (m, 2H), 6.11 (d, 1H), 4.37-4.15 (m, 3H), 3.76 (s, 3H), 3.25-3.10 (m, 3H), 2.97 (d, 1H), 1.84-1.67 (m, 2H), 1.66-1.57 (m, 1H), 1.51-1.41 (m, 1H). MS: 484 $(M + H)^+$. |
| 12 | (S)-1'-(6-amino-5-((2-amino-3-chloro pyridin-4-yl)thio) pyrazin-2-yl)-4,6-dihydrospiro[cyclopenta [b]thiophene-5, 4'-piperidin]-amine | 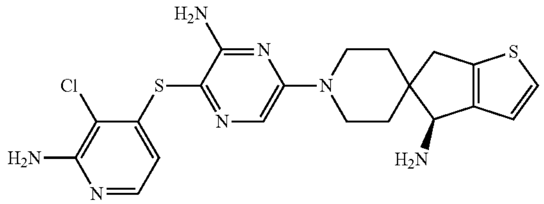 [SMILES: Nc1nc(N2CCC3(CC2)Cc2sccc2[C@H]3N)cnc1Sc1ccnc(N)c1Cl] | $^1$H NMR (400 MHz, MeOH-d4) δ 7.87 (s, 1H), 7.73 (d, 1H), 7.45 (d, 1H), 7.07 (d, 1H), 6.53 (d, 1H), 4.51 (d, 1H), 4.39 (d, 1H), 4.30 (s, 1H), 3.47-3.12 (m, 4H), 2.11-1.78 (m, 4H). MS: 460 $(M + H)^+$. |
| 13 | (S)-1-amino-1'-(6-amino-5-((2-amino-3-chloropyridin-4-yl)thio)pyrazin-2-yl)-1,3-dihydrospiro [indene-2,4'-piperidine]-6-carbonitrile | 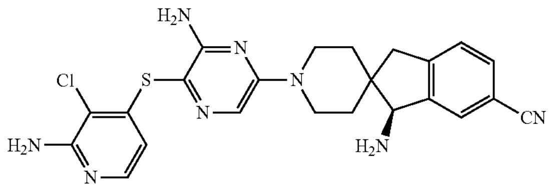 [SMILES: N#Cc1ccc2c(c1)[C@@H](N)C1(CCN(c3cnc(Sc4ccnc(N)c4Cl)c(N)n3)CC1)C2] | $^1$H NMR (400 MHz, DMSO-d6) δ 8.05 (s, 1H), 7.83 (d, 1H), 7.99 (d, 1H), 7.72 (s, 1H), 7.55 (d, 1H), 6.11 (d, 1H), 4.47 (s, 1H), 4.32 (d, 1H), 4.23 (d, 1H), 3.40-3.07 (m, 4H), 1.79-1.72 (m, 2H), 1.58-1.49 (m, 2H). MS: 479 $(M + H)^+$. |

TABLE 16-continued

| EX No | Chemical Name | Structure | $^1$HNMR & MS: $(M + H)^+$ |
|---|---|---|---|
| 14 | (S)-1'-(6-amino-5-((2-amino-3-chloro pyridin-4-yl)thio) pyrazin-2-yl)-4-methoxy-1,3-dihydrospiro[2,4'-piperidin]-1-amine | 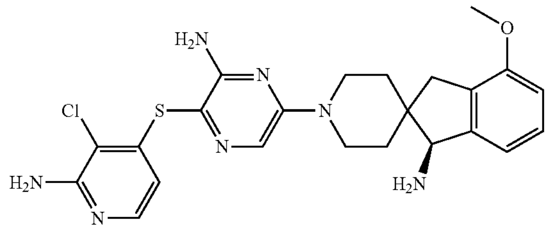 [SMILES: COc1cccc2c1CC1(CCN(c3cnc(Sc4ccnc(N)c4Cl)c(N)n3)CC1)[C@@H]2N] | $^1$H NMR (400 MHz, MeOH-d4) δ 7.89 (s, 1H), 7.75 (d, 1H), 7.35 (t, 1H), 7.12 (d, 1H), 7.01 (d, 1H), 6.58 (d, 1H), 4.48 (d, 1H), 4.44 (s, 1H), 4.37 (d, 1H), 3.87 (s, 3H), 3.51-3.38 (m, 2H), 3.19-3.07 (m, 2H), 1.99-1.87 (m, 2H), 1.79 (d, 1H), 1.66 (d, 1H). MS: 484 $(M + H)^+$. |
| 15 | (S)-1'-(6-amino-5-((2-amino-3-chloro pyridin-4-yl)thio) pyrazin-2-yl)-6-chloro-1,3-dihydrospiro[indene-2,4'-piperidin]-1-amine | 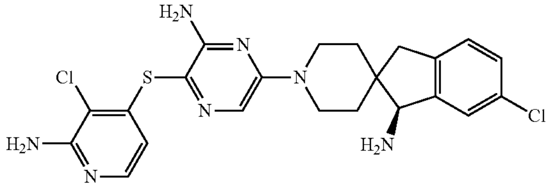 | $^1$H NMR (400 MHz, DMSO-d6) δ 7.80 (d, 1H), 7.72 (s, 1H), 7.70 (s, 1H), 7.41-7.35 (m, 2H), 6.12 (d, 1H), 4.39 (s, 1H), 4.32 (d, 1H), 4.24 (d, 1H), 3.23-2.94 (m, 4H), 1.86-1.70 (m, 2H), 1.58-1.49 (m, 2H). MS: 488 $(M + H)^+$. |
| 16 | (S)-1-amino-1'-(6-amino-5-((2-amino-3-chloropyridin-4-yl) thio)pyrazin-2-yl)-1,3-dihydrospiro [indene-2,4'-piperidine]-4-carbonitrile | 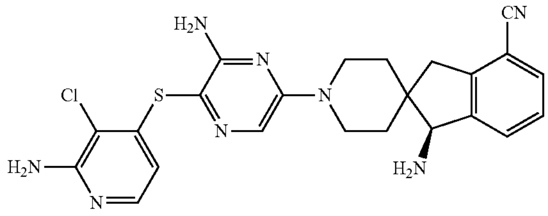 [SMILES: N#Cc1cccc2c1CC1(CCN(c3cnc(Sc4ccnc(N)c4Cl)c(N)n3)CC1)[C@@H]2N] | $^1$H NMR (400 MHz, MeOH-d4) δ 7.89-7.76 (m, 3H), 7.72 (d, 1H), 7.55 (t, 1H), 6.49 (d, 1H), 4.60 (s, 1H), 4.47 (d, 1H), 4.36 (d, 1H), 3.52-3.36 (m, 4H), 1.99-1.86 (m, 2H), 1.85-1.75 (m, 1H), 1.73-1.61 (m, 1H). MS: 479 $(M + H)^+$. |
| 17 | (S)-1-amino-1'-(6-amino-5-((2-amino-3-chloropyridin-4-yl)thio)pyrazin-2-yl)-1,3-dihydrospiro [indene-2,4'-piperidine]-4-carboxamide | 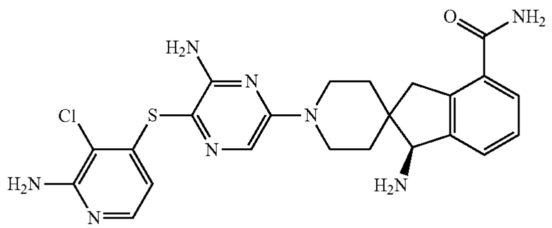 [SMILES: NC(=O)c1cccc2c1CC1(CCN(c3cnc(Sc4ccnc(N)c4Cl)c(N)n3)CC1)[C@@H]2N] | $^1$H NMR (400 MHz, MeOH-d4) δ 7.78-7.60 (m, 4H), 7.52-7.42 (m, 1H), 5.97 (d, 1H), 4.49-4.35 (m, 2H), 4.30 (d, 1H), 3.45-3.25 (m, 4H), 1.95-1.56 (m, 4H). MS: 497 $(M + H)^+$. |
| 18 | (R)-1'-(6-amino-5-((2-amino-3-chloro pyridin-4-yl)thio) pyrazin-2-yl)-1,3-dihydrospiro[indene-2,4'-piperidin]-1-amine | 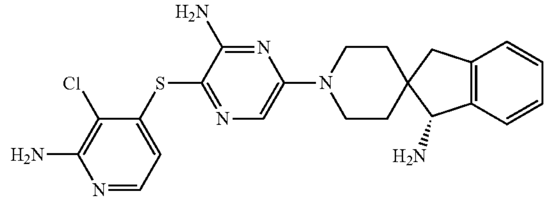 [SMILES: Nc1nc(N2CCC3(CC2)Cc2ccccc2[C@@H]3N)cnc1Sc1ccnc(N)c1Cl] | MS: 454 $(M + H)^+$. |
| 19 | (S)-1'-(6-amino-5-((2-amino-3-chloro pyridin-4-yl)thio) pyrazin-2-yl)-2-chloro-5,7-dihydrospiro[cyclopenta [b]pyridine-6,4'-piperidin]-5-amine | 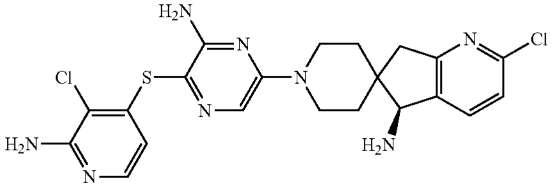 [SMILES: Nc1nc(N2CCC3(CC2)Cc2nc(Cl)ccc2[C@H]3N)cnc1Sc1ccnc(N)c1Cl] | $^1$H NMR (400 MHz, MeOH-d4) δ 7.86-7.80 (m, 1H), 7.66-7.59 (m, 2H), 7.34 (d, 1H), 5.96 (d, 1H), 4.41-4.29 (m, 2H), 4.08 (s, 1H), 3.32-3.18 (m, 3H), 2.97 (d, 1H), 1.93-1.79 (m, 2H), 1.65 (d, 1H), 1.49 (d, 1H). MS: 489 $(M + H)^+$. |
| 20 | (S)-1'-(6-amino-5-((2-amino-3-chloro pyridin-2-yl)thio) pyrazin-2-yl)-3-methoxy-5,7-dihydrospiro[cyclopenta] [c]pyridine-6,4'-piperidin]-7-amine | 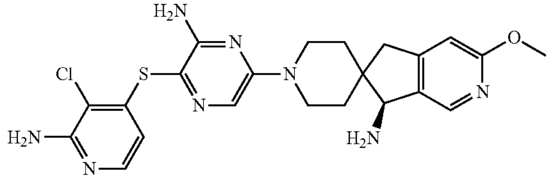 [SMILES: COc1cc2c(cn1)[C@@H](N)C1(CCN(c3cnc(Sc4ccnc(N)c4Cl)c(N)n3)CC1)C2] | $^1$H NMR (400 MHz, MeOH-d4) δ 8.08 (d, 1H), 7.82 (s, 1H), 7.71 (d, 1H), 7.02 (d, 1H), 6.47 (d, 1H), 4.49 (d, 2H), 4.37 (d, 1H), 4.06 (s, 3H), 3.47-3.34 (m, 4H), 2.05-1.95 (m, 1H), 1.93-1.83 (m, 2H), 1.71 (d, 1H). MS: 485 $(M + H)^+$. |

TABLE 16-continued

| EX No | Chemical Name | Structure | $^1$HNMR & MS: $(M + H)^+$ |
|---|---|---|---|
| 21 | (S)-1'-(6-amino-5-((2-amino-3-chloro pyridin-4-yl)thio) pyrazin-2-yl)-5,7-dihydrospiro[cyclopenta [c]pyridine-6,4'-piperidin]-7-amine | 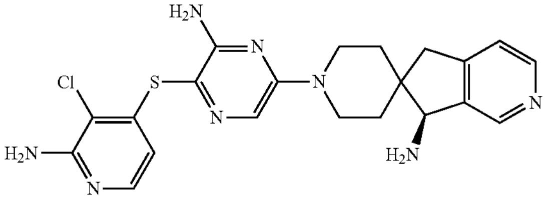 [SMILES: Nc1nc(N2CCC3(CC2)Cc2ccncc2[C@H]3N)cnc1Sc1ccnc(N)c1Cl] | $^1$H NMR (400 MHz, DMSO-d6) δ 9.16 (s, 1H), 8.88 (d, 1H), 8.04 (d, 1H), 7.81 (d, 1H), 7.74 (s, 1H), 6.11 (d, 1H), 4.72 (s, 1H), 4.43-4.13 (m, 2H), 3.73-3.12 (m, 4H), 1.91-1.75 (m, 2H), 1.72-1.64 (m, 1H), 1.53-1.40 (m, 1H). MS: 455 $(M + H)^+$. |
| 22 | (S)-1'-(6-amino-5-((2-amino-3-chloro pyridin-4-yl)thio) pyrazin-2-yl)-5,7-dihydrospiro [cyclopenta[c]pyridine-6,4'-piperidin]-5-amine | 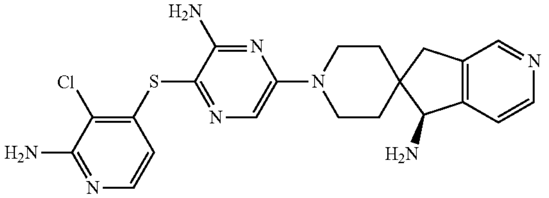 [SMILES: Nc1nc(N2CCC3(CC2)Cc2cnccc2[C@H]3N)cnc1Sc1ccnc(N)c1Cl] | $^1$H NMR (400 MHz, MeOH-d4) δ 8.92 (d, 2H), 8.26 (d, 1H), 7.83 (s, 1H), 7.72 (s, 1H), 6.49 (d, 1H), 4.97 (s, 1H), 4.52 (t, 2H), 3.70 (d, 1H), 3.46-3.29 (m, 3H), 2.19-1.65 (m, 4H). MS: 455 $(M + H)^+$. |
| 23 | (S)-1'-(6-amino-5-((2-amino-3-chloro pyridin-4-yl)thio) pyrazin-2-yl)-6-methyl-1,3-dihydro-spiro[indene-2,4'-piperidin]-1-amine | 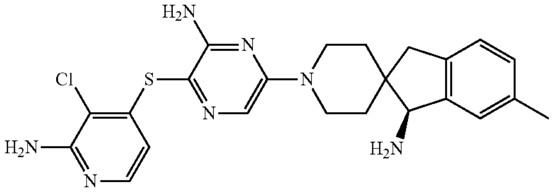 [SMILES: Cc1ccc2c(c1)[C@@H](N)C1(CCN(c3cnc(Sc4ccnc(N)c4Cl)c(N)n3)CC1)C2] | $^1$H NMR (400 MHz, DMSO-d6) δ 7.80 (d, 1H), 7.71 (s, 1H), 7.40 (s, 1H), 7.25-7.10 (m, 2H), 6.12 (d, 1H), 4.40-4.13 (m, 3H), 3.28-3.04 (m, 3H), 2.98-2.85 (d, 1H), 2.31 (s, 3H), 1.87-1.68 (m, 2H), 1.62-1.40 (m, 2H). MS: 468 $(M + H)^+$. |
| 24 | (S)-1'-(6-amino-5-((2-amino-3-chloro pyridin-4-yl)thio) pyrazin-2-yl)-6-(methylsulfonyl)-1,3-dihydrospiro[indene-2,4'-piperidin]-1-amine | 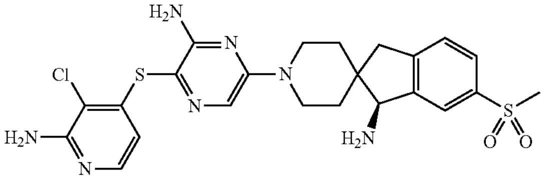 [SMILES: CS(=O)(=O)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 8.08 (s, 1H), 7.92 (d, 1H), 7.73-7.54 (m, 3H), 5.98 (d, 1H), 4.47-4.31 (m, 2H), 4.27 (s, 1H), 3.34-3.20 (m, 3H), 3.17 (s, 3H), 3.02 (d, 1H), 1.97-1.80 (m, 2H), 1.72-1.48 (m, 2H). MS: 532 $(M + H)^+$. |
| 25 | (1S)-1'-(6-amino-5-((2-amino-3-chloropyridin-4-yl)thio)pyrazin-2-yl)-6-(methylsulfinyl)-1,3-dihydrospiro [indene-2,4'-piperidin]-1-amine | 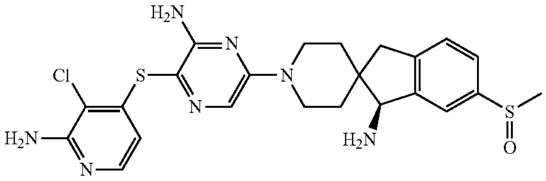 [SMILES: CS(=O)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.86-7.79 (m, 1H), 7.72-7.59 (m, 3H), 7.55 (d, 1H), 5.96 (d, 1H), 4.40-4.26 (m, 3H), 3.32-3.11 (m, 4H), 2.84 (s, 3H), 1.95-1.77 (m, 2H), 1.76-1.58 (m, 2H). MS: 516 $(M + H)^+$. |
| 26 | (S)-1-amino-1'-(6-amino-5-((2-amino-3-chloropyridin-4-yl)thio)pyrazin-1-yl)-1,3-dihydrospiro[indene-2,4'-piperidine]-6-carboxamide | 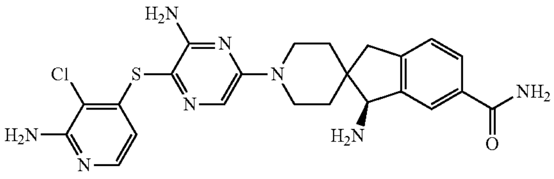 [SMILES: NC(=O)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 8.02 (s, 1H), 7.89 (d, 1H), 7.62-7.61 (m, 2H), 7.47 (d, 1H), 5.92 (d, 1H), 4.44 (s, 1H), 4.39-4.26 (m, 2H), 3.35-3.17 (m, 4H), 1.81-1.77 (m, 2H), 1.70 (d, 1H), 1.61 (d, 1H). MS: 497 $(M + H)^+$. |
| 27 | (S)-1-amino-1'-(6-amino-5-((2-amino-3-chloropyridin-4-yl)thio)pyrazin-2-yl)-N,N-dimethyl-1,3-dihydrospiro [indene-2,4'-piperidine]-6-carboxamide | 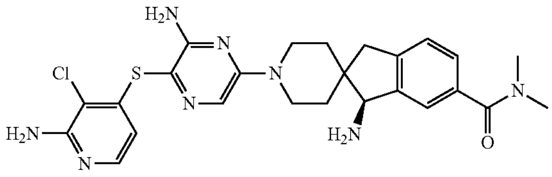 [SMILES: CN(C)C(=O)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.61 (s, 2H), 7.53 (s, 1H), 7.43 (s, 2H), 5.93 (d, 1H), 4.36-4.28 (m, 3H), 3.34-3.26 (m, 2H), 3.22-3.15 (d, 2H), 3.11 (s, 3H), 3.03 (s, 3H), 1.88-1.76 (m, 2H), 1.68-1.59 (m, 2H). MS: 525 $(M + H)^+$. |

TABLE 16-continued

| EX No | Chemical Name | Structure | $^1$HNMR & MS: $(M + H)^+$ |
|---|---|---|---|
| 28 | (S)-1'-(6-amino-5-((2-amino-3-chloro pyridin-4-yl)thio) pyrazin-2-yl)-6-bromo-1,3-dihydro-spiro[indene-2,4'-piperidin]-1-amine | 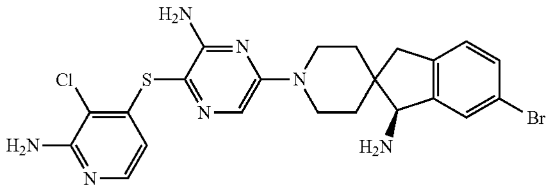 [SMILES: Nc1nc(N2CCC3(CC2)Cc2ccc(Br)cc2[C@H]3N)cnc1Sc1ccnc(N)c1Cl] | $^1$H NMR (600 MHz, MeOH-d4) δ 7.75 (s, 1H), 7.74 (s, 1H), 7.70 (d, 1H), 7.62-7.57 (m, 1H), 7.36 (d, 1H), 6.37 (d, 1H), 4.49 (s, 1H), 4.46 (d, 1H), 4.35 (d, 1H), 3.42-3.35 (m, 2H), 3.24-3.15 (m, 2H), 1.98-1.81 (m, 2H), 1.77 (d, 1H), 1.67 (d, 1H). MS: 532 $(M + H)^+$. |
| 29 | (S)-1'-(6-amino-5-((2-amino-3-chloro pyridin-4-yl)thio) pyrazin-2-yl)-4-bromo-1,3-dihydro-spiro[indene-2,4'-piperidin]-1-amine | 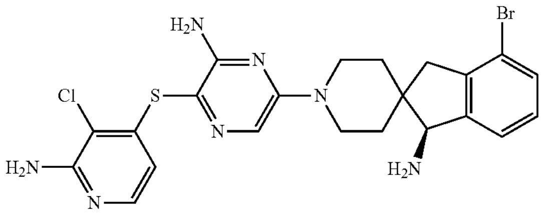 [SMILES: Nc1nc(N2CCC3(CC2)Cc2c(Br)cccc2[C@H]3N)cnc1Sc1ccnc(N)c1Cl] | $^1$H NMR (400 MHz, MeOH-d4) δ 7.77 (s, 1H), 7.68 (d, 1H), 7.61 (d, 1H), 7.52 (d, 1H), 7.30 (t, 1H), 6.39 (d, 1H), 4.57 (s, 1H), 4.44 (d, 1H), 4.33 (d, 1H), 3.46-3.34 (m, 2H), 3.21 (s, 2H), 2.03-1.62 (m, 4H). MS: 532 $(M + H)^+$. |
| 30 | (S)-1'-(5-((2-amino-3-chloropyridin-4-yl)thio)pyrazin-2-yl)-5,7-dihydrospiro [cyclopenta[b] pyridine-6,4'-piperidin]-5-amine | 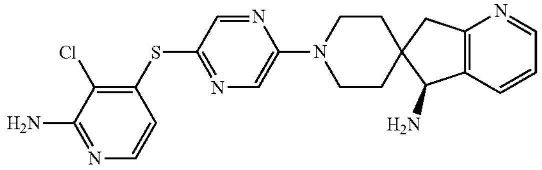 [SMILES: Nc1nccc(Sc2cnc(N3CCC4(CC3)Cc3ncccc3[C@H]4N)cn2)c1Cl] | $^1$H NMR (400 MHz, MeOH-d4) δ 8.39 (d, 1H), 8.37 (d, 1H), 8.28 (d, 1H), 7.86 (d, 1H), 7.60 (d, 1H), 7.31-7.28 (m, 1H), 5.95 (d, 1H), 4.42-4.36 (m, 2H), 4.12 (s, 1H), 3.37-3.33 (m, 2H), 3.26 (d, 1H), 3.00 (d, 1H), 1.94-1.81 (m, 2H), 1.69-1.45 (m, 2H). MS: 440 $(M + H)^+$. |
| 31 | (S)-1'-(6-amino-5-((2-amino-3-chloro pyridin-4-yl)thio) pyrazin-2-yl)-1,3-dihydrospiro[cyclopenta [a]naphthalene-2,4'-piperidin]-3-amine | 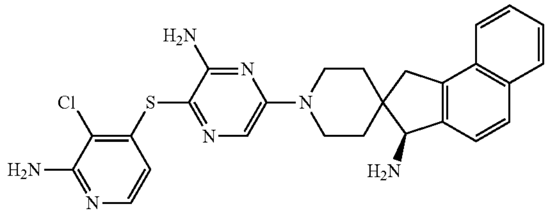 [SMILES: Nc1nc(N2CCC3(CC2)Cc2c(ccc4ccccc24)[C@H]3N)cnc1Sc1ccnc(N)c1Cl] | $^1$H NMR (600 MHz, MeOH-d4) δ 8.01-7.58 (m, 8H), 6.51 (d, 1H), 4.64 (s, 1H), 4.54 (d, 1H), 4.39 (d, 1H), 3.65-3.48 (m, 4H), 2.11-1.89 (m, 3H), 1.73 (d, 1H). MS: 504 $(M + H)^+$. |
| 32 | (S)-1'-(6-amino-5-((2-amino-3-chloro pyridin-4-yl)thio) pyrazin-2-yl)-6-chloro-5-methoxy-1,3-dihydrospiro[indene-2,4'-piperidin]-1-amine | 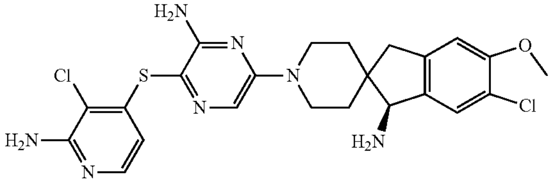 [SMILES: COc1cc2c(cc1Cl)[C@@H](N)C1(CCN(c3cnc(Sc4ccnc(N)c4Cl)c(N)n3)CC1)C2] | $^1$H NMR (400 MHz, DMSO-d6) δ 7.64-7.63 (m, 2H), 7.25 (s, 1H), 7.14 (s, 1H), 5.75 (d, 1H), 4.21 (d, 2H), 3.89 (s, 1H), 3.83 (s, 3H), 3.13-3.06 (m, 2H), 3.01 (d, 1H), 2.63 (d, 1H), 1.76-1.71 (m, 1H), 1.66-1.60 (m, 1H), 1.50 (d, 1H), 1.17 (d, 1H). MS: 518 $(M + H)^+$. |
| 33 | (S)-1'-(6-amino-5-((2-amino-3-chloro pyridin-4-yl)thio) pyrazin-2-yl)-1,3-dihydrospiro[indene-2,4'-piperidine]-1,6-diamine | 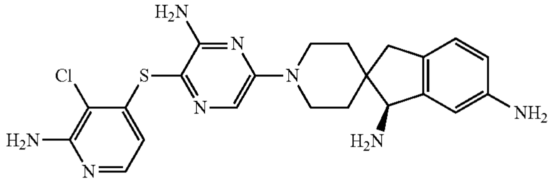 [SMILES: Nc1ccc2c(c1)[C@@H](N)C1(CCN(c3cnc(Sc4ccnc(N)c4Cl)c(N)n3)CC1)C2] | $^1$H NMR (600 MHz, MeOH-d4) δ 7.64 (d, 2H), 7.13 (d, 1H), 6.88 (s, 1H), 6.81 (d, 1H), 5.96 (d, 1H), 4.41 (d, 1H), 4.30 (d, 2H), 3.35-3.26 (m, 2H), 3.08 (d, 2H), 1.90-1.83 (m, 1H), 1.76 (d, 2H), 1.65 (d, 1H). MS: 469 $(M + H)^+$. |
| 34 | (S)-(1-amino-1'-(6-amino-5-((2-amino-3-chloropyridin-4-yl)thio)pyrazin-2-yl)-1,3-dihydrospiro [indene-2,4'-piperidin]-4-yl)dimethyl-phosphine oxide | 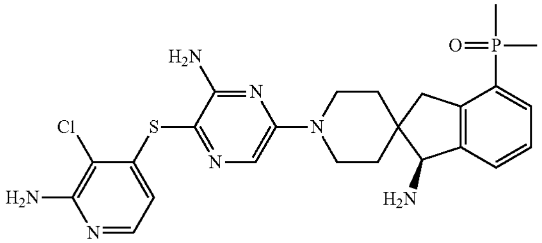 [SMILES: CP(C)(=O)c1cccc2c1CC1(CCN(c3cnc(Sc4ccnc(N)c4Cl)c(N)n3)CC1)[C@@H]2N] | $^1$H NMR (400 MHz, MeOH-d4) δ 7.80-7.68 (m, 2H), 7.67-7.59 (m, 2H), 7.51 (t, 1H), 5.96 (d, 1H), 4.41-4.24 (m, 3H), 3.48-3.31 (m, 4H), 1.96-1.79 (m, 8H), 1.71-1.55 (m, 2H). MS: 530 $(M + H)^+$. |

TABLE 16-continued

| EX No | Chemical Name | Structure | $^1$HNMR & MS: $(M + H)^+$ |
|---|---|---|---|
| 35 | (S)-1'-(6-amino-5-((2-amino-3-chloro pyridin-4-yl)thio) pyrazin-2-yl)-6-(trifluoromethyl)-1,3-dihydrospiro[indene-2,4'-piperidin]-1-amine | 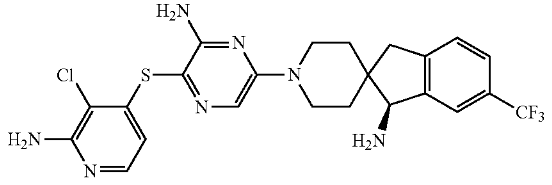 [SMILES: Nc1nc(N2CCC3(CC2)Cc2ccc(C(F)(F)F)cc2[C@H]3N)cnc1Sc1ccnc(N)c1Cl] | $^1$H NMR (400 MHz, DMSO-d6) δ 8.03 (s, 1H), 7.78 (d, 1H), 7.72-7.71 (m, 2H), 7.55 (d, 1H), 6.09 (d, 1H), 4.49 (d, 1H), 4.34-4.23 (m, 2H), 3.37-3.31 (d, 1H), 3.21-3.14 (m, 2H), 3.09-3.05 (d, 1H), 1.82-1.76 (m, 2H), 1.56-1.53 (m, 2H). MS: 522 $(M + H)^+$. |
| 36 | (S)-1'-(6-amino-5-((2-amino-3-chloro pyridin-4-yl)thio) pyrazin-2-yl)-6-(1H-imidazol-1-yl)-1,3-dihydrospiro [indene-2,4'-piperidin]-1-amine | 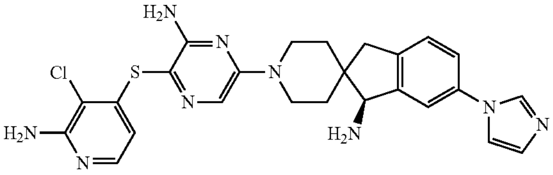 [SMILES: Nc1nc(N2CCC3(CC2)Cc2ccc(-n4ccnc4)cc2[C@H]3N)cnc1Sc1ccnc(N)c1Cl] | $^1$H NMR (400 MHz, MeOH-d4) δ 9.22 (s, 1H), 7.99 (s, 1H), 7.71-7.52 (m, 5H), 6.15 (d, 1H), 4.22 (d, 2H), 3.63-3.23 (m, 4H), 2.88 (d, 1H), 1.91 (d, 2H), 1.68 (d, 1H), 1.48 (d, 1H). MS: 520 $(M + H)^+$. |
| 37 | (S)-1'-(6-amino-5-((2-amino-3-chloro pyridin-4-yl)thio) pyrazin-2-yl)-6-(1H-pyrrol-1-yl)-1,3-dihydro-spiro[indene-2,4'-piperidin]-1-amine | 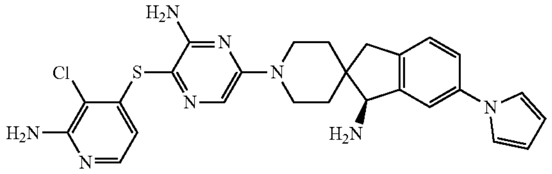 [SMILES: Nc1nc(N2CCC3(CC2)Cc2ccc(-n4cccc4)cc2[C@H]3N)cnc1Sc1ccnc(N)c1Cl] | $^1$H NMR (400 MHz, MeOH-d4) δ 7.81 (s, 1H), 7.75-7.70 (m, 2H), 7.66 (d, 1H), 7.58-7.53 (m, 1H), 7.48 (d, 1H), 7.22-7.19 (m, 1H), 6.46-6.43 (m, 1H), 6.34-6.29 (m, 2H), 4.53 (s, 1H), 4.47 (d, 1H), 4.37 (d, 1H), 3.42 (d, 2H), 3.24 (d, 2H), 1.98-1.90 (m, 2H), 1.81 (d, 1H), 1.72 (d, 1H). MS: 519 $(M + H)^+$. |
| 38 | (S)-1'-(6-amino-5-((2-amino-3-chloro pyridin-4-yl)thio) pyrazin-2-yl)-6-bromo-5-fluoro-1,3-dihydrospiro[indene-2,4'-piperidin]-1-amine | 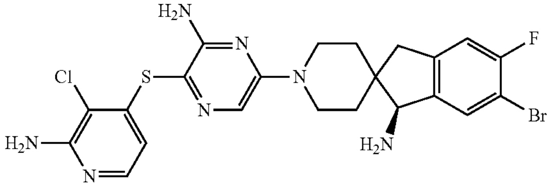 [SMILES: Nc1nc(N2CCC3(CC2)Cc2cc(F)c(Br)cc2[C@H]3N)cnc1Sc1ccnc(N)c1Cl] | $^1$H NMR (600 MHz, MeOH-d4) δ 7.84 (s, 1H), 7.81 (d, 1H), 7.73 (d, 1H), 7.28 (d, 1H), 6.50 (d, 1H), 4.51-4.42 (m, 2H), 4.35 (d, 1H), 3.47-3.39 (m, 2H), 3.27-3.20 (m, 2H), 2.00-1.93 (m, 1H), 1.92-1.84 (m, 1H), 1.84-1.73 (m, 1H), 1.72-1.63 (m, 1H). MS: 550 $(M + H)^+$. |
| 39 | (S)-1'-(6-amino-5-((2-amino-3-chloro pyridin-4-yl)thio) pyrazin-2-yl)-5,6-difluoro-1,3-dihydro-spiro[indene-2,4'-piperidin]-1-amine | 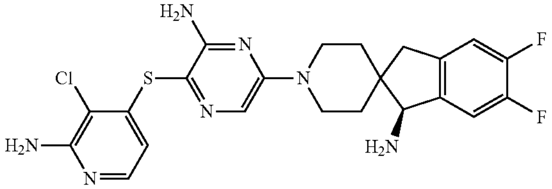 [SMILES: Nc1nc(N2CCC3(CC2)Cc2cc(F)c(F)cc2[C@H]3N)cnc1Sc1ccnc(N)c1Cl] | $^1$H NMR (400 MHz, DMSO-d6) δ 7.82 (d, 1H), 7.76-7.73 (m, 1H), 7.72 (s, 1H), 7.42-7.38 (m, 1H), 6.11 (d, 1H), 4.36-4.20 (m, 3H), 3.22-3.10 (m, 3H), 2.99-2.95 (d, 1H), 1.81-1.75 (m, 2H), 1.61-1.51 (m, 2H). MS: 490 $(M + H)^+$. |
| 40 | (S)-1'-(6-amino-5-((2-amino-3-chloro pyridin-4-yl)thio) pyrazin-2-yl)-6,7-difluoro-1,3-dihydro-spiro[indene-2,4'-piperidin]-1-amine | 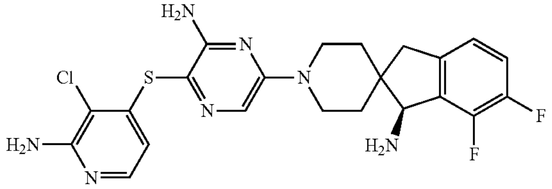 [SMILES: Nc1nc(N2CCC3(CC2)Cc2ccc(F)c(F)c2[C@H]3N)cnc1Sc1ccnc(N)c1Cl] | $^1$H NMR (400 MHz, DMSO-d6) δ 7.65-7.63 (m, 2H), 7.30-7.22 (m, 2H), 5.75 (d, 1H), 4.22-4.17 (m, 2H), 3.83 (s, 1H), 3.16-3.02 (m, 3H), 2.62 (d, 1H), 1.78-1.71 (m, 1H), 1.68-1.55 (m, 1H), 1.51 (d, 1H), 1.11 (d, 1H). MS: 490 $(M + H)^+$. |
| 41 | (S)-(1-amino-1'-(6-amino-((2-amino-3-chloropyridin-4-yl)thio)pyrazin-2-yl)-5-fluoro-1,3-dihydrospiro[indene-2,4'-piperidin]-6-yl) dimethylphosphine oxide | 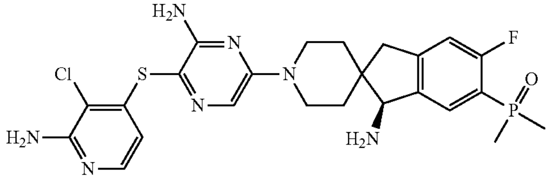 [SMILES: CP(C)(=O)c1cc2c(cc1F)CC1(CCN(c3cnc(Sc4ccnc(N)c4Cl)c(N)n3)CC1)[C@@H]2N] | $^1$H NMR (400 MHz, MeOH-d4) δ 7.97-7.92 (m, 1H), 7.64-7.63 (m, 2H), 7.34-7.31 (m, 1H), 5.96 (d, 1H), 4.44-4.38 (m, 2H), 4.31 (d, 1H), 3.34-3.21 (m, 4H), 1.93-1.80 (m, 8H), 1.75-1.71 (m, 1H), 1.66-1.62 (m, 1H). MS: 548 $(M + H)^+$. |
| 42 | (S)-1-amino-1'-(6-amino-5-((2-amino-3-chloropyridin-4-yl) thio)pyrazin-2-yl)-5-fluoro-1,3-dihydro-spiro[indene-2, 4'-piperidine]-6-carbonitrile | 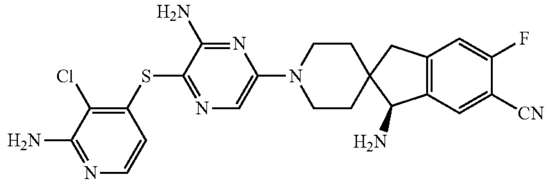 [SMILES: N#Cc1cc2c(cc1F)CC1(CCN(c3cnc(Sc4ccnc(N)c4Cl)c(N)n3)CC1)[C@@H]2N] | $^1$H NMR (400 MHz, MeOH-d4) δ 7.90 (d, 1H), 7.79 (s, 1H), 7.70 (d, 1H), 7.43 (d, 1H), 6.43 (d, 1H), 4.54 (s, 1H), 4.44 (d, 1H), 4.33 (d, 1H), 3.47-3.20 (m, 4H), 2.01-1.82 (m, 2H), 1.82-1.72 (m, 1H), 1.71-1.60 (m, 1H). MS: 497 $(M + H)^+$. |

TABLE 16-continued

| EX No | Chemical Name | Structure | $^1$HNMR & MS: $(M + H)^+$ |
|---|---|---|---|
| 43 | (S)-1-amino-1'-(6-amino-5-((2-amino-3-chloropyridin-4-yl)thio)pyrazin-2-yl)-5-fluoro-1,3-dihydro-spiro[indene-2,4'-piperidine]-6-carboxamide | 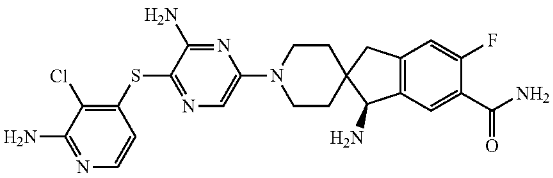 [SMILES: NC(=O)c1cc2c(cc1F)CC1(CCN(c3cnc(Sc4ccnc(N)c4Cl)c(N)n3)CC1)[C@@H]2N] | $^1$H NMR (400 MHz, MeOH-d4) δ 7.87 (d, 1H), 7.68-7.59 (m, 2H), 7.15 (d, 1H), 5.96 (d, 1H), 4.31-4.26 (d, 2H), 4.04 (s, 1H), 3.39-3.18 (m, 3H), 2.90-2.86 (d, 1H), 1.96-1.74 (m, 2H), 1.61-1.57 (m, 1H), 1.44-1.41 (m, 1H). MS: 515 $(M + H)^+$. |
| 44 | (S)-1'-(6-amino-5-((2-amino-3-chloro pyridin-4-yl)thio) pyrazin-2-yl)-2-chloro-4,6-dihydro-spiro[cyclopenta[d] thiazole-5,4'-piperidin]-4-amine | 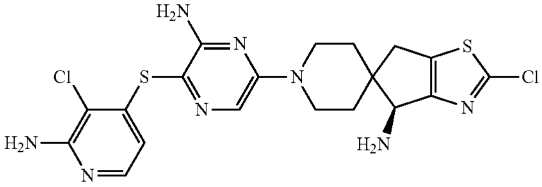 [SMILES: Nc1nc(N2CCC3(CC2)Cc2sc(Cl)nc2[C@H]3N)cnc1Sc1ccnc(N)c1Cl] | $^1$H NMR (400 MHz, DMSO-d6) δ 7.65 (s, 1H), 7.64 (d, 1H), 5.75 (d, 1H), 4.06-3.96 (m, 2H), 3.80 (s, 1H), 3.41-3.28 (m, 2H), 2.91-2.76 (m, 2H), 1.91-1.82 (m, 1H), 1.66-1.47 (m, 3H). MS: 495 $(M + H)^+$. |
| 45 | (R)-1'-(6-amino-5-((2-amino-3-chloro pyridin-4-yl)thio) pyrazin-2-yl)-3H-spiro[benzofuran-2,4'-piperidin]-3-amine | 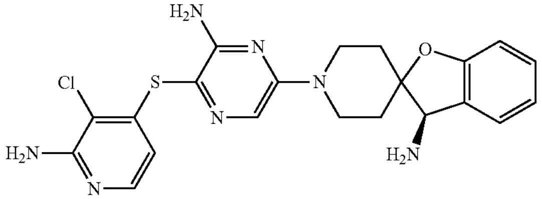 [SMILES: Nc1nc(N2CCC3(CC2)Oc2ccccc2[C@H]3N)cnc1Sc1ccnc(N)c1Cl] | $^1$H NMR (400 MHz, DMSO-d6) δ 7.70 (s, 1H), 7.65 (d, 1H), 7.42 (d, 1H), 7.20 (t, 1H), 6.90 (t, 1H), 6.84 (d, 1H), 5.77 (d, 1H), 4.32-4.20 (m, 3H), 3.33-3.29 (m, 2H), 1.99-1.90 (m, 1H), 1.84-1.70 (m, 3H). MS: 456 $(M + H)^+$. |
| 46 | (S)-1-(1-amino-1'-(6-amino-5-((2-amino-3-chloropyridin-4-yl)thio)pyrazin-2-yl)-1,3-dihydrospiro [indene-2,4'-piperidin]-6-yl)urea | 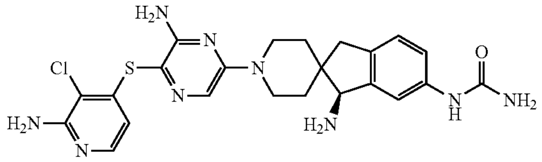 [SMILES: NC(=O)Nc1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.68 (s, 1H), 7.64-7.59 (m, 2H), 7.31-7.25 (m, 2H), 5.93 (d, 1H), 4.43-4.25 (m, 3H), 3.31-3.11 (m, 4H), 1.88-1.60 (m, 4H). MS: 512 (M + H)+. |
| 47 | (S)-1'-(6-amino-5-((2-amino-3-chloro pyridin-4-yl)thio) pyrazin-2-yl)-5-bromo-1,3-dihydro-spiro[indene-2,4'-piperidin]-1-amine | 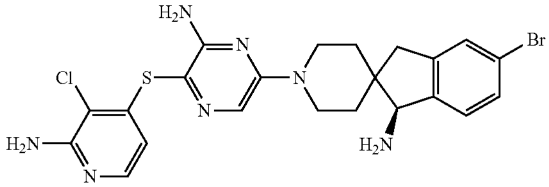 | $^1$H NMR (400 MHz, MeOH-d4) δ 7.84 (s, 1H), 7.74 (d, 1H), 7.58 (s, 1H), 7.53-7.41 (m, 2H), 6.51 (d, 1H), 4.50-4.28 (m, 3H), 3.51-3.35 (m, 2H), 3.30-3.17 (m, 2H), 2.02-1.83 (m, 2H), 1.81-1.71 (m, 1H), 1.70-1.57 (m, 1H). MS: 532 $(M + H)^+$. |
| 48 | (S)-1'-(5-((2-amino-3-chloropyridin-4-yl)thio)pyrazin-2-yl)-1,3-dihydro-spiro[indene-2,4'-piperidin]-1-amine | 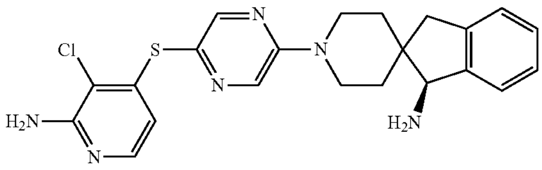 | $^1$H NMR (400 MHz, DMSO-d6) δ 8.55 (s, 1H), 8.38 (s, 1H), 7.80 (d, 1H), 7.60 (d, 1H), 7.35-7.28 (m, 3H), 6.23 (d, 1H), 4.43-4.31 (m, 3H), 3.38-3.23 (m, 3H), 3.03-2.99 (d, 1H), 1.93-1.78 (m, 2H), 1.61-1.54 (m, 2H). MS: 439 $(M + H)^+$. |
| 49 | (S)-1'-(5-((3-chloro-2-(dimethylamino) pyridin-4-yl)thio) pyrazin-2-yl)-1,3-dihydrospiro[indene-2,4'-piperidin]-1-amine | 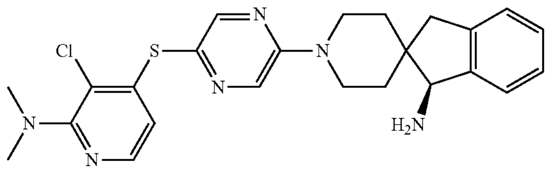 [SMILES: CN(C)c1nccc(Sc2cnc(N3CCC4(CC3)Cc3ccccc3[C@H]4N)cn2)c1Cl] | $^1$H NMR (600 MHz, MeOH-d4) δ 8.50 (s, 1H), 8.36 (s, 1H), 7.78 (d, 1H), 7.54 (d, 1H), 7.44-7.39 (m, 2H), 7.34 (m, 1H), 6.60 (d, 1H), 4.51 (d, 1H), 4.45 (s, 1H), 4.38 (d, 1H), 3.51-3.40 (m, 2H), 3.33 (s, 6H), 3.28-3.19 (m, 2H), 2.00-1.93 (m, 1H), 1.92-1.85 (m, 1H), 1.80 (d, 1H), 1.68 (d, 1H). MS: 467 $(M + H)^+$. |
| 50 | (S)-1'-(5-((3-amino-2-chlorophenyl) thio)pyrazin-2-yl)-1,3-dihydrospiro [indene-2,4'-piperidin]-1-amine | 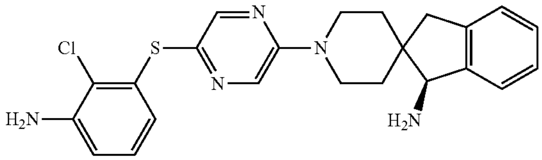 [SMILES: Nc1cccc(Sc2cnc(N3CCC4(CC3)Cc3ccccc3[C@H]4N)cn2)c1Cl] | $^1$H NMR (400 MHz, DMSO-d6) δ 8.43 (s, 1H), 8.19 (s, 1H), 7.59 (d, 1H), 7.35-7.29 (m, 3H), 6.97 (t, 1H), 6.78 (d, 1H), 6.22 (d, 1H), 4.35 (s, 1H), 4.32-4.22 (m, 2H), 3.28-3.19 (m, 3H), 3.02-2.98 (d, 1H), 1.82-1.71 (m, 2H), 1.60-1.46 (m, 2H). MS: 438 $(M + H)^+$. |

TABLE 16-continued

| EX No | Chemical Name | Structure | $^1$HNMR & MS: $(M + H)^+$ |
|---|---|---|---|
| 51 | (S)-1'-(5-((3-chloro-2-methoxypyridin-4-yl)thio)pyrazin-2-yl)-1,3-dihydro-spiro[indene-2,4'-piperidin]-1-amine | 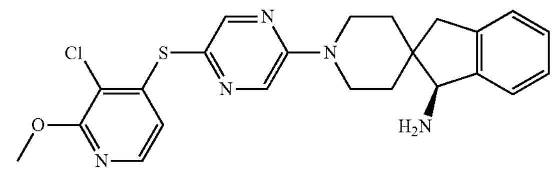 [SMILES: COc1nccc(Sc2cnc(N3CCC4(CC3)Cc3ccccc3[C@H]4N)cn2)c1Cl] | $^1$H NMR (400 MHz, DMSO-d6) δ 8.52 (d, 1H), 8.34 (s, 1H), 7.89 (d, 1H), 7.59 (d, 1H), 7.39-7.26 (m, 3H), 6.33 (d, 1H), 4.39 (m, 2H), 4.30 (d, 1H), 3.94 (d, 3H), 3.23 (m, 3H), 3.07-2.95 (m, 1H), 1.87-1.71 (m, 2H), 1.63-1.49 (m, 2H). MS: 454 $(M + H)^+$. |
| 52 | (S)-1'-(6-amino-5-((3-chloro-2-(dimethylamino)pyridin-4-yl)thio)pyrazin-2-yl)-1,3-dihydrospiro [indene-2,4'-piperidin]-1-amine | 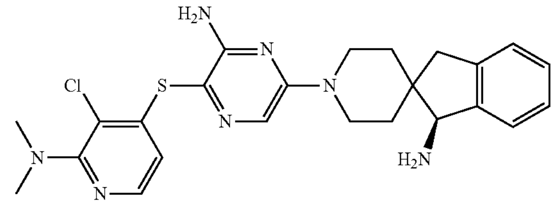 [SMILES: CN(C)c1nccc(Sc2ncc(N3CCC4(CC3)Cc3ccccc3[C@H]4N)nc2N)c1Cl] | $^1$H NMR (400 MHz, DMSO-d6) δ 7.89 (d, 1H), 7.72 (s, 1H), 7.60 (d, 1H), 7.41-7.20 (m, 3H), 6.24 (d, 1H), 4.35 (s, 1H), 4.33 (d, 1H), 4.23 (d, 1H), 3.27-3.11 (m, 3H), 3.05 (s, 6H), 3.02-2.93 (d, 1H), 1.85-1.70 (m, 2H), 1.62-1.46 (m, 2H). MS: 482 $(M + H)^+$. |
| 53 | (S)-1'-(6-amino-5-((3-amino-2-chloro phenyl)thio)pyrazin-2-yl)-1,3-dihydro spiro[2,4'-piperidin]-1-amine | 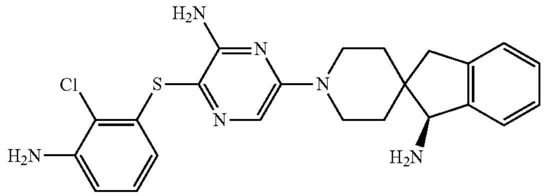 [SMILES: Nc1cccc(Sc2ncc(N3CCC4(CC3)Cc3ccccc3[C@H]4N)nc2N)c1Cl] | $^1$H NMR (400 MHz, DMSO-d6) δ 7.61 (d, 1H), 7.35-7.27 (m, 4H), 7.00-6.93 (t, 1H), 6.79 (d, 1H), 6.07 (d, 1H), 4.35 (s, 1H), 4.30 (d, 1H), 4.20 (d, 1H), 3.19-3.28 (m, 3H), 3.21 (d, 1H), 1.82-1.73 (m, 2H), 1.59-1.48 (m, 2H). MS: 453 $(M + H)^+$. |
| 54 | (S)-1'-(6-amino-5-((3-chloro-2-methoxypyridin-4-yl)thio)pyrazin-2-yl)-1,3-dihydrospiro [indene-2,4'-piperidin]-1-amine | 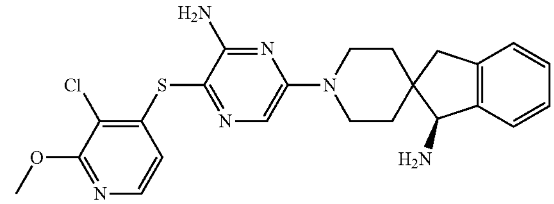 [SMILES: COc1nccc(Sc2ncc(N3CCC4(CC3)Cc3ccccc3[C@H]4N)nc2N)c1Cl] | $^1$H NMR (400 MHz, DMSO-d6) δ 7.87 (d, 1H), 7.66 (s, 1H), 7.37-7.32 (m, 1H), 7.22-7.17 (m, 3H), 6.19 (d, 1H), 4.22 (d, 2H), 3.92 (s, 4H), 3.19-3.06 (m, 3H), 2.71-2.67 (d, 1H), 1.82-1.58 (m, 2H), 1.48-1.39 (m, 1H), 1.19-1.16 (m, 1H). MS: 469 $(M + H)^+$. |
| 55 | (S)-1'-(6-amino-5-((2,3-dichloro-phenyl)thio) pyrazin-2-yl)-1,3-dihydrospiro[indene-2,4'-piperidin]-1-amine | 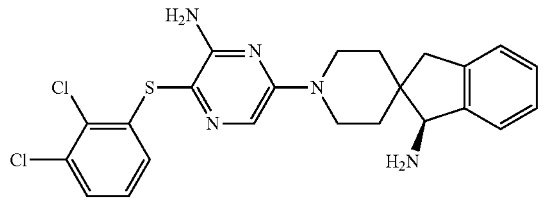 [SMILES: Nc1nc(N2CCC3(CC2)Cc2ccccc2[C@H]3N)cnc1Sc1cccc(Cl)c1Cl] | $^1$H NMR (400 MHz, DMSO-d6) δ 7.69 (s, 1H), 7.59 (d, 1H), 7.41 (d, 1H), 7.39-7.27 (m, 3H), 7.23 (t, 1H), 6.60 (d, 1H), 4.36 (s, 1H), 4.31 (d, 1H), 4.21 (d, 1H), 3.22-3.13 (m, 3H), 3.02-2.98 (d, 1H), 1.80-1.71 (m, 2H), 1.57-1.48 (m, 2H). MS: 472 $(M + H)^+$. |
| 56 | (R)-1'-(5-((2-amino-3-chloropyridin-4-yl)thio)pyrazin-2-yl)-3H-spiro[benzo furan-2,4'-piperidin]-3-amine | 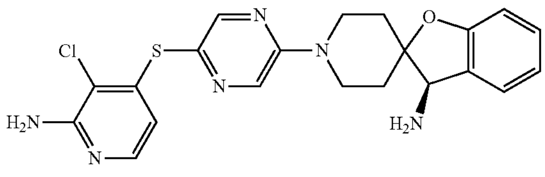 [SMILES: Nc1nccc(Sc2cnc(N3CCC4(CC3)Oc3ccccc3[C@H]4N)cn2)c1Cl] | $^1$H NMR (600 MHz, MeOH-d4) δ 8.38 (d, 1H), 8.30 (s, 1H), 7.61 (d, 1H), 7.42 (d, 1H), 7.24 (t, 1H), 6.94 (t, 1H), 6.85 (d, 1H), 5.96 (d, 1H), 4.53 (d, 1H), 4.40 (d, 1H), 4.24 (s, 1H), 3.54-3.45 (m, 2H), 2.01-1.83 (m, 4H). MS: 441 $(M + H)^+$. |
| 57 | (S)-(1-amino-1'-(6-amino-5-((2-amino-3-chloropyridin-4-yl)thio)pyrazin-2-yl)-1,3-dihydrospiro [indene-2,4'-piperidin]-6-yl)dimethyl-phosphine oxide | 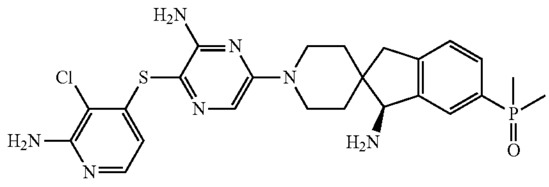 [SMILES: CP(C)(=O)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.77 (d, 1H), 7.69-7.63 (m, 1H), 7.61-7.59 (m, 2H), 7.44-7.42 (m, 1H), 5.94 (d, 1H), 4.32-4.27 (m, 2H), 4.01 (s, 1H), 3.32-3.23 (m, 2H), 2.86 (d, 1H), 2.58 (d, 1H), 1.94-1.73 (m, 8H), 1.51 (d, 1H), 1.37 (d, 1H). MS: 530 $(M + H)^+$. |

TABLE 16-continued

| EX No | Chemical Name | Structure | $^1$HNMR & MS: $(M + H)^+$ |
| --- | --- | --- | --- |
| 58 | (S)-1'-(6-amino-5-((2-amino-3-chloro pyridin-4-yl)thio) pyrazin-2-yl)-6-((tetrahydro-2H-pyran-4-yl)oxy)-1,3-dihydrospiro[indene-2,4'-piperidin]-1-amine | 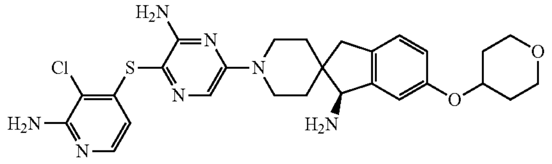 [SMILES: Nc1nc(N2CCC3(CC2)Cc2ccc(OC4CCOCC4)cc2[C@H]3N)cnc1Sc1ccnc(N)c1Cl] | $^1$H NMR (400 MHz, MeOH-d4) δ 7.62-7.60 (m, 2H), 7.26 (d, 1H), 7.13 (d, 1H), 7.07-6.97 (m, 1H), 5.92 (d, 1H), 4.59-4.54 (m, 2H), 4.37 (d, 1H), 4.32 (s, 1H), 4.28 (d, 1H), 3.98-3.93 (m, 2H), 3.63-3.56 (m, 2H), 3.35-3.22 (m, 2H), 3.14-3.03 (m, 2H), 2.06-2.01 (m, 2H), 1.86-1.58 (m, 5H). MS: 554 $(M + H)^+$. |
| 59 | (S)-(1-amino-1'-(6-amino-5-((2-amino-3-chloropyridin-4-yl)thio)pyrazin-2-yl)-1,3-dihydrospiro [indene-2,4'-piperidin]-6-yl)(piperidin-1-yl)methanone | 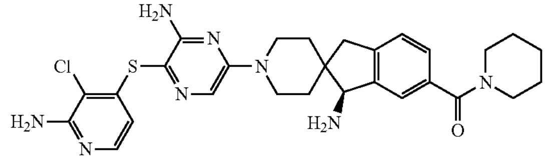 [SMILES: Nc1nc(N2CCC3(CC2)Cc2ccc(C(=O)N4CCCCC4)cc2[C@H]3N)cnc1Sc1ccnc(N)c1Cl] | $^1$H NMR (400 MHz, MeOH-d4) δ 7.61 (t, 2H), 7.51 (s, 1H), 7.45-7.38 (m, 2H), 5.93 (d, 1H), 4.39-4.27 (m, 3H), 3.80-3.64 (m, 2H), 3.43-3.37 (m, 2H), 3.32-3.25 (m, 2H), 3.24 (d, 1H), 3.10 (d, 1H), 1.88-1.50 (m, 10H). MS: 565 $(M + H)^+$. |
| 60 | (S)-1'-(6-amino-5-((2-amino-3-chloro pyridin-4-yl)thio) pyrazin-2-yl)-6-morpholino-1,3-dihydro-spiro[indene-2,4'-piperidin]-1-amine | 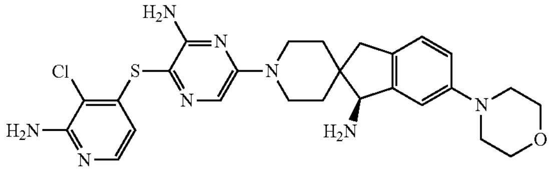 [SMILES: Nc1nc(N2CCC3(CC2)Cc2ccc(N4CCOCC4)cc2[C@H]3N)cnc1Sc1ccnc(N)c1Cl] | $^1$H NMR (400 MHz, MeOH-d4) δ 7.62-7.58 (m, 2H), 7.18 (d, 1H), 7.06 (d, 1H), 6.94-6.91 (m, 1H), 5.92 (d, 1H), 4.33-4.24 (m, 2H), 4.10 (s, 1H), 3.83 (t, 4H), 3.24 (t, 2H), 3.12 (t, 4H), 3.07 (d, 1H), 2.88 (d, 1H), 1.82-1.73 (m, 2H), 1.62-1.53 (m, 2H). MS: 539 $(M + H)^+$. |
| 61 | (S)-1'-(6-amino-5-((2-amino-3-choro pyridin-4-yl)thio) pyrazin-2-yl)-5,6,7-trifluoro-1,3-dihydro-spiro[indene-2,4'-piperidin]-1-amine | 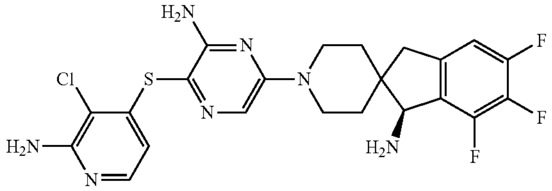 [SMILES: Nc1nc(N2CCC3(CC2)Cc2cc(F)c(F)c(F)c2[C@H]3N)cnc1Sc1ccnc(N)c1Cl] | $^1$H NMR (400 MHz, MeOH-d4) δ 7.63 (d, 2H), 7.27-7.17 (m, 1H), 5.95 (d, 1H), 4.67 (s, 1H), 4.39 (d, 1H), 4.27 (d, 1H), 3.30-3.12 (m, 4H), 1.94-1.88 (m, 1H), 1.85-1.70 (m, 2H), 1.61 (d, 1H). MS: 508 $(M + H)^+$. |
| 62 | (S)-4-(1-amino-1'-(6-amino-5-((2-amino-3-chloropyridin-4-yl)thio)pyrazin-2-yl)-1,3-dihydrospiro [indene-2,4'-piperidin]-6-yl) morpholin-3-one | 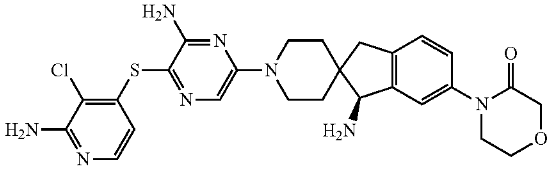 [SMILES: Nc1nc(N2CCC3(CC2)Cc2ccc(N4CCOCC4=O)cc2[C@H]3N)cnc1Sc1ccnc(N)c1Cl] | $^1$H NMR (400 MHz, MeOH-d4) δ 7.68-7.55 (m, 2H), 7.45-7.32 (m, 3H), 5.92 (d, 1H), 4.45-4.25 (m, 5H), 4.05 (t, 2H), 3.79 (d, 2H), 3.35 (s, 2H), 3.20 (d, 1H), 3.07 (d, 1H), 1.90-1.60 (m, 4H). MS: 553 $(M + H)^+$. |
| 63 | (S)-N-(1-amino-1'-(6-amino-5-((2-amino-3-chloropyridin-4-yl)thio)pyrazin-2-yl)-1,3-dihydrospiro [indene-2,4'-piperidin]-6-yl)methane-sulfonamide | 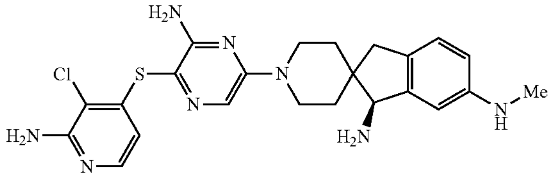 [SMILES: CNc1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.59 (t, 2H), 7.36 (s, 1H), 7.26 (d, 1H), 7.15-7.12 (m, 1H), 5.92 (d, 1H), 4.29 (t, 2H), 4.11 (s, 1H), 3.30-3.21 (m, 2H), 3.14 (d, 1H), 2.96 (s, 3H), 2.89 (d, 1H), 1.85-1.75 (m, 2H), 1.62-1.49 (m, 2H). MS: 547 $(M + H)^+$. |
| 64 | (S)-1'-(6-amino-5-((2-amino-3-chloro pyridin-4-yl)thio) pyrazin-2-yl)-1,3-dihydrospiro[cyclopenta [b]quinoline-2, 4'-piperidin]-1-amine | 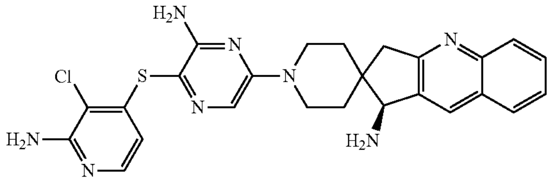 [SMILES: Nc1nc(N2CCC3(CC2)Cc2nc4ccccc4cc2[C@H]3N)cnc1Sc1ccnc(N)c1Cl] | $^1$H NMR (400 MHz, MeOH-d4) δ 9.26 (s, 1H), 8.42 (d, 1H), 8.30-8.20 (m, 2H), 8.02 (t, 1H), 7.83 (s, 1H), 7.71 (d, 1H), 6.46 (d, 1H), 5.01 (s, 1H), 4.54 (d, 1H), 4.43 (d, 1H), 3.98 (d, 1H), 3.78 (d, 1H), 3.45 (t, 2H), 2.06 (t, 2H), 1.97-1.83 (m, 2H). MS: 505 $(M + H)^+$. |
| 65 | (R)-1'-(6-amino-5-((2-amino-3-chloro pyridin-4-yl)thio) pyrazin-2-yl)-5,7-dihydrospiro[cyclopenta [c]pyridine-6,4'-piperidin]-5-amine | 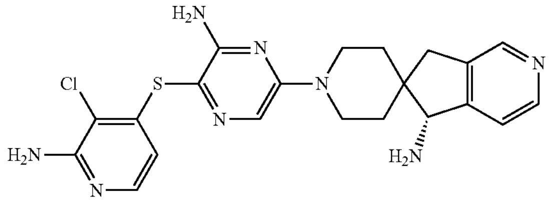 [SMILES: Nc1nc(N2CCC3(CC2)Cc2cnccc2[C@@H]3N)cnc1Sc1ccnc(N)c1Cl] | $^1$H NMR (400 MHz, MeOH-d4) δ 8.53 (s, 1H), 8.49 (d, 1H), 7.62-7.52 (m, 3H), 5.93 (d, 1H), 4.40-4.33 (m, 3H), 3.55-3.02 (m, 4H), 1.92-1.53 (m, 4H). MS: 455 $(M + H)^+$. |

TABLE 16-continued

| EX No | Chemical Name | Structure | $^1$HNMR & MS: $(M + H)^+$ |
|---|---|---|---|
| 66 | (S)-1'-(6-amino-5-((2,3-dichloropyridin-4-yl)thio)pyrazin-2-yl)-1,3-dihydro-spiro[indene-2,4'-piperidin]-1-amine | 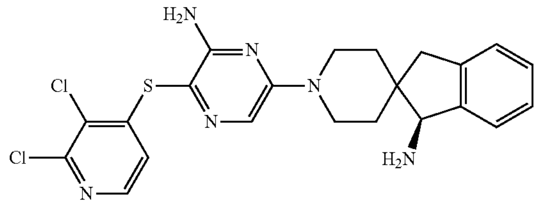 | $^1$H NMR (400 MHz, MeOH-d4) δ 8.05 (d, 1H), 7.74 (s, 1H), 7.52 (d, 1H), 7.42-7.32 (m, 3H), 6.73 (d, 1H), 4.45-4.43 (m, 3H), 3.42-3.20 (m, 4H), 2.02-1.62 (m, 4H). MS: 473 $(M + H)^+$. |
| 67 | (1R,3R)-1'-(6-amino-5-((2-amino-3-chloropyridin-4-yl)thio)pyrazin-2-yl)-1,3-dihydrospiro[indene-2,4'-piperidine]-1,3-diamine | 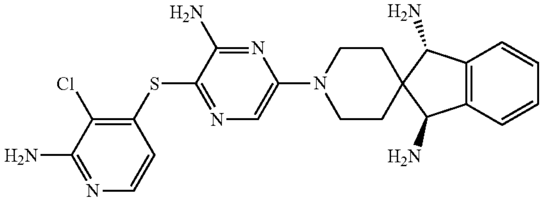 [SMILES: Nc1nc(N2CCC3(CC2)[C@H](N)c2ccccc2[C@H]3N)cnc1Sc1ccnc(N)c1Cl] | $^1$H NMR (400 MHz, MeOH-d4) δ 7.74-7.62 (m, 4H), 7.62-7.52 (m, 2H), 5.98 (d, 1H), 4.97 (s, 2H), 4.02-3.82 (m, 4H), 1.96-1.84 (m, 2H), 1.84-1.72 (m, 2H). MS: 469 $(M + H)^+$. |
| 68 | (S)-1'-(5-((2-amino-3-chloropyridin-4-yl)thio)pyrazin-2-yl)-2-chloro-4,6-dihydrospiro[cyclopenta[d]thiazole-5,4'-piperidin]-amine | 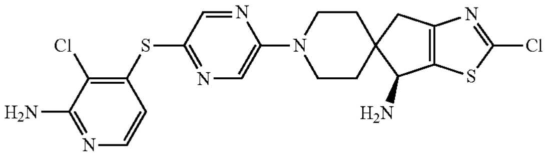 [SMILES: Nc1nccc(Sc2cnc(N3CCC4(CC3)Cc3nc(Cl)sc3[C@H]4N)cn2)c1Cl] | $^1$H NMR (400 MHz, DMSO-d6) δ 8.49 (d, 1H), 8.29 (d, 1H), 7.66 (d, 1H), 5.83 (d, 1H), 4.26-4.09 (m, 2H), 4.03 (s, 1H), 3.46-3.23 (m, 2H), 2.91-2.71 (m, 2H), 1.92-1.77 (m, 1H), 1.74-1.54 (m, 3H). MS: 480 $(M + H)^+$. |
| 69 | (S)-1'-(6-amino-5-((2-amino-3-chloro pyridin-4-yl)thio) pyrazin-2-yl)-2-chloro-4,6-dihydro-spiro[cyclopenta[d] thiazole-5,4'-piperidin]-6-amine | 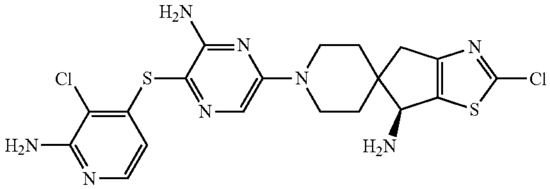 [SMILES: Nc1nc(N2CCC3(CC2)Cc2nc(Cl)sc2[C@H]3N)cnc1Sc1ccnc(N)c1Cl] | MS: 495 $(M + H)^+$. |
| 70 | (S)-1-amino-1'-(6-amino-5-((2-amino-3-chloropyridin-4-yl) thio)pyrazin-2-yl)-3H-spiro[indolizine-2,4'-piperidin]-5(1H)-one | 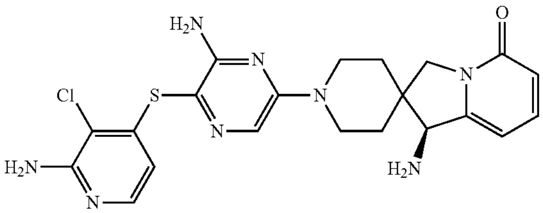 [SMILES: Nc1nc(N2CCC3(CC2)Cn2c(cccc2=O)[C@H]3N)cnc1Sc1ccnc(N)c1Cl] | $^1$H NMR (600 MHz, MeOH-d4) δ 7.84 (d, 1H), 7.91-7.87 (m, 1H), 7.77 (d, 1H), 6.97 (d, 1H), 6.84 (d, 1H), 6.68 (d, 1H), 4.92 (s, 1H), 4.61-4.38 (m, 4H), 3.50-3.40 (m, 2H), 2.27-2.16 (m, 1H), 2.10-2.00 (m, 1H), 1.99 (d, 1H), 1.81 (d, 1H). MS: 471 $(M + H)^+$. |
| 71 | (R)-1'-(5-((2-amino-3-chloropyridin-4-yl)thio)pyrazin-2-yl)spiro[indoline-2,4'-piperidin]-3-amine | 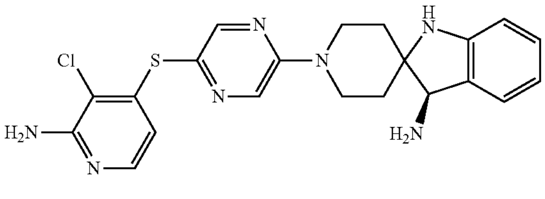 [SMILES: Nc1nccc(Sc2cnc(N3CCC4(CC3)Nc3ccccc3[C@H]4N)cn2)c1Cl] | $^1$H NMR (600 MHz, MeOH-d4) δ 8.37 (d, 1H), 8.30 (d, 1H), 7.61 (d, 1H), 7.30 (d, 1H), 7.11 (t, 1H), 6.75-6.69 (m, 2H), 5.95 (d, 1H), 4.38-4.26 (m, 2H), 4.13 (s, 1H), 3.52-3.49 (m, 2H), 1.83-1.74 (m, 4H). MS: 440 $(M + H)^+$. |
| 72 | (R)-1'-(6-amino-5-((2-amino-3-chloro pyridin-4-yl)thio) pyrazin-2-yl)-6,7-dihydrospiro[cyclopenta [b]pyridine-5,4'-piperidin]-6-amine | 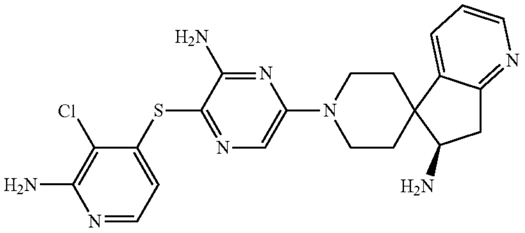 [SMILES: Nc1nc(N2CCC3(CC2)c2cccnc2C[C@H]3N)cnc1Sc1ccnc(N)c1Cl] | MS: 455 $(M + H)^+$. |

TABLE 16-continued

| EX No | Chemical Name | Structure | $^1$HNMR & MS: $(M + H)^+$ |
|---|---|---|---|
| 73 | (S)-1'-(6-amino-5-((2-amino-3-chloro pyridin-4-yl)thio) pyrazin-2-yl)-3-chloro-5,7-dihydro-spiro[cyclopenta[b] pyridine-6,4'-piperidin]-5-amine | 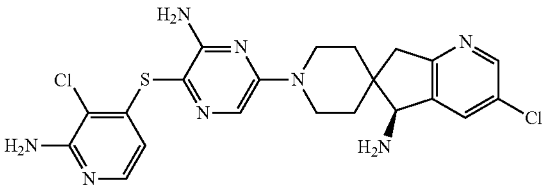 [SMILES: Nc1nc(N2CCC3(CC2)Cc2ncc(Cl)cc2[C@H]3N)cnc1Sc1ccnc(N)c1Cl] | MS: 489 $(M + H)^+$. |
| 74 | (S)-1'-(6-amino-5-((2-amino-3-chloro pyridin-4-yl)thio) pyrazin-2-yl)-6-(methylthio)-1,3-dihydro-spiro[indene-2,4'-piperidin]-1-amine | 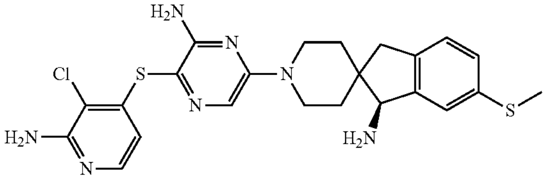 [SMILES: CSc1ccc2c(c1)[C@@H](N)C1(CCN(c3cnc(Sc4ccnc(N)c4Cl)c(N)n3)CC1)C2] | MS: 500 $(M + H)^+$. |
| 75 | (S)-1'-(6-amino-5-((2-amino-3-chloro pyridin-4-yl)thio) pyrazin-2-yl)-6-(4-methylpiperazin-1-yl)-1,3-dihydrospiro [indene-2,4'-piperidin]-1-amine | 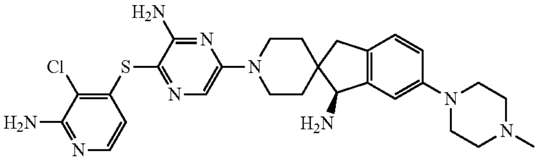 [SMILES: CN1CCN(c2ccc3c(c2)[C@@H](N)C2(CCN(c4cnc(Sc5ccnc(N)c5Cl)c(N)n4)CC2)C3)CC1] | MS: 552 $(M + H)^+$. |
| 76 | (S)-1'-(5-((2,3-dichloropyridin-4-yl) thio)pyrazin-2-yl)-1,3-dihydrospiro [indene-2,4'-piperidin]-1-amine | 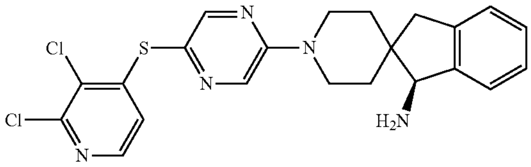 [SMILES: N[C@@H]1c2ccccc2CC12CCN(c1cnc(Sc3ccnc(Cl)c3Cl)cn1)CC2] | MS: 458 $(M + H)^+$. |
| 77 | (S)-1'-(6-amino-5-((2-(trifluoromethyl) pyridin-3-yl)thio) pyrazin-2-yl)-1,3-dihydrospiro[indene-2,4'-piperidin]-1-amine | 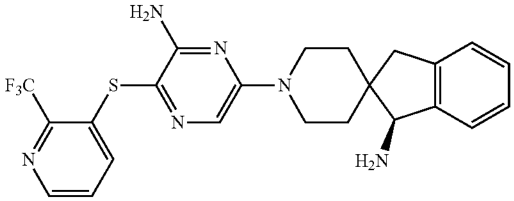 [SMILES: Nc1nc(N2CCC3(CC2)Cc2ccccc2[C@H]3N)cnc1Sc1cccnc1C(F)(F)F] | MS: 473 $(M + H)^+$. |
| 78 | (S)-1-(4-((3-amino-5-(1-amino-1,3-dihydrospiro[indene-2,4'-piperidin]-1'-yl)pyrazin-2-yl)thio)-3,3-difluoroindolin-1-yl)ethan-1-one | 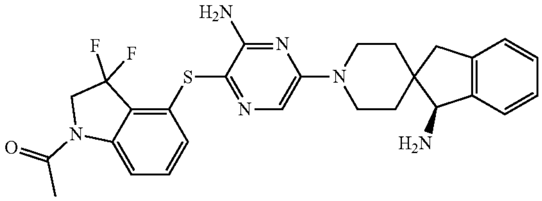 [SMILES: CC(=O)N1CC(F)(F)c2c(Sc3ncc(N4CCC5(CC4)Cc4ccccc4[C@H]5N)nc3N)cccc21] | MS: 523 $(M + H)^+$. |
| 79 | (S)-1'-(6-amino-5-((2-amino-3-chloro pyridin-4-yl)thio) pyrazin-2-yl)-2-(tert-butyl)-4,6-dihydro-spiro[cyclopenta [b]thiophene-5,4'-piperidin]-4-amine | 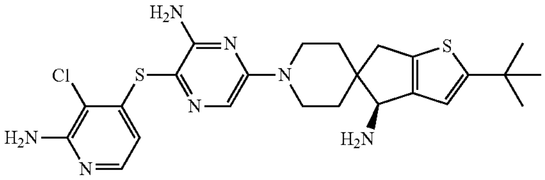 [SMILES: CC(C)(C)c1cc2c(s1)CC1(CCN(c3cnc(Sc4ccnc(N)c4Cl)c(N)n3)CC1)[C@@H]2N] | MS: 516 $(M + H)^+$. |
| 80 | (S)-1-amino-1'-(6-amino-5-((2-amino-3-chloropyridin-4-yl) thio)pyrazin-2-yl)-1,3-dihydrospiro [indene-2,4'-piperidine]-6-carboxylic acid | 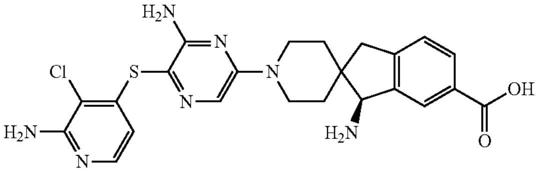 [SMILES: Nc1nc(N2CCC3(CC2)Cc2ccc(C(=O)O)cc2[C@H]3N)cnc1Sc1ccnc(N)c1Cl] | MS: 498 $(M + H)^+$. |

TABLE 16-continued

| EX No | Chemical Name | Structure | $^1$HNMR & MS: (M + H)$^+$ |
|---|---|---|---|
| 81 | (2R)-1'-(6-amino-5-((2-amino-3-chloropyridin-4-yl)thio) pyrazin-2-yl)spiro [bicyclo[3.1.0]hexane-3,4'-piperidin]-2-amine | 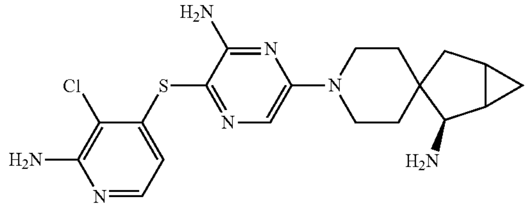 [SMILES: Nc1nc(N2CCC3(CC2)CC2CC2[C@H]3N)cnc1Sc1ccnc(N)c1Cl] | MS: 418 (M + H)$^+$. |

Example 82

(S)-1'-(6-amino-5-((2-amino-3-chloropyridin-4-yl) thio)pyrazin-2-yl)-5,7-dihydrospiro[cyclo penta[b] pyridine-6,4'-piperidin]-7-amine

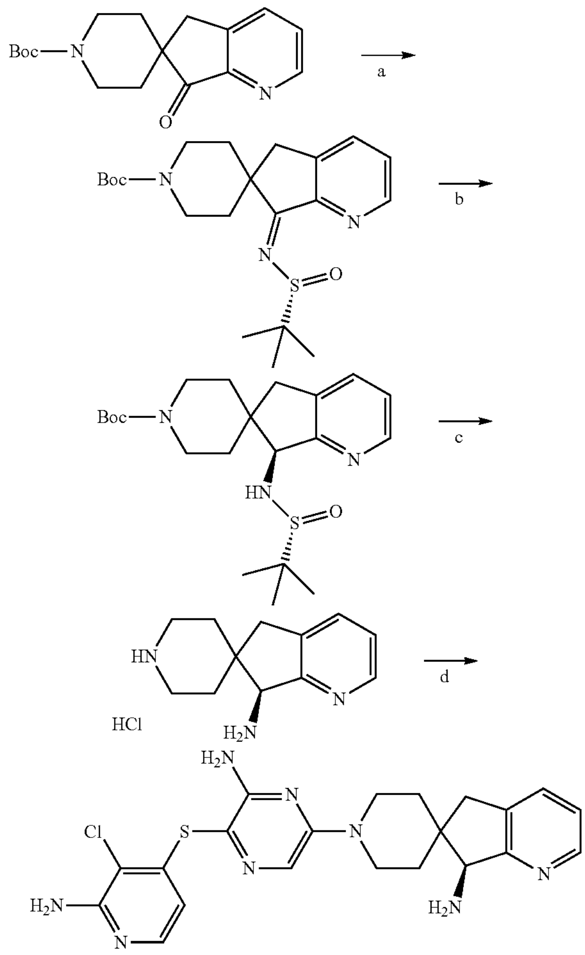

Step a: A mixture of tert-butyl 7-oxo-5,7-dihydrospiro [cyclopenta[b]pyridine-6,4'-piperidine]-1'-carboxylate (936 mg, 3.10 mmol) and (R)-(+)-2-Methyl-2-propanesulfinamide (1045 mg, 8.62 mmol) in $Ti(OEt)_4$ (8 mL) was stirred for 2 h at 100° C. After cooling to RT, the reaction mixture was diluted with EA (50 mL) and water (50 mL). The resulting mixture was filtered through a pad of Celite followed by EA wash. The organic layer was separated, dried over anhydrous $Na_2SO_4$, filtered and concentrated under reduced pressure to give tert-butyl (R,Z)-7-((tert-butylsulfinyl)imino)-5,7-dihydrospiro[cyclopenta[b]pyridine-6,4'-piperidine]-1'-carboxylate (1.41 g). MS: m/z 406 (M+H)$^+$.

Step b: To a −40° C. solution of tert-butyl (R,Z)-7-((tert-butylsulfinyl)imino)-5,7-dihydrospiro[cyclopenta[b]pyridine-6,4'-piperidine]-1'-carboxylate (1.41 g, 3.48 mmol) in THF (50 mL) was added $BH_3$ (1 M solution in THF, 10.00 mL, 10.00 mmol). The resulting mixture was allowed to warm to RT and stirred for 1 h. The reaction mixture was quenched with brine (100 mL). The aqueous layer was separated, extracted with EA (1×60 mL), the organic layers combined, dried over anhydrous $Na_2SO_4$, filtered and concentrated under reduced pressure. The residue was dissolved in MeOH (100 mL) and stirred for 15 h at 80° C. After cooling to RT, the reaction mixture was concentrated under reduced pressure. The residue was purified by silica chromatography (eluting with MeOH:DCM=1:60, v/v) to give tert-butyl (S)-7-(((R)-tert-butylsulfinyl)amino)-5,7-dihydrospiro[cyclopenta[b]pyridine-6,4'-piperidine]-1-carboxylate (309 mg). MS: m/z 408 (M+H)$^+$.

Step c: To solution of tert-butyl (S)-7-(((R)-tert-butylsulfinyl)amino)-5,7-dihydrospiro [cyclopenta[b]pyridine-6,4'-piperidine]-1'-carboxylate (309 mg, 0.76 mmol) in DCM (20 mL) was added HCl (4 M solution in EA, 2 mL, 8.00 mmol), and stirred for 1.5 h at RT. The resulting mixture was concentrated under reduced pressure to give (S)-5,7-dihydrospiro [cyclopenta [b]pyridine-6,4'-piperidin]-7-amine (227 mg). MS: m/z 204 (M+H)$^+$.

Step d: A mixture of (S)-5,7-dihydrospiro[cyclopenta[b] pyridine-6,4'-piperidin]-7-amine (HCl salt, 227 mg, 1.12 mmol), 3-((2-amino-3-chloropyridin-4-yl)thio)-6-chloropyrazin-2-amine (249 mg, 0.86 mmol) and $K_2CO_3$ (1149 mg, 8.31 mmol) in acetonitrile (15 mL) was stirred for 44 h at reflux temperature. After cooling to RT, the reaction mixture was diluted with brine (100 mL), extracted with EA (2×50 mL). The organic layers were combined, dried over anhydrous $Na_2SO_4$, filtered and concentrated under reduced pressure. The residue was purified by silica chromatography (eluting with MeOH:DCM=1:6, v/v) to give (S)-1'-(6-amino-5-((2-amino-3-chloropyridin-4-yl)thio)pyrazin-2-yl)-5,7-dihydrospiro[cyclopenta[b]pyridine-6,4'-piperidin]-7-amine (77 mg). MS: m/z 455 (M+H)$^+$. H NMR (400 MHz, MeOH-d4) δ 8.51 (s, 1H), 7.81 (d, 1H), 7.63 (s, 2H), 7.38 (s, 1H), 5.94 (d, 1H), 4.49-4.30 (m, 3H), 3.37-3.09 (m, 4H), 2.05-1.95 (m, 1H), 1.85-1.70 (m, 2H), 1.60-1.50 (m, 1H).

The following examples were synthesized using the above procedure or modification procedure using the corresponding Intermediate A and Intermediate B.

2-Methylpropane-2-sulfinamide, instead of (R)-(+)-2-Methyl-2-Propanesulfinamide, was used in step (a) of Example 82 to give the racemic compounds.

The following examples are compounds with free base, or a pharmaceutically acceptable salt.

TABLE 17

| EX No | Chemical Name | Structure | MS: $(M + H)^+$ & $^1$HNMR |
|---|---|---|---|
| 83 | (S)-1'-(6-amino-5-(quinolin-4-yl-thio)pyrazin-2-yl)-5,7-dihydrospiro [cyclopenta[b] pyridine-6,4'-piperidin]-5-amine | 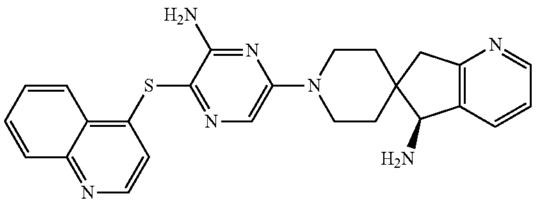 [SMILES: Nc1nc(N2CCC3(CC2)Cc2ncccc2[C@H]3N)cnc1Sc1ccnc2ccccc12] | $^1$H NMR (400 MHz, MeOH-d4) δ 8.57 (d, 1H), 8.42-8.38 (m, 1H), 8.34-8.29 (m, 1H), 8.06 (d, 1H), 7.90-7.82 (m, 2H), 7.75-7.67 (m, 2H), 7.35-7.29 (m, 1H), 6.89 (d, 1H), 4.38 (d, 2H), 4.10 (s, 1H), 3.34-3.23 (m, 3H), 2.98-2.94 (d, 1H), 1.98-1.83 (m, 2H), 1.68 (d, 1H), 1.48 (d, 1H). MS: 456 $(M + H)^+$. |
| 84 | (S)-1'-(6-amino-5-((2,3-dichloro-phenyl)thio)pyrazin-2-yl)-5,7-dihydrospiro[cyclopenta [b]pyridine-6, 4'-piperidin]-5-amine | 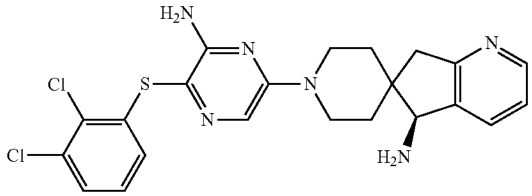 [SMILES: Nc1nc(N2CCC3(CC2)Cc2ncccc2[C@H]3N)cnc1Sc1cccc(Cl)c1Cl] | $^1$H NMR (400 MHz, MeOH-d4) δ 8.39-8.34 (m, 1H), 7.85 (d, 1H), 7.62 (s, 1H), 7.34-7.26 (m, 2H), 7.16-7.10 (t, 1H), 6.70-6.63 (m, 1H), 4.33 (d, 2H), 4.05 (s, 1H), 3.32-3.19 (m, 3H), 2.94-2.90 (d, 1H), 1.95-1.79 (m, 2H), 1.64 (d, 1H), 1.43 (d, 1H). MS: 473 $(M + H)^+$. |
| 85 | (S)-1'-(5-((3-chloro-2-(dimethyl-amino)pyridin-4-yl)thio)pyrazin-2-yl)-5,7-dihydrospiro [cyclopenta [b]pyridine-6,4'-piperidin]-5-amine | 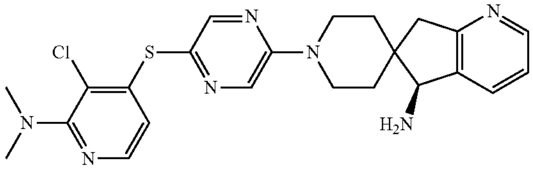 [SMILES: CN(C)c1nccc(Sc2cnc(N3CCC4(CC3)Cc3ncccc3[C@H]4N)cn2)c1Cl] | $^1$H NMR (400 MHz, MeOH-d4) δ 8.50-8.46 (m, 1H), 8.39 (d, 1H), 8.32 (d, 1H), 7.94 (d, 1H), 7.84 (d, 1H), 7.40-7.34 (m, 1H), 6.22 (d, 1H), 4.51-4.36 (m, 2H), 4.33 (s, 1H), 3.43-3.29 (m, 3H), 3.17-3.10 (d, 1H), 2.97 (s, 6H), 1.96-1.85 (m, 2H), 1.74-1.61 (m, 2H). MS: 468 $(M + H)^+$. |
| 86 | (S)-1'-(5-(pyridin-4-ylthio)pyrazin-2-yl)-5,7-dihydrospiro [cyclopenta [b]pyridine-6,4'-piperidin]-5-amine | 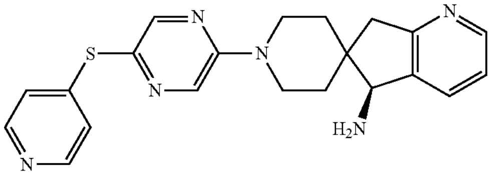 [SMILES: N[C@@H]1c2cccnc2CC12CCN(c1cnc(Sc3ccncc3)cn1)CC2] | $^1$H NMR (400 MHz, MeOH-d4) δ 8.46 (d, 1H), 8.33-8.28 (m, 3H), 7.94 (d, 1H), 7.66-7.61 (m, 1H), 7.36-7.32 (m, 1H), 7.16-7.12 (m, 1H), 7.07 (d, 1H), 4.43-4.31 (m, 3H), 3.36-3.28 (m, 3H), 3.10 (d, 1H), 1.92-1.84 (m, 2H), 1.67-1.60 (m, 2H). MS: 391 $(M + H)^+$. |
| 87 | (S)-1'-(6-amino-5-((3-fluoropyridin-4-yl)thio)pyrazin-2-yl)-5,7-dihydrospiro[cyclopenta [b]pyridine-6,4'-piperidin]-5-amine | 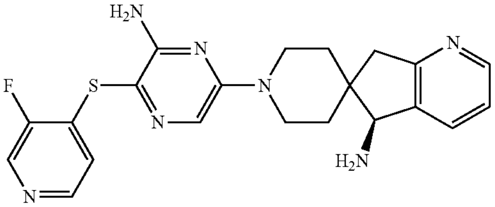 [SMILES: Nc1nc(N2CCC3(CC2)Cc2ncccc2[C@H]3N)cnc1Sc1ccncc1F] | $^1$H NMR (400 MHz, MeOH-d4) δ 8.58 (d, 1H), 8.34 (s, 1H), 8.15 (d, 1H), 8.03 (d, 1H), 7.69 (s, 1H), 7.48-7.39 (m, 1H), 6.87-6.77 (m, 1H), 4.54 (s, 1H), 4.47 (d, 1H), 4.37 (d, 1H), 3.33-3.20 (m, 4H), 1.99-1.81 (m, 2H), 1.81-1.62 (m, 2H). MS: 424 $(M + H)^+$. |
| 88 | (S)-1'-(6-amino-5-((3-fluoropyridin-4-yl)thio)pyrazin-2-yl)-4,6-dihydrospiro[cyclopenta [d]thiazole-5,4'-piperidin]-4-amine | 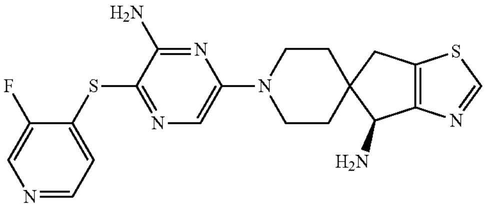 [SMILES: Nc1nc(N2CCC3(CC2)Cc2scnc2[C@H]3N)cnc1Sc1ccncc1F] | $^1$H NMR (400 MHz, MeOH-d4) δ 9.02 (s, 1H), 8.35 (s, 1H), 8.16 (s, 1H), 7.70 (s, 1H), 6.83 (s, 1H), 4.43-4.28 (m, 3H), 3.32-3.05 (m, 4H), 2.09-1.72 (m, 4H). MS: 430 $(M + H)^+$ |
| 89 | (S)-1'-(6-amino-5-((3-chloro-2-(methylamino)pyridin-4-yl)thio) pyrazin-2-yl)-5,7-dihydrospiro [cyclopenta[b]pyridine-6,4'-piperidin]-5-amine | 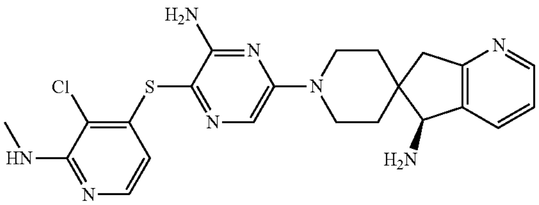 [SMILES: CNc1nccc(Sc2ncc(N3CCC4(CC3)Cc3ncccc3[C@H]4N)nc2N)c1Cl] | $^1$H NMR (400 MHz, MeOH-d4) δ 8.39 (d, 1H), 7.87 (d, 1H), 7.70 (d, 1H), 7.62 (s, 1H), 7.35-7.28 (m, 1H), 5.90 (d, 1H), 4.40-4.31 (m, 2H), 4.11 (s, 1H), 3.33-3.23 (m, 3H), 2.97-2.94 (d, 1H), 2.93 (s, 3H), 1.95-1.80 (m, 2H), 1.65 (d, 1H), 1.47 (d, 1H). MS: 469 $(M + H)^+$. |

TABLE 17-continued

| EX No | Chemical Name | Structure | MS: (M + H)$^+$ & $^1$HNMR |
|---|---|---|---|
| 90 | diethyl (S)-(1-amino-1'-(6-amino-5-((2-amino-3-chloropyridin-4-yl)thio)pyrazin-2-yl)-1,3-dihydrospiro[indene-2,4'-piperidin]-6-yl) phosphonate | 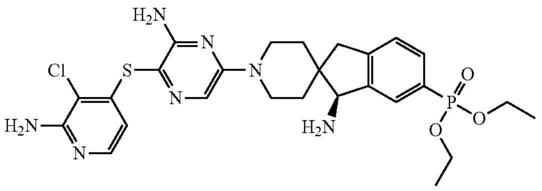 [SMILES: CCOP(=O)(OCC)c1ccc2c(c1)[C@@H](N)C1(CCN(c3cnc(Sc4ccnc(N)c4Cl)c(N)n3)CC1)C2] | $^1$H NMR (400 MHz, MeOH-d4) δ 7.93 (d, 1H), 7.81-7.76 (m, 1H), 7.61-7.53 (m, 3H), 5.92 (d, 1H), 4.42 (s, 1H), 4.37 (d, 1H), 4.29 (d, 1H), 4.18-4.09 (m, 4H), 3.38-3.13 (m, 4H), 1.90-1.80 (m, 2H), 1.70-1.60 (m, 2H), 1.36 (t, 6H). MS: 590 (M + H)$^+$. |
| 91 | (S)-1'-(6-amino-5-((2-amino-3-fluoropyridin-4-yl)thio)pyrazin-2-yl)-5,7-dihydrospiro[cyclopenta[b]pyridine-6,4'-piperidin]-5-amine | 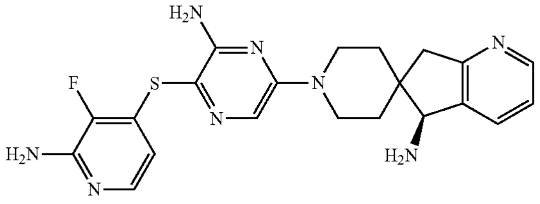 [SMILES: Nc1nc(N2CCC3(CC2)Cc2ncccc2[C@H]3N)cnc1Sc1ccnc(N)c1F] | $^1$H NMR (400 MHz, MeOH-d4) δ 8.40 (s, 1H), 7.88 (d, 1H), 7.63 (s, 1H), 7.53 (d, 1H), 7.39-7.27 (m, 1H), 6.10-5.97 (m, 1H), 4.36 (d, 2H), 4.10 (s, 1H), 3.28-3.16 (m, 3H), 2.98 (d, 1H), 1.98-1.77 (m, 2H), 1.67 (d, 1H), 1.47 (d, 1H). MS: 439 (M + H)$^+$. |
| 92 | (S)-1'-(5-((2-amino-3-fluoropyridin-4-yl)thio)pyrazin-2-yl)-5,7-dihydrospiro[cyclopenta[b]pyridine-6,4'-piperidin]-5-amine | 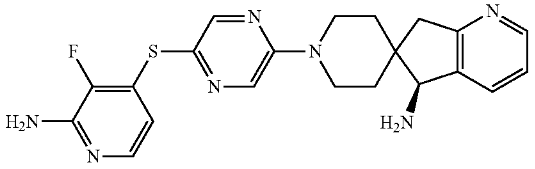 | $^1$H NMR (400 MHz, MeOH-d4) δ 8.42-8.37 (m, 1H), 8.34 (d, 1H), 8.31 (d, 1H), 7.88 (d, 1H), 7.55 (d, 1H), 7.35-7.29 (m, 1H), 6.14-6.10 (m, 1H), 4.45-4.35 (m, 2H), 4.11 (s, 1H), 3.38-3.27 (m, 2H), 3.22 (d, 1H), 3.00 (d, 1H), 1.99-1.82 (m, 2H), 1.75-1.65 (m, 1H), 1.54-1.46 (m, 1H). MS: 424 (M + H)$^+$. |
| 93 | (S)-1'-(6-amino-5-((3-chloropyridin-4-yl)thio)pyrazin-2-yl)-5,7-dihydrospiro[cyclopenta[b]pyridine-6,4'-piperidin]-5-amine | 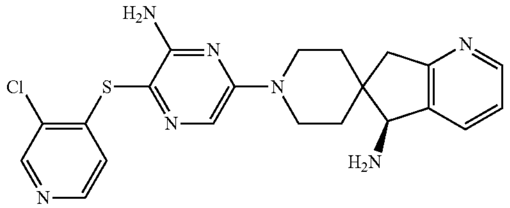 [SMILES: Nc1nc(N2CCC3(CC2)Cc2ncccc2[C@H]3N)cnc1Sc1ccncc1Cl] | $^1$H NMR (400 MHz, MeOH-d4) δ 8.43 (d, 1H), 8.39 (s, 1H), 8.16 (d, 1H), 7.92 (d, 1H), 7.64 (s, 1H), 7.33 (t, 1H), 6.70 (d, 1H), 4.38-4.25 (m, 3H) 3.40-3.00 (m, 4H), 1.92-1.79 (m, 2H), 1.65-1.54 (m, 2H). MS: 440 (M + H)$^+$. |
| 94 | (S)-1'-(6-amino-5-((3-chloro-2-(dimethylamino)pyridin-4-yl)thio)pyrazin-2-yl)-5,7-dihydrospiro[cyclopenta[b]pyridine-6,4'-piperidin]-5-amine | 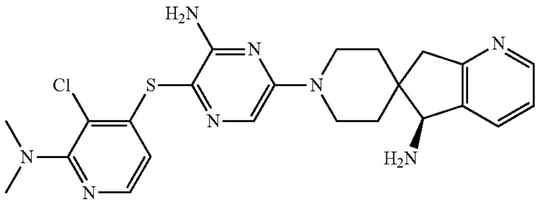 [SMILES: CN(C)c1nccc(Sc2ncc(N3CCC4(CC3)Cc3ncccc3[C@H]4N)nc2N)c1Cl] | $^1$H NMR (400 MHz, MeOH-d4) δ 8.41 (d, 1H), 7.88 (d, 1H), 7.84 (d, 1H), 7.63 (s, 1H), 7.36-7.28 (m, 1H), 6.21 (d, 1H), 4.41-4.31 (m, 2H), 4.14 (s, 1H), 3.34-3.23 (m, 3H), 3.02-2.99 (d, 1H), 2.98 (s, 6H), 1.95-1.80 (m, 2H), 1.65 (d, 1H), 1.50 (d, 1H). MS: 483 (M + H)$^+$. |
| 95 | (S)-1'-(5-((2-amino-3-chloropyridin-4-yl)thio)pyrazin-2-yl)-2-chloro-4,6-dihydrospiro[cyclopenta[d]thiazole-5,4'-piperidin]-4-amine | 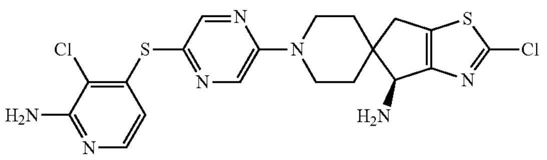 [SMILES: Nc1nccc(Sc2cnc(N3CCC4(CC3)Cc3sc(Cl)nc3[C@H]4N)cn2)c1Cl] | $^1$H NMR (400 MHz, DMSO-d6) δ 8.49 (s, 1H), 8.29 (s, 1H), 7.66 (s, 1H), 5.84 (s, 1H), 4.20-3.95 (m, 2H), 3.85 (s, 1H), 3.58-3.40 (m, 2H), 3.02-2.71 (m, 2H), 1.76-1.48 (m, 3H), 1.34-1.09 (m, 1H). MS: 480 (M + H)$^+$. |
| 96 | (R)-1'-(6-amino-5-((2-amino-3-chloropyridin-4-yl)thio)pyrazin-2-yl)-3H-spiro[2,3-b]pyridine-2,4'-piperidin]3-amine | 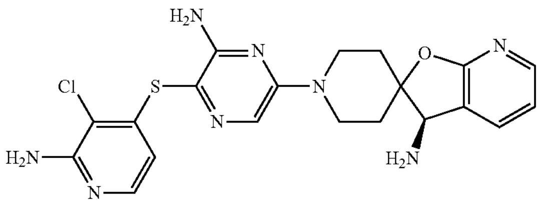 [SMILES: Nc1nc(N2CCC3(CC2)Oc2ncccc2[C@H]3N)cnc1Sc1ccnc(N)c1Cl] | $^1$H NMR (400 MHz, MeOH-d4) δ 8.07 (d, 1H), 7.90 (d, 1H), 7.69 (s, 1H), 7.64 (d, 1H), 7.08-6.99 (m, 1H), 6.00 (d, 1H), 4.52 (d, 1H), 4.43 (d, 1H), 4.28 (s, 1H), 3.58-3.41 (m, 2H), 2.16-1.81 (m, 4H). MS: 457 (M + H)$^+$. |

TABLE 17-continued

| EX No | Chemical Name | Structure | MS: $(M + H)^+$ & $^1$HNMR |
|---|---|---|---|
| 97 | (S)-1'-(5-((3-amino-2-chlorophenyl) thio)pyrazin-2-yl)-5,7-dihydro-spiro[cyclopenta [b]pyridine-6,4'-piperidin]-5-amine | 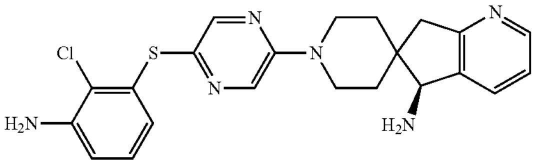 [SMILES: Nc1cccc(Sc2cnc(N3CCC4(CC3)Cc3ncccc3[C@H]4N)cn2)c1Cl] | $^1$H NMR (400 MHz, MeOH-d4) δ 8.37 (d, 1H), 8.24 (s, 1H), 8.14 (s, 1H), 7.85 (d, 1H), 7.38-7.20 (m, 1H), 6.98-6.85 (m, 1H), 6.70 (d, 1H), 6.27 (d, 1H), 4.41-4.21 (m, 2H), 4.08 (s, 1H), 3.44-3.19 (m, 3H), 3.04-2.89 (m, 1H), 1.98-1.72 (m, 2H), 1.73-1.58 (m, 1H), 1.55-1.38 (m, 1H). MS: 439 $(M + H)^+$. |
| 98 | (S)-1'-(6-amino-5-((3-amino-2-chlorophenyl)thio) pyrazin-2-yl)-5,7-dihydrospiro [cyclopenta[b] pyridine-6,4'-piperidin]-5-amine | 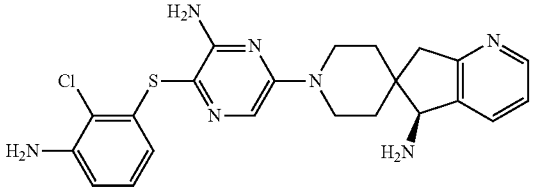 [SMILES: Nc1cccc(Sc2ncc(N3CCC4(CC3)Cc3ncccc3[C@H]4N)nc2N)c1Cl] | $^1$H NMR (400 MHz, MeOH-d4) δ 8.43 (d, 1H), 7.90 (d, 1H), 7.56 (s, 1H), 7.41-7.26 (m, 1H), 6.95-6.79 (m, 1H), 6.63 (d, 1H), 6.03 (d, 1H), 4.41-4.26 (m, 2H), 4.23 (s, 1H), 3.39-3.15 (m, 3H), 3.10-2.96 (m, 1H), 1.92-1.74 (m, 2H), 1.70-1.59 (m, 1H), 1.58-1.47 (m, 1H). MS: 454 $(M + H)^+$. |
| 99 | (S)-1'-(5-((3-chloro-2-methoxy-pyridin-4-yl)thio) pyrazin-2-yl)-5,7-dihydrospiro [cyclopenta[b]pyridine-6,4'-piperidin]-5-amine | 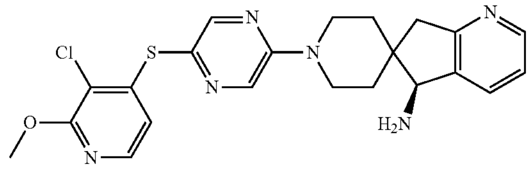 [SMILES: COc1nccc(Sc2cnc(N3CCC4(CC3)Cc3ncccc3[C@H]4N)cn2)c1Cl] | $^1$H NMR (400 MHz, MeOH-d4) δ 8.46-8.37 (m, 2H), 8.33 (d, 1H), 7.88 (d, 1H), 7.83 (d, 1H), 7.38-7.26 (m, 1H), 6.33 (d, 1H), 4.50-4.34 (m, 2H), 4.12 (s, 1H), 4.01 (s, 3H), 3.47-3.24 (m, 3H), 3.06-2.94 (m, 1H), 2.02-1.79 (m, 2H), 1.78-1.65 (m, 1H), 1.60-1.44 (m, 1H). MS: 455 $(M + H)^+$. |
| 100 | (S)-1'-(6-amino-5-((3-chloro-2-methoxypyridin-4-yl)thio)pyrazin-2-yl)-5,7-dihydro-spiro[cyclopenta [b]pyridine-6,4'-piperidin]-5-amine | 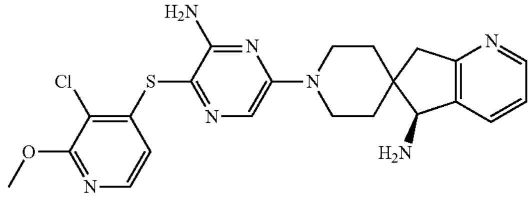 | $^1$H NMR (400 MHz, MeOH-d4) δ 8.41 (d, 1H), 7.87 (d, 1H), 7.79 (d, 1H), 7.63 (s, 1H), 7.36-7.24 (m, 1H), 6.25 (d, 1H), 4.43-4.29 (m, 2H), 4.16 (s, 1H), 3.98 (s, 3H), 3.43-3.17 (m, 3H), 3.09-2.95 (m, 1H), 1.93-1.76 (m, 2H), 1.70-1.59 (m, 1H), 1.56-1.42 (m, 1H). MS: 470 $(M + H)^+$. |
| 101 | (S)-1'-(5-((5-chloro-2-fluoro-pyridin-4-yl)thio) pyrazin-2-yl)-5,7-dihydrospiro[cyclopenta [b]pyridine-6,4'-piperidin]-5-amine | 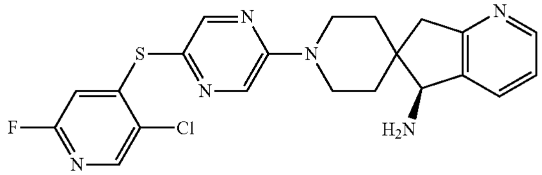 [SMILES: N[C@@H]1c2cccnc2CC12CCN(c1cnc(Sc3cc(F)ncc3Cl)cn1)CC2] | $^1$H NMR (400 MHz, MeOH-d4) δ 8.44 (d, 1H), 8.39 (d, 1H), 8.36 (d, 1H), 8.14 (s, 1H), 7.87 (d, 1H), 7.38-7.24 (m, 1H), 6.42 (d, 1H), 4.54-4.36 (m, 2H), 4.11 (s, 1H), 3.48-3.23 (m, 3H), 3.07-2.93 (m, 1H), 2.04-1.80 (m, 2H), 1.77-1.66 (m, 1H), 1.56-1.44 (m, 1H). MS: 443 $(M + H)^+$. |
| 102 | (S)-1'-(6-amino-5-((5-chloro-2-fluoropyridin-4-yl)thio)pyrazin-2-yl)-5,7-dihydro-spiro[cyclopenta[b] pyridine-6,4'-piperidin]-5-amine | 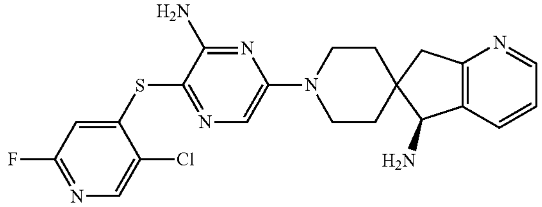 [SMILES: Nc1nc(N2CCC3(CC2)Cc2ncccc2[C@H]3N)cnc1Sc1cc(F)ncc1Cl] | $^1$H NMR (400 MHz, MeOH-d4) δ 8.40 (d, 1H), 8.13 (s, 1H), 7.87 (d, 1H), 7.70 (s, 1H), 7.40-7.25 (m, 1H), 6.28 (s, 1H), 4.40 (d, 2H), 4.11 (s, 1H), 3.47-3.16 (m, 3H), 3.08-2.89 (m, 1H), 2.00-1.81 (m, 2H), 1.72-1.60 (m, 1H), 1.54-1.42 (m, 1H). MS: 458 $(M + H)^+$. |
| 103 | (S)-1-(4-((3-amino-5-(5-amino-5,7-dihydrospiro [cyclopenta[b] pyridine-6,4'-piperidin]-1'-yl)pyrazin-2-yl)thio)-3,3-difluoroindolin-1-yl) ethan-1-one | 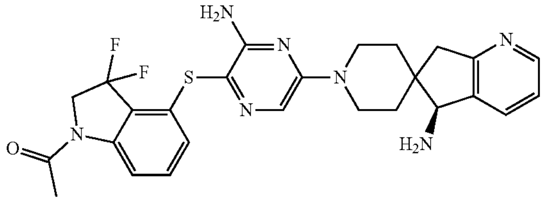 [SMILES: CC(=O)N1CC(F)(F)c2c(Sc3ncc(N4CCC5(CC4)Cc4ncccc4[C@H]5N)nc3N)cccc21] | $^1$H NMR (400 MHz, MeOH-d4) δ 8.34 (d, 1H), 8.07 (d, 1H), 7.83 (d, 1H), 7.58 (s, 1H), 7.33 (t, 1H), 7.28-7.25 (m, 1H), 6.64 (d, 1H), 4.52 (t, 2H), 4.30 (d, 1H), 4.04 (s, 1H), 3.25-3.21 (m, 3H), 2.92 (d, 1H), 2.28 (s, 3H), 1.90-1.80 (m, 2H), 1.62 (d, 1H), 1.41 (d, 1H). MS: 524 $(M + H)^+$. |

TABLE 17-continued

| EX No | Chemical Name | Structure | MS: $(M + H)^+$ & $^1$HNMR |
|---|---|---|---|
| 104 | (S)-1'-(5-((2,3-dichloropyridin-4-yl)thio)pyrazin-2-yl)-5,7-dihydrospiro [cyclopenta [b]pyridine-6,4'-piperidin]-5-amine | 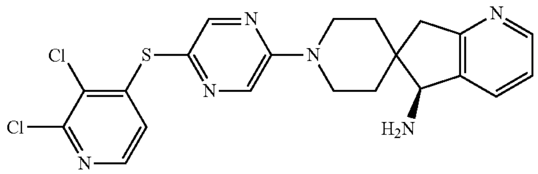 [SMILES: N[C@@H]1c2cccnc2CC12CCN(c1cnc(Sc3ccnc(Cl)c3Cl)cn1)CC2] | $^1$H NMR (400 MHz, MeOH-d4) δ 8.39 (s, 1H), 8.37 (d, 1H), 8.32 (s, 1H), 8.00 (d, 1H), 7.84 (d, 1H), 7.30-7.26 (m, 1H), 6.71 (d, 1H), 4.42-4.37 (m, 2H), 4.08 (s, 1H), 3.40-3.24 (m, 3H), 2.96 (d, 1H), 1.96-1.81 (m, 2H), 1.67 (d, 1H), 1.48 (d, 1H). MS: 459 $(M + H)^+$. |
| 105 | (S)-1'-(6-amino-5-((2,3-dichloro-pyridin-4-yl)thio) pyrazin-2-yl)-5,7-dihydrospiro[cyclo-penta[b]pyridine-6,4'-piperidin]-5-amine | 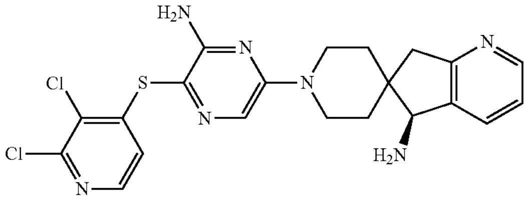 | $^1$H NMR (400 MHz, MeOH-d4) δ 8.34 (d, 1H), 8.00 (d, 1H), 7.82 (d, 1H), 7.63 (s, 1H), 7.28-7.24 (m, 1H), 6.64 (d, 1H), 4.32 (d, 2H), 4.03 (s, 1H), 3.31-3.21 (m, 3H), 2.92 (d, 1H), 1.94-1.77 (m, 2H), 1.62 (d, 1H), 1.41 (d, 1H). MS: 474 $(M + H)^+$. |
| 106 | (S)-1'-(5-((4-chloropyridin-3-yl) thio)pyrazin-2-yl)-5,7-dihydrospiro [cyclopenta[b] pyridine-6,4'-piperidin]-5-amine | 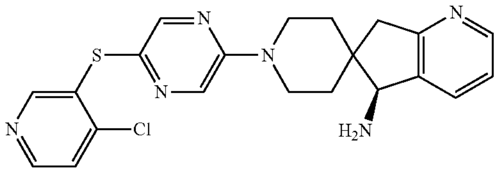 [SMILES: N[C@@H]1c2cccnc2CC12CCN(c1cnc(Sc3cnccc3Cl)cn1)CC2] | $^1$H NMR (400 MHz, MeOH-d4) δ 8.36-8.32 (m, 2H), 8.27 (d, 2H), 8.22 (s, 1H), 7.83 (d, 1H), 7.53 (d, 1H), 7.30-7.27 (m, 1H), 4.34 (d, 2H), 4.06 (s, 1H), 3.36-3.23 (m, 3H), 2.95 (d, 1H), 1.94-1.80 (m, 2H), 1.66 (d, 1H), 1.45 (d, 1H). MS: 425 $(M + H)^+$. |
| 107 | (S)-1'-(6-amino-5-((4-chloropyridin-3-yl)thio)pyrazin-2-yl)-5,7-dihydrospiro[cyclo-penta[b]pyridine-6,4'-piperidin]-5-amine | 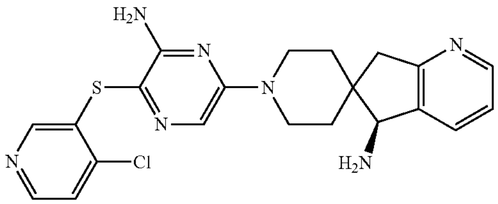 [SMILES: Nc1nc(N2CCC3(CC2)Cc2ncccc2[C@H]3N)cnc1Sc1cnccc1Cl] | $^1$H NMR (400 MHz, MeOH-d4) δ 8.36 (d, 1H), 8.26 (d, 1H), 7.88 (s, 1H), 7.84 (d, 1H), 7.62 (s, 1H), 7.47 (d, 1H), 7.30-7.26 (m, 1H), 4.34 (d, 2H), 4.06 (s, 1H), 3.36-3.23 (m, 3H), 2.95 (d, 1H), 1.94-1.80 (m, 2H), 1.66 (d, 1H), 1.45 (d, 1H). MS: 440 $(M + H)^+$. |
| 108 | (S)-1'-(5-((3-amino-pyridin-4-yl) thio)pyrazin-2-yl)-5,7-dihydrospiro [cyclopenta[b] pyridine-6,4'-piperidin]-5-amine | 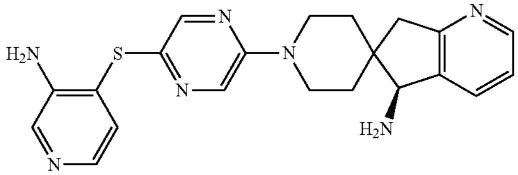 [SMILES: Nc1cnccc1Sc1cnc(N2CCC3(CC2)Cc2ncccc2[C@H]3N)cn1] | $^1$H NMR (400 MHz, MeOH-d4) δ 8.48 (d, 1H), 8.28 (d, 1H), 8.21 (d, 1H), 8.03 (s, 1H), 7.96 (d, 1H), 7.73 (d, 1H), 7.41-7.33 (m, 1H), 7.09 (d, 1H), 4.44-4.28 (m, 3H), 3.34-3.26 (m, 3H), 3.11 (d, 1H), 1.95-1.84 (m, 2H), 1.72-1.59 (m, 2H). MS: 406 $(M + H)^+$. |
| 109 | (S)-1'-(6-amino-5-((3-aminopyridin-4-yl)thio)pyrazin-2-yl)-5,7-dihydrospiro[cyclo-penta[b]pyridine-6,4'-piperidin]-5-amine | 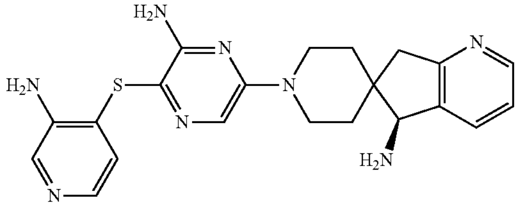 [SMILES: Nc1cnccc1Sc1ncc(N2CCC3(CC2)Cc2ncccc2[C@H]3N)nc1N] | $^1$H NMR (400 MHz, MeOH-d4) δ 8.40 (d, 1H), 7.96 (s, 1H), 7.88 (d, 1H), 7.68 (d, 1H), 7.60 (s, 1H), 7.35-7.27 (m, 1H), 6.84 (d, 1H), 4.38-4.27 (m, 2H), 4.11 (s, 1H), 3.32-3.20 (m, 3H), 2.98 (d, 1H), 1.96-1.78 (m, 2H), 1.64 (d, 1H), 1.46 (d, 1H). MS: 421 $(M + H)^+$. |
| 110 | (S)-1'-(5-((3,5-dichloropyridin-4-yl)thio)pyrazin-2-yl)-5,7-dihydrospiro [cyclopenta[b] pyridine-6,4'-piperidin]-5-amine | 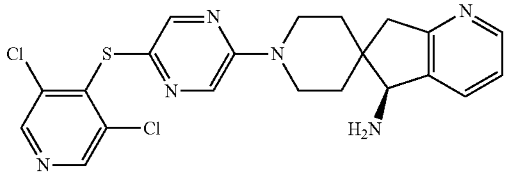 [SMILES: N[C@@H]1c2cccnc2CC12CCN(c1cnc(Sc3c(Cl)cncc3Cl)cn1)CC2] | $^1$H NMR (400 MHz, MeOH-d4) δ 8.53 (s, 2H), 8.36 (d, 1H), 8.15 (d, 1H), 8.11 (s, 1H), 7.83 (d, 1H), 7.30-7.26 (m, 1H), 4.29-4.25 (m, 2H), 4.06 (s, 1H), 3.36-3.21 (m, 3H), 2.94 (d, 1H), 1.92-1.78 (m, 2H), 1.63 (d, 1H), 1.44 (d, 1H). MS: 459 $(M + H)^+$. |
| 111 | (S)-1'-(6-amino-5-((3,5-dichloro-pyridin-4-yl)thio) pyrazin-2-yl)-5,7-dihydrospiro [cyclopenta[b] pyridine-6,4'-piperidin]-5-amine | 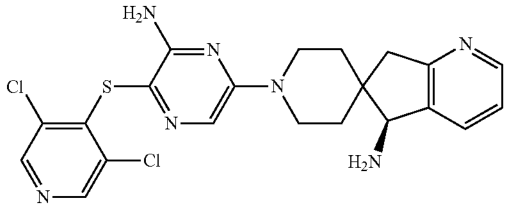 [SMILES: Nc1nc(N2CCC3(CC2)Cc2ncccc2[C@H]3N)cnc1Sc1c(Cl)cncc1Cl] | MS: 474 $(M + H)^+$. |

TABLE 17-continued

| EX No | Chemical Name | Structure | MS: (M + H)+ & 1HNMR |
|---|---|---|---|
| 112 | (S)-1'-(5-((2-amino-5-chloro-pyridin-4-yl)thio) pyrazin-2-yl)-5,7-dihydrospiro [cyclopenta [b]pyridine-6,4'-piperidin]-5-amine | 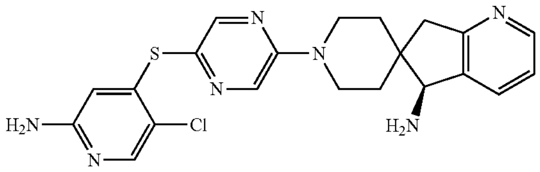 [SMILES: Nc1cc(Sc2cnc(N3CCC4(CC3)Cc3ncccc3[C@H]4N)cn2)c(Cl)cn1] | $^1$H NMR (400 MHz, MeOH-d4) δ 8.37 (s, 2H), 8.29 (d, 1H), 7.85 (d, 1H), 7.84 (s, 1H), 7.31-7.27 (m, 1H), 5.91 (s, 1H), 4.40-4.37 (m, 2H), 4.10 (s, 1H), 3.37-3.24 (m, 3H), 2.97 (d, 1H), 1.92-1.84 (m, 2H), 1.68 (d, 1H), 1.58 (d, 1H). MS: 440 $(M + H)^+$. |
| 113 | (S)-1'-(6-amino-5-((2-amino-5-chloropyridin-4-yl)thio)pyrazin-2-yl)-5,7-dihydrospiro [cyclopenta[b] pyridine-6,4'-piperidin]-5-amine | 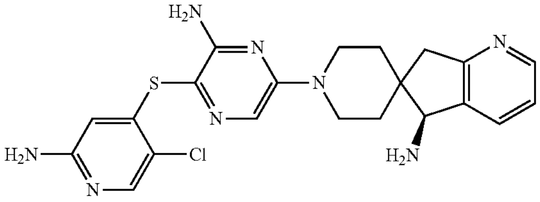 [SMILES: Nc1cc(Sc2ncc(N3CCC4(CC3)Cc3ncccc3[C@H]4N)nc2N)c(Cl)cn1] | $^1$H NMR (400 MHz, MeOH-d4) δ 8.36 (d, 1H), 7.84 (d, 1H), 7.74 (s, 1H), 7.62 (s, 1H), 7.30-7.26 (m, 1H), 5.90 (s, 1H), 4.32 (d, 2H), 4.07 (s, 1H), 3.35-3.21 (m, 3H), 2.94 (d, 1H), 1.92-1.78 (m, 2H), 1.62 (d, 1H), 1.43 (d, 1H). MS: 455 $(M + H)^+$. |
| 114 | (S)-1'-(6-amino-5-((2-(trifluoro-methyl)pyridin-3-yl)thio)pyrazin-2-yl)-5,7-dihydrospiro [cyclopenta [b]pyridine-6,4'-piperidin]-5-amine | 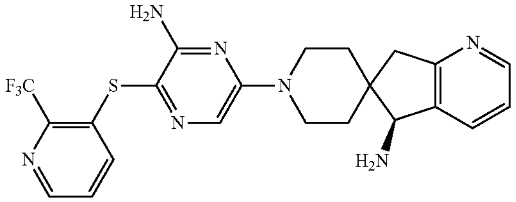 [SMILES: Nc1nc(N2CCC3(CC2)Cc2ncccc2[C@H]3N)cnc1Sc1cccnc1C(F)(F)F] | $^1$H NMR (400 MHz, MeOH-d4) δ 8.40 (d, 1H), 8.37 (d, 1H), 7.84 (d, 1H), 7.63 (s, 1H), 7.46-7.40 (m, 2H), 7.30-7.27 (m, 1H), 4.35-4.30 (m, 2H), 4.09 (s, 1H), 3.31-3.22 (m, 3H), 2.96 (d, 1H), 1.88-1.78 (m, 2H), 1.62 (d, 1H), 1.44 (d, 1H). MS: 474 $(M + H)^+$. |
| 115 | (S)-1'-(5-((3-chloro-2-fluoropyridin-4-yl)thio)pyrazin-2-yl)-5,7-dihydrospiro [cyclopenta[b]pyridine-6,4'-piperidin]-5-amine | 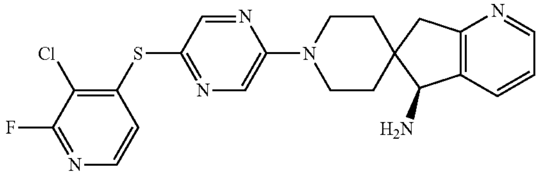 [SMILES: N[C@@H]1c2cccnc2CC12CCN(c1cnc(Sc3ccnc(F)c3Cl)cn1)CC2] | MS: 443 $(M + H)^+$. |
| 116 | (S)-1'-(6-amino-5-((3-chloro-2-fluoropyridin-4-yl)thio)pyrazin-2-yl)-5,7-dihydrospiro [cyclopenta[b] pyridine-6,4'-piperidin]-5-amine | 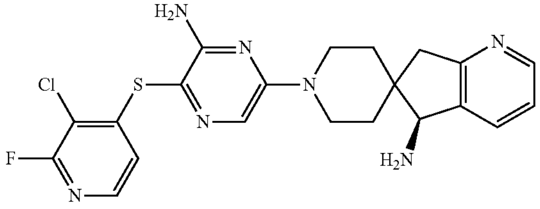 [SMILES: Nc1nc(N2CCC3(CC2)Cc2ncccc2[C@H]3N)cnc1Sc1ccnc(F)c1Cl] | $^1$H NMR (400 MHz, MeOH-d4) δ 8.36 (d, 1H), 7.84 (d, 1H), 7.78 (d, 1H), 7.61 (s, 1H), 7.30-7.26 (m, 1H), 6.24 (d, 1H), 4.33 (d, 2H), 4.07 (s, 1H), 3.35-3.22 (m, 3H), 2.94 (d, 1H), 1.89-1.81 (m, 2H), 1.62 (d, 1H), 1.44 (d, 1H). MS: 458 $(M + H)^+$. |
| 117 | (S)-3-((5-(5-amino-5,7-dihydrospiro [cyclopenta[b] pyridine-6,4'-piperidin]-1'-yl) pyrazin-2-yl)thio) picolinonitrile | 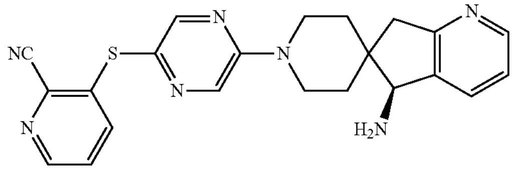 [SMILES: N#Cc1ncccc1Sc1cnc(N2CCC3(CC2)Cc2ncccc2[C@H]3N)cn1] | $^1$H NMR (400 MHz, MeOH-d4) δ 8.53-8.51 (m, 1H), 8.45 (d, 1H), 8.31-8.28 (m, 2H), 7.90 (d, 1H), 7.77-7.74 (m, 1H), 7.55-7.52 (m, 1H), 7.35-7.32 (m, 1H), 4.41-4.27 (m, 3H), 3.35-3.25 (m, 3H), 3.18 (d, 1H), 1.89-1.83 (m, 2H), 1.67-1.57 (m, 2H). MS: 416 $(M + H)^+$. |
| 118 | (S)-3-((3-amino-5-(5-amino-5,7-dihydrospiro [cyclopenta[b] pyridine-6,4'-piperidin]-1'-yl)pyrazin-2-yl) thio)picolinonitrile | 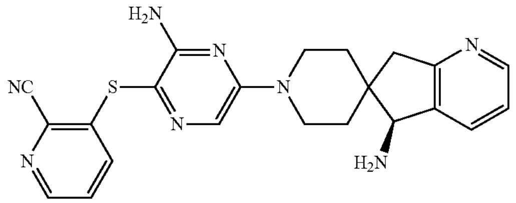 [SMILES: N#Cc1ncccc1Sc1ncc(N2CCC3(CC2)Cc2ncccc2[C@H]3N)nc1N] | $^1$H NMR (400 MHz, MeOH-d4) δ 8.43-8.42 (m, 1H), 8.37 (d, 1H), 7.85 (d, 1H), 7.61 (s, 1H), 7.49-7.45 (m, 1H), 7.41-7.39 (m, 1H), 7.30-7.27 (m, 1H), 4.34-4.30 (m, 2H), 4.10 (s, 1H), 3.32-3.22 (m, 3H), 2.96 (d, 1H), 1.91-1.78 (m, 2H), 1.62 (d, 1H), 1.45 (d, 1H). MS: 431 $(M + H)^+$. |

TABLE 17-continued

| EX No | Chemical Name | Structure | MS: $(M + H)^+$ & $^1$HNMR |
|---|---|---|---|
| 119 | (S)-1'-(5-((2-chloro-5-(trifluoro-methyl)pyridin-4-yl)thio)pyrazin-2-yl)-5,7-dihydro-spiro[cyclopenta[b]pyridine-6,4'-piperidin]-5-amine | 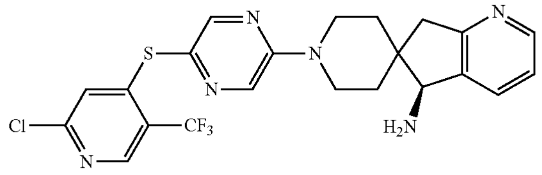 [SMILES: N[C@@H]1c2cccnc2CC12CCN(c1cnc(Sc3cc(Cl)ncc3C(F)(F)F)cn1)CC2] | MS: 493 $(M + H)^+$. |
| 120 | (S)-1'-(6-amino-5-((2-chloro-5-(trifluoromethyl)pyridin-4-yl)thio)pyrazin-2-yl)-5,7-dihydrospiro[cyclopenta[b]pyridine-6,4'-piperidin]-5-amine | 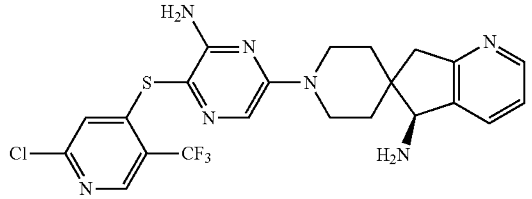 [SMILES: Nc1nc(N2CCC3(CC2)Cc2ncccc2[C@H]3N)cnc1Sc1cc(Cl)ncc1C(F)(F)F] | $^1$H NMR (400 MHz, MeOH-d4) δ 8.54 (s, 1H), 8.38 (d, 1H), 7.86 (d, 1H), 7.69 (s, 1H), 7.31-7.28 (m, 1H), 6.77 (d, 1H), 4.42-4.34 (m, 2H), 4.14 (s, 1H), 3.35-3.24 (m, 3H), 2.99 (d, 1H), 1.93-1.81 (m, 2H), 1.64 (d, 1H), 1.49 (d, 1H). MS: 508 $(M + H)^+$. |
| 121 | 1'-(6-amino-5-((2-amino-3-chloro pyridin-4-yl)thio) pyrazin-2-yl)-5,7-dihydrospiro [cyclopenta[b] pyridine-6,4'-piperidin]-5-amine | 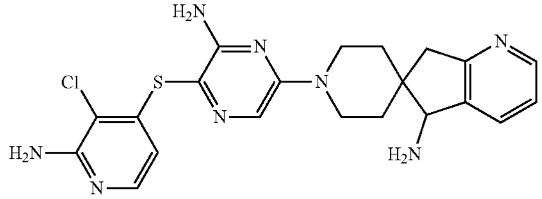 [SMILES: Nc1nc(N2CCC3(CC2)Cc2ncccc2C3N)cnc1Sc1ccnc(N)c1Cl] | $^1$H NMR (400 MHz, MeOH-d4) δ 8.41 (d, 1H), 7.89 (d, 1H), 7.73-7.57 (m, 2H), 7.38-7.25 (m, 1H), 5.97 (d, 1H), 4.45-4.27 (m, 2H), 4.14 (s, 1H), 3.46-3.18 (m, 3H), 3.09-2.93 (m, 1H), 2.00-1.78 (m, 2H), 1.72-1.60 (m, 1H), 1.55-1.45 (m, 1H). MS: 455 $(M + H)^+$. |
| 122 | 1'-(5-((2-amino-3-chloropyridin-4-yl)thio)pyrazin-2-yl)-5,7-dihydrospiro[cyclo-penta[b]pyridine-6,4'-piperidin]-5-amine | 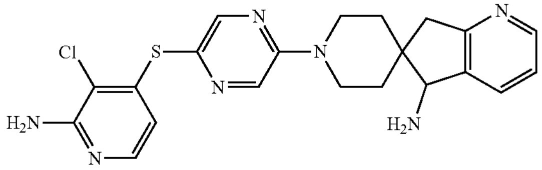 [SMILES: Nc1nccc(Sc2cnc(N3CCC4(CC3)Cc3ncccc3C4N)cn2)c1Cl] | $^1$H NMR (400 MHz, MeOH-d4) δ 8.45-8.35 (m, 2H), 8.32 (s, 1H), 7.89 (d, 1H), 7.64 (d, 1H), 7.39-7.27 (m, 1H), 5.99 (d, 1H), 4.52-4.33 (m, 2H), 4.14 (s, 1H), 3.48-3.18 (m, 3H), 3.11-2.94 (m, 1H), 2.01-1.82 (m, 2H), 1.76-1.65 (m, 1H), 1.59-1.46 (m, 1H). MS: 440 $(M + H)^+$. |
| 123 | 1'-(6-amino-5-((3-chloropyridin-4-yl)thio)pyrazin-2-yl)-5,7-dihydrospiro[cyclo-penta[b]pyridine-6,4'-piperidin]-5-amine | 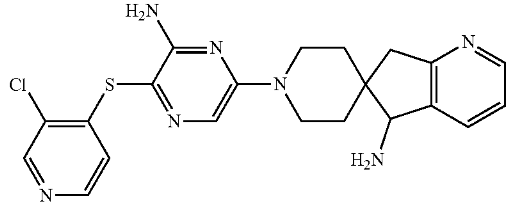 [SMILES: Nc1nc(N2CCC3(CC2)Cc2ncccc2C3N)cnc1Sc1ccncc1Cl] | $^1$H NMR (400 MHz, MeOH-d4) δ 8.36 (d, 1H), 8.25 (d, 1H), 7.87 (s, 1H), 7.84 (d, 1H), 7.61 (s, 1H), 7.48 (d, 1H), 7.30-7.26 (m, 1H), 4.34-4.30 (m, 2H), 4.09 (s, 1H), 3.29-3.21 (m, 3H), 2.95 (d, 1H), 1.88-1.79 (m, 2H), 1.62 (d, 1H), 1.45 (d, 1H). MS: 440 $(M + H)^+$. |
| 124 | 1'-(6-amino-5-((2-amino-3-chloro pyridin-4-yl)thio) pyrazin-2-yl)-1,3-dihydrospiro [indene-2,4'-piperidin]-1-amine | 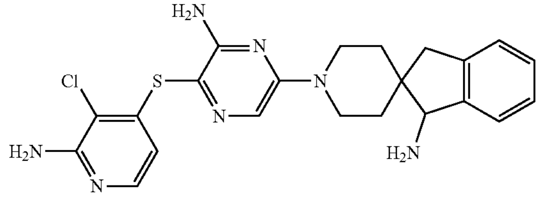 [SMILES: Nc1nc(N2CCC3(CC2)Cc2ccccc2C3N)cnc1Sc1ccnc(N)c1Cl] | $^1$H NMR (400 MHz, MeOH-d4) δ 7.68-7.57 (m, 2H), 7.50 (d, 1H), 7.41-7.26 (m, 3H), 5.95 (d, 1H), 4.43-4.21 (m, 3H), 3.41-3.16 (m, 3H), 3.15-3.00 (m, 1H), 1.91-1.74 (m, 2H), 1.74-1.58 (m, 2H). MS: 454 $(M + H)^+$. |
| 125 | 1'-(5-((2-amino-3-chloropyridin-4-yl)thio)pyrazin-2-yl)-1,3-dihydrospiro [indene-2,4'-piperidin]-1-amine | 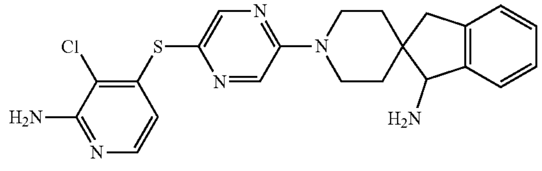 [SMILES: Nc1nccc(Sc2cnc(N3CCC4(CC3)Cc3ccccc3C4N)cn2)c1Cl] | $^1$H NMR (400 MHz, MeOH-d4) δ 8.33 (d, 1H), 8.27 (d, 1H), 7.60 (d, 1H), 7.37 (d, 1H), 7.23-7.18 (m, 3H), 5.95 (d, 1H), 4.34 (d, 2H), 3.95 (s, 1H), 3.34-3.15 (m, 3H), 2.81 (d, 1H), 1.88-1.84 (m, 2H), 1.63 (d, 1H), 1.45 (d, 1H). MS: 439 $(M + H)^+$. |

TABLE 17-continued

| EX No | Chemical Name | Structure | MS: $(M + H)^+$ & $^1$HNMR |
|---|---|---|---|
| 126 | 1'-(6-amino-5-((3-amino-2-chloro phenyl)thio) pyrazin-2-yl)-5,7-dihydrospiro[cyclo-penta[b]pyridine-6,4'-piperidin]-5-amine | 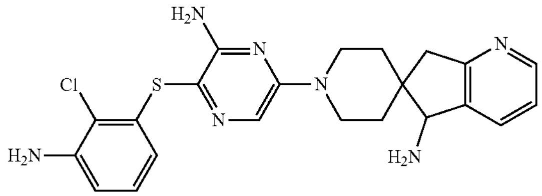 [SMILES: Nc1cccc(Sc2ncc(N3CCC4(CC3)Cc3ncccc3C4N)nc2N)c1Cl] | $^1$H NMR (400 MHz, MeOH-d4) δ 8.38 (d, 1H), 7.85 (d, 1H), 7.55 (s, 1H), 7.31-7.27 (m, 1H), 6.85 (t, 1H), 6.63-6.60 (m, 1H), 6.03 (d, 1H), 4.32-4.27 (m, 2H), 4.12 (s, 1H), 3.35-3.22 (m, 3H), 2.98 (d, 1H), 1.89-1.78 (m, 2H), 1.62 (d, 1H), 1.47 (d, 1H). MS: 454 $(M + H)^+$. |
| 127 | 1'-(6-amino-5-((2-amino-3-chloro pyridin-4-yl)thio) pyrazin-2-yl)-5,7-dihydrospiro [cyclopenta[c] pyridine-6,4'-piperidin]-5-amine | 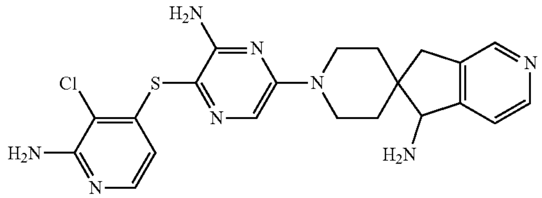 | $^1$H NMR (400 MHz, MeOH-d4) δ 8.43 (s, 1H), 8.41 (d, 1H), 7.60 (t, 2H), 7.48 (d, 1H), 5.93 (d, 1H), 4.36-4.31 (m, 2H), 4.11 (s, 1H), 3.35-3.21 (m, 3H), 2.90 (d, 1H), 1.91-1.89 (m, 1H), 1.77-1.72 (m, 1H), 1.66 (d, 1H), 1.34 (d, 1H). MS: 455 $(M + H)^+$. |
| 128 | 1'-(5-((3-amino-2-chlorophenyl) thio)pyrazin-2-yl)-5,7-dihydrospiro [cyclopenta[b] pyridine-6,4'-piperidin]-5-amine | 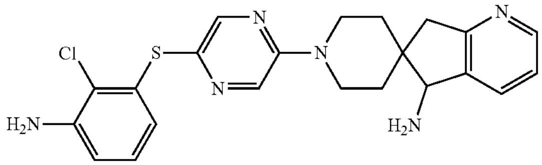 [SMILES: Nc1cccc(Sc2cnc(N3CCC4(CC3)Cc3ncccc3C4N)cn2)c1Cl] | $^1$H NMR (400 MHz, MeOH-d4) δ 8.39 (d, 1H), 8.23 (d, 1H), 8.13 (d, 1H), 7.85 (d, 1H), 7.31-7.28 (m, 1H), 6.91 (t, 1H), 6.69 (d, 1H), 6.27 (d, 1H), 4.34-4.28 (m, 2H), 4.13 (s, 1H), 3.35-3.26 (m, 3H), 3.00 (d, 1H), 1.92-1.80 (m, 2H), 1.65 (d, 1H), 1.49 (d, 1H). MS: 439 $(M + H)^+$. |
| 129 | 1'-(6-amino-5-((2-amino-3-chloro pyridin-4-yl)thio) pyrazin-2-yl)-5-bromo-1,3-dihydro-spiro[indene-2,4'-piperidin]-1-amine | 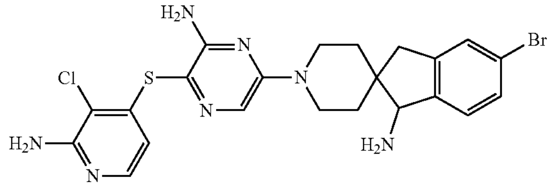 [SMILES: Nc1nc(N2CCC3(CC2)Cc2cc(Br)ccc2C3N)cnc1Sc1ccnc(N)c1Cl] | $^1$H NMR (400 MHz, MeOH-d4) δ 7.59 (t, 2H), 7.47 (s, 1H), 7.43-7.33 (m, 2H), 5.93 (d, 1H), 4.33-4.25 (m, 2H), 4.10 (s, 1H), 3.35-3.15 (m, 3H), 2.95 (d, 1H), 1.81-1.76 (m, 2H), 1.59 (d, 1H), 1.53 (d, 1H). MS: 532 $(M + H)^+$. |
| 130 | 1'-(6-amino-5-((2-amino-3-chloro pyridin-4-yl)thio) pyrazin-2-yl)-2-chloro-4,6-dihydro-spiro[cyclopenta [d]thiazole-5,4'-piperidin]-4-amine | 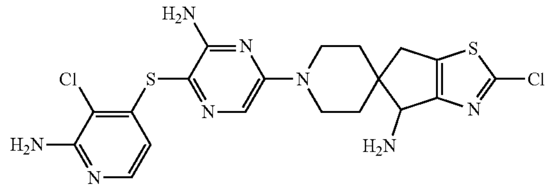 [SMILES: Nc1nc(N2CCC3(CC2)Cc2sc(Cl)nc2C3N)cnc1Sc1ccnc(N)c1Cl] | $^1$H NMR (400 MHz, MeOH-d4) δ 7.62-7.58 (m, 2H), 5.93 (d, 1H), 4.27-4.09 (m, 2H), 3.95 (s, 1H), 3.48-3.30 (m, 3H), 3.00 (d, 1H), 1.92-1.71 (m, 4H). MS: 495 $(M + H)^+$. |
| 131 | 1'-(5-((2-amino-3-chloropyridin-4-yl)thio)pyrazin-2-yl)-2-chloro-4,6-dihydrospiro [cyclopenta[d] thiazole-5,4'-piperidin]-4-amine | 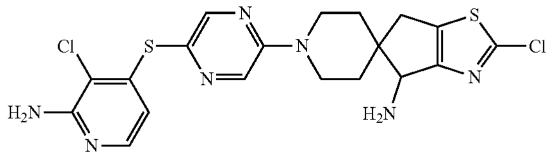 [SMILES: Nc1nccc(Sc2cnc(N3CCC4(CC3)Cc3sc(Cl)nc3C4N)cn2)c1Cl] | $^1$H NMR (400 MHz, MeOH-d4) δ 8.37 (s, 1H), 8.31 (s, 1H), 7.61 (d, 1H), 5.95 (d, 1H), 4.44-4.28 (m, 2H), 4.12 (s, 1H), 3.35-3.31 (m, 3H), 3.10 (d, 1H), 1.98-1.78 (m, 4H). MS: 480 $(M + H)^+$. |
| 132 | 1'-(5-((2-amino-3-chloropyridin-4-yl)thio)pyrazin-2-yl)-2,3-dihydrospiro[indene-1,4'-piperidin]-2-amine | 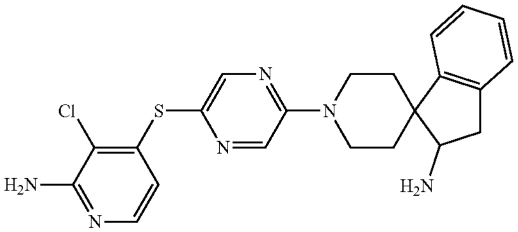 [SMILES: Nc1nccc(Sc2cnc(N3CCC4(CC3)c3ccccc3CC4N)cn2)c1Cl] | $^1$H NMR (400 MHz, MeOH-d4) δ 8.38 (d, 1H), 8.32 (s, 1H), 7.61 (d, 1H), 7.42-7.28 (m, 4H), 5.97 (d, 1H), 4.36-4.14 (m, 3H), 3.67-3.52 (m, 3H), 2.99 (d, 1H), 2.29-2.23 (m, 1H), 1.97-1.70 (m, 3H). MS: 439 $(M + H)^+$. |

Example 133

(S)-4-((5-(1-amino-1,3-dihydrospiro[indene-2,4'-piperidin]-1'-yl)pyrazin-2-yl)thio)-3-chloro pyridin-2-ol

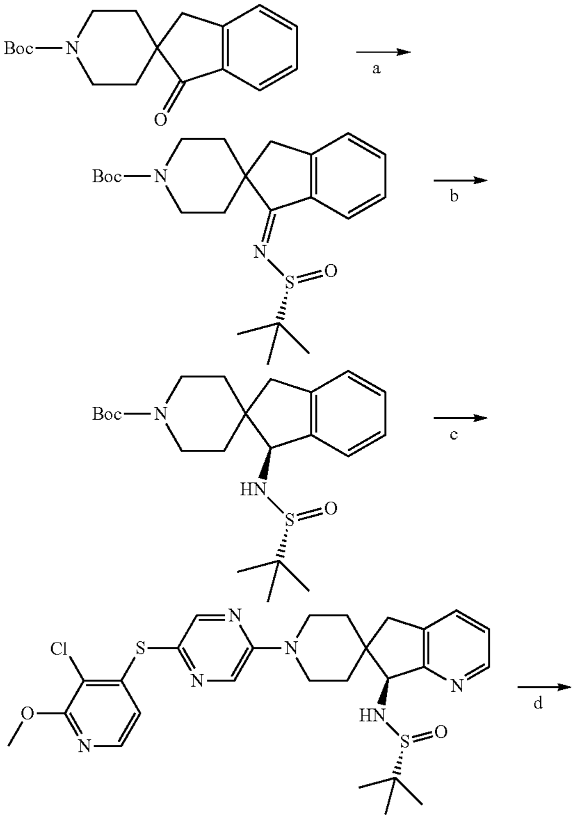

-continued

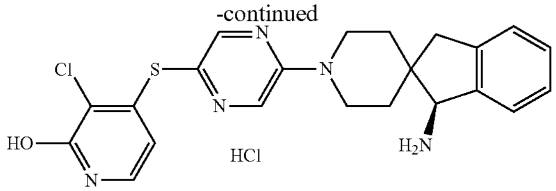

Step a-c: Step (a-c) of Example 5 was applied to provide (R)—N—((S)-1'-(5-((3-chloro-2-methoxypyridin-4-yl)thio)pyrazin-2-yl)-1,3-dihydrospiro[indene-2,4'-piperidin]-1-yl)-2-methylpropane-2-sulfinamide. MS: m/z 558 $(M+H)^+$.

Step d: A mixture of (R)—N—((S)-1'-(5-((3-chloro-2-methoxypyridin-4-yl)thio)pyrazin-2-yl)-1,3-dihydrospiro[indene-2,4'-piperidin]-1-yl)-2-methylpropane-2-sulfinamide (112 mg, 0.20 mmol), DCM (5 mL) and HCl (4 M solution in 1,4-dioxane, 10 mL) was stirred for 17 h at RT. The mixture was concentrated under reduced pressure, dissolved in MeOH (10 mL) and stirred for another 23 h at 60° C. After cooling to RT, the reaction mixture was concentrated under reduced pressure. The residue was suspended in MeOH (2 mL) and EA (20 mL), the resulting precipitate was collected by filtration and dried under reduced pressure to give (S)-4-((5-(1-amino-1,3-dihydrospiro[indene-2,4'-piperidin]-1'-yl)pyrazin-2-yl)thio)-3-chloropyridin-2-ol (73 mg). MS: m/z 440 $(M+H)^+$. H NMR (400 MHz, DMSO-d6) δ 8.51 (s, 1H), 8.34 (s, 1H), 7.59 (d, 1H), 7.37-7.28 (m, 3H), 7.23 (d, 1H), 5.52 (d, 1H), 4.40-4.28 (m, 3H), 3.38-3.21 (m, 3H), 3.02-2.99 (d, 1H), 1.82-1.75 (m, 2H), 1.60-1.52 (m, 2H).

The following examples were synthesized using the above procedure with the corresponding starting materials.

The following examples are compounds, or a pharmaceutically acceptable salt.

TABLE 18

| EX No. | Chemical Name | Structure | MS: $(M + H)^+$ & $^1$HNMR |
|---|---|---|---|
| 134 | (S)-4-((3-amino-5-(1-amino-1,3-dihydrospiro[indene-2,4'-piperidin]-1'-yl)pyrazin-2-yl)thio)-3-chloropyridin-2-ol | 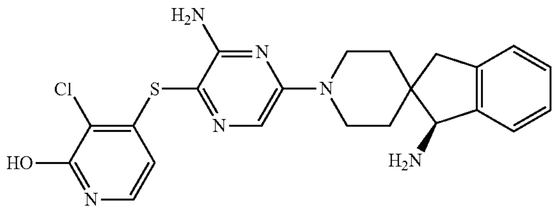 | $^1$H NMR (400 MHz, DMSO-d6) δ 7.68 (s, 1H), 7.52 (d, 1H), 7.39-7.29 (m, 3H), 7.23 (d, 1H), 5.45 (d, 1H), 4.36 (s, 1H), 4.29 (d, 1H), 4.21 (d, 1H), 3.19-3.00 (m, 4H), 1.78-1.63 (m, 2H), 1.46-1.58 (m, 2H). MS: $455(M + H)^+$. |
| 135 | (S)-4-((5-(5-amino-5,7-dihydrospiro[cyclopenta[b]pyridine-6,4'-piperidin]-1'-yl)pyrazin-2-yl)thio)-3-chloropyridin-2-ol | 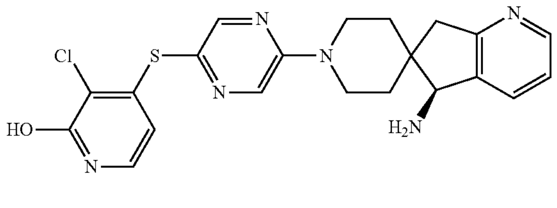 [SMILES: N[C@@H]1c2cccnc2CC12CCN(c1cnc(Sc3ccnc(O)c3Cl)cn1)CC2] | $^1$H NMR (400 MHz, DMSO-d6) δ 8.38-8.32 (m, 3H), 7.84 (d, 1H), 7.31-7.27 (m, 1H), 7.19 (d, 1H), 5.76 (d, 1H), 4.42-4.38 (d, 2H), 4.10 (s, 1H), 3.31-3.25 (m, 3H), 2.99 (d, 1H), 1.95-1.82 (m, 2H), 1.68 (d, 1H), 1.48 (d, 1H). MS: $441(M + H)^+$. |

TABLE 18-continued

| EX No. | Chemical Name | Structure | MS: $(M + H)^+$ & $^1$HNMR |
|---|---|---|---|
| 136 | (S)-4-((3-amino-5-(5-amino-5,7-dihydrospiro[cyclopenta[b]pyridine-6,4'-piperidin]-1'-yl)pyrazin-2-yl)thio)-3-chloropyridin-2-ol | 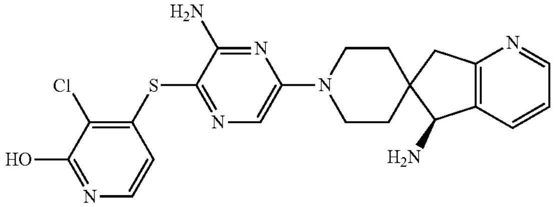 [SMILES: Nc1nc(N2CCC3(CC2)Cc2ncccc2[C@H]3N)cnc1Sc1ccnc(O)c1Cl] | $^1$H NMR (400 MHz, MeOH-d4) δ 8.41 (d, 1H), 7.89 (d, 1H), 7.64 (s, 1H), 7.38-7.28 (m, 1H), 7.24 (d, 1H), 5.77 (d, 1H), 4.44-4.29 (m, 2H), 4.15 (s, 1H), 3.43-3.19 (m, 3H), 3.08-2.92 (m, 1H), 1.99-1.78 (m, 2H), 1.74-1.58 (m, 1H), 1.56-1.43 (m, 1H). MS: 456$(M + H)^+$. |

Example 137

(S)-1-amino-1'-(6-amino-5-((2-amino-3-chloropyridin-4-yl)thio)pyrazin-2-yl)-1,3-dihydrospiro[indene-2,4'-piperidin]-6-ol

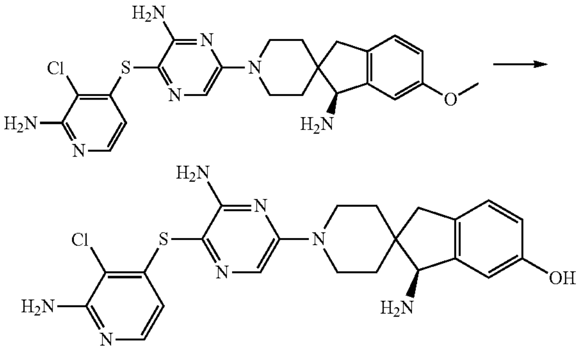

To a mixture of (S)-1'-(6-amino-5-((2-amino-3-chloropyridin-4-yl)thio)pyrazin-2-yl)-6-methoxy-1,3-dihydrospiro[indene-2,4'-piperidin]-1-amine (74 mg, 0.14 mmol) in DCM (2 mL) was added BBr3 (1 M solution in DCM, 0.71 mL). The resulting mixture was stirred for 6 h at RT. The volatiles were removed under reduced pressure, the residue suspended in water, the resulting solid was filtered off and the pH value of the filtrate was adjusted to 7 with sat.aq.$NaHCO_3$. The resulting precipitate was collected by filtration and dried in a vacuum oven to give (S)-1-amino-1'-(6-amino-5-((2-amino-3-chloropyridin-4-yl)thio)pyrazin-2-yl)-1,3-dihydrospiro[indene-2,4'-piperidin]-6-ol (7 mg). MS: m/z 470 $(M+H)^+$.

The following example was synthesized using the above procedure with the corresponding starting materials.

TABLE 19

| EX No. | Chemical name | Structure | MS: $(M + H)^+$ & $^1$HNMR |
|---|---|---|---|
| 138 | (S)-1-amino-1'-(6-amino-5-((2-amino-3-chloropyridin-4-yl)thio)pyrazin-2-yl)-1,3-dihydrospiro[indene-2,4'-piperidin]-4-ol | 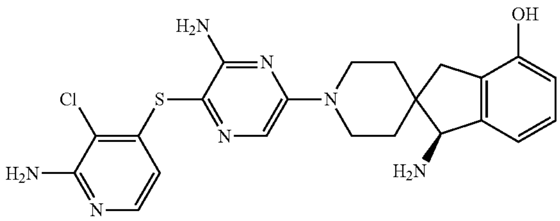 [SMILES: Nc1nc(N2CCC3(CC2)Cc2c(O)cccc2[C@H]3N)cnc1Sc1ccnc(N)c1Cl] | $^1$H NMR (400 MHz, DMSO-d6) δ 7.58-7.51 (m, 2H), 7.05 (t, 1H), 6.87 (d, 1H), 6.65 (d, 1H), 5.94 (d, 1H), 4.27 (d, 2H), 3.9 (s, 1H), 3.36-3.18 (m, 2H), 3.08 (d, 1H), 2.69 (d, 1H), 1.88-1.68 (m, 2H), 1.57 (d, 1H), 1.43 (d, 1H). MS: 470$(M + H)^+$. |

Example 139

1'-(6-amino-5-((2-amino-3-chloropyridin-4-yl)thio)pyrazin-2-yl)-5-methyl-5,7-dihydrospiro

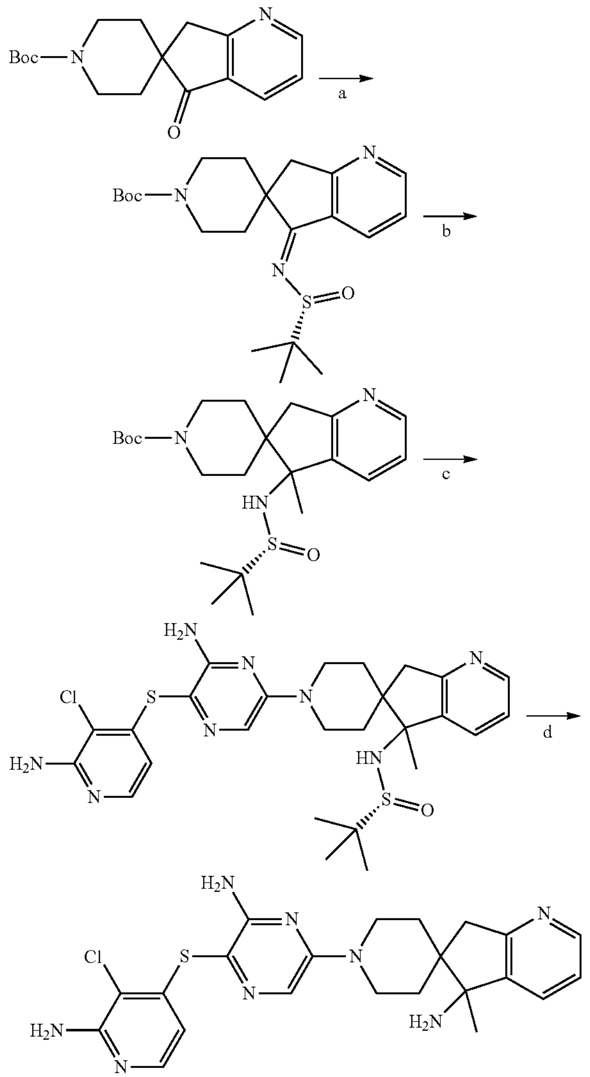

Step a: Step (a) of Example 5 was applied to provide tert-butyl (R,Z)-5-((tert-butylsulfinyl)imino)-5,7-dihydrospiro[cyclopenta[b]pyridine-6,4'-piperidine]-1'-carboxylate. MS: m/z 406 $(M+H)^+$.

Step b: To a −60° C. solution of tert-butyl (R,Z)-5-((tert-butylsulfinyl)imino)-5,7-dihydrospiro[cyclopenta[b]pyridine-6,4'-piperidine]-1'-carboxylate (1.49 g, 3.67 mmol) in THF (15 mL) was added methyllithium (1.3 M solution in diethyl ether, 14 mL, 18.20 mmol) dropwise. The resulting mixture was allowed to warm to RT and stirred for 20 h. The reaction mixture was diluted with water (10 mL) and EA (20 mL). The aqueous layer was collected, NaOH (1.00 g, 25.00 mmol) and $(Boc)_2O$ (0.50 mL) was added. The mixture was stirred for 1.5 h at RT. The reaction mixture was extracted with EA (2×50 mL), the organic layers combined, washed with brine (1×30 mL), dried over anhydrous $Na_2SO_4$, filtrated and concentrated under reduced pressure. The residue was purified by silica chromatography (eluting with EA:Hex=1:1, v/v) to give tert-butyl 5-(((S)-tert-butylsulfinyl)amino)-5-methyl-5,7-dihydrospiro[cyclopenta[b]pyridine-6,4'-piperidine]-1'-carboxylate (823 mg). MS: m/z 422 $(M+H)^+$.

Step (c-d): Step (c-d) of Example 5 was applied to provide 1'-(6-amino-5-((2-amino-3-chloropyridin-4-yl)thio)pyrazin-2-yl)-5-methyl-5,7-dihydrospiro[cyclopenta[b]pyridine-6,4'-piperidin]-5-amine (71 mg). MS: m/z 469 $(M+H)^+$. $^1H$ NMR (400 MHz, MeOH-d4) δ 8.50-8.44 (m, 1H), 7.93-7.87 (m, 1H), 7.67-7.61 (m, 2H), 7.41-7.35 (m, 1H), 5.97 (d, 1H), 4.54 (m, 2H), 3.35 (d, 1H), 3.23-3.08 (m, 3H), 1.92-1.78 (m, 2H), 1.57-1.48 (m, 2H), 1.44 (s, 3H).

Example 140

1-amino-1'-(6-amino-5-((2-amino-3-chloropyridin-4-yl)thio)pyrazin-2-yl)-3H-spiro[indolizine-2,4'-piperidin]-7(1H)-one

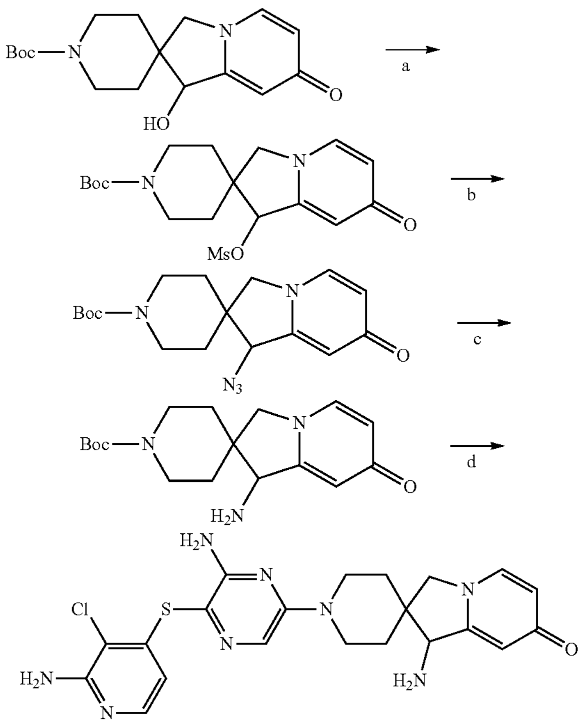

Step a: To a −10° C. solution of tert-butyl 1-hydroxy-7-oxo-1,7-dihydro-3H-spiro[indolizine-2,4'-piperidine]-1'-carboxylate (100 mg, 0.31 mmol), triethylamine (157 mg, 1.55 mmol) in THF (10 mL) and DCM (2 mL) was added MsCl (66 mg, 0.58 mmol). The resulting solution was stirred for 1 h at RT. The reaction solution was diluted with water (50 mL), extracted with DCM (3×50 mL). The combined organic layers were dried over anhydrous $Na_2SO_4$, filtrated and concentrated under reduced pressure to give tert-butyl 1-((methylsulfonyl)oxy)-7-oxo-1,7-dihydro-3H-spiro[indolizine-2,4'-piperidine]-1'-carboxylate (155 mg). MS: m/z 399 $(M+H)^+$.

Step b: A mixture of tert-butyl 1-((methylsulfonyl)oxy)-7-oxo-1,7-dihydro-3H-spiro[indolizine-2,4'-piperidine]-1'-carboxylate (155 mg, 0.39 mmol), sodium azide (136 mg, 2.09 mmol) and DMF (5 mL) was stirred for 1 h at 75° C. and 4 h at 85° C. After cooling to RT, the reaction mixture was diluted with EA (30 mL), filtered and the filtration was concentrated under reduced pressure. The residue was purified by silica chromatography (eluting with MeOH:DCM=1:10, v/v) to give tert-butyl 1-azido-7-oxo-1,7-dihydro-3H-spiro[indolizine-2,4'-piperidine]-1'-carboxylate (32 mg). MS: m/z 346 $(M+H)^+$.

Step c: A mixture of tert-butyl 1-azido-7-oxo-1,7-dihydro-3H-spiro[indolizine-2,4'-piperidine]-1'-carboxylate (32 mg, 0.093 mmol), Pd (10% on carbon, 15 mg) in EtOH (6 mL) was stirred for 3 h under hydrogen atmosphere. The reaction mixture filtrated follow by EtOH wash and the filtration was concentrated under reduced pressure to give tert-butyl 1-amino-7-oxo-1,7-dihydro-3H-spiro[indolizine-2,4'-piperidine]-1'-carboxylate (26 mg). MS: m/z 320 $(M+H)^+$.

Step d: To solution of tert-butyl 1-amino-7-oxo-1,7-dihydro-3H-spiro[indolizine-2,4'-piperidine]-1'-carboxylate (26 mg, 0.081 mmol) in DCM (2 mL) was added TFA (2 mL), and stirred for 30 min at RT. The resulting mixture was concentrated under reduced pressure. The residue was dissolved in NMP (2.5 mL), 3-((2-amino-3-chloropyridin-4-yl)thio)-6-chloropyrazin-2-amine (46 mg, 0.16 mmol) and $K_2CO_3$ (395 mg, 2.86 mmol) was added, stirred for 16 h at 95° C. After cooling to RT, the reaction mixture was diluted DCM (30 mL), filtered and concentrated under reduced pressure. The residue was purified by Pre-TLC (eluting with MeOH:DCM=1:3, v/v) to give 1-amino-1'-(6-amino-5-((2-amino-3-chloropyridin-4-yl)thio)pyrazin-2-yl)-3H-spiro[indolizine-2,4'-piperidin]-7(1H)-one (2 mg). MS: m/z 471 $(M+H)^+$.

The following example was synthesized using the above procedure with the corresponding starting materials.

-continued

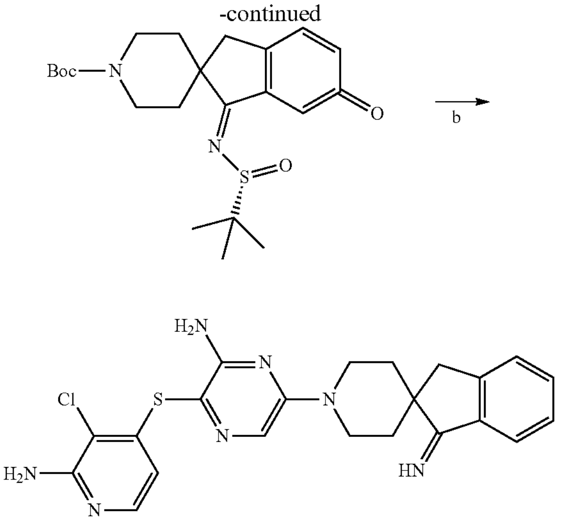

Step a: Step (a) of Example 5 was applied to provide tert-butyl (R,Z)-1-((tert-butylsulfinyl)imino)-1,3-dihydrospiro[indene-2,4'-piperidine]-1'-carboxylate. MS: m/z 405 $(M+H)^+$.

Step b: To solution of tert-butyl (R,Z)-1-((tert-butylsulfinyl)imino)-1,3-dihydrospiro[indene-2,4'-piperidine]-1'-carboxylate (405 mg, 1.00 mmol) in DCM (10 mL) was added TFA (1 mL), and stirred for 1.5 h at RT. The resulting mixture was concentrated under reduced pressure. The residue was dissolved in NMP (10 mL), 3-((2-amino-3-chloropyridin-4-yl)thio)-6-chloropyrazin-2-amine (288 mg, 1.00

TABLE 20

| EX No. | Chemical Name | Structure | MS: $(M + H)^+$ & $^1$HNMR |
|---|---|---|---|
| 141 | 1-amino-1'-(6-amino-5-((2-amino-3-chloropyridin-4-yl)thio)pyrazin-2-yl)-3H-spiro[indolizine-2,4'-piperidin]-5(1H)-one | 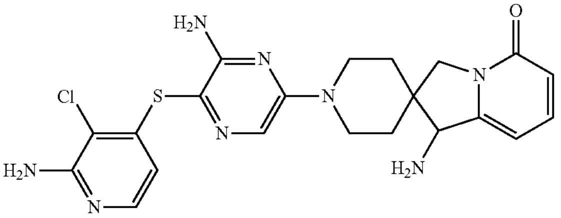 [SMILES: Nc1nc(N2CCC3(CC2)Cn2c(cccc2=O)C3N)cnc1Sc1ccnc(N)c1Cl] | $^1$H NMR (400 MHz, MeOH-d4) δ 7.61-7.57 (m, 3H), 6.53 (d, 1H), 6.45 (d, 1H), 5.93 (d, 1H), 4.46 (d, 1H), 4.39-4.32 (m, 2H), 4.14-4.08 (m, 1H), 3.84 (d, 1H), 3.28-3.11 (m, 2H), 1.99-1.91 (m, 1H), 1.83-1.75 (m, 1H), 1.70 (d, 1H), 1.30 (d, 1H). MS: 471$(M + H)^+$. |

Example 142

3-((2-amino-3-chloropyridin-4-yl)thio)-6-(1-imino-1,3-dihydrospiro[indene-2,4'-piperidin]-1'-yl) pyrazin-2-amine

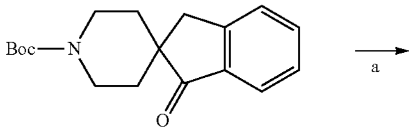

mmol) and $K_2CO_3$ (1.38 g, 10.00 mmol) was added. The resulting mixture was stirred for 18 h at 100° C. After cooling to RT, the reaction mixture was diluted with water (50 mL) and extracted with EA (3×30 mL). The combined organic layers were washed with brine (1×100 mL), dried over anhydrous $Na_2SO_4$, filtered and concentrated under reduced pressure. The residue was purified by silica chromatography (eluting with MeOH:DCM=1:5, v/v) to give 3-((2-amino-3-chloropyridin-4-yl)thio)-6-(1-imino-1,3-dihydrospiro[indene-2,4'-piperidin]-1'-yl) pyrazin-2-amine (50 mg). MS: m/z 452 $(M+H)^+$. H NMR (400 MHz, MeOH-d4) δ 7.83 (d, 1H), 7.74-7.37 (m, 5H), 5.96 (d, 1H), 4.58-4.43 (m, 2H), 3.28-3.12 (m, 4H), 2.06-2.01 (m, 2H), 1.60-1.56 (m, 2H).

The following examples were synthesized using the above procedure with the corresponding starting materials.

TABLE 21

| EX No. | Chemical Name | Structure | MS: $(M+H)^+$ & $^1$HNMR |
|---|---|---|---|
| 143 | 3-((2-amino-3-chloropyridin-4-yl) thio)-6-(1-imino-5-methoxy-1,3-dihydro-spiro[indene-2,4'-piperidin]-1'-yl)pyrazin-2-amine | 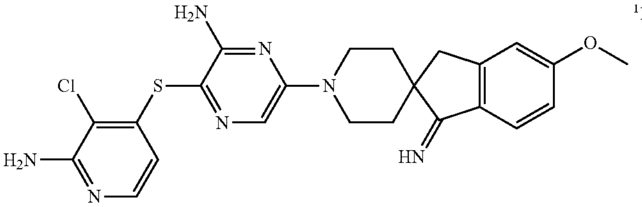 | $^1$H NMR (400 MHz, MeOH-d4) δ 7.81 (d, 1H), 7.65 (s, 1H), 7.61(d, 1H), 7.06 (s, 1H), 7.00 (dd, 1H), 5.95 (d, 1H), 4.57 (d, 2H), 3.91 (s, 3H), 3.26 (s, 2H), 3.21-3.14 (m, 211), 2.05-1.98 (m, 2H), 1.61 (d, 2H). MS: 482$(M+H)^+$. |
| 144 | 3-((2-amino-3-chloropyridin-4-yl) thio)-6-(4-imino-4,6-dihydrospiro [cyclopenta[b]thiophene-5,4'-piperidin]-1'-yl)pyrazin-2-amine | 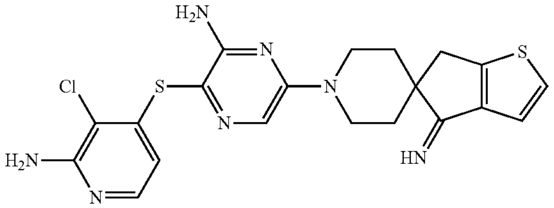 [SMILES: N=C1c2ccsc2CC12CCN(c1cnc(Sc3ccnc(N)c3Cl)c(N)n1)CC2] | $^1$H NMR (400 MHz, DMSO-d6) δ 7.83 (d, 1H), 7.70 (s, 1H), 7.66 (d, 1H), 7.46 (d, 1H), 6.04 (d, 1H), 4.68 (d, 2H), 3.59 (s, 2H), 3.21 (t, 2H), 2.14-2.07 (m, 2H), 1.91 (d, 2H). MS: 458$(M+H)^+$. |
| 145 | 3-((2-amino-3-chloropyridin-4-yl) thio)-6-(1-bromo-4-imino-4H,6H-spiro [cyclopenta[c]thiophene-5,4'-piperidin]-1'-yl)pyrazin-2-amine | 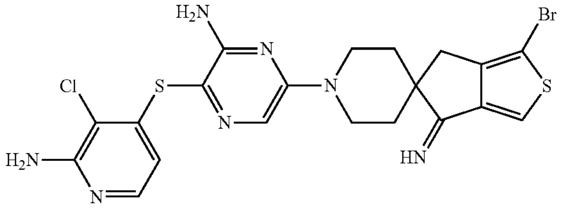 [SMILES: N=C1c2csc(Br)c2CC12CCN(c1cnc(Sc3ccnc(N)c3Cl)c(N)n1)CC2] | $^1$H NMR (400 MHz, DMSO-d6) δ 7.69 (s, 1H), 7.65 (d, 1H), 6.15 (s, 1H), 5.81-5.74 (m, 1H), 4.49-4.32 (m, 2H), 3.17-2.93 (m, 4H), 1.90-1.80 (m, 1H), 1.79-1.66 (m, 1H), 1.61-1.43 (m, 2H). MS: 536$(M+H)^+$. |
| 146 | 3-((2-amino-3-chloropyridin-4-yl) thio)-6-(4-imino-4H,6H-spiro [cyclopenta[c]thiophene-5,4'-piperidin]-1'-yl)pyrazin-2-amine | 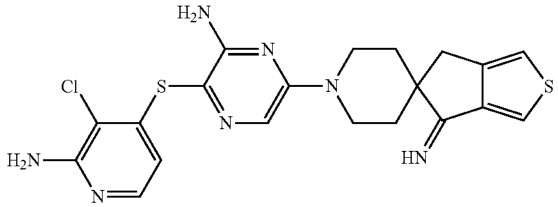 [SMILES: N=C1c2cscc2CC12CCN(c1cnc(Sc3ccnc(N)c3Cl)c(N)n1)CC2] | $^1$H NMR (400 MHz, DMSO-d6) δ 7.69 (s, 1H), 7.65 (d, 1H), 6.20-6.12 (m, 2H), 5.80-5.73 (m, 1H), 4.51-4.28 (m, 2H), 3.13-2.96 (m, 4H), 1.83-1.66 (m, 2H), 1.59-1.46 (m, 2H). MS: 458$(M+H)^+$. |
| 147 | 3-((2-amino-3-chloropyridin-4-yl) thio)-6-(2-bromo-4-imino-4,6-dihydro-spiro[cyclopenta[b] thiophene-5,4'-piperidin]-1'-yl) pyrazin-2-amine | 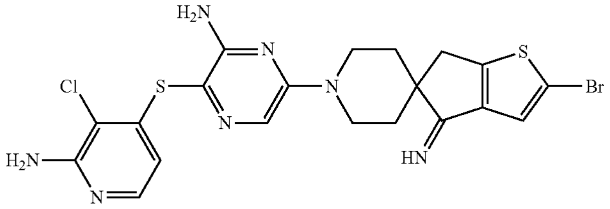 [SMILES: N=C1c2cc(Br)sc2CC12CCN(c1cnc(Sc3ccnc(N)c3Cl)c(N)n1)CC2] | MS: 536$(M+H)^+$. |

Example 148

1'-(6-amino-5-((2-amino-3-chloropyridin-4-yl)thio) pyrazin-2-yl)-7-methoxy-1,3-dihydrospiro[indene-2, 4'-piperidin]-1-amine

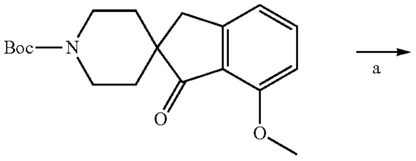

-continued

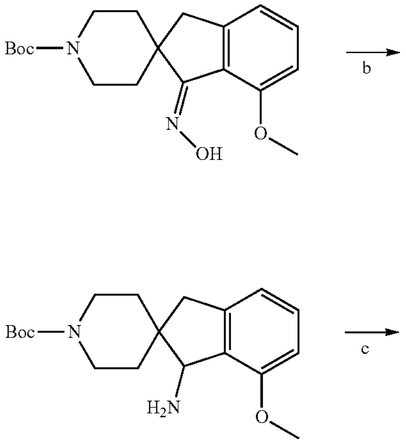

-continued

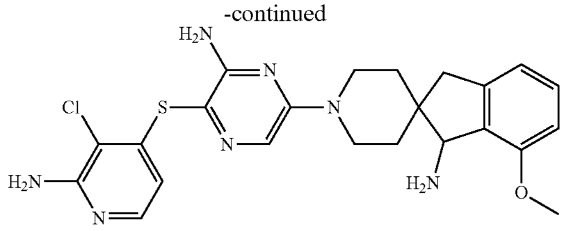

Step a: To a solution of tert-butyl 7-methoxy-1-oxo-1,3-dihydrospiro[indene-2,4'-piperidine]-1'-carboxylate (552 mg, 1.07 mmol) in MeOH (10 mL) was added hydroxylamine hydrochloride (348 mg, 5.01 mmol) and AcONa (822 mg, 10.02 mmol). The resulting mixture was stirred for 4 h at RT. The reaction mixture was concentrated under reduced pressure. The residue was dissolved in EA (15 mL) and water (15 mL), the organic layer was separated, washed with brine (1×15 mL), dried over anhydrous $Na_2SO_4$, filtered and concentrated under reduced pressure to give tert-butyl (Z)-1-(hydroxyimino)-7-methoxy-1,3-dihydrospiro[indene-2,4'-piperidine]-1'-carboxylate (520 mg) as a yellow solid. MS: m/z 347 $(M+H)^+$.

Step b: A suspension of tert-butyl (Z)-1-(hydroxyimino)-7-methoxy-1,3-dihydrospiro[indene-2,4'-piperidine]-1'-carboxylate (510 mg, 1.47 mmol) and $PtO_2$ (30 mg) in AcOH (10 mL) was stirred for 17 h at 60° C. under hydrogen atmosphere. After cooling to RT, the reaction mixture was diluted with EA (45 mL) and water (45 mL), the aqueous layer was separated and the pH value was taken to 10 with $K_2CO_3$ solid. The resulting mixture was extracted with DCM (2×30 mL), the combined organic layers were washed with brine (1×50 mL), dried over anhydrous $Na_2SO_4$, filtered and concentrated under reduced pressure to give tert-butyl 1-amino-7-methoxy-1,3-dihydrospiro[indene-2,4'-piperidine]-1'-carboxylate (202 mg) as a colorless oil. MS: m/z 333 $(M+H)^+$.

Step c: To solution of tert-butyl 1-amino-7-methoxy-1,3-dihydrospiro[indene-2,4'-piperidine]-1'-carboxylate (199 mg, 0.60 mmol) in DCM (10 mL) was added TFA (1 mL), and stirred for 1.5 h at RT. The resulting mixture was concentrated under reduced pressure. The residue was dissolved in NMP (5 mL), 3-((2-amino-3-chloropyridin-4-yl)thio)-6-chloropyrazin-2-amine (144 mg, 0.50 mmol) and $K_2CO_3$ (691 mg, 5.90 mmol) was added. The resulting mixture was stirred for 3 h at 95° C. After cooling to RT, the reaction mixture was diluted with water (50 mL) and extracted with EA (1×50 mL). The organic layer was washed with brine (1×50 mL), dried over anhydrous $Na_2SO_4$, filtered and concentrated under reduced pressure. The residue was purified by Pre-TLC (eluting with MeOH:DCM=1:5, v/v) to give 1'-(6-amino-5-((2-amino-3-chloropyridin-4-yl)thio)pyrazin-2-yl)-7-methoxy-1,3-dihydrospiro[indene-2,4'-piperidin]-1-amine (20 mg). MS: m/z 484 $(M+H)^+$. $^1H$ NMR (400 MHz, DMSO-d6) δ 7.66 (s, 1H), 7.64 (d, 1H), 7.36-7.28 (m, 1H), 6.90 (d, 1H), 6.88 (d, 1H), 5.75 (d, 1H), 4.29 (s, 1H), 4.20 (d, 1H), 4.09 (d, 1H), 3.83 (s, 3H), 3.30-3.15 (m, 2H), 3.10 (d, 1H), 2.96 (d, 1H), 1.87-1.76 (m, 1H), 1.70-1.54 (m, 2H), 1.41 (d, 1H).

The following example was synthesized using the above procedure with the corresponding starting materials.

TABLE 22

| EX No. | Chemical Name | Structure | MS: (M + H)$^+$ & $^1$HNMR |
|---|---|---|---|
| 149 | (Z)-1'-(6-amino-5-((2-amino-3-chloropyridin-4-yl)thio)pyrazin-2-yl)spiro[indene-2,4'-piperidin]-1(3H)-one oxime | 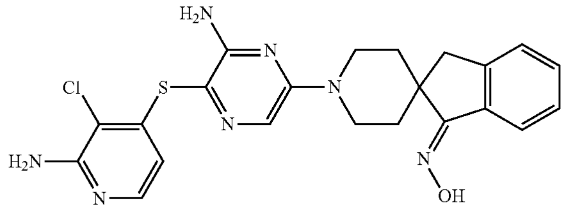 [SMILES: Nc1nc(N2CCC3(CC2)Cc2ccccc2/C3=N\O)cnc1Sc1ccnc(N)c1Cl] | $^1$H NMR (400 MHz, MeOH-d4) δ 8.40 (d, 1H), 7.63-7.58 (m, 3H), 7.41-7.34 (m, 2H), 5.96 (d, 1H), 4.38 (d, 2H), 3.31-3.14 (m, 4H), 1.96-1.92 (m, 2H), 1.72-1.63 (m, 2H). MS: 468(M + H)$^+$. |

Example 150

(S)-1'-(6-amino-5-((2-amino-3-chloropyridin-4-yl)thio)pyrazin-2-yl)-2-methoxy-4,6-dihydro spiro[cyclopenta[d]thiazole-5,4'-piperidin]-4-amine

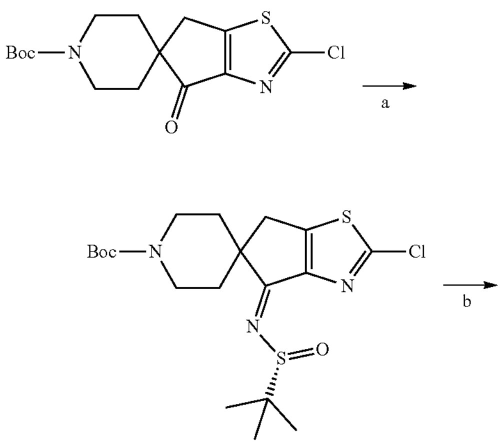

-continued

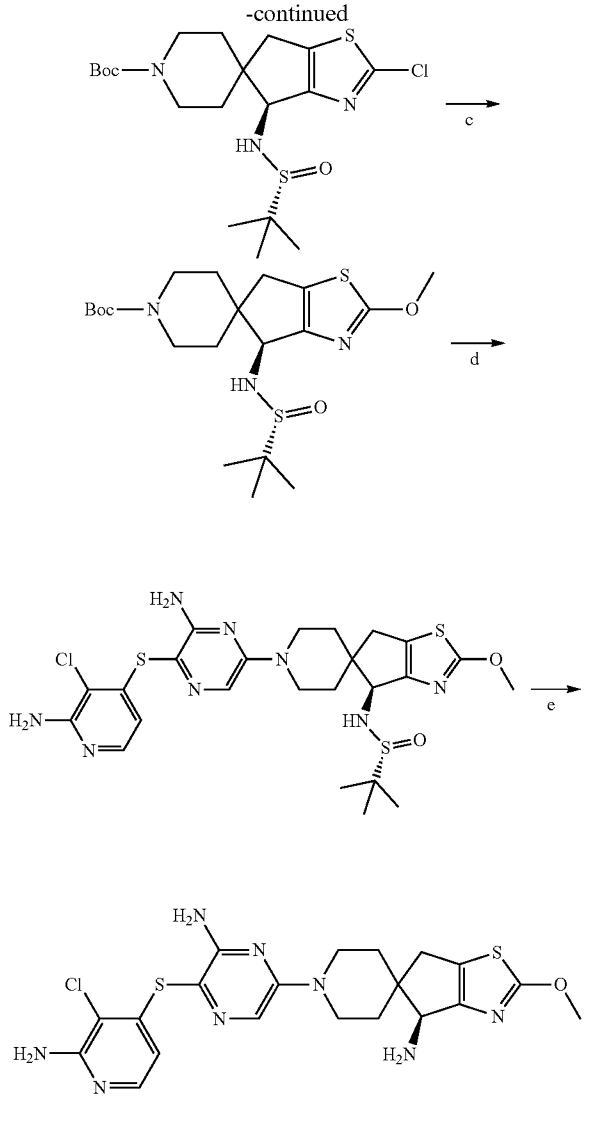

Step (a-b): Step (a-b) of Example 5 was applied to provide tert-butyl (S)-4-(((R)-tert-butylsulfinyl)amino)-2-chloro-4,6-dihydrospiro[cyclopenta[d]thiazole-5,4'-piperidine]-1'-carboxylate. MS: m/z 448 $(M+H)^+$.

Step c: A mixture of tert-butyl(S)-4-(((R)-tert-butylsulfinyl)amino)-2-chloro-4,6-dihydrospiro[cyclopenta[d]thiazole-5,4'-piperidine]-1'-carboxylate (403 mg, 0.90 mmol) and NaOH (358 mg, 8.95 mmol) in MeOH (15 mL) was stirred for 5 h at 65° C. After cooling to RT, the volatiles were removed under reduced pressure. The residue was dissolved in water and the pH value was taken to 7 by the addition of aq. citric acid. The resulting mixture was extracted with EA (3×30 mL), the combined organic layers were dried over anhydrous $Na_2SO_4$, filtered and concentrated under reduced pressure to give tert-butyl(S)-4-(((R)-tert-butylsulfinyl)amino)-2-methoxy-4,6-dihydrospiro[cyclopenta[d]thiazole-5,4'-piperidine]-1'-carboxylate (360 mg) as a brown oil. MS: m/z 444 $(M+H)^+$.

Step (d-e): Step (c-d) of Example 5 was applied to provide(S)-1'-(6-amino-5-((2-amino-3-chloropyridin-4-yl)thio)pyrazin-2-yl)-2-methoxy-4,6-dihydrospiro[cyclopenta[d]thiazole-5,4'-piperidin]-4-amine. MS: m/z 491 $(M+H)^+$.

Example 151

(S)-1'-(6-amino-5-((2-amino-3-chloropyridin-4-yl)thio)pyrazin-2-yl)-4,6-dihydrospiro[cyclo penta[d]thiazole-5,4'-piperidin]-4-amine

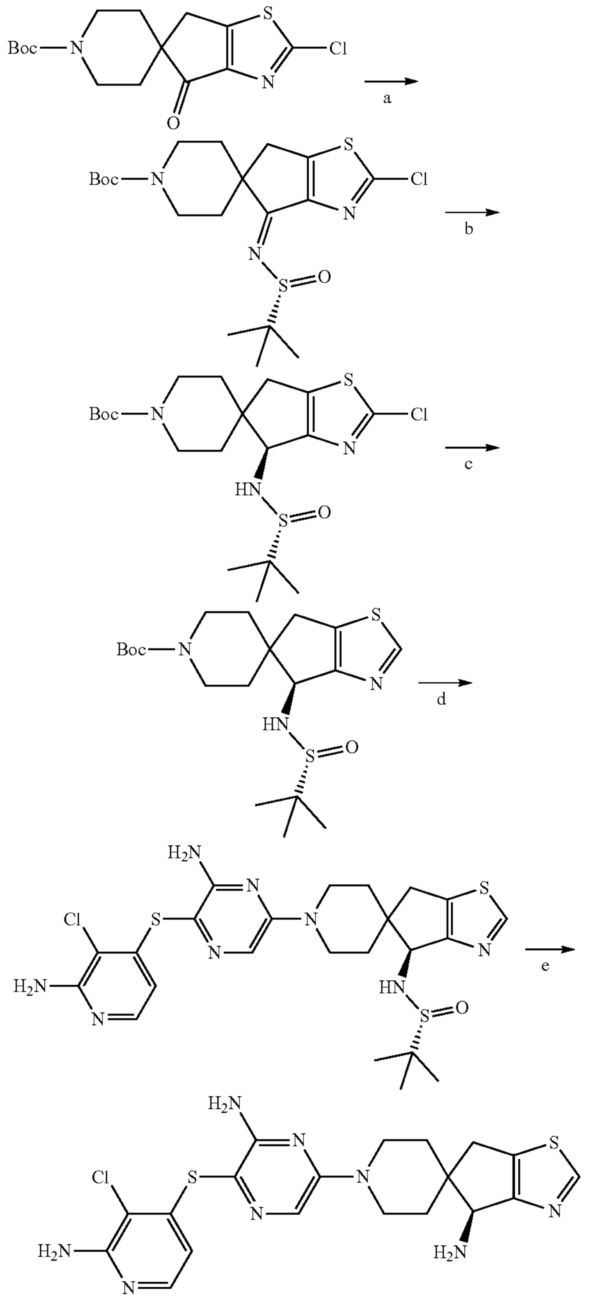

Step (a-b): Step (a-b) of Example 5 was applied to provide tert-butyl (S)-4-(((R)-tert-butylsulfinyl)amino)-2-chloro-4,6-dihydrospiro[cyclopenta[d]thiazole-5,4'-piperidine]-1'-carboxylate. MS: m/z 448 $(M+H)^+$.

Step c: A suspension of tert-butyl (S)-4-(((R)-tert-butylsulfinyl)amino)-2-chloro-4,6-dihydrospiro[cyclopenta[d]thiazole-5,4'-piperidine]-1'-carboxylate (2.50 g, 5.58 mmol), TEA (2 mL) and Pd (10% on carbon, 690 mg) in MeOH (50 mL) was stirred for 24 h at 40° C. under hydrogen atmosphere. The resulting mixture was filtered, and an additional portion of Pd (10 on carbon, 1.32 g) was added to the filtration. The resulting mixture was stirred for another 16 h at 50° C. under hydrogen atmosphere. The resulting mixture was filtered, the filtration was concentrated under reduced pressure. The residue was purified by silica chromatography (eluting with EA:Hex=1:1, v/v) to give tert-butyl (4S)-4-((tert-butylsulfinyl)amino)-4,6-dihydrospiro[cyclopenta[d]thiazole-5,4'-piperidine]-1'-carboxylate (1.28 g). MS: m/z 414 $(M+H)^+$.

Step (d-e): Step (c-d) of Example 5 was applied to provide(S)-1'-(6-amino-5-((2-amino-3-chloropyridin-4-yl)thio)pyrazin-2-yl)-4,6-dihydrospiro[cyclopenta[d]thiazole-5,4'-piperidin]-4-a mine. MS: m/z 461 $(M+H)^+$. H NMR (400 MHz, DMSO-d6) δ 8.94 (s, 1H), 7.66-7.63 (m, 2H), 5.76 (d, 1H), 4.07-3.99 (m, 2H), 3.87 (s, 1H), 3.38-3.28 (m, 2H), 2.93-2.78 (m, 2H), 1.87-1.47 (m, 4H).

2-Methylpropane-2-sulfinamide, instead of (R)-(+)-2-Methyl-2-Propanesulfinamide, was used in step (a) of Example 5 to give the racemic compounds.

The following example was synthesized using the above procedure with the corresponding starting materials.

-continued

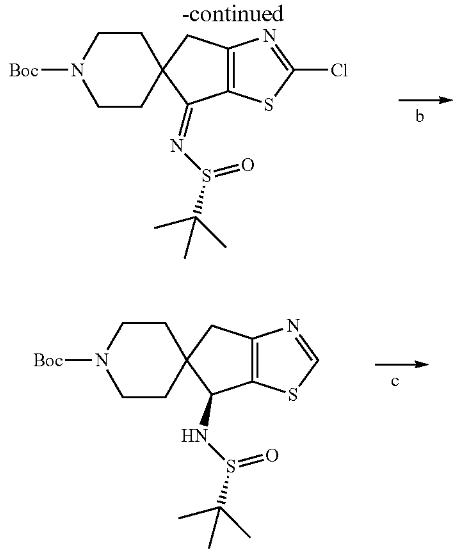

TABLE 23

| EX No. | Chemical Name | Structure | MS: $(M + H)^+$ & $^1$HNMR |
|---|---|---|---|
| 152 | (S)-1'-(5-((2-amino-3-chloropyridin-4-yl)thio)pyrazin-2-yl)-4,6-dihydro-spiro[cyclopenta[d]thiazole-5,4'-piperidin]-4-amine | 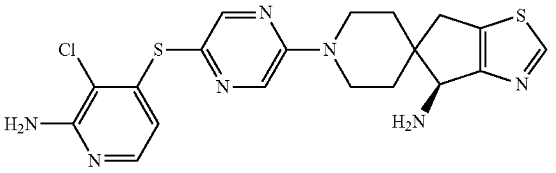 [SMILES: Nc1nccc(Sc2cnc(N3CCC4(CC3)Cc3scnc3[C@H]4N)cn2)c1Cl] | $^1$H NMR (400 MHz, MeOH-d4) δ 8.97 (s, 1H), 8.34 (d, 2H), 7.60 (d, 1H), 5.94 (d, 1H), 4.43 (d, 1H), 4.33 (d, 1H), 4.23 (s, 1H), 3.48-3.31 (m, 2H), 3.12-3.09 (m, 2H), 2.01-1.79 (m, 4H). MS: 446$(M + H)^+$. |
| 153 | 1'-(6-amino-5-((2-amino-3-chloropyridin-4-yl)thio)pyrazin-2-yl)-4,6-dihydro-spiro[cyclopenta[d]thiazole-5,4'-piperidin]-4-amine | 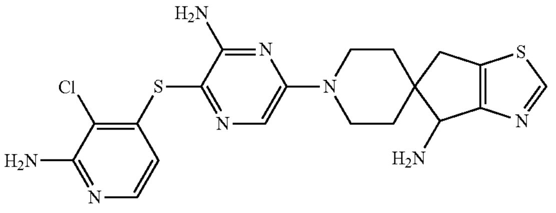 [SMILES: Nc1nc(N2CCC3(CC2)Cc2scnc2C3N)cnc1Sc1ccnc(N)c1Cl] | $^1$H NMR (400 MHz, MeOH-d4) δ 8.88 (s, 1H), 7.62-7.58 (d, 2H), 5.94 (d, 1H), 4.33-4.14 (m, 2H), 3.98 (s, 1H), 3.44-3.30 (m, 2H), 3.05-2.95 (m, 2H), 1.96-1.69 (m, 4H). MS: 461 $(M + H)^+$. |
| 154 | 1'-(5-((2-amino-3-chloro pyridin-4-yl)thio)pyrazin-2-yl)-4,6-dihydrospiro [cyclopenta[d]thiazole-5,4'-piperidin]-4-amine | 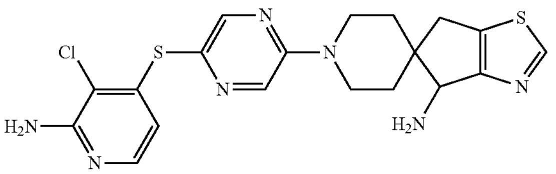 [SMILES: Nc1nccc(Sc2cnc(N3CCC4(CC3)Cc3scnc3C4N)cn2)c1Cl] | $^1$H NMR (400 MHz, MeOH-d4) δ 8.91 (s, 1H), 8.36 (d, 1H), 8.30 (d, 1H), 7.61 (d, 1H), 5.95 (d, 1H), 4.35-4.24 (m, 2H), 4.06 (s, 1H), 3.52-3.38 (m, 2H), 3.06 (s, 2H), 2.00-1.75 (m, 4H). MS: 446 $(M + H)^+$. |

Example 155

(S)-1'-(6-amino-5-((2-amino-3-chloropyridin-4-yl)thio)pyrazin-2-yl)-4,6-dihydrospiro[cyclo penta[d]thiazole-5,4'-piperidin]-6-amine

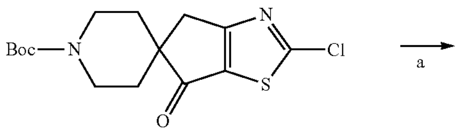

-continued

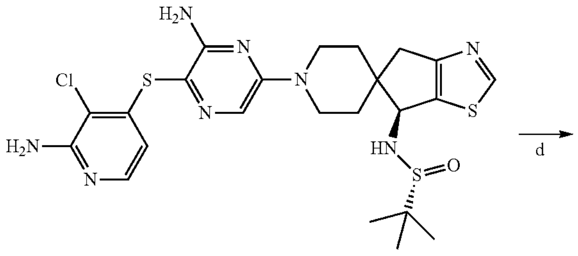

-continued

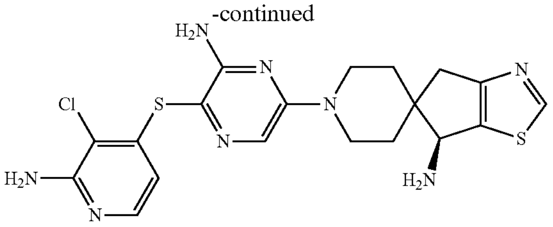

Step a: Step (a) of Example 5 was applied to provide tert-butyl (R,Z)-6-((tert-butylsulfinyl)imino)-2-chloro-4,6-dihydrospiro[cyclopenta[d]thiazole-5,4'-piperidine]-1'-carboxylate. MS: m/z 446 $(M+H)^+$.

Step b: To a −50° C. solution of tert-butyl (R,Z)-6-((tert-butylsulfinyl)imino)-2-chloro-4,6-dihydrospiro[cyclopenta[d]thiazole-5,4'-piperidine]-1'-carboxylate (4.25 g, 9.53 mmol) in THF (30 mL) was added $BH_3$ (1 M solution in THF, 30.00 mL, 30.00 mmol). The resulting mixture was allowed to warm to RT and stirred for 18 h. The reaction mixture was quenched with brine (50 mL). The organic layer was separated, dried over anhydrous $Na_2SO_4$, filtered and concentrated under reduced pressure. The residue was purified by silica chromatography eluting with (EA:Hex=1:2, v/v) to give tert-butyl (S)-6-(((R)-tert-butylsulfinyl)amino)-4,6-dihydrospiro [cyclopenta[d]thiazole-5,4'-piperidine]-1'-carboxylate (1.12 g). MS: m/z 414 $(M+H)^+$.

Step (c-d): Step (c-d) of Example 5 was applied to provide (S)-1'-(6-amino-5-((2-amino-3-chloropyridin-4-yl)thio)pyrazin-2-yl)-4,6-dihydrospiro[cyclopenta[d]thiazole-5,4'-piperidin]-6-amine. $^1H$ NMR (400 MHz, DMSO-d6) δ 9.01 (s, 1H), 7.66-7.63 (m, 2H) 5.76 (d, 1H), 4.23-4.19 (m, 2H), 4.09 (s, 1H), 3.32-3.15 (m, 2H), 2.93-2.80 (m, 2H), 1.87-1.60 (m, 4H). MS: m/z 461 $(M+H)^+$.

The following example was synthesized using the above procedure or modification procedure with the corresponding starting materials.

-continued

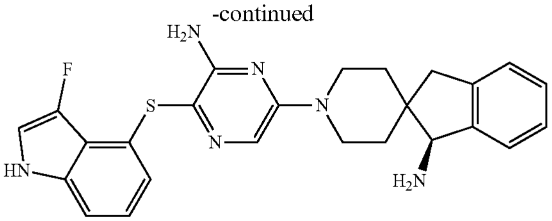

A mixture of (S)-1-(4-((3-amino-5-(1-amino-1,3-dihydrospiro[indene-2,4'-piperidin]-1'-yl)pyrazin-2-yl)thio)-3,3-difluoroindolin-1-yl)ethan-1-one (86 mg, 0.14 mmol), DCM (5 mL) and HCl (4 M solution in 1,4-dioxane, 0.50 mL) was stirred for 0.5 h at RT. The mixture was concentrated under reduced pressure. The residue was dissolved in MeOH (8 mL) and NaOH (17 mg, 0.43 mmol) was added. The resulting mixture was stirred for another 21 h at 65° C. After cooling to RT, the reaction mixture was concentrated under reduced pressure. The residue was diluted with water (10 mL) and EA (20 mL). The separated organic layer was washed with brine (10 mL), dried over anhydrous $Na_2SO_4$, filtered and concentrated under pressure. EA (5 mL) and Hex (3 mL) was added and the resulting precipitate was collected by filtration and dried under reduced pressure to give (S)-1'-(6-amino-5-((3-fluoro-1H-indol-4-yl)thio)pyrazin-2-yl)-1,3-dihydrospiro[indene-2,4'-piperidin]-1-amine (14 mg). $^1H$ NMR (400 MHz, DMSO-d6) δ 7.59 (s, 1H), 7.37-7.21 (m, 5H), 7.13 (d, 1H), 7.00-6.93 (m, 1H), 6.40 (d, 1H), 4.18 (d, 2H), 3.97 (s, 1H), 3.09 (m, 3H), 2.72 (m, 1H), 1.77-1.62 (m, 2H), 1.50-1.47 (m, 1H), 1.20-1.16 (m, 1H) MS: 461 $(M+H)^+$.

TABLE 24

| EX No. | Chemical Name | Structure | MS: $(M + H)^+$ & $^1$HNMR |
|---|---|---|---|
| 156 | (S)-1'-(5-((2-amino-3-chloropyridin-4-yl)thio)pyrazin-2-yl)-4,6-dihydrospiro[cyclopenta[d]thiazole-5,4'-piperidin]-6-amine | 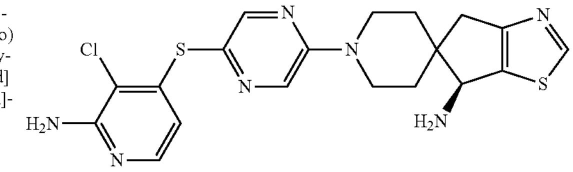 | $^1H$ NMR (400 MHz, MeOH-d4) δ 9.07 (s, 1H), 8.37 (d, 1H), 8.30 (d, 1H), 7.60 (d, 1H), 5.95 (d, 1H), 4.48 (d, 1H), 4.38-4.34 (m, 2H), 3.45-3.27(m, 2H), 3.13-3.02 (m, 2H), 2.00-1.76 (m, 4H). MS: $446(M + H)^+$. |

Example 157

(S)-1'-(6-amino-5-((3-fluoro-1H-indol-4-yl)thio)pyrazin-2-yl)-1,3-dihydrospiro[indene-2,4'-piperidin]-1-amine

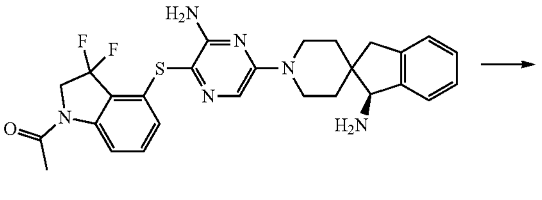

Example 158

(S)-1-(1-amino-1'-(6-amino-5-((2-amino-3-chloropyridin-4-yl)thio)pyrazin-2-yl)-1,3-dihydrospiro[indene-2,4'-piperidin]-6-yl)ethan-1-one

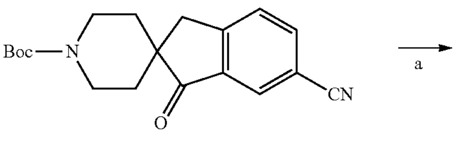

-continued

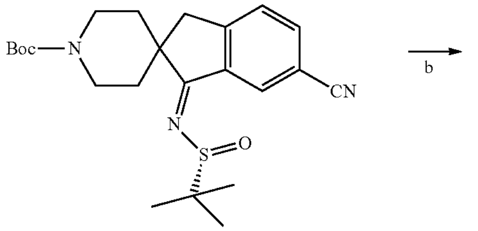

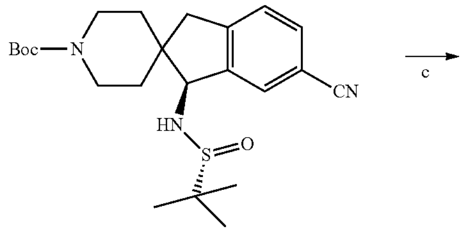

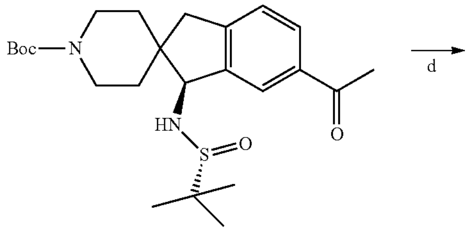

-continued

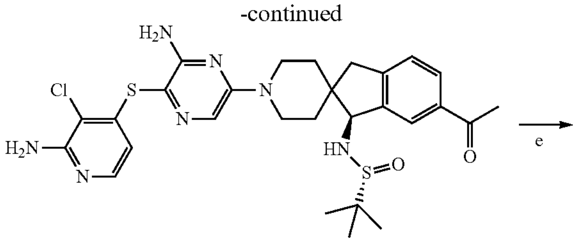

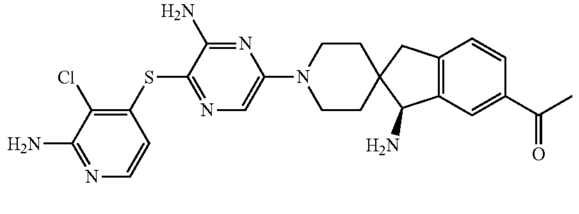

Step a-b: Step (a-b) of Example 5 was applied to provide tert-butyl (1S)-1-((tert-butylsulfinyl)amino)-6-cyano-1,3-dihydrospiro[indene-2,4'-piperidine]-1'-carboxylate. MS: m/z 432 $(M+H)^+$.

Step c: To a −50° C. solution of tert-butyl (1S)-1-((tert-butylsulfinyl)amino)-6-cyano-1,3-dihydrospiro[indene-2,4'-piperidine]-1'-carboxylate (430 mg, 1.00 mmol) in THF (10 mL) was added methylmagnesium bromide (3 M solution in THF/Hex, 0.50 mL, 1.50 mmol) dropwise. The resulting mixture was allowed to warmed to RT and stirred for 24 h. The reaction mixture was quenched with brine (10 mL). The organic layer was separated, dried over anhydrous $Na_2SO_4$, filtered and concentrated under reduced pressure to give tert-butyl (1S)-6-acetyl-1-((tert-butylsulfinyl)amino)-1,3-dihydrospiro[indene-2,4'-piperidine]-1'-carboxylate (0.72 g) which was used in next step without any further purification. MS: m/z 449 $(M+H)^+$.

Step d-e: Step (c-d) of Example 5 was applied to provide (S)-1-(1-amino-1'-(6-amino-5-((2-amino-3-chloropyridin-4-yl)thio)pyrazin-2-yl)-1,3-dihydrospiro[indene-2,4'-piperidin]-6-yl)ethan-1-one. MS: 496 $(M+H)^+$.

The following example was synthesized using the above procedure or modification procedure with the corresponding starting materials.

TABLE 25

| EX No. | Chemical Name | Structure | MS: $(M + H)^+$ & $^1$HNMR |
|---|---|---|---|
| 159 | (S)-1-(1-amino-1'-(6-amino-5-((2-amino-3-chloropyridin-4-yl)thio)pyrazin-2-yl)-1,3-dihydrospiro[indene-2,4'-piperidin]-4-yl)ethan-1-one | 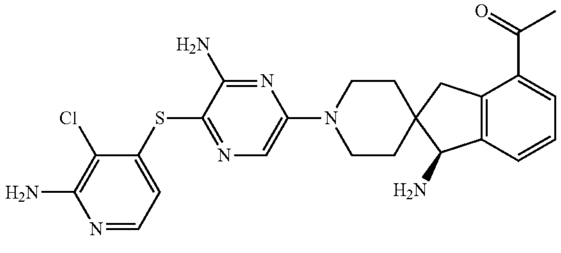 [SMILES: CC(=O)c1cccc2c1CC1(CCN(c3cnc(Sc4ccnc(N)c4Cl)c(N)n3)CC1)[C@@H]2N] | $^1$H NMR (400 MHz, DMSO-d6) δ 7.99 (d, 1H), 7.73 (d, 1H), 7.67 (s, 1H), 7.64 (d, 1H), 7.50 (t, 1H), 5.75 (d, 1H), 4.40 (s, 1H), 4.24 (d, 1H), 4.16 (d, 1H), 3.41-3.17 (m, 4H), 2.60 (s, 3H), 1.74-1.66 (m, 2H), 1.53-1.45 (m, 2H). MS: 496$(M + H)^+$. |

The following examples can be synthesized using the above methods and appropriate starting materials:

TABLE 26

| EX No. | Chemical Name | Structure | MS(M + H)+ |
|---|---|---|---|
| 160 | (R)-1'-(5-((2-amino-3-chloropyridin-4-yl)thio)pyrazin-2-yl)-1-methyl spiro[indoline-2,4'-piperidin]-3-amine | 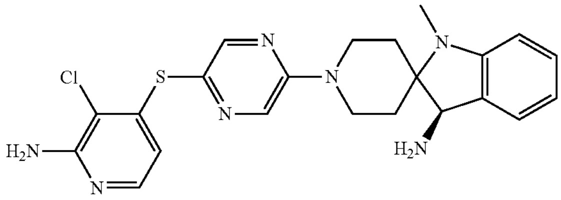 [SMILES: CN1c2ccccc2[C@@H](N)C12CCN(c1cnc(Sc3ccnc(N)c3Cl)cn1)CC2] | 454 |
| 161 | 1'-(6-amino-5-((2-amino-3-chloro-pyridin-4-yl)thio)pyrazin-2-yl)-2,3-dihydrospiro[indene-1,4'-piperidin]-2-amine | 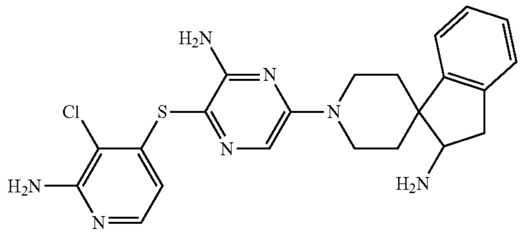 [SMILES: Nc1nc(N2CCC3(CC2)c2ccccc2CC3N)cnc1Sc1ccnc(N)c1Cl] | 454 |
| 162 | 1'-(6-amino-5-((2-amino-3-chloro-pyridin-4-yl)thio)pyrazin-2-yl)-3,4-dihydro-2H-spiro[naphthalene-1,4'-piperidin]-2-amine | 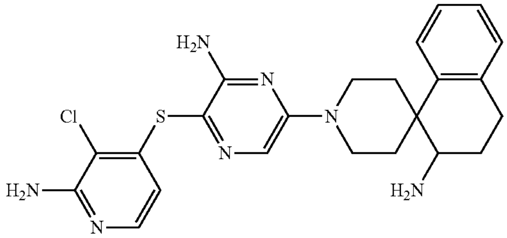 [SMILES: Nc1nc(N2CCC3(CC2)c2ccccc2CCC3N)cnc1Sc1ccnc(N)c1Cl] | 468 |
| 163 | 1'-(6-amino-5-((2-amino-3-chloro-pyridin-4-yl)thio)pyrazin-2-yl)-5,6-dihydrospiro[cyclopenta[b]pyridine-7,4'-piperidin]-6-amine | 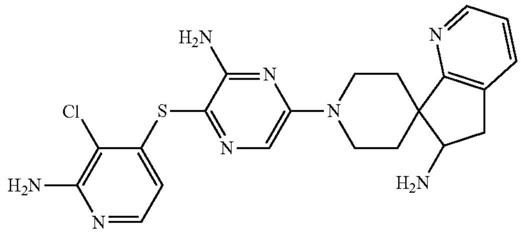 [SMILES: Nc1nc(N2CCC3(CC2)c2ncccc2CC3N)cnc1Sc1ccnc(N)c1Cl] | 455 |
| 164 | 1-(6-amino-5-((2-amino-3-chloro-pyridin-4-yl)thio)pyrazin-2-yl)tetra-hydro-1'H,3'H-spiro[piperidine-4,2'-pyrrolizin]-1'-amine | 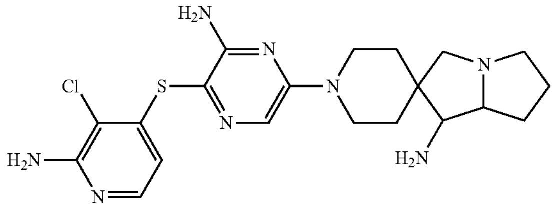 [SMILES: Nc1nc(N2CCC3(CC2)CN2CCCC2C3N)cnc1Sc1ccnc(N)c1Cl] | 447 |
| 165 | (1'S)-1-(6-amino-5-((2-amino-3-chloropyridin-4-yl)thio)pyrazin-2-yl) tetrahydro-1'H,3'H-spiro[piperidine-4,2'-pyrrolizin]-1'-amine | 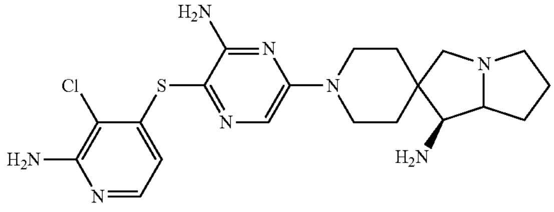 [SMILES: Nc1nc(N2CCC3(CC2)CN2CCCC2[C@H]3N)cnc1Sc1ccnc(N)c1Cl] | 447 |

TABLE 26-continued

| EX No. | Chemical Name | Structure | MS(M + H)+ |
|---|---|---|---|
| 166 | 1'-(6-amino-5-((2-amino-3-chloro-pyridin-4-yl)thio)pyrazin-2-yl)-4,6-dihydrospiro[cyclopenta[b]furan-5,4'-pipcridin]-4-amine | 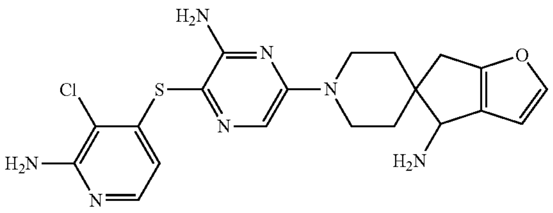 | 444 |
| 167 | (S)-1'-(6-amino-5-((2-amino-3-chloropyridin-4-yl)thio)pyrazin-2-yl)-4,6-dihydrospiro[cyclopenta[b]furan-5,4'-piperidin]-4-amine | 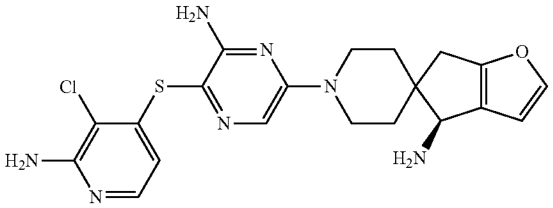 [SMILES: Nc1nc(N2CCC3(CC2)Cc2occc2[C@H]3N)cnc1Sc1ccnc(N)c1Cl] | 444 |
| 168 | 1'-(6-amino-5-((2-amino-3-chloro-pyridin-4-yl)thio)pyrazin-2-yl)-6,7-dihydrospiro[cyclopenta[b]pyridine-5,4'-piperidin]-6-amine | 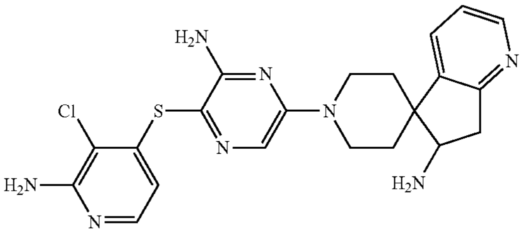 [SMILES: Nc1nc(N2CCC3(CC2)c2cccnc2CC3N)cnc1Sc1ccnc(N)c1Cl] | 455 |
| 169 | 1'-(6-amino-5-((2-amino-3-chloro-pyridin-4-yl)thio)pyrazin-2-yl)hexahydrospiro[cyclopenta[b]furan-5,4'-piperidin]-4-amine | 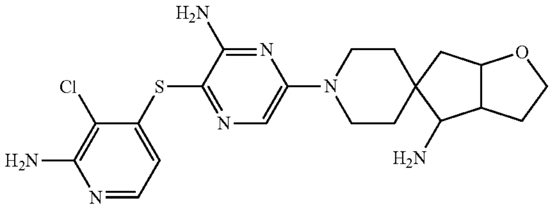 [SMILES: Nc1nc(N2CCC3(CC2)CC2OCCC2C3N)cnc1Sc1ccnc(N)c1Cl] | 448 |
| 170 | (4R)-1'-(6-amino-5-((2-amino-3-chloropyridin-4-yl)thio)pyrazin-2-yl)hexahydrospiro[cyclopenta[b]furan-5,4'-piperidin]-4-amine | 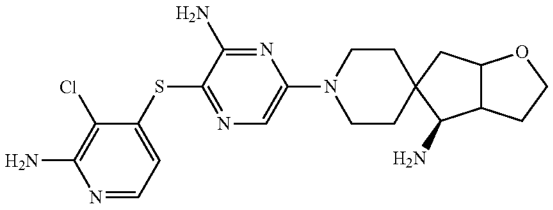 | 448 |
| 171 | 1'-(6-amino-5-((2-amino-3-chloro-pyridin-4-yl)thio)pyrazin-2-yl)spiro[bicyclo[3.1.0]hexane-3,4'-piperidin]-2-amine | 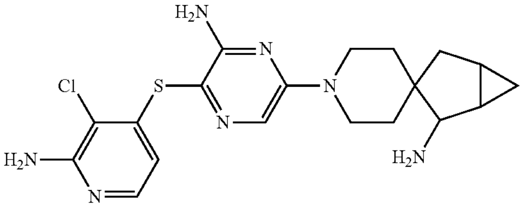 [SMILES: Nc1nc(N2CCC3(CC2)CC2CC2C3N)cnc1Sc1ccnc(N)c1Cl] | 418 |
| 172 | 1'-amino-1-(6-amino-5-((2-amino-3-chloropyridin-4-yl)thio)pyrazin-2-yl)tetrahydro-1'H,3'H-spiro[piperidine-4,2'-pyrrolizin]-3'-one | 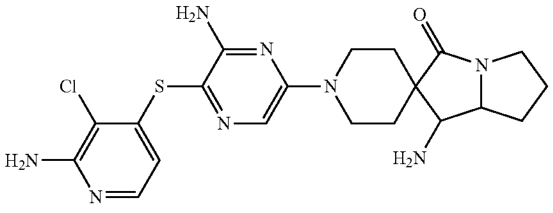 [SMILES: Nc1nc(N2CCC3(CC2)C(=O)N2CCCC2C3N)cnc1Sc1ccnc(N)c1Cl] | 461 |

TABLE 26-continued

| EX No. | Chemical Name | Structure | MS(M + H)+ |
| --- | --- | --- | --- |
| 173 | (1'S)-1'-amino-1-(6-amino-5-((2-amino-3-chloropyridin-4-yl)thio) pyrazin-2-yl)tetrahydro-1'H,3'H-spiro [piperidine-4,2'-pyrrolizin]-3'-one | 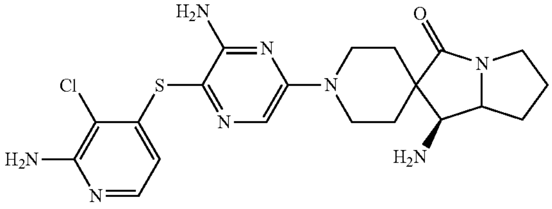 [SMILES: Nc1nc(N2CCC3(CC2)C(=O)N2CCCC2[C@H]3N)cnc1Sc1ccnc(N)c1Cl] | 461 |
| 174 | 1'-(6-amino-5-((2-amino-3-chloro-pyridin-4-yl)thio)pyrazin-2-yl)spiro [bicyclo[3.1.0]hexane-2,4'-piperidin]-3-amine | 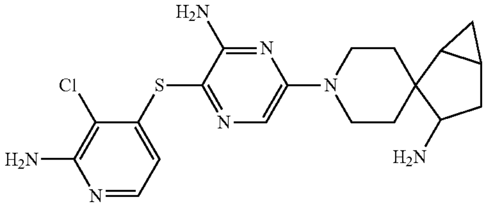 [SMILES: Nc1nc(N2CCC3(CC2)C(N)CC2CC23)cnc1Sc1ccnc(N)c1Cl] | 418 |
| 175 | (3R)-1'-(6-amino-5-((2-amino-3-chloropyridin-4-yl)thio)pyrazin-2-yl) spiro[bicyclo[3.1.0]hexane-2,4'-piperidin]-3-amine | 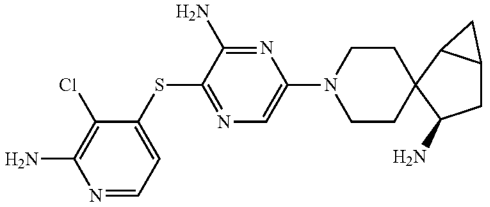 [SMILES: Nc1nc(N2CCC3(CC2)C2CC2C[C@H]3N)cnc1Sc1ccnc(N)c1Cl] | 418 |
| 176 | 3-((2-amino-3-chloropyridin-4-yl) thio)-6-(11-oxa-1,7-diazadispiro[2.0.$5^4$.$3^3$]dodecan-7-yl)pyrazin-2-amine | 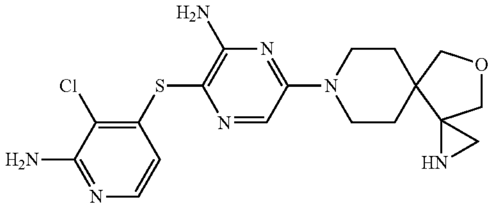 [SMILES: Nc1nc(N2CCC3(CC2)COCC32CN2)cnc1Sc1ccnc(N)c1Cl] | 420 |
| 177 | 1-(4-((3-amino-5-(2-aminospiro [bicyclo[3.1.0]hexane-3,4'-piperidin]-1-yl)pyrazin-2-yl)thio)-3,3-difluoro-indolin-1-yl)ethan-1-one | 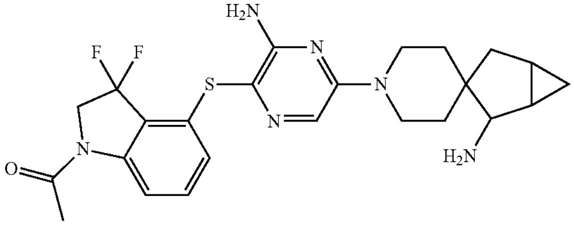 [SMILES: CC(=O)N1CC(F)(F)c2c(Sc3ncc(N4CCC5(CC4)CC4CC4C5N)nc3N)cccc21] | 487 |
| 178 | 1'-(6-amino-5-((2-amino-3-chloro-pyridin-4-yl)thio)pyrazin-2-yl)-1-methylspiro[bicyclo[3.1.0]hexane-3,4'-piperidin]-4-amine | 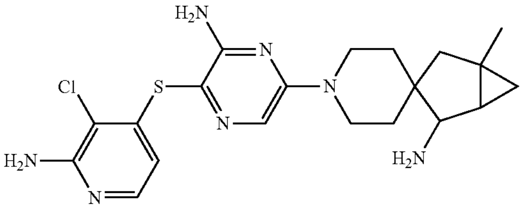 | 432 |
| 179 | (4R)-1'-(6-amino-5-((2-amino-3-chloropyridin-4-yl)thio)pyrazin-2-yl)-1-methylspiro[bicyclo[3.1.0] hexane-3,4'-piperidin]-4-amine | 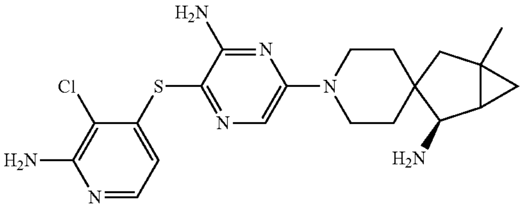 [SMILES: CC12CC1[C@@H](N)C1(CCN(c3cnc(Sc4ccnc(N)c4Cl)c(N)n3)CC1)C2] | 432 |

TABLE 26-continued

| EX No. | Chemical Name | Structure | MS(M + H)+ |
|---|---|---|---|
| 180 | 1'-(6-amino-5-((2-amino-3-chloro-pyridin-4-yl)thio)pyrazin-2-yl)spiro[bicyclo[3.2.0]heptane-3,4'-piperidin]-2-amine | 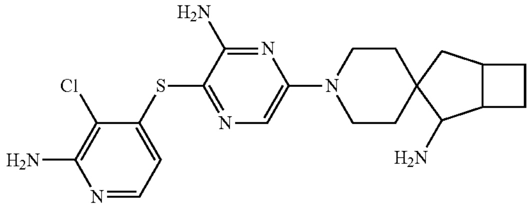 [SMILES: Nc1nc(N2CCC3(CC2)CC2CCC2C3N)cnc1Sc1ccnc(N)c1Cl] | 432 |
| 181 | (2R)-1'-(6-amino-5-((2-amino-3-chloropyridin-4-yl)thio)pyrazin-2-yl)spiro[bicyclo[3.2.0]heptane-3,4'-piperidin]-2-amine | 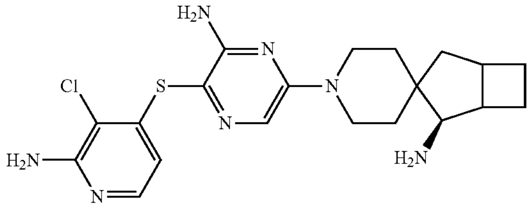 [SMILES: Nc1nc(N2CCC3(CC2)CC2CCC2[C@H]3N)cnc1Sc1ccnc(N)c1Cl] | 432 |
| 182 | 1'-(6-amino-5-((2-amino-3-chloro-pyridin-4-yl)thio)pyrazin-2-yl)hexa-hydro-1H-spiro[pentalene-2,4'-piperidin]-1-amine | 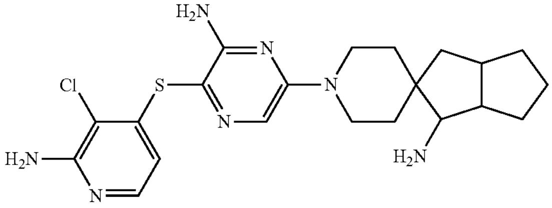 [SMILES: Nc1nc(N2CCC3(CC2)CC2CCCC2C3N)cnc1Sc1ccnc(N)c1Cl] | 446 |
| 183 | (1R)-1'-(6-amino-5-((2-amino-3-chloropyridin-4-yl)thio)pyrazin-2-yl)hexahydro-1H-spiro[pentalene-2,4'-piperidin]-1-amine | 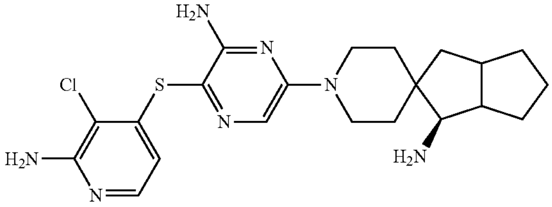 | 446 |
| 184 | 1-(4-((3-amino-5-(2-amino-2,3-dihydrospiro[indene-1,4'-piperidin]-1'-yl)pyrazin-2-yl)thio)-3,3-difluoro-indolin-1-yl)ethan-1-one | 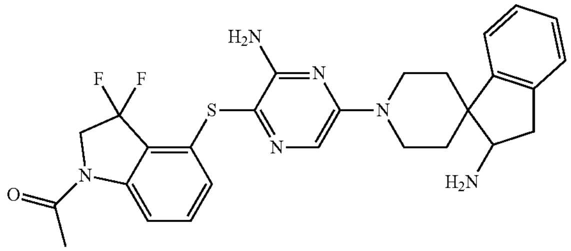 [SMILES: CC(=O)N1CC(F)(F)c2c(Sc3ncc(N4CCC5(CC4)c4ccccc4CC5N)nc3N)cccc21] | 523 |
| 185 | 1'-(6-amino-5-((2-amino-3-chloro-pyridin-4-yl)thio)pyrazin-2-yl)-4-methoxy-2,3-dihydrospiro[indene-1,4'-piperidin]-2-amine | 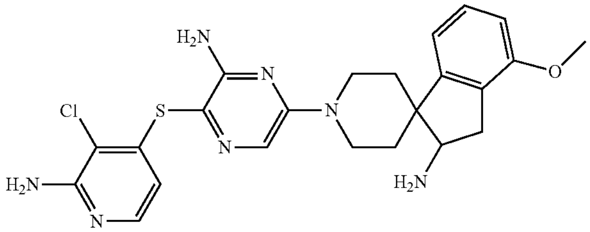 [SMILES: COc1cccc2c1CC(N)C21CCN(c2cnc(Sc3ccnc(N)c3Cl)c(N)n2)CC1] | 484 |

TABLE 26-continued

| EX No. | Chemical Name | Structure | MS(M + H)+ |
|---|---|---|---|
| 186 | (R)-1'-(6-amino-5-((2-amino-3-chloropyridin-4-yl)thio)pyrazin-2-yl)-4-methoxy-2,3-dihydrospiro[indene-1,4'-piperidin]-2-amine | 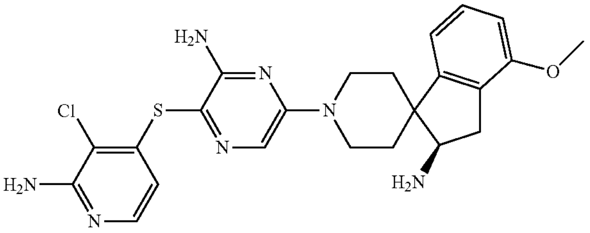 [SMILES: COc1cccc2c1C[C@@H](N)C21CCN(c2cnc(Sc3ccnc(N)c3Cl)c(N)n2)CC1] | 484 |
| 187 | 1'-(6-amino-5-((2-amino-3-chloro-pyridin-4-yl)thio)pyrazin-2-yl)-4,5-dihydrospiro[cyclopenta[b]furan-6,4'-piperidin]-5-amine | 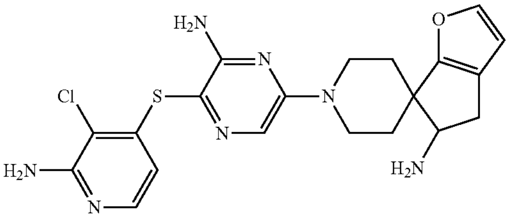 [SMILES: Nc1nc(N2CCC3(CC2)c2occc2CC3N)cnc1Sc1ccnc(N)c1Cl] | 444 |
| 188 | (R)-1'-(6-amino-5-((2-amino-3-chloropyridin-4-yl)thio)pyrazin-2-yl)-4,5-dihydrospiro[cyclopenta[b]furan-6,4'-piperidin]-5-amine | 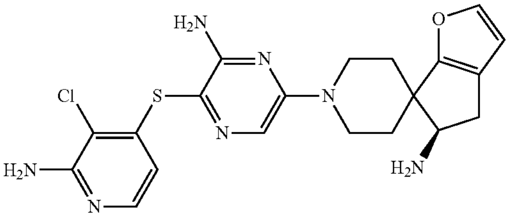 [SMILES: Nc1nc(N2CCC3(CC2)c2occc2C[C@H]3N)cnc1Sc1ccnc(N)c1Cl] | 444 |
| 189 | 1-(4-((3-amino-5-(11-oxa-1,7-diazadispiro[2.0.5$^4$.3$^3$]dodecan-7-yl)pyrazin-2-yl)thio)-3,3-difluoroindolin-1-yl)ethan-1-one | 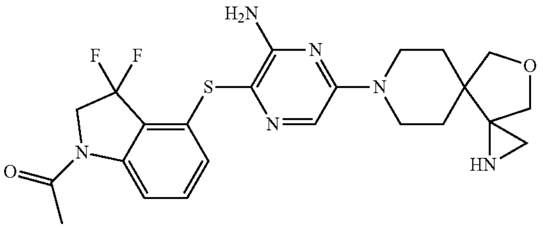 [SMILES: CC(=O)N1CC(F)(F)c2c(Sc3ncc(N4CCC5(CC4)COCC54CN4)nc3N)cccc21] | 489 |
| 190 | 1'-(6-amino-5-((2-amino-3-chloro-pyridin-4-yl)thio)pyrazin-2-yl)hexahydrospiro[cyclopenta[b][1,4]dioxine-6,4'-piperidin]-5-amine | 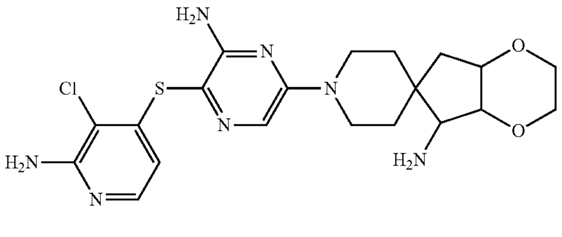 [SMILES: Nc1nc(N2CCC3(CC2)CC2OCCOC2C3N)cnc1Sc1ccnc(N)c1Cl] | 464 |
| 191 | (5S)-1'-(6-amino-5-((2-amino-3-chloropyridin-4-yl)thio)pyrazin-2-yl)hexahydrospiro[cyclopenta[b][1,4]dioxine-6,4'-piperidin]-5-amine | 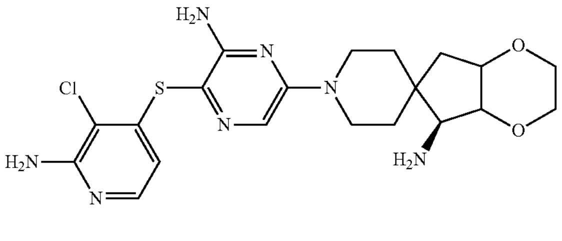 [SMILES: Nc1nc(N2CCC3(CC2)CC2OCCOC2[C@H]3N)cnc1Sc1ccnc(N)c1Cl] | 464 |

TABLE 26-continued

| EX No. | Chemical Name | Structure | MS(M + H)+ |
|---|---|---|---|
| 192 | 6-amino-1'-(6-amino-5-((2-amino-3-chloropyridin-4-yl)thio)pyrazin-2-yl)-6,7-dihydrospiro[cyclopenta[b]pyridine-5,4'-piperidin]-2(1H)-one | 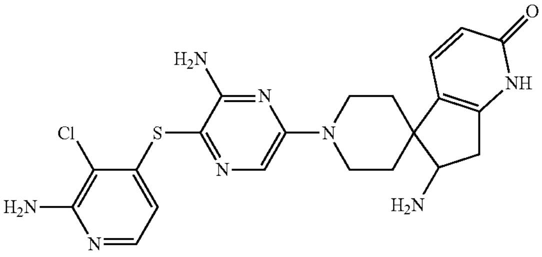 [SMILES: Nc1nc(N2CCC3(CC2)c2ccc(=O)[nH]c2CC3N)cnc1Sc1ccnc(N)c1Cl] | 471 |
| 193 | (R)-6-amino-1'-(6-amino-5-((2-amino-3-chloropyridin-4-yl)thio)pyrazin-2-yl)-6,7-dihydrospiro[cyclopenta[b]pyridine-5,4'-piperidin]-2(1H)-one | 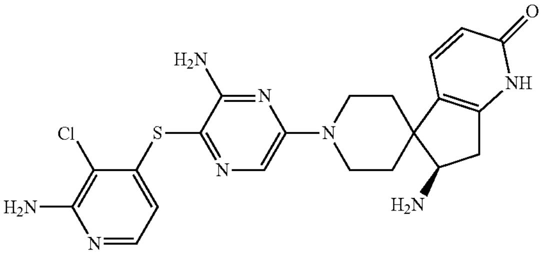 [SMILES: Nc1nc(N2CCC3(CC2)c2ccc(=O)[nH]c2C[C@H]3N)cnc1Sc1ccnc(N)c1Cl] | 471 |
| 194 | 2-amino-1'-(6-amino-5-((2-amino-3-chloropyridin-4-yl)thio)pyrazin-2-yl)-2,3-dihydro-5H-spiro[indolizine-1,4'-piperidin]-5-one | 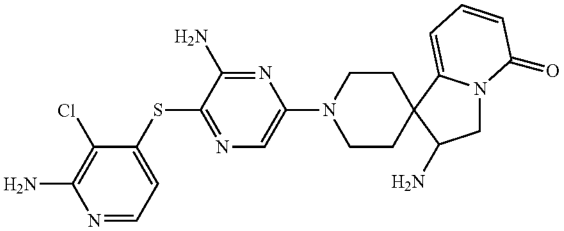 [SMILES: Nc1nc(N2CCC3(CC2)c2cccc(=O)n2CC3N)cnc1Sc1ccnc(N)c1Cl] | 471 |
| 195 | (S)-2-amino-1'-(6-amino-5-((2-amino-3-chloropyridin-4-yl)thio)pyrazin-2-yl)-2,3-dihydro-5H-spiro[indolizine-1,4'-piperidin]-5-one | 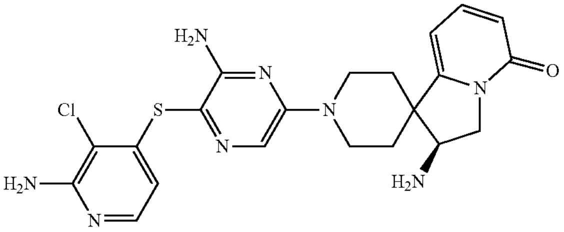 [SMILES: Nc1nc(N2CCC3(CC2)c2cccc(=O)n2C[C@H]3N)cnc1Sc1ccnc(N)c1Cl] | 471 |
| 196 | 1'-(6-amino-5-((2-amino-3-chloropyridin-4-yl)thio)pyrazin-2-yl)spiro[chromane-4,4'-piperidin]-3-amine | 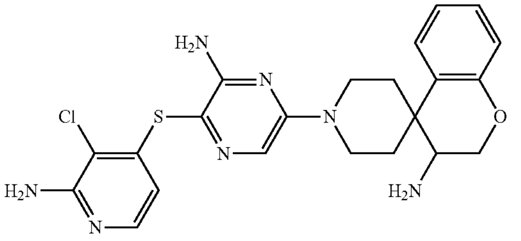 [SMILES: Nc1nc(N2CCC3(CC2)c2ccccc2OCC3N)cnc1Sc1ccnc(N)c1Cl] | 470 |
| 197 | (S)-1'-(6-amino-5-((2-amino-3-chloropyridin-4-yl)thio)pyrazin-2-yl)spiro[chromane-4,4'-piperidin]-3-amine | 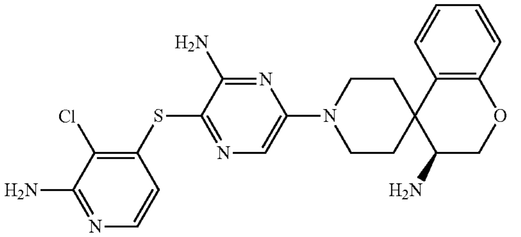 [SMILES: Nc1nc(N2CCC3(CC2)c2ccccc2OC[C@H]3N)cnc1Sc1ccnc(N)c1Cl] | 470 |

TABLE 26-continued

| EX No. | Chemical Name | Structure | MS(M + H)+ |
|---|---|---|---|
| 198 | 1'-(6-amino-5-((2-amino-3-chloro-pyridin-4-yl)thio)pyrazin-2-yl)-6-methoxy-1,3-dihydrospiro[indene-2,4'-piperidin]-1-amine | 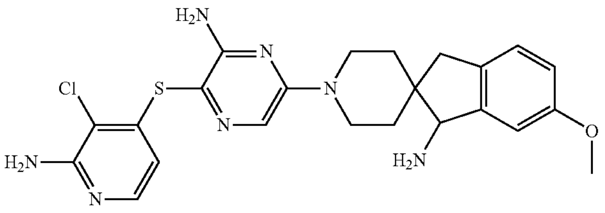 [SMILES: COc1ccc2c(c1)C(N)C1(CCN(c3cnc(Sc4ccnc(N)c4Cl)c(N)n3)CC1)C2] | 484 |
| 199 | 1'-(6-amino-5-((2-amino-3-chloro-pyridin-4-yl)thio)pyrazin-2-yl)-3,4-dihydro-1H-spiro[naphthalene-2,4'-piperidin]-1-amine | 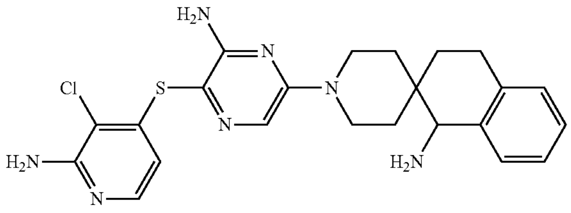 [SMILES: Nc1nc(N2CCC3(CCc4ccccc4C3N)CC2)cnc1Sc1ccnc(N)c1Cl] | 468 |
| 200 | 1-(6-amino-5-((2-amino-3-chloro-pyridin-4-yl)thio)pyrazin-2-yl)-7',8'-dihydro-5'H-spiro[piperidine-4,6'-quinolin]-7'-amine | 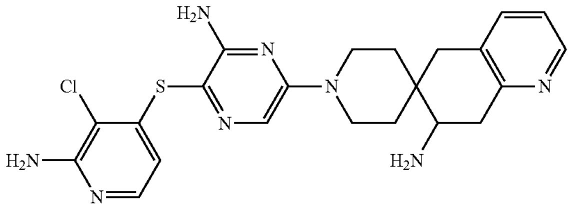 [SMILES: Nc1nc(N2CCC3(CC2)Cc2cccnc2CC3N)cnc1Sc1ccnc(N)c1Cl] | 469 |
| 201 | 1'-(6-amino-5-((2-amino-3-chloro-pyridin-4-yl)thio)pyrazin-2-yl)-6,7-dihydrospiro[cyclopenta[c]pyridine-5,4'-piperidin]-6-amine | 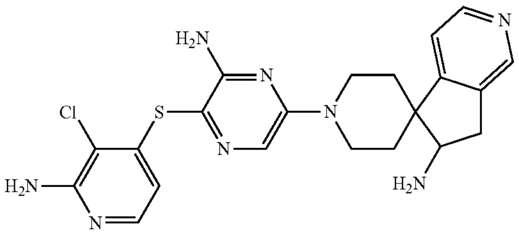 [SMILES: Nc1nc(N2CCC3(CC2)c2ccncc2CC3N)cnc1Sc1ccnc(N)c1Cl] | 455 |
| 202 | (R)-1'-(6-amino-5-((2-amino-3-chloropyridin-4-yl)thio)pyrazin-2-yl)-6,7-dihydrospiro[cyclopenta[c]pyridine-5,4'-piperidin]-6-amine | 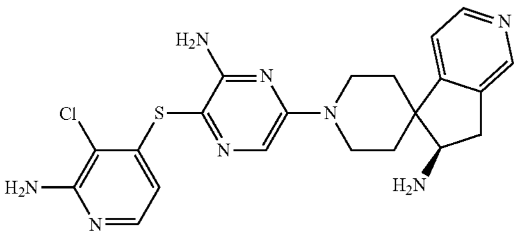 [SMILES: Nc1nc(N2CCC3(CC2)c2ccncc2C[C@H]3N)cnc1Sc1ccnc(N)c1Cl] | 455 |
| 203 | 1'-(6-amino-5-((2-amino-3-chloro-pyridin-4-yl)thio)pyrazin-2-yl)-6-methoxy-3,4-dihydro-1H-spiro[naphthalene-2,4'-piperidin]-1-amine | 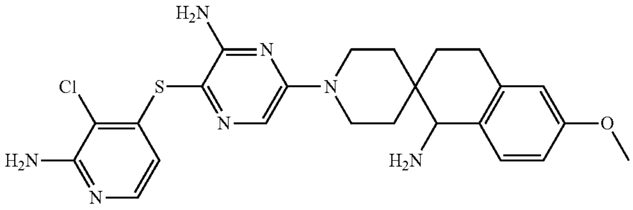 [SMILES: COc1ccc2c(c1)CCC1(CCN(c3cnc(Sc4ccnc(N)c4Cl)c(N)n3)CC1)C2N] | 498 |
| 204 | (S)-1'-(6-amino-5-((2-amino-3-chloropyridin-4-yl)thio)pyrazin-2-yl)-6-methoxy-3,4-dihydro-1H-spiro[naphthalene-2,4'-piperidin]-1-amine | 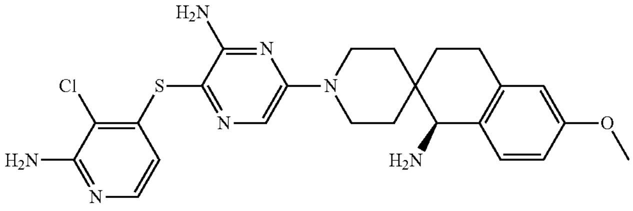 [SMILES: COc1ccc2c(c1)CCC1(CCN(c3cnc(Sc4ccnc(N)c4Cl)c(N)n3)CC1)[C@@H]2N] | 498 |

TABLE 26-continued

| EX No. | Chemical Name | Structure | MS(M + H)+ |
|---|---|---|---|
| 205 | 1'-(6-amino-5-((2-amino-3-chloro-pyridin-4-yl)thio)pyrazin-2-yl)-5,6-dimethoxy-1,3-dihydrospiro[indene-2,4'-piperidin]-1-amine | 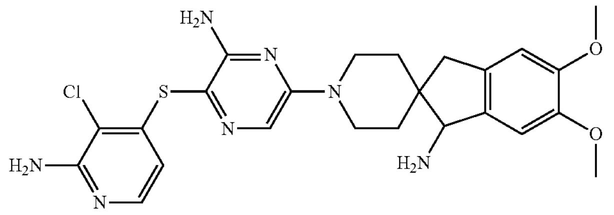 [SMILES: COc1cc2c(cc1OC)C(N)C1(CCN(c3cnc(Sc4ccnc(N)c4Cl)c(N)n3)CC1)C2] | 514 |
| 206 | (S)-1'-(6-amino-5-((2-amino-3-chloropyridin-4-yl)thio)pyrazin-2-yl)-5,6-dimethoxy-1,3-dihydrospiro[indene-2,4'-piperidin]-1-amine | 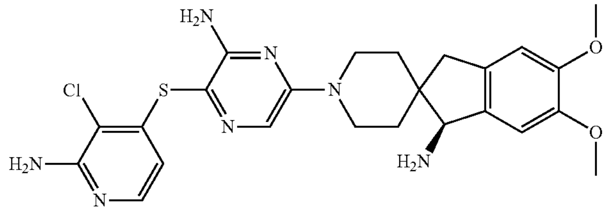 [SMILES: COc1cc2c(cc1OC)[C@@H](N)C1(CCN(c3cnc(Sc4ccnc(N)c4Cl)c(N)n3)CC1)C2] | 514 |
| 207 | 1-amino-1'-(6-amino-5-((2-amino-3-chloropyridin-4-yl)thio)pyrazin-2-yl)-1,3-dihydrospiro[indene-2,4'-piperidin]-6-ol | 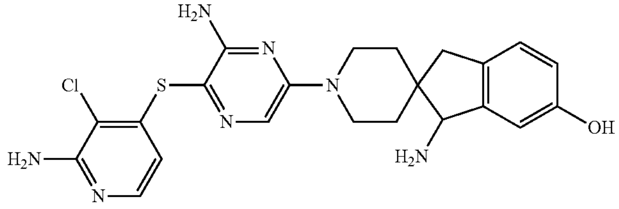 [SMILES: N#Cc1ccc2c(c1)C(N)C1(CCN(c3cnc(Sc4ccnc(N)c4Cl)c(N)n3)CC1)C2] | 470 |
| 208 | 1'-(6-amino-5-((2-amino-3-chloro-pyridin-4-yl)thio)pyrazin-2-yl)-5-methoxy-1,3-dihydrospiro[indene-2,4'-piperidin]-1-amine | 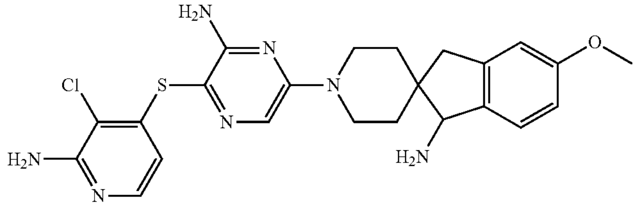 | 484 |
| 209 | 1'-(6-amino-5-((2-amino-3-chloro-pyridin-4-yl)thio)pyrazin-2-yl)-4,6-dihydrospiro[cyclopenta[b]thio-phene-5,4'-piperidin]-4-amine | 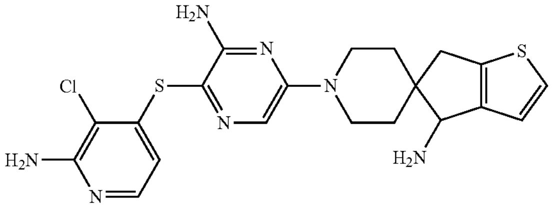 | 460 |
| 210 | 1-amino-1'-(6-amino-5-((2-amino-3-chloropyridin-4-yl)thio)pyrazin-2-yl)-1,3-dihydrospiro[indene-2,4'-piperidine]-6-carbonitrile | 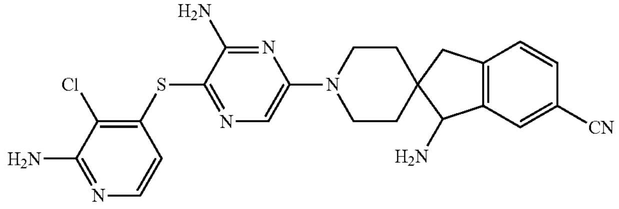 | 479 |
| 211 | 1'-(6-amino-5-((2-amino-3-chloro-pyridin-4-yl)thio)pyrazin-2-yl)-4-methoxy-1,3-dihydrospiro[indene-2,4'-piperidin]-1-amine | 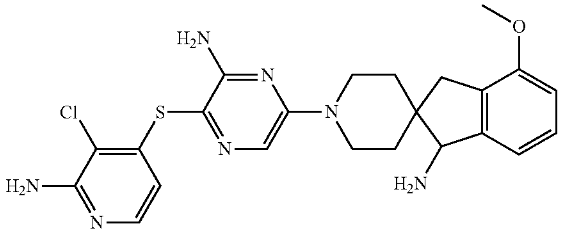 [SMILES: COc1cccc2c1CC1(CCN(c3cnc(Sc4ccnc(N)c4Cl)c(N)n3)CC1)C2N] | 484 |

TABLE 26-continued

| EX No. | Chemical Name | Structure | MS(M + H)+ |
| --- | --- | --- | --- |
| 212 | 1'-(6-amino-5-((2-amino-3-chloro-pyridin-4-yl)thio)pyrazin-2-yl)-1,3-dihydrospiro[indene-2,4'-piperidine]-1,6-diamine | 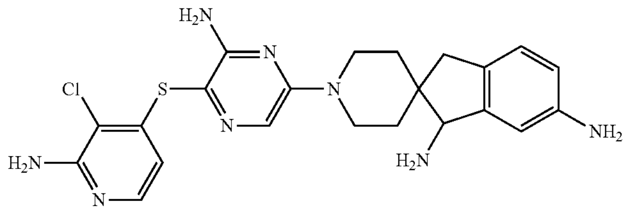 [SMILES: Nc1ccc2c(c1)C(N)C1(CCN(c3cnc(Sc4ccnc(N)c4Cl)c(N)n3)CC1)C2] | 469 |
| 213 | 1-amino-1'-(6-amino-5-((2-amino-3-chloropyridin-4-yl)thio)pyrazin-2-yl)-1,3-dihydrospiro[indene-2,4'-piperidin]-4-ol | 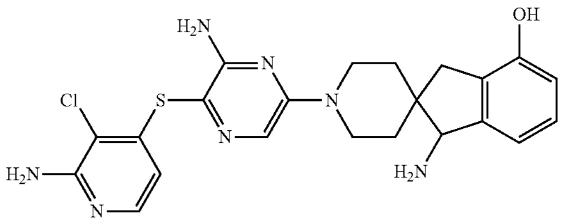 [SMILES: Nc1nc(N2CCC3(CC2)Cc2c(O)cccc2C3N)cnc1Sc1ccnc(N)c1Cl] | 470 |
| 214 | 1'-(6-amino-5-((2-amino-3-chloro-pyridin-4-yl)thio)pyrazin-2-yl)-6-chloro-1,3-dihydrospiro[indene-2,4'-piperidin]-1-amine | 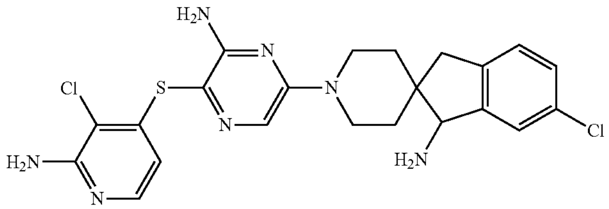 [SMILES: Nc1nc(N2CCC3(CC2)Cc2ccc(Cl)cc2C3N)cnc1Sc1ccnc(N)c1Cl] | 488 |
| 215 | 1'-(6-amino-5-((2-amino-3-chloro-pyridin-4-yl)thio)pyrazin-2-yl)-6-bromo-1,3-dihydrospiro[indene-2,4'-piperidin]-1-amine | 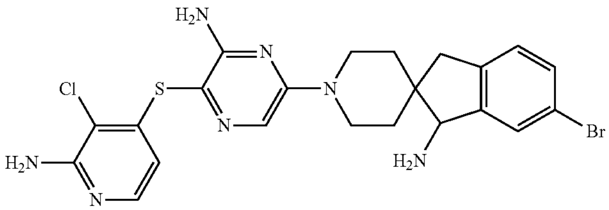 | 532 |
| 216 | 1'-(6-amino-5-((2-amino-3-chloro-pyridin-4-yl)thio)pyrazin-2-yl)-2,3-dihydrospiro[indene-1,4'-piperidine]-2,5-diamine | 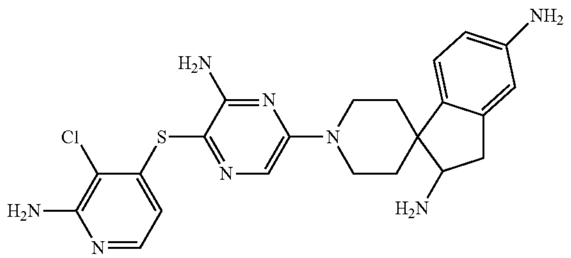 [SMILES: Nc1ccc2c(c1)CC(N)C21CCN(c2cnc(Sc3ccnc(N)c3Cl)c(N)n2)CC1] | 469 |
| 217 | (R)-1'-(6-amino-5-((2-amino-3-chloropyridin-4-yl)thio)pyrazin-2-yl)-2,3-dihydrospiro[indene-1,4'-piperidine]-2,5-diamine | 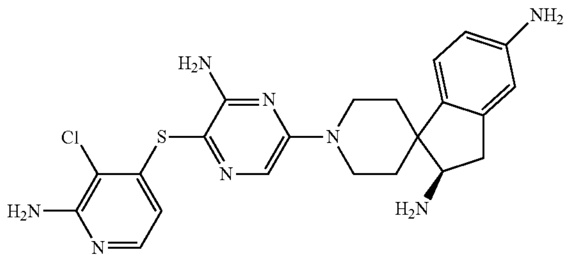 [SMILES: Nc1ccc2c(c1)C[C@@H](N)C21CCN(c2cnc(Sc3ccnc(N)c3Cl)c(N)n2)CC1] | 469 |

TABLE 26-continued

| EX No. | Chemical Name | Structure | MS(M + H)+ |
|---|---|---|---|
| 218 | 1'-(6-amino-5-((2-amino-3-chloro-pyridin-4-yl)thio)pyrazin-2-yl)-6-methoxy-2,3-dihydrospiro[indene-1,4'-piperidin]-2-amine | 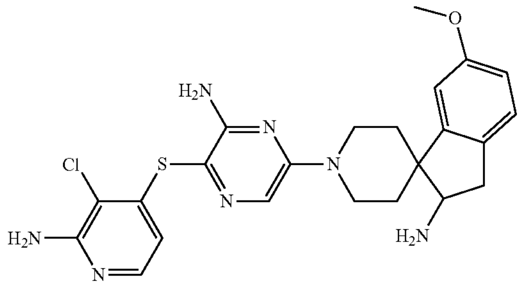 [SMILES: COc1ccc2c(c1)C1(CCN(c3cnc(Sc4ccnc(N)c4Cl)c(N)n3)CC1)C(N)C2] | 484 |
| 219 | (R)-1'-(6-amino-5-((2-amino-3-chloropyridin-4-yl)thio)pyrazin-2-yl)-6-methoxy-2,3-dihydrospiro[indene-1,4'-piperidin]-2-amine | 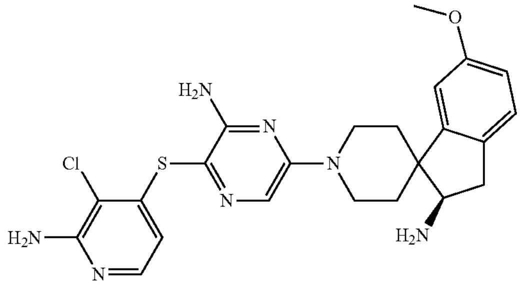 [SMILES: COc1ccc2c(c1)C1(CCN(c3cnc(Sc4ccnc(N)c4Cl)c(N)n3)CC1)[C@H](N)C2] | 484 |
| 220 | 1-(6-amino-5-((2-amino-3-chloro pyridin-4-yl)thio)pyrazin-2-yl)-1'H,3'H-spiro[piperidine-4,2'-pyrrolizin]-1'-amine | 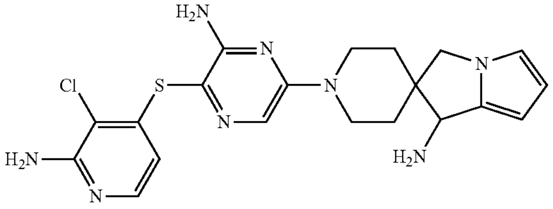 [SMILES: Nc1nc(N2CCC3(CC2)Cn2cccc2C3N)cnc1Sc1ccnc(N)c1Cl] | 443 |
| 221 | (S)-1-(6-amino-5-((2-amino-3-chloropyridin-4-yl)thio)pyrazin-2-yl)-1'H,3'H-spiro[piperidine-4,2'-pyrrolizin]-1'-amine | 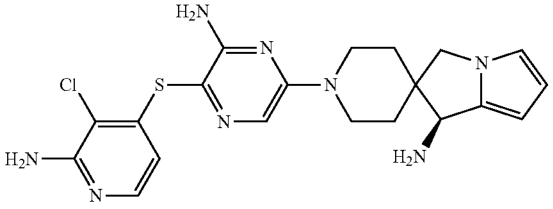 [SMILES: Nc1nc(N2CCC3(CC2)Cn2cccc2[C@H]3N)cnc1Sc1ccnc(N)c1Cl] | 443 |
| 222 | 1'-(6-amino-5-((2-amino-3-chloro-pyridin-4-yl)thio)pyrazin-2-yl)-5,7-dihydrospiro[cyclopenta[c]pyridine-6,4'-piperidin]-7-amine | 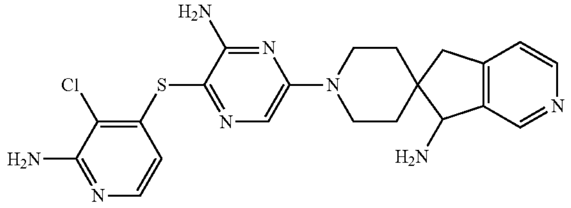 [SMILES: Nc1nc(N2CCC3(CC2)Cc2ccncc2C3N)cnc1Sc1ccnc(N)c1Cl] | 455 |
| 223 | 2-amino-1'-(6-amino-5-((2-amino-3-chloropyridin-4-yl)thio)pyrazin-2-yl)-2,3-dihydrospiro[indene-1,4'-piperidine]-4-carboxamide | 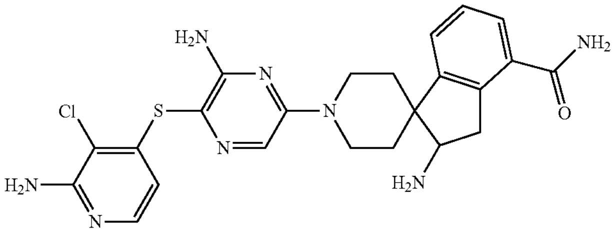 [SMILES: NC(=O)c1cccc2c1CC(N)C21CCN(c2cnc(Sc3ccnc(N)c3Cl)c(N)n2)CC1] | 497 |

TABLE 26-continued

| EX No. | Chemical Name | Structure | MS(M + H)+ |
|---|---|---|---|
| 224 | (R)-2-amino-1'-(6-amino-5-((2-amino-3-chloropyridin-4-yl)thio)pyrazin-2-yl)-2,3-dihydrospiro[indene-1,4'-piperidine]-4-carboxamide | 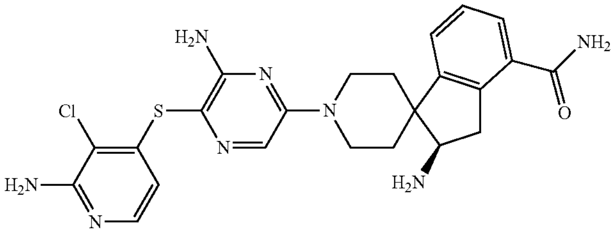 [SMILES: NC(=O)c1cccc2c1C[C@@H](N)C21CCN(c2cnc(Sc3ccnc(N)c3Cl)c(N)n2)CC1] | 497 |
| 225 | 2-amino-1'-(6-amino-5-((2-amino-3-chloropyridin-4-yl)thio)pyrazin-2-yl)-2,3-dihydrospiro[indene-1,4'-piperidine]-4-carbonitrile | 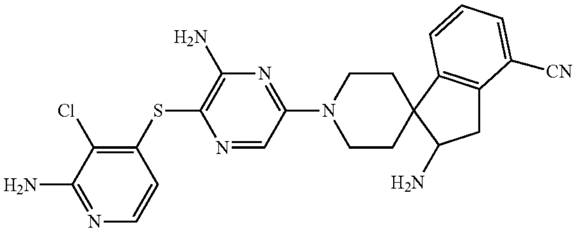 [SMILES: N#Cc1cccc2c1CC(N)C21CCN(c2cnc(Sc3ccnc(N)c3Cl)c(N)n2)CC1] | 479 |
| 226 | (R)-2-amino-1'-(6-amino-5-((2-amino-3-chloropyridin-4-yl)thio)pyrazin-2-yl)-2,3-dihydrospiro[indene-1,4'-piperidine]-4-carbonitrile | 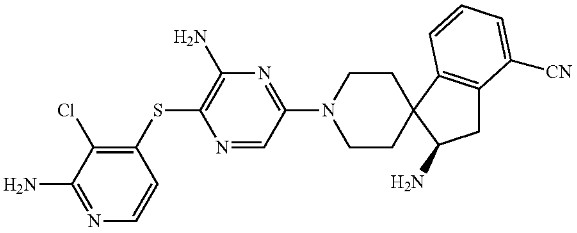 [SMILES: N#Cc1cccc2c1C[C@@H](N)C21CCN(c2cnc(Sc3ccnc(N)c3Cl)c(N)n2)CC1] | 479 |
| 227 | N-(2-amino-1'-(6-amino-5-((2-amino-3-chloropyridin-4-yl)thio)pyrazin-2-yl)-2,3-dihydrospiro[indene-1,4'-piperidin]-4-yl)acetamide | 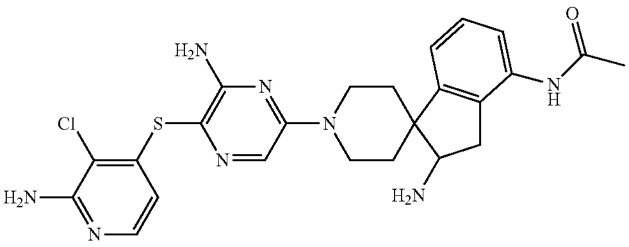 [SMILES: CC(=O)Nc1cccc2c1CC(N)C21CCN(c2cnc(Sc3ccnc(N)c3Cl)c(N)n2)CC1] | 511 |
| 228 | (R)-N-(2-amino-1'-(6-amino-5-((2-amino-3-chloropyridin-4-yl)thio)pyrazin-2-yl)-2,3-dihydrospiro[indene-1,4'-piperidin]-4-yl)acetamide | 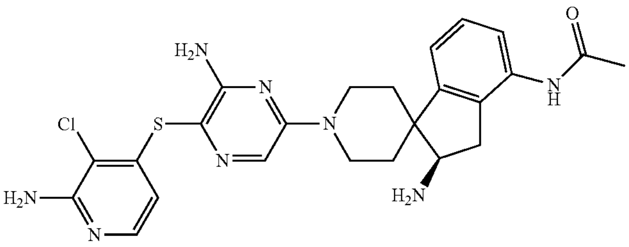 [SMILES: CC(=O)Nc1cccc2c1C[C@@H](N)C21CCN(c2cnc(Sc3ccnc(N)c3Cl)c(N)n2)CC1] | 511 |
| 229 | 1'-(6-amino-5-((2-amino-3-chloropyridin-4-yl)thio)pyrazin-2-yl)-6-(pyrrolidin-1-yl)-1,3-dihydrospiro[indene-2,4'-piperidin]-1-amine | 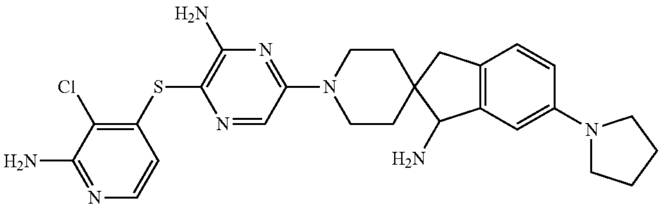 [SMILES: Nc1nc(N2CCC3(CC2)Cc2ccc(N4CCCC4)cc2C3N)cnc1Sc1ccnc(N)c1Cl] | 523 |

TABLE 26-continued

| EX No. | Chemical Name | Structure | MS(M + H)+ |
|---|---|---|---|
| 230 | (S)-1'-(6-amino-5-((2-amino-3-chloropyridin-4-yl)thio)pyrazin-2-yl)-6-(pyrrolidin-1-yl)-1,3-dihydrospiro[indene-2,4'-piperidin]-1-amine | 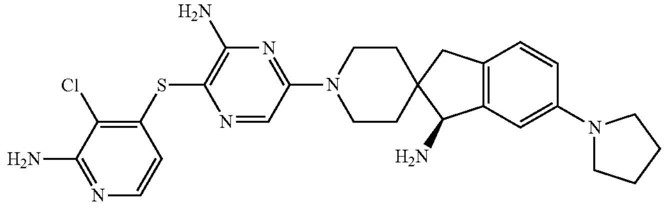 [SMILES: Nc1nc(N2CCC3(CC2)Cc2ccc(N4CCCC4)cc2[C@H]3N)cnc1Sc1ccnc(N)c1Cl] | 523 |
| 231 | 1'-(6-amino-5-((2-amino-3-chloro-pyridin-4-yl)thio)pyrazin-2-yl)-6-(1,4-dimethyl-1H-1,2,3-triazol-5-yl)-1,3-dihydrospiro[indene-2,4'-piperidin]-1-amine | 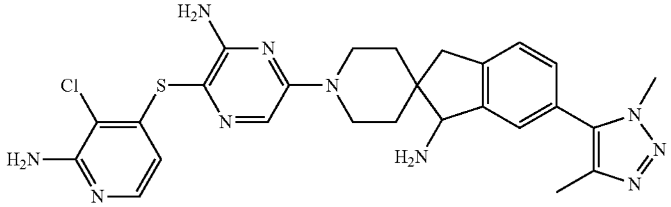 [SMILES: Cc1nnn(C)c1-c1ccc2c(c1)C(N)C1(CCN(c3cnc(Sc4ccnc(N)c4Cl)c(N)n3)CC1)C2] | 549 |
| 232 | (S)-1'-(6-amino-5-((2-amino-3-chloropyridin-4-yl)thio)pyrazin-2-yl)-6-(1,4-dimethyl-1H-1,2,3-triazol-5-yl)-1,3-dihydrospiro[indene-2,4'-piperidinl-1-amine | 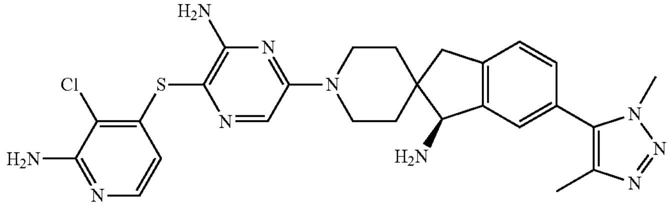 [SMILES: Cc1nnn(C)c1-c1ccc2c(c1)[C@@H](N)C1(CCN(c3cnc(Sc4ccnc(N)c4Cl)c(N)n3)CC1)C2] | 549 |
| 233 | 1'-(6-amino-5-((2-amino-3-chloro-pyridin-4-yl)thio)pyrazin-2-yl)-6-(methylthio)-1,3-dihydrospiro[indene-2,4'-piperidin]-1-amine | 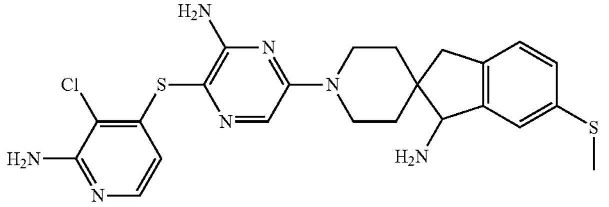 [SMILES: CSc1ccc2c(c1)C(N)C1(CCN(c3cnc(Sc4ccnc(N)c4Cl)c(N)n3)CC1)C2] | 500 |
| 234 | 2-(1-amino-1'-(6-amino-5-((2-amino-3-chloropyridin-4-yl)thio)pyrazin-2-yl)-1,3-dihydrospiro[indene-2,4'-piperidin]-6-yl)propan-2-ol | 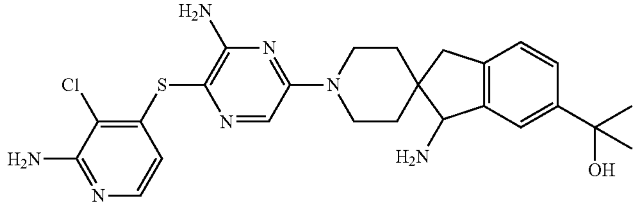 [SMILES: CC(C)(O)c1ccc2c(c1)C(N)C1(CCN(c3cnc(Sc4ccnc(N)c4Cl)c(N)n3)CC1)C2] | 512 |
| 235 | (S)-2-(1-amino-1'-(6-amino-5-((2-amino-3-chloropyridin-4-yl)thio)pyrazin-2-yl)-1,3-dihydrospiro[indene-2,4'-piperidin]-6-yl)propan-2-ol | 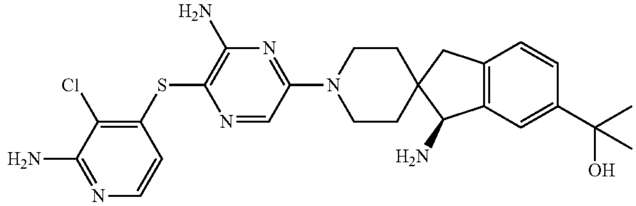 [SMILES: CC(C)(O)c1ccc2c(c1)[C@@H](N)C1(CCN(c3cnc(Sc4ccnc(N)c4Cl)c(N)n3)CC1)C2] | 512 |
| 236 | 1'-(6-amino-5-((2-amino-3-chloro-pyridin-4-yl)thio)pyrazin-2-yl)-6-(methylsulfonyl)-1,3-dihydrospiro[indene-2,4'-piperidin]-1-amine | 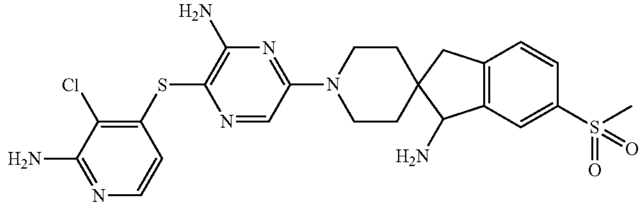 [SMILES: CS(=O)(=O)c1ccc2c(c1)C(N)C1(CCN(c3cnc(Sc4ccnc(N)c4Cl)c(N)n3)CC1)C2] | 532 |

TABLE 26-continued

| EX No. | Chemical Name | Structure | MS(M + H)+ |
|---|---|---|---|
| 237 | N-(1-amino-1'-(6-amino-5-((2-amino-3-chloropyridin-4-yl)thio)pyrazin-2-yl)-1,3-dihydrospiro[indene-2,4'-piperidin]-6-yl)acetamide | 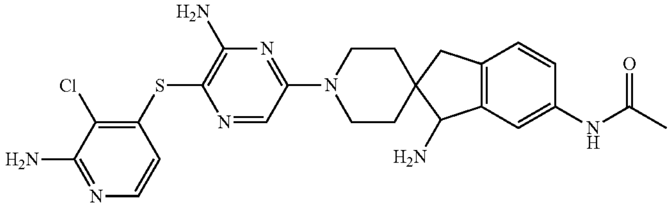 [SMILES: CC(=O)Nc1ccc2c(c1)C(N)C1(CCN(c3cnc(Sc4ccnc(N)c4Cl)c(N)n3)CC1)C2] | 511 |
| 238 | (S)-N-(1-amino-1'-(6-amino-5-((2-amino-3-chloropyridin-4-yl)thio) pyrazin-2-yl)-1,3-dihydrospiro[indene-2,4'-piperidin]-6-yl)acetamide | 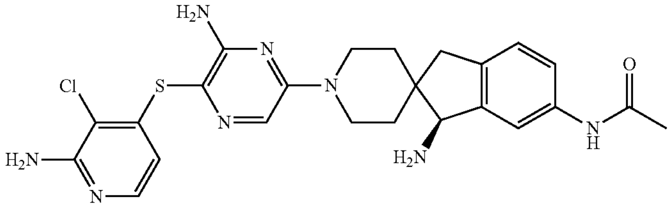 [SMILES: CC(=O)Nc1ccc2c(c1)[C@@H](N)C1(CCN(c3cnc(Sc4ccnc(N)c4Cl)c(N)n3)CC1)C2] | 511 |
| 239 | 1-amino-1'-(6-amino-5-((2-amino-3-chloropyridin-4-yl)thio)pyrazin-2-yl)-1,3-dihydrospiro[indene-2,4'-piperidine]-6-carboxamide | 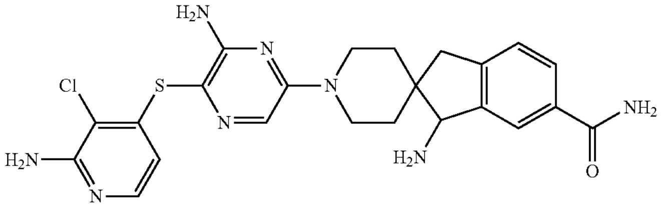 [SMILES: NC(=O)c1ccc2c(c1)C(N)C1(CCN(c3cnc(Sc4ccnc(N)c4Cl)c(N)n3)CC1)C2] | 497 |
| 240 | 1'-(6-amino-5-((2-amino-3-chloropyridin-4-yl)thio)pyrazin-2-yl)-6-(cyclopentyloxy)-1,3-dihydrospiro[indene-2,4'-piperidin]-1-amine | 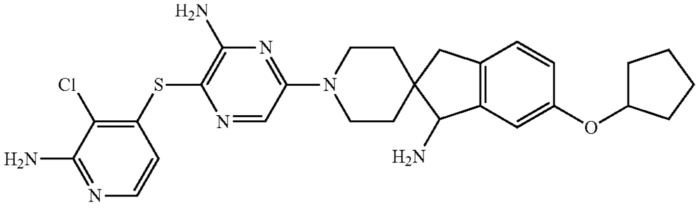 [SMILES: Nc1nc(N2CCC3(CC2)Cc2ccc(OC4CCCC4)cc2C3N)cnc1Sc1ccnc(N)c1Cl] | 538 |
| 241 | (S)-1'-(6-amino-5-((2-amino-3-chloropyridin-4-yl)thio)pyrazin-2-yl)-6-(cyclopentyloxy)-1,3-dihydrospiro[indene-2,4'-piperidin]-1-amine | 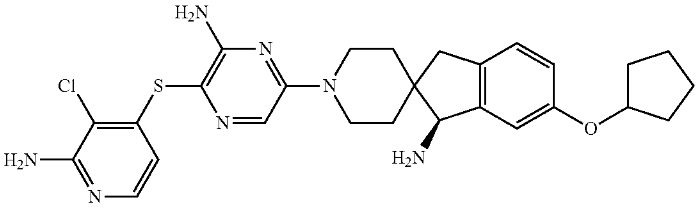 [SMILES: Nc1nc(N2CCC3(CC2)Cc2ccc(OC4CCCC4)cc2[C@H]3N)cnc1Sc1ccnc(N)c1Cl] | 538 |
| 242 | (S)-1-amino-1'-(6-amino-5-((2-amino-3-chloropyridin-4-yl)thio)pyrazin-2-yl)-3H-spiro[indolizine-2,4'-piperidin]-7(1H)-one | 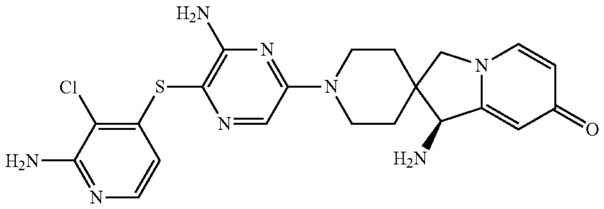 [SMILES: Nc1nc(N2CCC3(CC2)Cn2ccc(=O)cc2[C@H]3N)cnc1Sc1ccnc(N)c1Cl] | 471 |
| 243 | 1-amino-1'-(6-amino-5-((2-amino-3-chloropyridin-4-yl)thio)pyrazin-2-yl)-5-fluoro-1,3-dihydrospiro[indene-2,4'-piperidin]-6-ol | 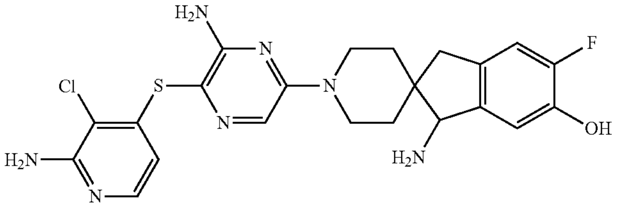 [SMILES: Nc1nc(N2CCC3(CC2)Cc2cc(F)c(O)cc2C3N)cnc1Sc1ccnc(N)c1Cl] | 488 |

TABLE 26-continued

| EX No. | Chemical Name | Structure | MS(M + H)+ |
|---|---|---|---|
| 244 | (S)-1-amino-1'-(6-amino-5-((2-amino-3-chloropyridin-4-yl)thio)pyrazin-2-yl)-5-fluoro-1,3-dihydrospiro [indene-2,4'-piperidin]-6-ol | 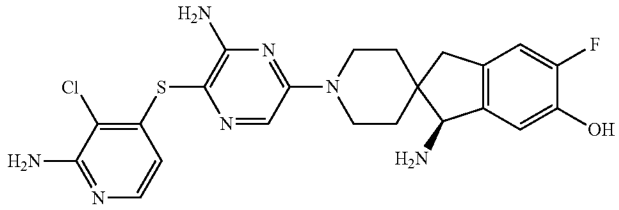 [SMILES: Nc1nc(N2CCC3(CC2)Cc2cc(F)c(O)cc2[C@H]3N)cnc1Sc1ccnc(N)c1Cl] | 488 |
| 245 | 1'-(6-amino-5-((2-amino-3-chloro-pyridin-4-yl)thio)pyrazin-2-yl)-5,7-dihydro-1H-spiro[cyclopenta[f] indole-6,4'-piperidin]-7-amine | 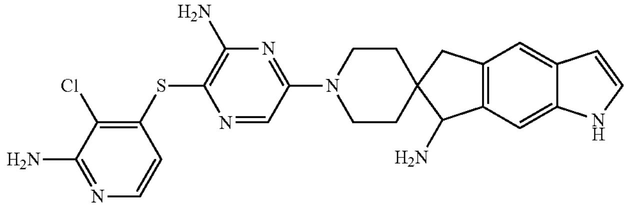 [SMILES: Nc1nc(N2CCC3(CC2)Cc2cc4cc[nH]c4cc2C3N)cnc1Sc1ccnc(N)c1Cl] | 493 |
| 246 | (S)-1'-(6-amino-5-((2-amino-3-chloropyridin-4-yl)thio)pyrazin-2-yl)-5,7-dihydro-1H-spiro[cyclopenta[f] indole-6,4'-piperidin]-7-amine | 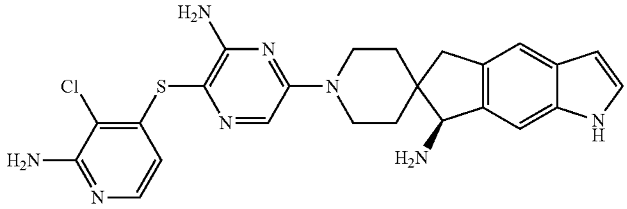 [SMILES: Nc1nc(N2CCC3(CC2)Cc2cc4cc[nH]c4cc2[C@H]3N)cnc1Sc1ccnc(N)c1Cl] | 493 |
| 247 | 1'-(6-amino-5-((2-amino-3-chloro-pyridin-4-yl)thio)pyrazin-2-yl)-5,7-dihydro-1H-spiro[indeno[5,6-d] imidazole-6,4'-piperidin]-7-amine | 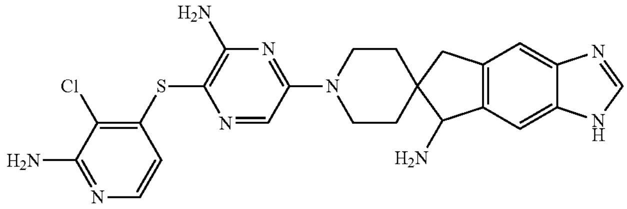 [SMILES: Nc1nc(N2CCC3(CC2)Cc2cc4nc[nH]c4cc2C3N)cnc1Sc1ccnc(N)c1Cl] | 494 |
| 248 | (S)-1'-(6-amino-5-((2-amino-3-chloropyridin-4-yl)thio)pyrazin-2-yl)-5,7-dihydro-1H-spiro[indeno[5,6-d] imidazole-6,4'-piperidin]-7-amine | 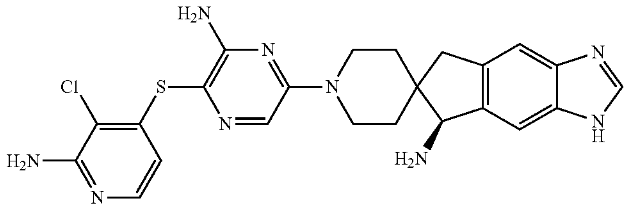 [SMILES: Nc1nc(N2CCC3(CC2)Cc2cc4nc[nH]c4cc2[C@H]3N)cnc1Sc1ccnc(N)c1Cl] | 494 |
| 249 | 1'-(6-amino-5-((2-amino-3-chloro-pyridin-4-yl)thio)pyrazin-2-yl)-6-(1H-tetrazol-5-yl)-1,3-dihydrospiro [indene-2,4'-piperidin]-1-amine | 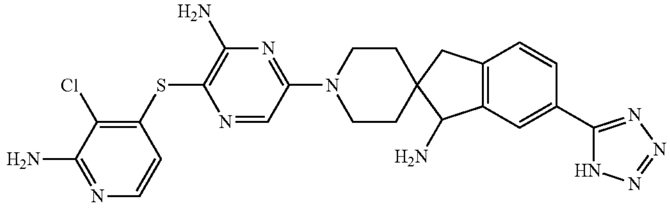 [SMILES: Nc1nc(N2CCC3(CC2)Cc2ccc(-c4nnn[nH]4)cc2C3N)cnc1Sc1ccnc(N)c1Cl] | 522 |
| 250 | (S)-1'-(6-amino-5-((2-amino-3-chloropyridin-4-yl)thio)pyrazin-2-yl)-6-(1H-tetrazol-5-yl)-1,3-dihydrospiro [indene-2,4'-piperidin]-1-amine | 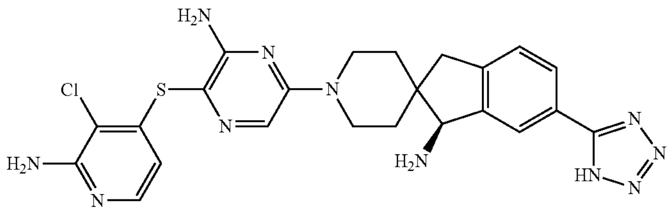 [SMILES: Nc1nc(N2CCC3(CC2)Cc2ccc(-c4nnn[nH]4)cc2[C@H]3N)cnc1Sc1ccnc(N)c1Cl] | 522 |

TABLE 26-continued

| EX No. | Chemical Name | Structure | MS(M + H)+ |
|---|---|---|---|
| 251 | 1-(1-amino-1'-(6-amino-5-((2-amino-3-chloropyridin-4-yl)thio)pyrazin-2-yl)-1,3-dihydrospiro[indene-2,4'-piperidin]-6-yl)-3-methylurea | 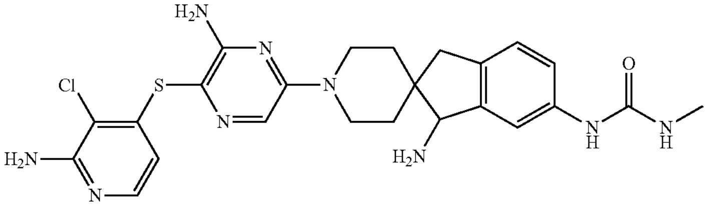 [SMILES: CNC(=O)Nc1ccc2c(c1)C(N)C1(CCN(c3cnc(Sc4ccnc(N)c4Cl)c(N)n3)CC1)C2] | 526 |
| 252 | (S)-1-(1-amino-1'-(6-amino-5-((2-amino-3-chloropyridin-4-yl)thio) pyrazin-2-yl)-1,3-dihydrospiro[indene-2,4'-piperidin]-6-yl)-3-methylurea | 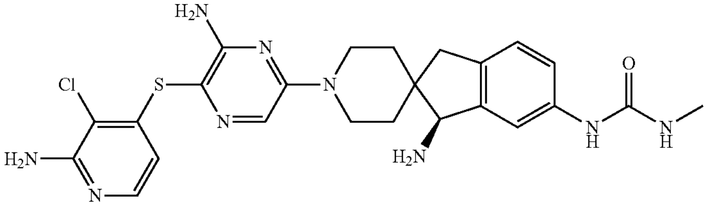 [SMILES: CNC(=O)Nc1ccc2c(c1)[C@@H](N)C1(CCN(c3cnc(Sc4ccnc(N)c4Cl)c(N)n3)CC1)C2] | 526 |
| 253 | (R)-1'-(5-((2-amino-3-chloropyridin-4-yl)thio)pyrazin-2-yl)-2,3-dihydro-spiro[indene-1,4'-piperidin]-2-amine | 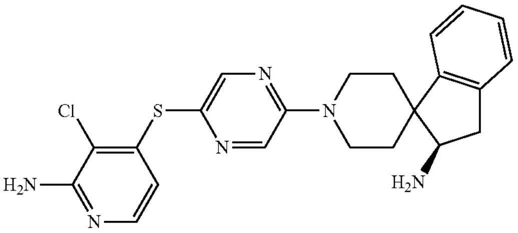 [SMILES: Nc1nccc(Sc2cnc(N3CCC4(CC3)c3ccccc3C[C@H]4N)cn2)c1Cl] | 439 |

Pharmacological Testing

Example A. Phosphatase Assay (Single Dose Inhibition)

Assay Protocol:

For single dose inhibition assays using 6,8-difluoro-4-methylumbelliferyl phosphate (DiFMUP) as substrate, SHP2 samples (diluted to 0.5 nM in reaction buffer) we incubated with dPEG8 peptide for 30 min in reaction buffer[60 mM 3,3-dimethyl glutarate (pH7.2), 75 mM NaCl, 75 mM KCl, and 1 mM EDTA, 0.05% Tween 20, 2 mM dithiothreitol (DTT)] to active the PIP. DMSO [0.5% (v/v)] or compounds (100 nM) were added to the mixture and incubated for 30 min at room temperature. Reactions were initiated by the addition of DiFMUP (12 μM; total reaction volume of 100 μL), and the fluorescence (excitation at 340 nm, emission at 450 nm) of the resulting solutions was measured on a 2104-0020 EnVision Xcite Multilabel Reader (PerkinElmer) after 30 min. The experiment is carried out in triplicate. The value for the control sample (DMSO) was set to 100%, and the values for the compound-treated samples were expressed as activity relative to the control sample. The inhibition of SHP2 by compounds of the invention were shown in table A

TABLE A

| Example | SHP2 inhibition (%)@0.1 μM |
|---|---|
| 1 | 87 |
| 2 | 75 |
| 3 | 42 |
| 4 | 20 |
| 5 | 84 |

TABLE A-continued

| Example | SHP2 inhibition (%)@0.1 μM |
|---|---|
| 6 | 66 |
| 7 | 81 |
| 8 | 60 |
| 9 | 54 |
| 11 | 74 |
| 12 | 76 |
| 13 | 72 |
| 14 | 82 |
| 15 | 83 |
| 16 | 75 |
| 17 | 81 |
| 18 | 35 |
| 19 | 86 |
| 20 | 86 |
| 21 | 49 |
| 22 | 30 |
| 23 | 71 |
| 24 | 70 |
| 25 | 72 |
| 26 | 57 |
| 27 | 79 |
| 28 | 75 |
| 29 | 77 |
| 31 | 70 |
| 32 | 85 |
| 33 | 81 |
| 34 | 71 |
| 35 | 70 |
| 36 | 65 |
| 37 | 76 |
| 38 | 75 |
| 39 | 67 |
| 40 | 74 |
| 41 | 69 |
| 42 | 49 |
| 43 | 79 |
| 44 | 88 |

TABLE A-continued

| Example | SHP2 inhibition (%)@0.1 μM |
|---|---|
| 45 | 68 |
| 46 | 69 |
| 47 | 81 |
| 48 | 81 |
| 49 | 85 |
| 50 | 77 |
| 51 | 85 |
| 53 | 84 |
| 54 | 69 |
| 56 | 71 |
| 57 | 55 |
| 58 | 73 |
| 59 | 69 |
| 60 | 70 |
| 61 | 74 |
| 62 | 76 |
| 63 | 93 |
| 64 | 66 |
| 65 | 0 |
| 66 | 72 |
| 67 | 63 |
| 68 | 82 |
| 69 | 89 |
| 70 | 30 |
| 71 | 86 |
| 72 | 28 |
| 73 | 80 |
| 74 | 76 |
| 75 | 16 |
| 78 | 67 |
| 79 | 58 |
| 80 | 75 |
| 81 | 75 |
| 82 | 72 |
| 83 | 91 |
| 89 | 90 |
| 90 | 71 |
| 91 | 88 |
| 92 | 92 |
| 93 | 94 |
| 94 | 64 |
| 95 | 73 |
| 96 | 66 |
| 97 | 86 |
| 98 | 81 |
| 99 | 89 |
| 100 | 88 |
| 101 | 83 |
| 102 | 81 |
| 103 | 76 |
| 104 | 87 |
| 106 | 82 |
| 107 | 77 |
| 108 | 71 |
| 109 | 71 |
| 110 | 61 |
| 111 | 82 |
| 112 | 87 |
| 113 | 80 |
| 114 | 96 |
| 115 | 86 |
| 116 | 79 |
| 117 | 81 |
| 118 | 81 |
| 119 | 61 |
| 120 | 87 |
| 122 | 88 |
| 123 | 50 |
| 124 | 84 |
| 125 | 86 |
| 126 | 81 |
| 127 | 83 |
| 128 | 84 |
| 129 | 74 |
| 130 | 94 |
| 131 | 83 |
| 132 | 78 |
| 133 | 76 |

TABLE A-continued

| Example | SHP2 inhibition (%)@0.1 μM |
|---|---|
| 134 | 78 |
| 135 | 86 |
| 136 | 83 |
| 137 | 89 |
| 138 | 82 |
| 140 | 14 |
| 141 | 41 |
| 142 | 17 |
| 143 | 72 |
| 144 | 80 |
| 145 | 79 |
| 146 | 82 |
| 148 | 72 |
| 149 | 28 |
| 150 | 84 |
| 151 | 86 |
| 153 | 82 |
| 154 | 82 |
| 156 | 80 |
| 157 | 78 |
| 158 | 90 |
| 159 | 88 |

Example B. Phosphatase Assays (IC50)

$IC_{50}$ values were estimated using 6,8-difluoro-4-methylumbelliferyl phosphate (DiFMUP) as a substrate, SHP2 samples (diluted to 0.5 nM in reaction buffer) were incubated with dPEG8 peptide for 30 min in reaction buffer[60 mM 3,3-dimethyl glutarate (pH7.2), 75 mM NaCl, 75 mM KCl, and 1 mM EDTA, 0.05% Tween 20, 2 mM dithiothreitol (DT)] to active the PP. DMSO [0.5% (v/v)] or compounds (concentrations ranging from 0.3 nM to 1 M) were added to the mixture and incubated for 30 min at room temperature. Reactions were initiated by the addition of DiFMUP (12 μM; total reaction volume of 100 μL), and the fluorescence (excitation at 340 nm, emission at 450 nm) of the resulting solutions was measured on a 2104-0020 EnVision Xcite Multilabel Reader (PerkinElmer) after 30 min. The $IC_{50}$ results of the compounds of the invention were shown by table B.

TABLE B

| Example | $IC_{50}$(nM) |
|---|---|
| 1 | 8 |
| 2 | 4 |
| 5 | 6 |
| 7 | 22 |
| 10 | 7 |
| 19 | 7 |
| 26 | 11 |
| 30 | 3 |
| 44 | 4 |
| 57 | 16 |
| 81 | 8 |
| 84 | 3 |
| 85 | 6 |
| 86 | 14 |
| 87 | 9 |
| 88 | 36 |
| 121 | 56 |
| 146 | 12 |
| 151 | 7 |
| 152 | 3 |
| 155 | 3 |

Example C. Cell Proliferation Assay

MV-4-11 (4000 cells/well) were plated onto 96-well plates in 100 μL medium (IMDM containing 3% FBS, Gibco). For drug treatment, compounds of the invention at various concentrations were added 24 hours after cell plating. At day 8, 30 μL MTS/PMS reagents (Promega/Sigma) were added, and the absorbance value was determined according to the supplier's instruction (Promega). The $IC_{50}$ results of the compounds of the invention were shown by table C.

TABLE C

| Example | $IC_{50}$(nM) |
|---|---|
| 2 | 2.7 |
| 5 | 4.8 |
| 10 | 4.0 |
| 14 | 6.0 |
| 30 | 2.2 |
| 44 | 7.4 |
| 45 | 2.5 |
| 56 | 10.4 |
| 64 | 8.1 |
| 68 | 4.9 |
| 69 | 4.0 |
| 71 | 13.0 |
| 83 | 16.0 |
| 89 | 5.0 |
| 91 | 12.0 |
| 92 | 9.0 |
| 93 | 11.0 |
| 94 | 10.9 |
| 95 | 10.0 |
| 99 | 18.0 |
| 100 | 30.0 |
| 104 | 9.0 |
| 105 | 11.0 |
| 112 | 30.0 |
| 137 | 3.3 |
| 156 | 46.1 |

Example D. p-ERK Cellular Assay

ERK1/2 activation is determined by immunoblotting analysis of cell lysates with an anti-p-ERK1/2 antibody. In brief, MV-4-11 cells were treated with a series of compounds (concentrations ranging from 0.3 nM to 100 nM) for 2 hours. Total protein was extracted using a RIPA buffer with Halt Protease Inhibitor Cocktail (Thermo Fisher Scientific, Rockford, Ill., USA). 10 μL of total protein was resolved by SDS-PAGE under reducing conditions and transferred onto polyvinylidene difluoride membranes (Bio-Rad). After blocking in Tris-buffered saline containing 5% BSA, the membrane was incubated overnight with primary antibodies at 4° C., followed by 1 h incubation with horseradish peroxidase (HRP)-conjugated secondary antibody. The bound secondary antibody was detected using chemiluminescence.

Example E. MV-4-11 Xenograft Model

MV-4-11 cells were expanded in culture, harvested and injected subcutaneously into 5-8 week old female NOD/SCID mice ($5\times10^6$ cells/each mouse, n=6-10/group). Subsequent administration of compound by oral gavage (0.1-10 mpk/dose) started when the mean tumor size reached approximately 100-200 $mm^3$. During the treatment (once or twice a day for 2-4 weeks), the tumor volumes were measured using a caliper. Statistical analysis of difference in tumor volume among the groups were evaluated using a one-way ANOVA. Vehicle alone was the negative control.

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19$^{th}$ ed., Mack Publishing Co., 1995). The compounds of Formula I, II, III or IV are generally effective over a wide dosage range.

In summary, the most of compounds descripted here is very potent and selective, with IC50 below 10 nM. They also showed a great anti-tumor efficacy in vivo models. For example, dosages per day normally fall within the range of about 0.2 mg to about 100 mg total daily dose, preferably 0.2 mg to 50 mg total daily dose, more preferably 0.2 mg to 20 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A compound which is:

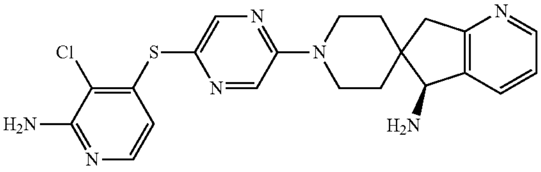

;

or a pharmaceutically acceptable salt thereof.

2. A compound which is:

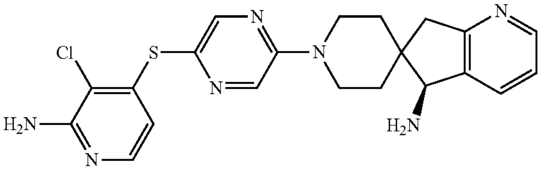

.

* * * * *